(12) United States Patent
Green et al.

(10) Patent No.: US 7,709,503 B2
(45) Date of Patent: May 4, 2010

(54) PYRROL DERIVATIVES WITH ANTIBACTERIAL ACTIVITY

(75) Inventors: Oluyinka Morenike Green, Waltham, MA (US); Kenneth Gregory Hull, Waltham, MA (US); Haihong Ni, Waltham, MA (US); Sheila Irene Hauck, Waltham, MA (US); George Byron Mullen, Waltham, MA (US); Alexander Louis Breeze, Macclesfield (GB); Neil James Hales, Macclesfield (GB); David Timms, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 1087 days.

(21) Appl. No.: 10/571,212

(22) PCT Filed: Sep. 10, 2004

(86) PCT No.: PCT/GB2004/003874

§ 371 (c)(1),
(2), (4) Date: Mar. 9, 2006

(87) PCT Pub. No.: WO2005/026149

PCT Pub. Date: Mar. 24, 2005

(65) Prior Publication Data

US 2006/0223801 A1    Oct. 5, 2006

(30) Foreign Application Priority Data

Sep. 13, 2003  (GB) ................. 0321509.2
May 12, 2004  (GB) ................. 0410527.6

(51) Int. Cl.
*A61K 31/4468* (2006.01)
(52) U.S. Cl. ............... 514/326; 514/327; 546/208; 546/216; 546/222; 546/224; 548/523
(58) Field of Classification Search ............ 514/326, 514/327; 546/201, 208, 209, 212, 214, 216, 546/222, 224, 210; 548/518, 523
See application file for complete search history.

(56) References Cited

U.S. PATENT DOCUMENTS

| | | | |
|---|---|---|---|
| 3,963,480 A | 6/1976 | Bailey | |
| 4,046,775 A | 9/1977 | Bailey | |
| 4,791,112 A | 12/1988 | Bagley et al. | |
| 4,912,109 A | 3/1990 | Bagley et al. | |
| 5,712,279 A | 1/1998 | Biller et al. | |
| 5,739,135 A | 4/1998 | Biller et al. | |
| 2005/0234033 A1 | 10/2005 | Anandan et al. | |
| 2005/0250784 A1 | 11/2005 | Anandan et al. | |

FOREIGN PATENT DOCUMENTS

| | | |
|---|---|---|
| EP | 0894805 A1 | 2/1999 |
| EP | 1253142 A1 | 10/2002 |
| EP | 1431267 A1 | 6/2004 |
| WO | 96/26205 A1 | 8/1996 |
| WO | 01/12601 A1 | 2/2001 |
| WO | 01/52845 A1 | 7/2001 |
| WO | 01/52846 A1 | 7/2001 |
| WO | 01/53267 A1 | 7/2001 |
| WO | 01/96307 A2 | 12/2001 |
| WO | 02/085886 A2 | 10/2002 |
| WO | 02/096908 A1 | 12/2002 |
| WO | 03/016254 A1 | 2/2003 |
| WO | 03/048129 A1 | 6/2003 |
| WO | 03/072553 A1 | 9/2003 |
| WO | 03/072554 A1 | 9/2003 |
| WO | 2004/002490 A2 | 1/2004 |
| WO | 2004/083177 A2 | 9/2004 |
| WO | 2004/089947 A2 | 10/2004 |
| WO | 2004/089954 A1 | 10/2004 |
| WO | 2005/014579 A1 | 2/2005 |
| WO | 2005/044797 A1 | 5/2005 |
| WO | 2005/086898 A2 | 9/2005 |
| WO | 2006/030975 A1 | 3/2006 |
| WO | 2006/047277 A2 | 5/2006 |
| WO | 2006/047504 A1 | 5/2006 |
| WO | 2006/087543 A1 | 8/2006 |
| WO | 2006/087544 A2 | 8/2006 |
| WO | 2006/087548 A2 | 8/2006 |
| WO | 2006/092599 A2 | 9/2006 |
| WO | 2006/092608 A1 | 9/2006 |
| WO | 2007/071965 A2 | 6/2007 |

OTHER PUBLICATIONS

Gilles Klopman et al, Computer Automated Structure Evaluation of Quinolone Antibacterial Agents, Antimicrobial Agents and Chemotherapy, 1987, 1831-1840, 31 (11).
Patrick Laurin et al, Structure-Activity Relationship in Two Series of Aminoalkyl Substituted Coumarin Inhibitors of Gyrase B, Bioorganic & Medicinal Chemistry Letters, 1999, 2875-2880, 9.
Laurent Schio et al, Fine Tuning of Physico-Chemical Parameters to Optimise a New Series of Novobiocin Analogues, Bioorganic & Medicinal Chemistry Letters, 2001, 1461-1464, 11.
Richard L. Wynn, Evaluation of the Morphine Reversal Actions and Antinociceptive Activity of a New Class of Opiate Antagonists Structurally Related to Fentanyl, Drug Development Research, 1991, 189-195, 22.

(Continued)

*Primary Examiner*—Janet L Andres
*Assistant Examiner*—David E Gallis

(57) ABSTRACT

Compounds of Formula (1) and their pharmaceutically acceptable salts are described: Formula (1) Processes for their preparation, pharmaceutical compositions containing them, their use as medicaments and their use in the treatment of bacterial infections are also described.

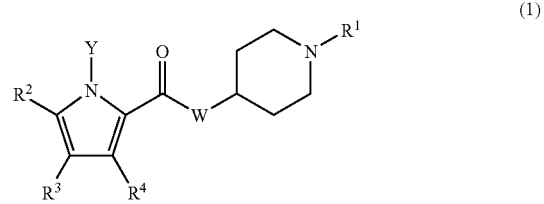

(1)

12 Claims, No Drawings

OTHER PUBLICATIONS

Yuichi Kanaoka et al, Synthesis of Thieno[2,3-c]-, Pyrrolo[2,3-c]- and Indolo[2,3-c]diazanaphthalenes by Photocyclization of Acylaminopyridines, Heterocycles, 1977, 29-32, 6 (1).

John M. Domagala et al, New Structure-Activity Relationships of the Quinolone Antibacterials Using the Target Enzyme. The Development and Application of an DNA Gyrase Assay, J. Med. Chem., 1986, 394-404, 29.

James A. Waters et al, Anticonvulsant Activity of Piperidinol and (Dialkylamino)alkanol Esters, J. Med. Chem., 1986, 1512-1516, 29.

Krzysztof Sieradzki et al, Suppression of B-Lactam Antibiotic Resistance in a Methicillin-Resistant *Staphyloccous aureus* through synergic action of early cell wall inhibitors and some other antibiotics, Journal of Antimicrobial Chemotherapy, 1997, 47-51, 39 Suppl. A.

Branislav Musick et al, Noviose Mimics of the Coumarin Inhibitors of Gyrase B, Tetrahedron Letters, 2003, 9259-9262, 44.

Beccalli, Egle M., et al., Pd-catalyzed intramolecular cyclization of pyrrolo-2-carboxamides: regiodivergent routes to pyrrolo-pyrazines and pyrrolo-pyridines, Tetrahedon, 2005, pp. 1077-1082, vol. 61.

Brown, J.W. et al., Some Three-Ring Esters Containing a Five-Membered Heteroaromatic Ring. A Comparison of Liquid Crystal Properties, Mol. Cryst. Liq. Cryst., 1989, pp. 121-140, vol. 173.

XP002397870 retrieved from STN, Database accession No. 784198-11-4 abstract; 784198-11-4 compounds, Nov. 19, 2004, Database Registry [Online], Chemical Abstracts Service, Columbus, OH.

XP002397871 retrieved from STN, Database accession No. 785802-22-4 abstract; 785802-22-4 compounds, Nov. 22, 2004, Database Registry [Online], Chemical Abstracts Service, Columbus, OH.

XP002397872 retrieved from STN, Database accession No. 784198-41-0 abstract; 784198-41-0 compounds, Nov. 19, 2004, Database Registry [Online], Chemical Abstracts Service, Columbus, OH.

XP002397873 retrieved from MDL, Database accession No. 432931, compounds 13254-12-1 & NL 6 510 290 a, Feb. 8, 2006, Database Beilstein [Online], Chemical Abstracts Service, Columbus, OH.

PYRROL DERIVATIVES WITH ANTIBACTERIAL ACTIVITY

CROSS-REFERENCE TO RELATED APPLICATIONS

This application is a US National Stage under 35 U.S.C §371 of International Application No.: PCT/GB2004/003874 (filed Sep. 10, 2004), which claims priority under 35 U.S.C. §111 to Application No. 0321509.2 filed on Sep. 13, 2003, the specification of which is incorporated by reference herein.

The present invention relates to compounds which demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular this invention relates to compounds useful for the treatment of bacterial infections in warm-blooded animals such as humans, more particularly to the use of these compounds in the manufacture of medicaments for use in the treatment of bacterial infections in warm-blooded animals such as humans.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus aureus* (MRSA), methicillin resistant coagulase negative staphylococci (MRCNS), penicillin resistant *Streptococcus pneumoniae* and multiple resistant *Enterococcus faecium*.

The preferred clinically effective antibiotic for treatment of last resort of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Consequently, in order to overcome the threat of widespread multi-drug resistant organisms, there is an on-going need to develop new antibiotics, particularly those with either a novel mechanism of action and/or containing new pharmacophoric groups.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

DNA gyrase is a well-validated target of antibacterials, including the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials may also inhibit topoisomerase IV and as a result, the primary target of these compounds varies among species. Although the quinolones are successful antibacterials, resistance generated primarily by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, clorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, J. *Antibiot*. 47: 32-36). Despite potent activity against DNA gyrase, cyclothialidine is a poor antibacterial agent showing activity only against some eubacterial species (Nakada, N, 1993, *Antimicrob. Agents Chemother.* 37: 2656-2661).

Synthetic inhibitors that target the B subunit of DNA gyrase are known in the art. For example, coumarin-containing compounds are described in patent application number WO 99/35155, 5,6-bicyclic heteroaromatic compounds are described in patent application WO 02/060879, and pyrazole compounds are described in patent application WO 01/52845 (U.S. Pat. No. 6,608,087).

We have discovered a new class of compounds which are useful for inhibiting DNA gyrase.

Therefore the current invention provides a compound of the formula (1) or a pharmaceutically acceptable salt thereof;

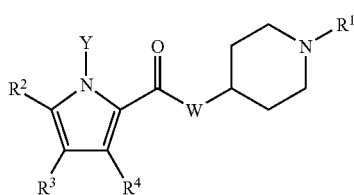

wherein:

W is O or $NR^5$;

Y is hydrogen;

$R^1$ is selected from $R^1a$, $R^1b$, $R^1c$, $R^1d$, $R^1e$ and $R^1f$;

$R^1a$ is a 4 to 7 membered saturated, partially unsaturated or unsaturated heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from:

nitro, cyano, sulfo, formyl, hydroxyiminomethyl, (2-6C)alkenyl, (2-6C)alkynyl, —CO(1-6C)alkyl, —COO(1-6C)alkyl (optionally substituted with —COO(1-6C)alkyl), trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy-, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, aryl, —NHC(O)O(1-4C)alkyl, —C(=NOR$^7$)(1-4C)alkyl, —C(=NOR$^7$)NR$^6$R$^7$, —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl, —NR$^6$R$^7$, —CH$_2$CH(CO$_2$R$^6$)OH, -(1-4C)alkylCH(NR$^6$R$^7$)CO$_2$R$^6$ and -(1-4C)alkylCH(NR$^6$R$^7$)CO(NR$^6$R$^7$);

wherein any aryl or heterocyclyl group in any of the preceding values for substituents on $R^1a$ may optionally be substituted by 1 or 2 substituents independently selected from (1-4C) alkyl, (2-4C)alkenyl, (2-4C)alkynyl, hydroxy, (1-4C)alkoxy, halo, cyano, nitro, carboxy, hydroxy(1-4C)alkyl-, (1-4C)alkoxy(1-4C)alkyl-, halo(1-4C)alkyl-, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl and —S(O)$_2$N[di(1-4C)alkyl];

$R^1b$ is an 8-10 membered bicyclic heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from the substituents listed for $R^1a$ above;

$R^1c$ is a phenyl ring, substituted by 1, 2 or 3 substituents independently selected from the substituents listed for $R^1a$ above;

$R^1d$ is selected from —CH$_2$R$^1a$, —C(O)R$^1a$, —OR$^1a$, S(O)qR$^1a$ (wherein q is 1 or 2);

$R^1e$ is selected from —CH$_2$R$^1b$, —C(O)R$^1b$, —OR$^1b$, S(O)qR$^1b$ (wherein q is 1 or 2);

$R^1f$ is selected from —CH$_2$R$^1c$, —C(O)R$^1c$ —OR$^1c$, S(O)qR$^1c$ (wherein q is 1 or 2);

$R^2$ is selected from hydrogen, (1-4C)alkyl, cyclopropyl, (2-4C)alkenyl, (2-4C)alkynyl, halo, cyano, fluoromethyl, difluoromethyl and trifluoromethyl;

$R^3$ is selected from hydrogen, (1-4C)alkyl, cyclopropyl, (2-4C)alkenyl, (2-4C)alkynyl, halo, hydroxy, cyano, fluoromethyl, difluoromethyl trifluoromethyl, —CO(1-6C)alkyl, and (1-6C)alkoxy;

$R^4$ is selected from hydrogen, (1-4C)alkyl, (2-4C)alkenyl, (2-4C)alkynyl, nitro, hydroxy, halo, cyano, (3-6C)cycloalkyl, -(1-6C)alkyl(3-6C)cycloalkyl, halo(1-4C)alkyl-, difluoromethyl, trifluoromethyl, —CO(1-6C)alkyl, and (1-6C)alkoxy;

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —N [di(1-4C)alkyl], (1-4C)alkoxy, (1-4C)alkoxy(1-4C)alkoxy, (1-4C)alkoxy(1-4C)alkoxy(1-4C)alkoxy, (1-4C)alkoxy(1-4C)alkyl-, (1-4C)alkylthio(1-4C)alkyl-, hydroxy(1-4C)alkyl-, -(1-4C)alkylNH$_2$, -(1-4C)alkylNH(1-4C)alkyl, -(1-4C)alkylN[di(1-4C)alkyl], and -(1-4C)alkylheterocyclyl;

$R^7$ is independently at each occurrence selected from hydrogen and (1-6C)alkyl;

or $R^6$ and $R^7$ may together with the nitrogen to which they are attached form a 5 or 6-membered heterocyclyl ring, optionally substituted with 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl-, (1-4C)alkoxy(1-4C)alkyl-, halo(1-4C)alkyl-, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl;

$R^5$ is selected from hydrogen and (1-4C)alkyl;

p is (independently at each occurrence) 0, 1 or 2.

In a further aspect of the invention there is provided a compound of the formula (1) or a pharmaceutically-acceptable salt thereof, wherein:

W is O or $NR^5$;

Y is hydrogen or methyl;

$R^1$ is selected from $R^1a$, $R^1b$, $R^1c$, $R^1d$, $R^1e$ and $R^1f$;

$R^1a$ is a 4 to 7 membered saturated, partially unsaturated or unsaturated heterocyclic ring containing 1, 2, 3, or 4 heteroatoms independently selected from O, S and N (provided that such a ring does not contain O—O or S—S bonds), wherein said ring is substituted by 1, 2 or 3 substituents independently selected from:

nitro, cyano, (2-6C)alkenyl, (2-6C)alkynyl, —CO(1-6C)alkyl, —COO(1-6C)alkyl, —O(1-6C)alkyl, trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —O(1-6C)alkyl, trifluoromethyl, —CONR$^6$R$^7$, carboxy, —NHC(O)O(1-4C)alkyl, —C(=NOH)(1-4C)alkyl, —C(=NOH)NR$^6$R$^7$, —S(O)p(1-4C)alkyl, —S(O)pNR$^6$R$^7$, —NR$^6$R$^7$, and heterocyclyl {optionally substituted by 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl}], heterocyclyl [optionally substituted by 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl], aryl [optionally substituted by 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl], —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl, —NR$^6$R$^7$, —CH$_2$CH(CO$_2$R$^6$)OH, -(1-4C)alkylCH(NR$^6$R$^7$)CO$_2$R$^6$, and -(1-4C)alkylCH(NR$^6$R$^7$)CO(NR$^6$R$^7$);

$R^1b$ is an 8-10 membered bicyclic heterocyclic ring containing 1, 2, 3, or 4 heteroatoms independently selected from O, S and N (provided that such a ring does not contain O—O or S—S bonds), wherein said ring is substituted by 1, 2 or 3 substituents independently selected from the substituents listed for $R^1a$ above;

$R^1c$ is a phenyl ring, substituted by 1, 2 or 3 substituents independently selected from the substituents listed for $R^1a$ above;

$R^1d$ is selected from —CH$_2$R$^1$a, —C(O)R$^1$a, —OR$^1$a, S(O)qR$^1$a (wherein q is 1 or 2);

$R^1e$ is selected from —CH$_2$R$^1$b, —C(O)R$^1$b, —OR$^1$b, S(O)qR$^1$b (wherein q is 1 or 2);

$R^1f$ is selected from —CH$_2$R$^1$c, —C(O)R$^1$c —OR$^1$c, S(O)qR$^1$c (wherein q is 1 or 2);

$R^2$ is selected from hydrogen, (1-4C)alkyl, cyclopropyl, (2-4C)alkenyl, (2-4C)alkynyl, halo, fluoromethyl, difluoromethyl and trifluoromethyl;

$R^3$ is selected from hydrogen, (1-4C)alkyl, cyclopropyl, (2-4C)alkenyl, (2-4C)alkynyl, halo, hydroxy, cyano, fluoromethyl, difluoromethyl trifluoromethyl, —CO(1-6C)alkyl, and (1-6C)alkoxy;

$R^4$ is selected from hydrogen, (1-4C)alkyl, (2-4C)alkenyl, (2-4C)alkynyl, nitro, hydroxy, halo, cyano, (3-6C)cycloalkyl, -(1-6C)alkyl(3-6C)cycloalkyl, halo(1-4C)alkyl, difluoromethyl, trifluoromethyl, —CO(1-6C)alkyl, and (1-6C)alkoxy;

$R^6$ is independently at each occurrence selected from hydrogen, (1-4C)alkyl, (3-6C)cycloalkyl, -(1-4C)alkylC(O)O(1-4C)alkyl, hydroxy, amino, (1-4C)alkoxy, (1-4C)alkoxy(1-4C)alkoxy, (1-4C)alkoxy(1-4C)alkoxy(1-4C)alkoxy, (1-4C)alkoxy(1-4C)alkyl, (1-4C)alkylthio(1-4C)alkyl, hydroxy(1-4C)alkyl, -(1-4C)alkylNH$_2$, -(1-4C)alkylNH(1-4C)alkyl, -(1-4C)alkylN[di(1-4C)alkyl], and -(1-4C)alkylheterocyclyl;

$R^7$ is independently at each occurrence selected from hydrogen and (1-6C)alkyl;

or $R^6$ and $R^7$ may together form a 5 or 6-membered heterocyclyl ring, optionally substituted with 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl;

$R^5$ is selected from hydrogen and (1-4C)alkyl;

p is (independently at each occurrence) 0, 1 or 2.

Therefore the current invention provides a compound of the formula (1) or a pharmaceutically acceptable salt thereof; wherein:

W is O or NR$^5$;

Y is hydrogen;

$R^1$ is selected from $R^1a$, $R^1b$, $R^1c$, $R^1d$, $R^1e$ and $R^1f$;

$R^1a$ is a 4 to 7 membered saturated, partially unsaturated or unsaturated heterocyclic ring containing 1, 2, 3, or 4 heteroatoms independently selected from O, S and N (provided that such a ring does not contain O—O or S—S bonds), wherein said ring is substituted by 1, 2 or 3 substituents independently selected from:

nitro, cyano, (2-6C)alkenyl, (2-6C)alkynyl, —CO(1-6C)alkyl, —COO(1-6C)alkyl (optionally substituted with —COO(1-6C)alkyl), trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, aryl, —NHC(O)O(1-4C)alkyl, —C(=NOR$^7$)(1-4C)alkyl, —C(═NOR$^7$)NR$^6$R$^7$, —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl, —NR$^6$R$^7$, —CH$_2$CH(CO$_2$R$^6$)OH, -(1-4C)alkylCH(NR$^6$R$^7$)CO$_2$R$^6$ and -(1-4C)alkylCH(NR$^6$R$^7$)CO(NR$^6$R$^7$);

wherein any aryl or heterocyclyl group in any of the preceding values for substituents on R$^1$a may optionally be substituted by 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl and —S(O)$_2$N[di(1-4C)alkyl];

R$^1$b is an 8-10 membered bicyclic heterocyclic ring containing 1, 2, 3, or 4 heteroatoms independently selected from O, S and N (provided that such a ring does not contain O—O or S—S bonds), wherein said ring is substituted by 1, 2 or 3 substituents independently selected from the substituents listed for R$^1$a above;

R$^1$c is a phenyl ring, substituted by 1, 2 or 3 substituents independently selected from the substituents listed for R$^1$a above;

R$^1$d is selected from —CH$_2$R$^1$a, —C(O)R$^1$a, —OR$^1$a, S(O)qR$^1$a (wherein q is 1 or 2);

R$^1$e is selected from —CH$_2$R$^1$b, —C(O)R$^1$b, —OR$^1$b, S(O)qR$^1$b (wherein q is 1 or 2);

R$^1$f is selected from —CH$_2$R$^1$c, —C(O)R$^1$c —OR$^1$c, S(O)qR$^1$c (wherein q is 1 or 2);

R$^2$ is selected from hydrogen, (1-4C)alkyl, cyclopropyl, (2-4C)alkenyl, (2-4C)alkynyl, halo, fluoromethyl, difluoromethyl and trifluoromethyl;

R$^3$ is selected from hydrogen, (1-4C)alkyl, cyclopropyl, (2-4C)alkenyl, (2-4C)alkynyl, halo, hydroxy, cyano, fluoromethyl, difluoromethyl trifluoromethyl, —CO(1-6C)alkyl, and (1-6C)alkoxy;

R$^4$ is selected from hydrogen, (1-4C)alkyl, (2-4C)alkenyl, (2-4C)alkynyl, nitro, hydroxy, halo, cyano, (3-6C)cycloalkyl, -(1-6C)alkyl(3-6C)cycloalkyl, halo(1-4C)alkyl, difluoromethyl, trifluoromethyl, —CO(1-6C)alkyl, and (1-6C)alkoxy;

R$^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —N[di(1-4C)alkyl, (1-4C)alkoxy, (1-4C)alkoxy(1-4C)alkoxy, (1-4C)alkoxy(1-4C)alkoxy(1-4C)alkoxy, (1-4C)alkoxy(1-4C)alkyl, (1-4C)alkylthio(1-4C)alkyl, hydroxy(1-4C)alkyl, -(1-4C)alkylNH$_2$, -(1-4C)alkylNH(1-4C)alkyl, -(1-4C)alkylN[di(1-4C)alkyl], and -(1-4C)alkylheterocyclyl;

R$^7$ is independently at each occurrence selected from hydrogen and (1-6C)alkyl;

or R$^6$ and R$^7$ may together with the nitrogen to which they are attached form a 5 or 6-membered heterocyclyl ring, optionally substituted with 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl;

R$^5$ is selected from hydrogen and (1-4C)alkyl;

p is (independently at each occurrence) 0, 1 or 2.

In this specification the term alkyl includes both straight and branched chain alkyl groups but references to individual alkyl groups such as propyl are specific for the straight chain version only. An analogous convention applies to other generic terms. Unless otherwise stated the term alkyl advantageously refers to chains with 1-6 carbon atoms, preferably 1-4 carbon atoms. In this specification, the terms alkenyl, alkynyl and cycloalkenyl include all positional and geometrical isomers.

In this specification the term alkoxy means an alkyl group as defined hereinbefore linked to an oxygen atom.

Where optional substituents are chosen from 0, 1, 2 or 3 groups it is to be understood that this definition includes all substituents being chosen from one of the specified groups or the substituents being chosen from two or more of the specified groups. An analogous convention applies to substituents chose from 0, 1 or 2 groups; 1, 2 or 3 substituents; and 1 or 2 groups.

It is to be understood that where substituents contain two substituents on an alkyl chain, in which both are linked by a heteroatom (for example two alkoxy substituents), then these two substituents are not substituents on the same carbon atom of the alkyl chain. It will be understood that unstable compounds are not contemplated as part of this invention.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

Where "R$^6$ and R$^7$ may together with the nitrogen to which they are attached form a 5 or 6-membered heterocyclyl ring" said "5 or 6-membered heterocyclyl ring" is a saturated, partially saturated or fully unsaturated, monocyclic ring one atom of which is the nitrogen atom to which R$^6$ and R$^7$ are attached, and the other atoms are either all carbon atoms or they are carbon atoms and 1, 2 or 3 heteroatoms chosen from nitrogen, sulphur or oxygen, wherein a —CH$_2$— group can optionally be replaced by a —C(O)—, and a ring nitrogen atom or a ring sulphur atom may be optionally oxidised to form the N- and/or S-oxide(s). Examples and suitable values of "R$^6$ and R$^7$ may together with the nitrogen to which they are attached form a 5 or 6-membered heterocyclyl ring" are piperazinyl and morpholino.

Particular examples of "4 to 7 membered saturated, partially unsaturated or unsaturated heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide" include pyridinyl, N-oxopyridinyl, pyrimidinyl, thiazolyl, thiadiazolyl, tetrazolyl, imidazolyl, triazinyl, pyrrolidinyl, thienyl, furanyl, oxadiazolyl, isoxazolyl, oxazolyl and pyrrolyl.

Particular examples of an "8-10 membered bicyclic heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide" include quinolinyl, purinyl, benzothiazolyl, indolyl, 4-oxoquinolinyl, 2,7-naphthyridinyl and quinazolinyl.

Heterocyclyl is a saturated, partially saturated or unsaturated, optionally substituted monocyclic ring containing 5 to 7 atoms of which 1, 2, 3 or 4 ring atoms are chosen from nitrogen, sulphur or oxygen, which may, unless otherwise specified, be carbon or nitrogen linked, wherein a —$CH_2$— group can optionally be replaced by a —C(O)—, a ring sulphur atom may be optionally oxidised to form the S-oxide(s), and a ring nitrogen atom may be optionally oxidised to form the N-oxide. Examples and suitable values of the term heterocyclyl are morpholino, morpholinyl, piperidino, piperidyl, pyridyl, pyridyl-N-oxide, pyranyl, pyrrolyl, imidazolyl, thiazolyl, thienyl, dioxolanyl, thiadiazolyl, piperazinyl, isothiazolidinyl, triazolyl, tetrazolyl, pyrrolidinyl, 2-oxazolidinonyl, 5-isoxazolonyl, thiomorpholino, pyrrolinyl, homopiperazinyl, 3,5-dioxapiperidinyl, 3-oxopyrazolin-5-yl, tetrahydropyranyl, tetrahydrothiopyranyl, 1-oxotetrahydrothiopyranyl, 1,1-dioxotetrahydrothiopyranyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, oxadiazolyl, 2-[(5-oxo)-1-oxa-3,4-diazolyl] and 3-[oxa-2,4-diazolyl].

Suitably a heterocyclyl is morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, 1,2,4-oxadiazolyl 2-[(5-oxo)-1-oxa-3,4-diazolyl] and 3-[oxa-2,4-diazolyl].

Conveniently heterocyclyl is oxazolyl, 1,3,4-oxadiazolyl, 1,2,4-oxadiazolyl, 2-[(5-oxo)-1-oxa-3,4-diazolyl]], 3-[oxa-2,4-diazolyl], tetrazolyl, thiazolyl, thiadiazolyl, pyridyl, imidazolyl, furyl, thienyl, morpholine, pyrimidyl, pyrazinyl, pyridazinyl, pyrazolyl, pyrazolinyl, and piperazinyl.

Suitable optional substituents for heterocyclyl as a saturated or partially saturated ring are, unless otherwise defined, 1, 2 or 3 substituents independently selected from halo, cyano, hydroxy, (1-4C)alkyl, (1-4C)alkoxy and (1-4C)alkylS(O)$_b$ (wherein b is 0, 1 or 2). Further suitable substituents for "heterocyclyl" as a saturated or partially saturated ring are 1, 2 or 3 substituents independently selected from fluoro, chloro, cyano, hydroxy, methyl, ethyl, methoxy, methylthio, methylsulfinyl and methylsulfonyl.

Suitable optional substituents for heterocyclyl as an unsaturated ring are, unless otherwise defined, 1, 2 or 3 substituents independently selected from halo, cyano, nitro, amino, hydroxy, (1-4C)alkyl, (1-4C)alkoxy, (1-4C)alkylS(O)$_b$ (wherein b is 0, 1 or 2), N-((1-4C)alkyl)amino and N,N-((1-4C)alkyl)$_2$amino. Further suitable optional substituents for "heterocyclyl" as an unsaturated ring are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

For the avoidance of doubt, optional substituents on heterocyclyl groups are generally substituents on carbon atoms of the ring, but may where appropriate be on an N atom, for example N-alkylpyridine.

Examples of (heterocyclyl)(1-4C)alkyl are morpholinomethyl, morpholinethyl, morpholinylmethyl, morpholinylethyl, piperidinomethyl, piperidinoethyl, piperidylmethyl, piperidylethyl, imidazolylmethyl, imidazolylethyl, tetrazolylmethyl, tetrazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl.

Aryl is a partially saturated or unsaturated, mono or bicyclic carbon ring that contains 3-12 atoms; wherein a —$CH_2$— group can optionally be replaced by a —C(O)—. Particularly aryl is a monocyclic ring containing 5 or 6 atoms or a bicyclic ring containing 9 or 10 atoms. In another aspect aryl is a totally unsaturated ring. Suitable values for aryl include cyclopentenyl, cyclohexenyl, phenyl, naphthyl, indanyl or 1-oxoindanyl. Examples of aryl are optionally substituted phenyl and naphthyl.

Examples of aryl((1-4C)alkyl are benzyl, phenethyl, naphthylmethyl and naphthylethyl.

Examples of (1-4C)alkyl include methyl, ethyl, propyl, butyl, tert-butyl and isopropyl; examples of (1-6C)alkyl include (1-4C)alkyl, pentyl and hexyl; examples of (2-4C)alkenyl include vinyl, propenyl, allyl, but-2-enyl and but-3-enyl; examples of (3-4C)alkenyl include propenyl, allyl, but-2-enyl and but-3-enyl; examples of (2-6C)alkenyl include (2-4C)alkenyl, pent-2-enyl, pent-3-enyl, and hex-5-enyl; examples of (2-4C)alkynyl include ethynyl, prop-2-ynyl, but-2-ynyl and but-3-ynyl; examples of (2-6C)alkynyl include (2-4C)alkynyl, pent-3-ynyl and hex-4-ynyl; examples of (1-6C)alkoxy and —O(1-6C)alkyl include methoxy, ethoxy, propoxy, iso-propoxy, butoxy, tert-butoxy and pentoxy; examples of (1-4C)alkoxy include methoxy, ethoxy and propoxy; examples of (1-4C)alkoxy(1-4C)alkyl include methoxymethyl, ethoxymethyl, methoxyethyl and propoxymethyl; examples of (3-6C)cycloalkyl include cyclopropyl, cyclobutyl, cyclopentyl and cyclohexyl; examples of -(1-6C)alkyl(3-6C)cycloalkyl include cyclopropylmethyl, cyclopropylethyl, cyclobutylmethyl, cyclopentylmethyl and cyclohexylmethyl; examples of halo groups include fluoro, chloro and bromo; examples of halo(1-4C)alkyl groups include fluoromethyl, fluoroethyl, chloromethyl, chloroethyl and bromomethyl; examples of hydroxy(1-4C)alkyl and hydroxy(1-6C)alkyl include hydroxymethyl, 1-hydroxyethyl, 2-hydroxyethyl and 3-hydroxypropyl; examples of (1-4C)alkoxy-(1-4C)alkoxy and (1-6C)alkoxy-(1-6C)alkoxy include methoxymethoxy, 2-methoxyethoxy, 2-ethoxyethoxy and 3-methoxypropoxy; examples of (1-4C)alkoxy-(1-4C)alkoxy-(1-4C)alkoxy include 2-(methoxymethoxy)ethoxy, 2-(2-methoxyethoxy)ethoxy; 3-(2-methoxyethoxy)propoxy and 2-(2-ethoxyethoxy)ethoxy; examples of (1-4C)alkylS(O)$_p$— wherein p is 0, 1 or 2 include methylthio, ethylthio, methylsulfinyl, ethylsulfinyl, methylsulfonyl and ethylsulfonyl; examples of (1-4C)alkylthio(1-4C)alkyl include methylthioethyl, methylthiomethyl, ethylthiomethyl, propylthiomethyl and propylthioethyl; examples of cyano(1-4C)alkyl include cyanomethyl, 1-cyanoethyl, 2-cyanoethyl and 3-cyanopropyl; examples of —CO(1-4C)alkyl include methylcarbonyl, ethylcarbonyl, propylcarbonyl, isopropylcarbonyl and tert-butylcarbonyl; examples of —CO(1-6C)alkyl include —CO(1-4C)alkyl and pentylcarbonyl; examples of —COO(1-4C)alkyl include methoxycarbonyl, ethoxycarbonyl, propoxycarbonyl, isopropoxycarbonyl and tert-butoxycarbonyl; examples of —COO(1-C)alkyl include —COO(1-4C)alkyl and pentoxycarbonyl; examples of —OCO(1-4C)alkyl include methylcarbonyloxy, ethylcarbonyloxy, propylcarbonyloxy, isopropylcarbonyloxy and tert-butylcarbonyloxy; examples of —OCO(1-6C)alkyl include —OCO(1-4C)alkyl and pentylcarbonyloxy; examples of -(1-4C)alkylCOO(1-4C)alkyl include methoxycarbonylmethyl, ethoxycarbonylmethyl, methoxycarbonylethyl, propoxycarbonylmethyl, isopropoxycarbonylmethyl and tert-butoxycarbonylmethyl; examples of —NH(1-4C)alkyl include methylamino, ethylamino, propylamino and butylamino; examples of —N[di(1-4C)alkyl] include N,N-dimethylamino, N-methyl-N-ethylamino, N,N-diethylamino, and N,N-dipropylamino; examples of -(1-4C)alkylNH(1-4C)alkyl include methylaminomethyl, ethylaminomethyl, methylaminoethyl, propylaminomethyl and isopropylaminomethyl; examples of -(1-4C)alkylN[di(1-4C)alkyl] include N,N-dimethylaminomethyl, N,N-dimethylaminoethyl, N-methyl-N-ethylaminomethyl and dimethylaminopropyl; examples of —CONH(1-4C)alkyl include methylaminocarbonyl, ethylaminocarbonyl, propylaminocarbonyl, isopropylaminocarbonyl and tert-butylaminocarbonyl; examples of —CON[di(1-4C)alkyl] include N-dimethylaminocarbonyl and N-methyl-N-ethylaminocarbonyl; examples of —S(O)$_2$NH(1-4C)alkyl include N-methylaminosulfonyl and N-ethylaminosulfonyl; examples of —S(O)$_2$N[di(1-4C)alkyl] include N,N-dimethylaminosulfonyl, N,N-diethylaminosulfonyl and N-methyl-N-ethylaminosulfonyl; examples of —S(O)p(1-4C)alkyl include methylthio, methylsulfinyl, methylsulfonyl, ethylthio, propylthio, isopropylthio, ethylsulfinyl and ethylsulfonyl; examples of —NHC(O)(1-4C)alkyl include acetylamino and propionylamino; examples of —NHC(O)heterocyclyl include pyrimidin-2-ylcarbonylamino and piperazin-1-ylcarbonylamino; examples of —NHC(O)aryl include benzoylamino and naphth-3-ylcarbonylamino; examples of —NHS(O)p(1-4C)alkyl include mesylamino and isopropylsulphonylamino.

Within this specification composite terms are used to describe groups comprising more that one functionality such as -(1-4C)alkylSO$_2$(1-4C)alkyl. Such terms are to be interpreted in accordance with the meaning which is understood by a person skilled in the art for each component part. For example -(1-4C)alkylSO$_2$(1-4C)alkyl includes -methylsulphonylmethyl, -methylsulphonylethyl, -ethylsulphonylmethyl, and -propylsulphonylbutyl.

A compound of formula (1) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate. fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form which inhibits DNA gyrase and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (1) contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DNA gyrase, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DNA gyrase by the standard tests described hereinafter.

It is also to be understood that certain compounds of the formula (1) and salts thereof can exist in solvated as well as unsolvated forms such as, for example, hydrated forms. It is to be understood that the invention encompasses all such solvated forms which inhibit DNA gyrase.

As stated before, we have discovered a range of compounds that are good inhibitors of DNA gyrase. They have good physical and/or pharmacokinetic properties in general. The following compounds possess preferred pharmaceutical and/or physical and/or pharmacokinetic properties.

Particularly preferred compounds of the invention comprise a compound of formula (1), or a pharmaceutically-acceptable salt thereof, wherein the substituents W and $R^1$ to $R^7$ and other substituents mentioned above have values disclosed hereinbefore, or any of the following values (which may be used where appropriate with any of the definitions and embodiments disclosed hereinbefore or hereinafter):

In one embodiment of the invention are provided compounds of formula (1), in an alternative embodiment are provided pharmaceutically-acceptable salts of compounds of formula (1).

In one aspect of the invention, W is O. In another aspect, W is $NR^5$.

In one embodiment, $R^1$ is selected from $R^1a$.
In another embodiment, $R^1$ is selected from $R^1b$.
In another embodiment, $R^1$ is selected from $R^1c$.
In another embodiment, $R^1$ is selected from $R^1d$.
In another embodiment, $R^1$ is selected from $R^1e$.
In another embodiment, $R^1$ is selected from $R^1f$.

In one aspect $R^1a$ is a 5 membered heterocyclic ring containing 1, 2, 3 or 4 heteroatoms independently selected from O, S and N (provided that such a ring does not contain any O—O or S—S bonds). In another aspect $R^1a$ is a 5 membered heterocyclic ring containing 1, 2 or 3 heteroatoms independently selected from O, S and N (provided that such a ring does not contain any O—O or S—S bonds). In another aspect $R^1a$ is a 5 membered heterocyclic ring containing 1 or 2 heteroatoms independently selected from O, S and N (provided that such a ring does not contain any O—O or S—S bonds). In another aspect $R^1a$ is a 5 membered heterocyclic ring containing 1 heteroatom independently selected from O, S and N.

In one aspect $R^1a$ is a 6 membered heterocyclic ring containing 1, 2, 3 or 4 heteroatoms independently selected from O, S and N (provided that such a ring does not contain any O—O or S—S bonds). In another aspect $R^1a$ is a 6 membered heterocyclic ring containing 1, 2 or 3 heteroatoms independently selected from O, S and N (provided that such a ring does not contain any O—O or S—S bonds). In another aspect $R^1a$ is a 6 membered heterocyclic ring containing 1 or 2 heteroatoms independently selected from O, S and N (provided that such a ring does not contain any O—O or S—S bonds). In another aspect $R^1a$ is a 6 membered heterocyclic ring containing 1 heteroatom independently selected from O, S and N.

Suitable values for $R^1a$ as a 5-membered heterocyclyl ring include furyl, thienyl, oxazolyl, isoxazolyl, imidazolyl, thiazolyl, triazolyl, tetrazolyl, 1-oxa-3,4-diazolyl, 2-oxo-[1-oxa-3,4-diazolyl], oxa-2,4-diazolyl, thia-2,4-diazolyl and pyrrolyl.

Suitable values for $R^1a$ as a 6-membered heterocyclyl ring include morpholinyl, thiomorpholinyl, pyridyl, pyrimidinyl, triazinyl, piperidinyl and piperazinyl.

Suitable values for $R^1a$ as a 6-membered heterocyclyl ring include morpholinyl, thiomorpholinyl, pyridyl, pyridinonyl (for example pyridin-2(1H)-one), pyrimidinyl, pyrimidinonyl (for example pyrimidin-2(1H)-one), triazinyl, piperidinyl and piperazinyl.

Further suitable values for $R^1a$ are imidazolyl, pyrimidinyl, pyridinyl, thiazolyl, triazinyl, pyrrolyl, thiadiazolyl and tetrazolyl.

$R^1a$ is 5 or 6 membered saturated, partially unsaturated or unsaturated heterocyclic ring containing 1, 2, 3, or 4 heteroatoms independently selected from O, S and N (provided that such a ring does not contain O—O or S—S bonds), wherein a —$CH_2$— group can optionally be replaced by a —C(O)—, a ring sulphur atom may be optionally oxidised to form the S-oxide(s), and a ring nitrogen atom may be optionally oxidised to form the N-oxide.

$R^1a$ is pyridinyl, N-oxopyridinyl, pyrimidinyl, thiazolyl, thiadiazolyl, tetrazolyl, imidazolyl, triazinyl, pyrrolidinyl, thienyl, furanyl, oxadiazolyl, isoxazolyl, oxazolyl or pyrrolyl.

$R^1a$ is 5 or 6 membered saturated, partially unsaturated or unsaturated heterocyclic ring containing 1, 2, 3, or 4 heteroatoms independently selected from O, S and N (provided that such a ring does not contain O—O or S—S bonds), wherein a —$CH_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl and —NR$^6$R$^7$;

wherein any aryl or heterocyclyl group in any of the preceding values for substituents on $R^1a$ may optionally be substituted by 1 or 2 substituents independently selected from (1-4C)alkyl and carboxy.

$R^1a$ is pyridinyl, N-oxopyridinyl, pyrimidinyl, thiazolyl, thiadiazolyl, tetrazolyl, imidazolyl, triazinyl, pyrrolidinyl, thienyl, furanyl, oxadiazolyl, isoxazolyl, oxazolyl or pyrrolyl, wherein said $R^1a$ may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)tetrahydrofuranyl, —NHC(O)phenyl, —NHS(O)p(1-4C)alkyl, —S(O)p(1-4C)alkyl, —S(O)pNR$^6$R$^7$, —NHSO$_2$R$^6$, —NR$^6$R$^7$, morpholino, 1,3-dioxo-1,3-dihydro-2H-isoindolyl and 1,3-dioxolanyl], cyclopropyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), tetrazolyl, 2-oxo-1,3,4-oxadiazolyl, 1,2,4-oxadiazolyl, morpholino, piperazinyl, pyrrolidinyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl and —NR$^6$R$^7$;

wherein any phenyl, tetrahydrofuranyl, morpholino, 1,3-dioxo-1,3-dihydro-2H-isoindolyl, 1,3-dioxolanyl, tetrazolyl, 2-oxo-1,3,4-oxadiazolyl, 1,2,4-oxadiazolyl, morpholino, piperazinyl, pyrrolidinyl, in any of the preceding values for substituents on $R^1a$ may optionally be substituted by 1 or 2 substituents independently selected from (1-4C)alkyl and carboxy.

In one aspect $R^1b$ is a 8 membered heterocyclic ring containing 1, 2, 3 or 4 heteroatoms independently selected from O, S and N (provided that such a ring does not contain any O—O or S—S bonds). In another aspect $R^1b$ is a 8 membered heterocyclic ring containing 1, 2 or 3 heteroatoms independently selected from O, S and N (provided that such a ring does not contain any O—O or S—S bonds). In another aspect $R^1b$ is a 8 membered heterocyclic ring containing 1 or 2 heteroatoms independently selected from O, S and N (provided that such a ring does not contain any O—O or S—S bonds). In another aspect $R^1b$ is a 8 membered heterocyclic ring containing 1 heteroatom independently selected from O, S and N.

In one aspect $R^1b$ is a 9 membered heterocyclic ring containing 1, 2, 3 or 4 heteroatoms independently selected from O, S and N (provided that such a ring does not contain any O—O or S—S bonds). In another aspect $R^1b$ is a 9 membered heterocyclic ring containing 1, 2 or 3 heteroatoms independently selected from O, S and N (provided that such a ring does not contain any O—O or S—S bonds). In another aspect $R^1b$ is a 9 membered heterocyclic ring containing 1 or 2 heteroatoms independently selected from O, S and N (provided that such a ring does not contain any O—O or S—S bonds). In another aspect $R^1b$ is a 9 membered heterocyclic ring containing 1 heteroatom independently selected from O, S and N.

In one aspect $R^1b$ is a 10 membered heterocyclic ring containing 1, 2, 3 or 4 heteroatoms independently selected from O, S and N (provided that such a ring does not contain any O—O or S—S bonds). In another aspect $R^1b$ is a 10 membered heterocyclic ring containing 1, 2 or 3 heteroatoms independently selected from O, S and N (provided that such a ring does not contain any O—O or S—S bonds). In another aspect $R^1b$ is a 10 membered heterocyclic ring containing 1 or 2 heteroatoms independently selected from O, S and N (provided that such a ring does not contain any O—O or S—S bonds). In another aspect $R^1b$ is a 10 membered heterocyclic ring containing 1 heteroatom independently selected from O, S and N.

Examples of $R^1b$ as an 8-10 membered bicyclic heterocyclic ring containing 1, 2, 3, or 4 heteroatoms independently selected from O, S and N (provided that such a ring does not contain O—O or S—S bonds) include, for example, bicyclic benzo-fused systems containing a 5- or 6-membered heteroaryl ring containing one nitrogen atom and optionally 1-3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine, 1,4-benzoxazine, and cinnoline. Further examples of such ring systems are isomers of the above named examples, such as isoquinoline and isoindole; it will be understood that references to such ring systems are intended to encompass such isomers.

$R^1b$ is a 10 membered bicyclic heterocyclic ring containing 1, 2 or 4 heteroatoms independently selected from S and N (provided that such a ring does not contain S—S bonds), wherein a —$CH_2$— group can optionally be replaced by a —C(O)—.

$R^1b$ is quinolinyl, purinyl, benzothiazolyl, indolyl, 4-oxoquinolinyl, 2,7-naphthyridinyl or quinazolinyl.

$R^1b$ is a 10 membered bicyclic heterocyclic ring containing 1, 2 or 4 heteroatoms independently selected from S and N (provided that such a ring does not contain S—S bonds), wherein a —$CH_2$— group can optionally be replaced by a —C(O)—, wherein said ring may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —$CONR^6R^7$, —$N(R^7)COR^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)$NR^6R^7$, —NHC(O)$NR^6R^7$, —NHC(O)(1-4C)alkyl, —NHC(O)heterocyclyl, —NHC(O)aryl, —NHS(O)p(1-4C)alkyl, —S(O)p(1-4C)alkyl, —S(O)p$NR^6R^7$, —$NHSO_2R^6$, —$NR^6R^7$, and heterocyclyl], (3-6C)cycloalkyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=$NOR^7$)(1-4C)alkyl, —C(=$NOR^7$)$NR^6R^7$, —S(O)p(1-4C)alkylCONHR$^7$, —C(O)NHS(O)p(1-4C)alkyl and —$NR^6R^7$;

wherein any aryl or heterocyclyl group in any of the preceding values for substituents on $R^1a$ may optionally be substituted by 1 or 2 substituents independently selected from (1-4C)alkyl and carboxy.

$R^1b$ is quinolinyl, purinyl, benzothiazolyl, indolyl, 4-oxoquinolinyl, 2,7-naphthyridinyl or quinazolinyl wherein said $R^1b$ may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —$CONR^6R^7$, —$N(R^7)COR^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)$NR^6R^7$, —NHC(O)$NR^6R^7$, —NHC(O)(1-4C)alkyl, —NHC(O)tetrahydrofuranyl, —NHC(O)phenyl, —NHS(O)p(1-4C)alkyl, —S(O)p(1-4C)alkyl, —S(O)p$NR^6R^7$, —$NHSO_2R^6$, —$NR^6R^7$, morpholino, 1,3-dioxo-1,3-dihydro-2H-isoindolyl and 1,3-dioxolanyl], cyclopropyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), tetrazolyl, 2-oxo-1,3,4-oxadiazolyl, 1,2,4-oxadiazolyl, morpholino, piperazinyl, pyrrolidinyl, —NHC(O)O(1-4C)alkyl, —C(=$NOR^7$)(1-4C)alkyl, —C(=$NOR^7$)$NR^6R^7$, —S(O)p(1-4C)alkylCONHR$^7$, —C(O)NHS(O)p(1-4C)alkyl and —$NR^6R^7$;

wherein any phenyl, tetrahydrofuranyl, morpholino, 1,3-dioxo-1,3-dihydro-2H-isoindolyl, 1,3-dioxolanyl, tetrazolyl, 2-oxo-1,3,4-oxadiazolyl, 1,2,4-oxadiazolyl, morpholino, piperazinyl, pyrrolidinyl, in any of the preceding values for substituents on $R^1a$ may optionally be substituted by 1 or 2 substituents independently selected from (1-4C)alkyl and carboxy.

Further examples of $R^1b$ as an 8-10 membered heterocyclic ring include 5/5-, 5/6 and 6/6 bicyclic ring systems containing heteroatoms in both of the rings. Further examples of $R^1b$ as an 8-10 membered heterocyclic ring include bicyclic heteroaryl ring systems with at least one bridgehead nitrogen and optionally a further 1-3 heteroatoms chosen from oxygen, sulfur and nitrogen.

Specific examples of such ring systems include, for example, purine, naphthyridine, pyrido[2,3-d]pyrimidinyl, pyrimido[4,5-d]pyrimidinyl, indolizine, quinolizine, indazole, indan-2-yl, carbazole, pyrrolo[1,2-c]pyrimidine, pyrazolo[3,4-b]pyridine, 1H-pyrazolo[3,4-d]pyrimidine, thiadiazolo[3,4-b]pyridine, 1H-imidazo[4,5-b]pyridine, azapurine, furazanopyrimidines, coumarin, benzopyran, thiazolo[4,5-d]pyrimidine, pyrido[2,3-b]pyrazin-3(2H)-one, H-pyrimido[5,4-b][1,4]oxazin-7(6H)-one, 3H-pyrrolo[1,2-a]pyrrole, pyrrolo[2,1-b]thiazole, 1H-imidazo[1,2-a]pyrrole, 1H-imidazo[1,2-a]imidazole, 1H, 3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazole[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazole, [3H]-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, such as imidazo[5,1-b]thiazole, imidazo[2,1-b]thiazole, imidazo[5,1-b]oxazole or imidazo[2,1-b]oxazole.

Further examples of $R^1b$ as an 8-10 membered heterocyclic ring include ring systems where one or both of the rings is partially or fully saturated, for example indoline, 1,3,4,6,9, 9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

The nomenclature used is that found in, for example, "Heterocyclic Compounds (Systems with bridgehead nitrogen)", W. L. Mosby (Interscience Publishers Inc., New York), 1961, Parts 1 and 2.

Further examples of suitable values for $R^1b$ may be found in Handbook of Heterocyclic Chemistry 2nd Ed—by A. R. Katritzky and A. F. Pozharskii.

Suitable values for $R^1b$ are quinolinyl, purinyl, benzothiazolyl and indolyl.

In one aspect $R^1d$ is selected from —$CH_2R^1a$.

In another aspect $R^1d$ is selected from —$C(O)R^1a$.

In another aspect $R^1d$ is selected from —$OR^1a$.

In a further aspect $R^1d$ is selected from $S(O)qR^1a$ (wherein q is 1 or 2).

$R^1d$ is selected from —$CH_2R^1a$ or —$C(O)R^1a$.

In one aspect $R^1e$ is selected from —$CH_2R^1b$.

In another aspect $R^1e$ is selected from —$C(O)R^1b$.

In another aspect $R^1e$ is selected from —$OR^1b$.

In a further aspect $R^1e$ is selected from $S(O)qR^1b$ (wherein q is 1 or 2).

In one aspect $R^1f$ is selected from —$CH_2R^1c$.

In another aspect $R^1f$ is selected from —$C(O)R^1c$.

In another aspect $R^1f$ is selected from —$OR^1c$.

In a further aspect $R^1f$ is selected from $S(O)qR^1c$ (wherein q is 1 or 2).

In one aspect, $R^1$ contains one substituent selected from the optional substituents listed in any aspect or embodiment hereinbefore or hereinafter. In another aspect $R^1$ contains two substituents independently selected from the optional substituents listed in any aspect or embodiment hereinbefore or hereinafter. In a further aspect, $R^1$ is unsubstituted.

In one aspect the optional substituents for $R^1$ (wherein $R^1$ is selected from $R^1a$, $R^1b$, $R^1c$, $R^1d$, $R^1e$ and $R^1d$) are selected from nitro, cyano, (2-6C)alkenyl, (2-6C)alkynyl, —CO(1-6C)alkyl, —COO(1-6C)alkyl, —O(1-6C)alkyl, trifluoromethyl, —$CONR^6R^7$, —$OCONR^6R^7$, —$N(R^7)COR^6$, —$CONHCH(CO_2R^7)R^6$, halo, hydroxy, carboxy, (1-6C)alkyl [optionally substituted by 1 or 2 substituents independently selected from hydroxy, halo, cyano, nitro, —COO(1-6C)alkyl, —O(1-6C)alkyl, trifluoromethyl, —$CONR^6R^7$, carboxy, —NHC(O)O(1-4C)alkyl, —C(=NOH)(1-4C)alkyl, —C(=NOH)$NR^6R^7$, —S(O)p(1-4C)alkyl, —S(O)p$NR^6R^7$ and —$NR^6R^7$], heterocyclyl [optionally substituted by 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, (1-4C)alkylcarbonyl, (1-4C)alkoxycarbonyl, —C(O)$NH_2$, —C(O)NH(1-4C)alkyl, —C(O)N[di(1-4C)alkyl], —$S(O)_2NH_2$, —$S(O)_2NH$(1-4C)alkyl, —$S(O)_2N$[di(1-4C)alkyl] and —S(O)p(1-4C)alkyl], aryl [optionally substituted by 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, (1-4C)alkylcarbonyl, (1-4C)alkoxycarbonyl, —C(O)$NH_2$, —C(O)NH(1-4C)alkyl, —C(O)N[di(1-4C)alkyl], —$S(O)_2NH_2$, —$S(O)_2NH$(1-4C)alkyl, —$S(O)_2N$[di(1-4C)alkyl] and —S(O)p(1-4C)alkyl], —NHC(O)O(1-4C)alkyl, —C(=$NOR^7$)(1-4C)alkyl, —C(=$NOR^7$)$NR^6R^7$, —S(O)p(1-4C)alkyl (optionally substituted by hydroxy), —S(O)p$NR^6R^7$, —S(O)p(1-4C)alkylCONHR$^7$, —$NR^7S(O)pNR^6R^7$, —$NR^7S(O)p$(1-4C)alkyl, —$NR^7S(O)$p-aryl, —C(O)NHS(O)p(1-4C)alkyl, —C(O)NHS(O)p-aryl, —$NR^6R^7$, —$CH_2CH(CO_2R^6)OH$, -(1-4C)alkylCH($NR^6R^7$)$CO_2R^6$ and -(1-4C)alkylCH($NR^6R^7$)CO($NR^6R^7$).

In another aspect the optional substituents for $R^1$ (wherein $R^1$ is selected from $R^1a$, $R^1b$, $R^1c$, $R^1d$, $R^1e$ and $R^1d$) are selected from nitro, cyano, (2-6C)alkenyl, (2-6C)alkynyl, —CO(1-6C)alkyl, —COO(1-6C)alkyl, —O(1-6C)alkyl, trifluoromethyl, —$CONR^6R^7$, —$OCONR^6R^7$, —$N(R^7)COR^6$, —$CONHCH(CO_2R^7)R^6$, halo, hydroxy, carboxy, (1-6C)alkyl [optionally substituted by 1 or 2 substituents independently selected from hydroxy, halo, —COO(1-6C)alkyl, —O(1-6C)alkyl, trifluoromethyl, —$CONR^6R^7$, —NHC(O)O(1-4C)alkyl, —C(=NOH)(1-4C)alkyl, —C(=NOH)$NR^6R^7$, —S(O)p(1-4C)alkyl, —S(O)p$NR^6R^7$ and —$NR^6R^7$], heterocyclyl [optionally substituted by 1 or 2 substituents independently selected from (1-4C)alkyl, hydroxy, (1-4C)alkoxy, halo, cyano, nitro, carboxy, hydroxy(1-4C)alkyl, halo(1-4C)alkyl, difluoromethyl, trifluoromethyl, trifluoromethoxy, (1-4C)alkylcarbonyl, (1-4C)alkoxycarbonyl, —C(O)$NH_2$, —C(O)NH(1-4C)alkyl, —C(O)N[di(1-4C)alkyl], —$S(O)_2NH_2$, —$S(O)_2NH$(1-4C)alkyl, —$S(O)_2N$[di(1-4C)alkyl] and —S(O)p(1-4C)alkyl], aryl [optionally substituted by 1 or 2 substituents independently selected from (1-4C)alkyl, hydroxy, (1-4C)alkoxy, halo, cyano, nitro, carboxy, hydroxy(1-4C)alkyl, halo(1-4C)alkyl, difluoromethyl, trifluoromethyl, trifluoromethoxy, (1-4C)alkylcarbonyl, (1-4C)alkoxycarbonyl, —C(O)$NH_2$, —C(O)NH(1-4C)alkyl, —C(O)N[di(1-4C)alkyl], —$S(O)_2NH_2$, —$S(O)_2NH$(1-4C)alkyl, —$S(O)_2N$[di(1-4C)alkyl] and —S(O)p(1-4C)alkyl], —NHC(O)O(1-4C)alkyl, —C(=$NOR^7$)(1-4C)alkyl, —C(=$NOR^7$)$NR^6R^7$, —S(O)p(1-4C)alkyl (optionally substituted by hydroxy), —S(O)p$NR^6R^7$, —S(O)p(1-4C)alkylCONHR$^7$, —$NR^7S(O)pNR^6R^7$, —$NR^7S(O)p$(1-4C)alkyl, —$NR^7S$(O)p-aryl, —C(O)NHS(O)p(1-4C)alkyl, —C(O)NHS(O)p-aryl and —$NR^6R^7$.

In another aspect the optional substituents for $R^1$ (wherein $R^1$ is selected from $R^1a$, $R^1b$, $R^1c$, $R^1d$, $R^1e$ and $R^1d$) are selected from nitro, cyano, —CO(1-6C)alkyl, —COO(1-6C)alkyl, —O(1-6C)alkyl, trifluoromethyl, —$CONR^6R^7$, —$OCONR^6R^7$, —$N(R^7)COR^6$, —$CONHCH(CO_2R^7)R^6$, halo, hydroxy, carboxy, (1-6C)alkyl [optionally substituted by 1 or 2 substituents independently selected from hydroxy, halo, —COO(1-6C)alkyl, —O(1-6C)alkyl, trifluoromethyl, —$CONR^6R^7$, —S(O)p(1-4C)alkyl, —S(O)p$NR^6R^7$ and —$NR^6R^7$], heterocyclyl [optionally substituted by 1 or 2 substituents independently selected from (1-4C)alkyl, hydroxy, (1-4C)alkoxy, halo, cyano, nitro, carboxy, halo(1-4C)alkyl, difluoromethyl, trifluoromethyl and trifluoromethoxy], aryl [optionally substituted by 1 or 2 substituents independently selected from (1-4C)alkyl, hydroxy, (1-4C)alkoxy, halo, cyano, nitro, carboxy, halo(1-4C)alkyl, difluoromethyl, trifluoromethyl and trifluoromethoxy],
—NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl and —NR$^6$R$^7$.

In another aspect the optional substituents for R$^1$ (wherein R$^1$ is selected from R$^1$a, R$^1$b, R$^1$c, R$^1$d, R$^1$e and R$^1$d) are selected from nitro, cyano, —CO(1-6C)alkyl, —COO(1-6C)alkyl, —O(1-6C)alkyl, trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl, heterocyclyl, aryl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl and —NR$^6$R$^7$.

In another aspect the optional substituents for R$^1$ (wherein R$^1$ is selected from R$^1$a, R$^1$b, R$^1$c, R$^1$d, R$^1$e and R$^1$d) are selected from nitro, cyano, —CO(1-6C)alkyl, —COO(1-6C)alkyl, —O(1-6C)alkyl, trifluoromethyl, —CONR$^6$R$^7$, —OCONR$^6$R$^7$, —N(R$^7$)COR$^6$, halo, hydroxy, carboxy, (1-6C)alkyl, heterocyclyl, aryl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, and —NR$^6$R$^7$.

In another aspect the optional substituents for R$^1$ (wherein R$^1$ is selected from R$^1$a, R$^1$b, R$^1$c, R$^1$d, R$^1$e and R$^1$d) are selected from nitro, cyano, —CO(1-4C)alkyl, —COO(1-4C)alkyl, —O(1-4C)alkyl, trifluoromethyl, —CONR$^6$R$^7$, —N(R$^7$)COR$^6$, fluoro, chloro, bromo, hydroxy, carboxy, (1-4C)alkyl, heterocyclyl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)p(1-4C)alkylCONHR$^7$, and —NR$^6$R$^7$.

In another aspect the optional substituents for R$^1$ (wherein R$^1$ is selected from R$^1$a, R$^1$b, R$^1$c, R$^1$d, R$^1$e and R$^1$d) are selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl],
(3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —NR$^7$S(O)p-aryl, —C(O)NH S(O)p(1-4C)alkyl, —C(O)NHS(O)p-aryl, and —NR$^6$R$^7$;

wherein any heterocyclyl or aryl group in any of the preceding values for substituents on R$^1$a may optionally be substituted by 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl and —S(O)$_2$N[di(1-4C)alkyl].

In another aspect the optional substituents for R$^1$ (wherein R$^1$ is selected from R$^1$a, R$^1$b, R$^1$c, R$^1$d, R$^1$e and R$^1$d) are selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, —CONHCH(CO$_2$R$^7$)R$^6$, halo, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl],
(3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —C(O)NHS(O)p(1-4C)alkyl, and —NR$^6$R$^7$;

wherein any heterocyclyl or aryl group in any of the preceding values for substituents on R$^1$a may optionally be substituted by 1 or 2 substituents independently selected from (1-4C)alkyl, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl and trifluoromethoxy.

In another aspect the optional substituents for R$^1$ (wherein R$^1$ is selected from R$^1$a, R$^1$b, R$^1$c, R$^1$d, R$^1$e and R$^1$d) are selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, halo, carboxy,
(1-6C)alkyl [optionally substituted by 1 or 2 substituents independently selected from hydroxy, halo, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl],
(3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —C(O)NHS(O)p(1-4C)alkyl, and —NR$^6$R$^7$;

wherein any heterocyclyl or aryl group in any of the preceding values for substituents on R$^1$a may optionally be substituted by 1 or 2 substituents independently selected from (1-4C)alkyl, (1-4C)alkoxy, halo, cyano, nitro, carboxy, halo(1-4C)alkyl, difluoromethyl, trifluoromethyl and trifluoromethoxy.

In another aspect the optional substituents for R$^1$ (wherein R$^1$ is selected from R$^1$a, R$^1$b, R$^1$c, R$^1$d, R$^1$e and R$^1$d) are selected from nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl and —NR$^6$R$^7$;

wherein any aryl or heterocyclyl group in any of the preceding values for substituents on R$^1$a may optionally be substituted by 1 or 2 substituents independently selected from (1-4C)alkyl and carboxy.

In another aspect the optional substituents for R$^1$ (wherein R$^1$ is selected from R$^1$a, R$^1$b, R$^1$c, R$^1$d, R$^1$e and R$^1$d) are selected from nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)tetrahydrofuranyl, —NHC(O)phenyl, —NHS(O)p(1-4C)alkyl, —S(O)p(1-4C)alkyl, —S(O)pNR$^6$R$^7$, —NHSO$_2$R$^6$, —NR$^6$R$^7$, morpholino, 1,3-dioxo-1,3-dihydro-2H-isoindolyl and 1,3-dioxolanyl], cyclopropyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), tetrazolyl, 2-oxo-1,3,4-oxadiazolyl, 1,2,4-oxadiazolyl, morpholino, piperazinyl, pyrrolidinyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl and —NR$^6$R$^7$;

wherein any phenyl, tetrahydrofuranyl, morpholino, 1,3-dioxo-1,3-dihydro-2H-isoindolyl, 1,3-dioxolanyl, tetrazolyl, 2-oxo-1,3,4-oxadiazolyl, 1,2,4-oxadiazolyl, morpholino, piperazinyl, pyrrolidinyl, in any of the preceding values for substituents on R$^1$a may optionally be substituted by 1 or 2 substituents independently selected from (1-4C)alkyl and carboxy.

In another aspect R$^1$ is substituted by 2 substituents; wherein one substituent is selected from carboxy, —CONHSO$_2$Me and —CONHR$^6$ (wherein R$^6$ is selected from any of the values listed in any aspect or embodiment hereinbefore or hereinafter) and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore), wherein R$^6$ and R$^7$ are selected from any of the values listed in any aspect or embodiment hereinbefore or hereinafter.

In another aspect R$^1$ is substituted by 2 substituents; wherein one substituent is selected from carboxy, —CONHSO$_2$Me and —CONHR$^6$ (wherein R$^6$ is selected from —OMe, hydrogen, amino and 3-4C alkenyl); and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore), wherein R$^6$ and R$^7$ are selected from any of the values listed in any aspect or embodiment hereinbefore or hereinafter.

In another aspect R$^1$ is substituted by 2 substituents; wherein one substituent is selected from carboxy, —CONHSO$_2$Me and —CONHR$^6$ (wherein R$^6$ is selected from —OMe, hydrogen, amino, (3-4C alkenyl and —SO$_2$Me); and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore), wherein R$^6$ is selected from hydrogen and (1-4C)alkyl, and R$^7$ is hydrogen or methyl, or wherein R$^6$ and R$^7$ together from a piperidine, morpholine or piperazine ring, which ring may optionally be substituted with methyl on an available carbon or nitrogen atom (provided a nitrogen atom is not thereby quaternised) and a carbon atom may optionally be oxidised to form a carbonyl group.

R$^1$ is selected from R$^1$a, R$^1$b, R$^1$c and R$^1$d; wherein
R$^1$a is a 5 or 6 membered saturated, partially unsaturated or unsaturated heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl, and —NR$^6$R$^7$, wherein any aryl or heterocyclyl group in any of the preceding values for substituents on R$^1$a may optionally be substituted by 1 or 2 substituents independently selected from (1-4C)alkyl and carboxy;

R$^1$b is a 10 membered bicyclic heterocyclic ring containing 1, 2 or 4 heteroatoms independently selected from S and N (provided that such a ring does not contain S—S bonds), wherein a —CH$_2$— group can optionally be replaced by a —C(O)—, and wherein said ring may be optionally substituted by 1, 2 or 3 substituents independently selected from the substituents listed for R$^1$a above;

R$^1$c is a phenyl ring, substituted by 1, 2 or 3 substituents independently selected from the substituents listed for R$^1$a above;

R$^1$d is selected from —CH$_2$R$^1$a, and —C(O)R$^1$a.

R$^1$ is selected from R$^1$a, R$^1$b, R$^1$c and R$^1$d; wherein

R$^1$a is pyridinyl, N-oxopyridinyl, pyrimidinyl, thiazolyl, thiadiazolyl, tetrazolyl, imidazolyl, triazinyl, pyrrolidinyl, thienyl, furanyl, oxadiazolyl, isoxazolyl, oxazolyl or pyrrolyl, wherein said R$^1$a may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)tetrahydrofuranyl, —NHC(O)phenyl, —NHS(O)p(1-4C)alkyl, —S(O)p(1-4C)alkyl, —S(O)pNR$^6$R$^7$, —NHSO$_2$R$^6$, —NR$^6$R$^7$, morpholino, 1,3-dioxo-1,3-dihydro-2H-isoindolyl and 1,3-dioxolanyl], cyclopropyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), tetrazolyl, 2-oxo-1,3,4-oxadiazolyl, 1,2,4-oxadiazolyl, morpholino, piperazinyl, pyrrolidinyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl and —NR$^6$R$^7$;

wherein any phenyl, tetrahydrofuranyl, morpholino, 1,3-dioxo-1,3-dihydro-2H-isoindolyl, 1,3-dioxolanyl, tetrazolyl, 2-oxo-1,3,4-oxadiazolyl, 1,2,4-oxadiazolyl, morpholino, piperazinyl, pyrrolidinyl, in any of the preceding values for substituents on R$^1$a may optionally be substituted by 1 or 2 substituents independently selected from (1-4C)alkyl and carboxy;

R$^1$b is R$^1$b is quinolinyl, purinyl, benzothiazolyl, indolyl, 4-oxoquinolinyl, 2,7-naphthyridinyl or quinazolinyl, and wherein said R$^1$b may be optionally substituted by 1, 2 or 3 substituents independently selected from the substituents listed for R$^1$a above;

R$^1$c is a phenyl ring, substituted by 1, 2 or 3 substituents independently selected from the substituents listed for R$^1$a above;

R$^1$d is selected from —CH$_2$R$^1$a, and —C(O)R$^1$a.

In one aspect R$^2$ is selected from hydrogen, (1-4C)alkyl, cyclopropyl, halo, fluoromethyl, difluoromethyl and trifluoromethyl.

In another aspect R$^2$ is selected from (1-4C)alkyl, cyclopropyl, halo, and trifluoromethyl.

In another aspect R$^2$ is selected from (1-4C)alkyl, halo, and trifluoromethyl.

In another aspect R$^2$ is selected from (1-4C)alkyl, chloro and bromo.

In another aspect R$^2$ is selected from (1-4C)alkyl, halo and cyano.

In a further aspect R$^2$ is selected from methyl, ethyl, isopropyl and chloro.

In another aspect R$^2$ is selected from methyl, ethyl, isopropyl, chloro and cyano.

In one aspect R$^3$ is selected from hydrogen, (1-4C)alkyl, cyclopropyl, halo, cyano, fluoromethyl, difluoromethyl, trifluoromethyl and —CO(1-4C)alkyl.

In another aspect R$^3$ is selected from hydrogen, (1-4C)alkyl, halo, cyano, trifluoromethyl and —CO(1-4C)alkyl.

In another aspect R$^3$ is selected from hydrogen, (1-4C)alkyl, halo, cyano, trifluoromethyl and —COMe.

In another aspect R$^3$ is selected from hydrogen, (1-4C)alkyl, halo, cyano and —CO(1-6C)alkyl.

In another aspect R$^3$ is selected from hydrogen, methyl, ethyl, chloro, bromo, cyano, trifluoromethyl and —COMe.

In a further aspect R$^3$ is selected from hydrogen, methyl, ethyl, chloro, bromo, cyano and —COMe.

In one aspect R$^4$ is selected from hydrogen, (1-4C)alkyl, nitro, hydroxy, halo, cyano, halo(1-4C)alkyl, difluoromethyl, trifluoromethyl, —CO(1-4C)alkyl, and (1-4C)alkoxy.

In another aspect R$^4$ is selected from hydrogen, (1-4C)alkyl, halo, cyano, halo(1-4C)alkyl, difluoromethyl, trifluoromethyl and —CO(1-4C)alkyl.

In another aspect R$^4$ is selected from hydrogen, (1-4C)alkyl, halo, cyano, fluoromethyl, difluoromethyl, trifluoromethyl and —CO(1-4C)alkyl.

In another aspect R$^4$ is selected from hydrogen, (1-4C)alkyl, halo, cyano, trifluoromethyl and —COMe.

In another aspect R$^4$ is selected from hydrogen, (1-4C)alkyl, halo and cyano. In another aspect R$^4$ is selected from hydrogen, methyl, ethyl, chloro, bromo, cyano and —COMe.

In a further aspect R$^4$ is selected from hydrogen, methyl, ethyl, chloro, bromo and cyano.

In another aspect R$^4$ is selected from hydrogen, chloro, methyl, ethyl and cyano.

A preferred value of R$^4$ as halo(1-4C)alkyl is fluoromethyl.

In one aspect $R^5$ is hydrogen or methyl.

In one aspect $R^5$ is hydrogen. In another aspect $R^5$ is methyl.

In one aspect $R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkoxy, (1-4C)alkoxy(1-4C)alkyl, hydroxy(1-4C)alkyl, -(1-4C)alkylNH$_2$, -(1-4C)alkylNH(1-4C)alkyl, -(1-4C)alkylN[di(1-4C)alkyl], and -(1-4C)alkylheterocyclyl.

In another aspect $R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkoxy, (1-4C)alkoxy(1-4C)alkyl, hydroxy(1-4C)alkyl, -(1-4C)alkylNH$_2$, -(1-4C)alkylNH(1-4C)alkyl, -(1-4C)alkylN[di(1-4C)alkyl], and -(1-4C)alkylheterocyclyl.

In another aspect $R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl.

In another aspect $R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl.

In another aspect $R^6$ is independently at each occurrence selected from hydrogen, (1-4C)alkyl, cyclopropyl, -(1-4C)alkylC(O)O(1-4C)alkyl, amino, —NHMe, —NMe$_2$, (1-4C)alkoxy, and -(1-4C)alkylheterocyclyl.

In another aspect $R^6$ is independently at each occurrence selected from hydrogen, (1-4C)alkyl, (3-4C)alkenyl, cyclopropyl, -(1-4C)alkylC(O)O(1-4C)alkyl, amino, —NHMe, —NMe$_2$, (1-4C)alkoxy, and -(1-4C)alkylheterocyclyl.

In another aspect $R^6$ is independently at each occurrence selected from hydrogen, (1-4C)alkyl, cyclopropyl, -(1-4C)alkylC(O)OMe, amino, —NHMe, —NMe$_2$, (1-4C)alkoxy, and -(1-4C)alkylheterocyclyl.

In another aspect $R^6$ is independently at each occurrence selected from hydrogen, (1-4C)alkyl, allyl, cyclopropyl, -(1-4C)alkylC(O)OMe, amino, —NHMe, —NMe$_2$, (1-4C)alkoxy, and -(1-4C)alkylheterocyclyl.

When $R^6$ is -(1-4C)alkylheterocyclyl, the heterocyclyl group is preferably selected from morpholinyl, piperidinyl, piperazinyl, thiomorpholinyl and tetrahydropyranyl. Such a heterocyclyl group may optionally be substituted with a methyl group.

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —N[di(1-4C)alkyl], (1-4C)alkoxy and -(1-4C)alkylheterocyclyl.

$R^6$ is independently at each occurrence selected from hydrogen, (1-4C)alkyl, (3-4C)alkenyl, cyclopropyl, -(1-4C)alkylC(O)O(1-4C)alkyl, hydroxy, amino, —N[di(1-4C)alkyl], (1-4C)alkoxy and -(1-4C)alkylmorpholino.

In another aspect, $R^6$ and $R^7$ together with the nitrogen to which they are attached form a 5-membered heterocyclyl ring, optionally substituted with 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, (1-4C)alkylcarbonyl, (1-4C)alkoxycarbonyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl.

In another aspect, $R^6$ and $R^7$ together with the nitrogen to which they are attached form a 5-membered heterocyclyl ring, optionally substituted with 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl and trifluoromethoxy.

In another aspect, $R^6$ and $R^7$ together with the nitrogen to which they are attached form a 5-membered heterocyclyl ring, optionally substituted with 1 or 2 substituents independently selected from (1-4C)alkyl, hydroxy, (1-4C)alkoxy, halo, cyano, nitro and carboxy.

In another aspect, $R^6$ and $R^7$ together with the nitrogen to which they are attached form a 5-membered heterocyclyl ring, optionally substituted with 1 or 2 substituents independently selected from (1-4C)alkyl and halo.

In another aspect, $R^6$ and $R^7$ together with the nitrogen to which they are attached form a 5-membered heterocyclyl ring, optionally substituted with 1 or 2 substituents independently selected from formyl, (1-4C)alkylcarbonyl, (1-4C)alkoxycarbonyl, —C(O)NH$_2$, —C(O)NH(1-4C)alkyl, —C(O)N [di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl.

In another aspect, $R^6$ and $R^7$ together with the nitrogen to which they are attached form a 6-membered heterocyclyl ring, optionally substituted with 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, (1-4C)alkylcarbonyl, (1-4C)alkoxycarbonyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl.

In another aspect, $R^6$ and $R^7$ together with the nitrogen to which they are attached form a 6-membered heterocyclyl ring, optionally substituted with 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl and trifluoromethoxy.

In another aspect, $R^6$ and $R^7$ together with the nitrogen to which they are attached form a 6-membered heterocyclyl ring, optionally substituted with 1 or 2 substituents independently selected from (1-4C)alkyl, hydroxy, (1-4C)alkoxy, halo, cyano, nitro and carboxy.

In another aspect, $R^6$ and $R^7$ together with the nitrogen to which they are attached form a 6-membered heterocyclyl ring, optionally substituted with 1 or 2 substituents independently selected from (1-4C)alkyl and halo.

In another aspect, $R^6$ and $R^7$ together with the nitrogen to which they are attached form a 6-membered heterocyclyl ring, optionally substituted with 1 or 2 substituents independently selected from formyl, (1-4C)alkylcarbonyl, (1-4C)alkoxycarbonyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl.

When $R^6$ and $R^7$ together with the nitrogen to which they are attached form a 5-membered heterocyclyl ring, suitable values for such a ring are pyrrolidine, pyrazole, pyrrole, tetrazole, imidazole, imidazoline and triazole. Further suitable values are the afore-mentioned rings wherein a ring carbon atom is oxidised to form a carbonyl group, such as 2-pyrrolidone.

When $R^6$ and $R^7$ together with the nitrogen to which they are attached form a 6-membered heterocyclyl ring, suitable values for such a ring are morpholinyl, piperidinyl, piperazinyl, thiomorpholinyl and tetrahydropyridinyl. Further suitable values are the afore-mentioned rings wherein a ring carbon atom is oxidised to form a carbonyl group, such as 2-piperidinone, 2-piperazinone and 2-tetrahydropyridone.

$R^6$ and $R^7$ may together with the nitrogen to which they are attached form a 5 or 6-membered heterocyclyl ring, optionally substituted with 1 or 2 substituents independently selected from (1-4C)alkyl.

$R^6$ and $R^7$ may together with the nitrogen to which they are attached form piperazinyl or morpholino optionally substituted with 1 or 2 substituents independently selected from (1-4C)alkyl.

In one aspect $R^7$ is independently at each occurrence selected from hydrogen and (1-4C)alkyl.

In a further aspect of the invention $R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —N[di(1-4C)alkyl], (1-4C)alkoxy and -(1-4C)alkylheterocyclyl;

$R^7$ is independently at each occurrence selected from hydrogen and (1-6C)alkyl;

or $R^6$ and $R^7$ may together with the nitrogen to which they are attached form a 5 or 6-membered heterocyclyl ring, optionally substituted with 1 or 2 substituents independently selected from (1-4C)alkyl.

In one embodiment is provided a compound of the formula (1) or a pharmaceutically-acceptable salt thereof, wherein:
Y is H;
W is O;
$R^1$ is selected from $R^1a$ and $R^1b$;
$R^2$ is selected from hydrogen, (1-4C)alkyl, cyclopropyl, halo, fluoromethyl, difluoromethyl and trifluoromethyl;
$R^3$ is selected from hydrogen, (1-4C)alkyl, cyclopropyl, halo, cyano, fluoromethyl, difluoromethyl, trifluoromethyl and —CO(1-4C)alkyl;
$R^4$ is selected from hydrogen, (1-4C)alkyl, halo, cyano, halo(1-4C)alkyl, difluoromethyl, trifluoromethyl and —CO(1-4C)alkyl;
$R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;
$R^7$ is independently at each occurrence selected from hydrogen and (1-4C)alkyl.

In another embodiment is provided a compound of the formula (1) or a pharmaceutically-acceptable salt thereof, wherein:
Y is H;
W is O;
$R^1$ is selected from $R^1a$ and $R^1b$, optionally substituted by 1 or 2 substituents independently selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —N HC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —N H SO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl, and —NR$^6$R$^7$;

wherein any heterocyclyl or aryl group in any of the preceding values for substituents on $R^1a$ may optionally be substituted by 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl and —S(O)$_2$N[di(1-4C)alkyl];
$R^2$ is selected from hydrogen, (1-4C)alkyl, cyclopropyl, halo, fluoromethyl, difluoromethyl and trifluoromethyl;
$R^3$ is selected from hydrogen, (1-4C)alkyl, cyclopropyl, halo, cyano, fluoromethyl, difluoromethyl, trifluoromethyl and —CO(1-4C)alkyl;
$R^4$ is selected from hydrogen, (1-4C)alkyl, halo, cyano, halo(1-4C)alkyl, difluoromethyl, trifluoromethyl and —CO(1-4C)alkyl;
$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;
$R^7$ is independently at each occurrence selected from hydrogen and (1-4C)alkyl; and
p is (independently at each occurrence) 0, 1 or 2.

In another embodiment is provided a compound of the formula (1) or a pharmaceutically-acceptable salt thereof, wherein:
Y is H;
W is O;
$R^1$ is selected from $R^1a$ and $R^1b$, optionally substituted by 1 or 2 substituents independently selected from nitro, cyano, —CO(1-6C)alkyl, —COO(1-6C)alkyl, —O(1-6C)alkyl, trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl, heterocyclyl, aryl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl and —NR$^6$R$^7$;
$R^2$ is selected from hydrogen, (1-4C)alkyl, cyclopropyl, halo, fluoromethyl, difluoromethyl and trifluoromethyl;
$R^3$ is selected from hydrogen, (1-4C)alkyl, cyclopropyl, halo, cyano, fluoromethyl, difluoromethyl, trifluoromethyl and —CO(1-4C)alkyl;
$R^4$ is selected from hydrogen, (1-4C)alkyl, halo, cyano, halo(1-4C)alkyl, difluoromethyl, trifluoromethyl and —CO(1-4C)alkyl;
$R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di (1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is O;

$R^1$ is selected from $R^1a$ and $R^1b$, optionally substituted by 1 or 2 substituents independently selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, halo, carboxy, (1-6C)alkyl [optionally substituted by 1 or 2 substituents independently selected from hydroxy, halo, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —C(O)NHS(O)p(1-4C)alkyl, and —NR$^6$R$^7$;

wherein any heterocyclyl or aryl group in any of the preceding values for substituents on $R^1a$ may optionally be substituted by 1 or 2 substituents independently selected from (1-4C) alkyl, (1-4C)alkoxy, halo, cyano, nitro, carboxy, halo(1-4C) alkyl, difluoromethyl, trifluoromethyl and trifluoromethoxy;

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl;

$R^4$ is selected from hydrogen, (1-4C)alkyl, halo, cyano, halo (1-4C)alkyl, difluoromethyl, trifluoromethyl and —CO(1-4C)alkyl;

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is O;

$R^1$ is selected from $R^1a$ and $R^1b$, optionally substituted by 1 or 2 substituents independently selected from nitro, cyano, —CO(1-4C)alkyl, —COO(1-4C)alkyl, —O(1-4C)alkyl, trifluoromethyl, —CONR$^6$R$^7$, —N(R$^7$)COR$^6$, fluoro, chloro, bromo, hydroxy, carboxy, (1-4C)alkyl, heterocyclyl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)p(1-4C)alkylCONHR$^7$, and —NR$^6$R$^7$;

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl;

$R^4$ is selected from hydrogen, (1-4C)alkyl, halo, cyano, fluoromethyl, difluoromethyl, trifluoromethyl and —CO(1-4C)alkyl;

$R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is O;

$R^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 1 or 2 substituents independently selected from nitro, cyano, —CO(1-4C)alkyl, —COO(1-4C)alkyl, —O(1-4C)alkyl, trifluoromethyl, —CONR$^6$R$^7$, —N(R$^7$)COR$^6$, fluoro, chloro, bromo, hydroxy, carboxy, (1-4C)alkyl, heterocyclyl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)p(1-4C)alkylCONHR$^7$, and —NR$^6$R$^7$;

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl;

$R^4$ is selected from hydrogen, (1-4C)alkyl, halo, cyano, fluoromethyl, difluoromethyl, trifluoromethyl and —CO(1-4C)alkyl;

$R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is O;

$R^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 2 substituents; wherein one substituent is selected from carboxy, —CONHSO$_2$Me and —CONHR$^6$ and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR⁶R⁷, —C(=NOH)(1-4C)alkyl, —C(=NOH)NR⁶R⁷, —S(O)p(1-4C)alkyl, —S(O)pNR⁶R⁷, —NHSO₂R⁶, —NR⁶R⁷, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore);

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl.

$R^4$ is selected from hydrogen, (1-4C)alkyl, halo, cyano, fluoromethyl, difluoromethyl, trifluoromethyl and —CO(1-4C)alkyl;

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;
W is O;

$R^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 1 or 2 substituents independently selected from nitro, cyano, —CO(1-4C)alkyl, —COO(1-4C)alkyl, —O(1-4C)alkyl, trifluoromethyl, —CONR⁶R⁷, —N(R⁷)COR⁶, fluoro, chloro, bromo, hydroxy, carboxy, (1-4C)alkyl, heterocyclyl, —NHC(O)O(1-4C)alkyl, —C(=NOR⁷)(1-4C)alkyl, —C(=NOR⁷)NR⁶R⁷, —S(O)p(1-4C)alkyl (optionally substituted by hydroxy), —S(O)p(1-4C)alkylCONHR⁷, and —NR⁶R⁷;

$R^2$ is selected from (1-4C)alkyl, chloro and bromo;

$R^3$ is selected from hydrogen, methyl, ethyl, chloro, bromo, cyano, trifluoromethyl and —COMe;

$R^4$ is selected from hydrogen, methyl, ethyl, chloro, bromo, cyano and —COMe;

$R^6$ is independently at each occurrence selected from hydrogen, (1-4C)alkyl, cyclopropyl, -(1-4C)alkylC(O)OMe, amino, —NHMe, —NMe₂, (1-4C)alkoxy, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;
W is O;

$R^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 2 substituents; wherein one substituent is selected from carboxy, —CONHSO₂Me and —CONHR⁶ (wherein R⁶ is selected from —OMe, hydrogen, amino and 3-4C alkenyl); and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR⁶R⁷, carboxy, —NHC(O)O(1-4C)alkyl, —OCONR⁶R⁷, —C(=NOH)(1-4C)alkyl, —C(=NOH)NR⁶R⁷, —S(O)p(1-4C)alkyl, —S(O)pNR⁶R⁷, —NHSO₂R⁶, —NR⁶R⁷, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore);

$R^2$ is selected from (1-4C)alkyl, chloro and bromo;

$R^3$ is selected from hydrogen, methyl, ethyl, chloro, bromo, cyano, trifluoromethyl and —COMe;

$R^4$ is selected from hydrogen, methyl, ethyl, chloro, bromo, cyano and —COMe;

$R^6$ is independently at each occurrence selected from hydrogen, (1-4C)alkyl, allyl, cyclopropyl, -(1-4C)alkylC(O)OMe, amino, —NHMe, —NMe₂, (1-4C)alkoxy, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;
W is O;

$R^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 1 or 2 substituents independently selected from nitro, cyano, —CO(1-4C)alkyl, —COO(1-4C)alkyl, —O(1-4C)alkyl, trifluoromethyl, —CONR⁶R⁷, fluoro, chloro, bromo, hydroxy, carboxy, (1-4C)alkyl, heterocyclyl, —NHC(O)O(1-4C)alkyl, —C(=NOH)NR⁶R⁷, —S(O)p(1-4C)alkyl (optionally substituted by hydroxy), —S(O)p(1-4C)alkylCONHMe, and —NR⁶R⁷;

$R^2$ is selected from (1-4C)alkyl, chloro and bromo;

$R^3$ is selected from hydrogen, methyl, ethyl, chloro, bromo, cyano, trifluoromethyl and —COMe;

$R^4$ is selected from hydrogen, methyl, ethyl, chloro, bromo, cyano and —COMe;

$R^6$ and $R^7$ together form a 5- or 6-membered heterocyclyl ring, optionally substituted with 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl and trifluoromethoxy; and p is (independently at each occurrence) 0, 1 or 2.

In one embodiment is provided a compound of the formula (1) or a pharmaceutically-acceptable salt thereof, wherein:

Y is H;
W is NR⁵;

$R^1$ is selected from $R^1a$ and $R^1b$;

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl.

$R^4$ is selected from hydrogen, (1-4C)alkyl, halo, cyano, halo(1-4C)alkyl, difluoromethyl, trifluoromethyl and —CO(1-4C)alkyl;

$R^5$ is hydrogen or methyl;

$R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl.

In another embodiment is provided a compound of the formula (1) or a pharmaceutically-acceptable salt thereof, wherein:

Y is H;

W is $NR^5$;

$R^1$ is selected from $R^1a$ and $R^1b$, optionally substituted by 1 or 2 substituents independently selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl, and —NR$^6$R$^7$;

wherein any heterocyclyl or aryl group in any of the preceding values for substituents on $R^1a$ may optionally be substituted by 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl and —S(O)$_2$N[di(1-4C)alkyl];

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl;

$R^4$ is selected from hydrogen, (1-4C)alkyl, halo, cyano, halo(1-4C)alkyl, difluoromethyl, trifluoromethyl and —CO(1-4C)alkyl;

$R^5$ is hydrogen or methyl;

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is $NR^5$;

$R^1$ is selected from $R^1a$ and $R^1b$, optionally substituted by 1 or 2 substituents independently selected from nitro, cyano, —CO(1-6C)alkyl, —COO(1-6C)alkyl, —O(1-6C)alkyl, trifluoromethyl, —CONR$^6$R$^7$, —OCONR$^6$R$^7$, —N(R$^7$)COR$^6$, —CONHCH(CO$_2$R$^7$)R$^6$, halo, hydroxy, carboxy, (1-6C)alkyl, heterocyclyl, aryl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl and —NR$^6$R$^7$;

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl.

$R^4$ is selected from hydrogen, (1-4C)alkyl, halo, cyano, halo(1-4C)alkyl, difluoromethyl, trifluoromethyl and —CO(1-4C)alkyl;

$R^5$ is hydrogen or methyl;

$R^6$ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

$R^7$ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is $NR^5$;

$R^1$ is selected from $R^1a$ and $R^1b$, optionally substituted by 1 or 2 substituents independently selected from nitro, cyano, —CO(1-6C)alkyl, —COO(1-6C)alkyl (optionally substituted with —COO(1-4C)alkyl), trifluoromethyl, —CONR$^6$R$^7$, —OCONR$^6$R$^7$, —N(R$^7$)COR$^6$, halo, carboxy, (1-6C)alkyl [optionally substituted by 1 or 2 substituents independently selected from hydroxy, halo, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)pNR$^6$R$^7$, —NR$^7$S(O)p(1-4C)alkyl, —C(O)NHS(O)p(1-4C)alkyl, and —NR$^6$R$^7$;

wherein any heterocyclyl or aryl group in any of the preceding values for substituents on $R^1a$ may optionally be substituted by 1 or 2 substituents independently selected from (1-4C)alkyl, (1-4C)alkoxy, halo, cyano, nitro, carboxy, halo(1-4C)alkyl, difluoromethyl, trifluoromethyl and trifluoromethoxy;

$R^2$ is selected from hydrogen, (1-4C)alkyl, cyclopropyl, halo, fluoromethyl, difluoromethyl and trifluoromethyl;

$R^3$ is selected from hydrogen, (1-4C)alkyl, cyclopropyl, halo, cyano, fluoromethyl, difluoromethyl, trifluoromethyl and —CO(1-4C)alkyl;

R⁴ is selected from hydrogen, (1-4C)alkyl, halo, cyano, halo (1-4C)alkyl, difluoromethyl, trifluoromethyl and —CO(1-4C)alkyl;

R⁵ is hydrogen or methyl;

R⁶ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

R⁷ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is NR⁵;

R¹ is selected from R¹a and R¹b, optionally substituted by 1 or 2 substituents independently selected from nitro, cyano, —CO(1-4C)alkyl, —COO(1-4C)alkyl, —O(1-4C)alkyl, trifluoromethyl, —CONR⁶R⁷, —N(R⁷)COR⁶, fluoro, chloro, bromo, hydroxy, carboxy, (1-4C)alkyl, heterocyclyl, —NHC(O)O(1-4C)alkyl, —C(=NOR⁷)(1-4C)alkyl, —C(=NOR⁷)NR⁶R⁷, —S(O)p(1-4C)alkyl (optionally substituted by hydroxy), —S(O)p(1-4C)alkylCONHR⁷, and —NR⁶R⁷;

R² is selected from hydrogen, (1-4C)alkyl, cyclopropyl, halo, fluoromethyl, difluoromethyl and trifluoromethyl;

R³ is selected from hydrogen, (1-4C)alkyl, cyclopropyl, halo, cyano, fluoromethyl, difluoromethyl, trifluoromethyl and —CO(1-4C)alkyl.

R⁴ is selected from hydrogen, (1-4C)alkyl, halo, cyano, fluoromethyl, difluoromethyl, trifluoromethyl and —CO(1-4C)alkyl;

R⁵ is hydrogen or methyl;

R⁶ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

R⁷ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is NR⁵;

R¹ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 1 or 2 substituents independently selected from nitro, cyano, —CO(1-4C)alkyl, —COO(1-4C)alkyl, —O(1-4C)alkyl, trifluoromethyl, —CONR⁶R⁷, —N(R⁷)COR⁶, fluoro, chloro, bromo, hydroxy, carboxy, (1-4C)alkyl, heterocyclyl, —NHC(O)O(1-4C)alkyl, —C(=NOR⁷)(1-4C)alkyl, —C(=NOR⁷)NR⁶R⁷, —S(O)p(1-4C)alkyl (optionally substituted by hydroxy), —S(O)p(1-4C)alkylCONHR⁷, and —NR⁶R⁷;

R² is selected from hydrogen, (1-4C)alkyl, cyclopropyl, halo, fluoromethyl, difluoromethyl and trifluoromethyl;

R³ is selected from hydrogen, (1-4C)alkyl, cyclopropyl, halo, cyano, fluoromethyl, difluoromethyl, trifluoromethyl and —CO(1-4C)alkyl.

R⁴ is selected from hydrogen, (1-4C)alkyl, halo, cyano, fluoromethyl, difluoromethyl, trifluoromethyl and —CO(1-4C)alkyl;

R⁵ is hydrogen or methyl;

R⁶ is independently at each occurrence selected from hydrogen, (1-4C)alkyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

R⁷ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is NR⁵;

R¹ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 2 substituents; wherein one substituent is selected from carboxy, —CONHSO₂Me and —CONHR⁶ and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR⁶R⁷, carboxy, —NHC(O)O(1-4C)alkyl, —OCONR⁶R⁷, —C(=NOH)(1-4C)alkyl, —C(=NOH)NR⁶R⁷, —S(O)p(1-4C)alkyl, —S(O)pNR⁶R⁷, —NHSO₂R⁶, —NR⁶R⁷, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore);

R² is selected from hydrogen, (1-4C)alkyl, cyclopropyl, halo, fluoromethyl, difluoromethyl and trifluoromethyl;

R³ is selected from hydrogen, (1-4C)alkyl, cyclopropyl, halo, cyano, fluoromethyl, difluoromethyl, trifluoromethyl and —CO(1-4C)alkyl.

R⁴ is selected from hydrogen, (1-4C)alkyl, halo, cyano, fluoromethyl, difluoromethyl, trifluoromethyl and —CO(1-4C)alkyl;

R⁵ is hydrogen or methyl;

R⁶ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —(N[di(1-4C)alkyl], (1-4C)alkoxy, (1-4C)alkoxy(1-4C)alkyl, hydroxy(1-4C)alkyl, and -(1-4C)alkylheterocyclyl;

R⁷ is independently at each occurrence selected from hydrogen and (1-4C)alkyl; and p is (independently at each occurrence) 0, 1 or 2.

In another embodiment is provided a compound of the formula (1) or a pharmaceutically-acceptable salt thereof, wherein:

Y is H;

W is NR⁵;

R¹ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 1 or 2 substituents independently selected from nitro, cyano, —CO(1-4C)alkyl, —COO(1-4C)alkyl, —O(1-4C)alkyl, trifluoromethyl, —CONR⁶R⁷, —N(R⁷)COR⁶, fluoro, chloro, bromo, hydroxy, carboxy, (1-4C)alkyl, heterocyclyl, —NHC(O)O(1-4C)alkyl, —C(=NOR⁷)(1-4C)alkyl, —C(=NOR⁷)NR⁶R⁷, —S(O)

p(1-4C)alkyl (optionally substituted by hydroxy), —S(O)p(1-4C)alkylCONHR$^7$, and —NR$^6$R$^7$;
R$^2$ is selected from (1-4C)alkyl, chloro and bromo;
R$^3$ is selected from hydrogen, methyl, ethyl, chloro, bromo, cyano, trifluoromethyl and —COMe;
R$^4$ is selected from hydrogen, methyl, ethyl, chloro, bromo, cyano and —COMe;
R$^5$ is hydrogen or methyl;
R$^6$ is independently at each occurrence selected from hydrogen, (1-4C)alkyl, cyclopropyl, -(1-4C)alkylC(O)OMe, amino, —NHMe, —NMe$_2$, (1-4C)alkoxy, and -(1-4C)alkylheterocyclyl;
R$^7$ is independently at each occurrence selected from hydrogen and (1-4C)alkyl; and
p is (independently at each occurrence) 0, 1 or 2.

In another embodiment is provided a compound of the formula (1) or a pharmaceutically-acceptable salt thereof, wherein:
Y is H;
W is NR$^5$;
R$^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 2 substituents; wherein one substituent is selected from carboxy, —CONHSO$_2$Me and —CONHR$^6$ (wherein R$^6$ is selected from —OMe, hydrogen, amino and 3-4C alkenyl); and wherein the other substituent is selected from (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —S(O)p(1-4C)alkyl, —S(O)pNR$^6$R$^7$, —NHSO$_2$R$^6$, —NR$^6$R$^7$, and heterocyclyl], —O(1-6C)alkyl (optionally substituted by 1 or 2 substituents as described for (1-6C)alkyl hereinbefore) and —S(O)p(1-4C)alkyl (optionally substituted by 1 or 2 substituents as described for (1-6C)alkyl hereinbefore);
R$^2$ is selected from (1-4C)alkyl, chloro and bromo;
R$^3$ is selected from hydrogen, methyl, ethyl, chloro, bromo, cyano, trifluoromethyl and —COMe;
R$^4$ is selected from hydrogen, methyl, ethyl, chloro, bromo, cyano and —COMe;
R$^5$ is hydrogen or methyl;
R$^6$ is independently at each occurrence selected from hydrogen, (1-4C)alkyl, allyl, cyclopropyl, -(1-4C)alkylC(O)OMe, amino, —NHMe, —NMe$_2$, (1-4C)alkoxy, and -(1-4C)alkylheterocyclyl;
R$^7$ is independently at each occurrence selected from hydrogen and (1-4C)alkyl; and
p is (independently at each occurrence) 0, 1 or 2.

In another embodiment is provided a compound of the formula (1) or a pharmaceutically-acceptable salt thereof, wherein:
Y is H;
W is NR$^5$;
R$^1$ is selected from imidazolyl, pyrimidinyl, pyridinyl, thiazolyl, triazinyl, pyrrolyl, thiadiazolyl, tetrazolyl, quinolinyl, purinyl, benzothiazolyl and indolyl; optionally substituted by 1 or 2 substituents independently selected from nitro, cyano, —CO(1-4C)alkyl, —COO(1-4C)alkyl, —O(1-4C)alkyl, trifluoromethyl, —CONR$^6$R$^7$, —N(R$^7$)COR$^6$, fluoro, chloro, bromo, hydroxy, carboxy, (1-4C)alkyl, heterocyclyl, —NHC(O)O(1-4C)alkyl, —C(=NOR$^7$)(1-4C)alkyl, —C(=NOR$^7$)NR$^6$R$^7$, —S(O)p(1-4C)alkyl (optionally substituted by hydroxy), —S(O)p(1-4C)alkylCONHR$^7$, and —NR$^6$R$^7$;
R$^2$ is selected from (1-4C)alkyl, chloro and bromo;
R$^3$ is selected from hydrogen, methyl, ethyl, chloro, bromo, cyano, trifluoromethyl and —COMe;
R$^4$ is selected from hydrogen, methyl, ethyl, chloro, bromo, cyano and —COMe;
R$^5$ is hydrogen or methyl;
R$^6$ and R$^7$ together with the nitrogen to which they are attached form a 5- or 6-membered heterocyclyl ring, optionally substituted with 1 or 2 substituents independently selected from (1-4C)alkyl, hydroxy, (1-4C)alkoxy, halo, cyano, nitro, carboxy, hydroxy(1-4C)alkyl, (1-4C)alkoxy(1-4C)alkyl, halo(1-4C)alkyl, difluoromethyl, trifluoromethyl and trifluoromethoxy; and
p is (independently at each occurrence) 0, 1 or 2.

In one embodiment of the invention there is provided a compound of formula (1) or a pharmaceutically acceptable salt thereof, wherein:
R$^1$ is selected from R$^1$a, R$^1$b, R$^1$c and R$^1$d; wherein
R$^1$a is a 5 or 6 membered saturated, partially unsaturated or unsaturated heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from:
nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl, and —NR$^6$R$^7$, wherein any aryl or heterocyclyl group in any of the preceding values for substituents on R$^1$a may optionally be substituted by 1 or 2 substituents independently selected from (1-4C)alkyl and carboxy;
R$^1$b is a 10 membered bicyclic heterocyclic ring containing 1, 2 or 4 heteroatoms independently selected from S and N (provided that such a ring does not contain S—S bonds), wherein a —CH$_2$— group can optionally be replaced by a —C(O)—, and wherein said ring may be optionally substituted by 1, 2 or 3 substituents independently selected from the substituents listed for R$^1$a above;
R$^1$c is a phenyl ring, substituted by 1, 2 or 3 substituents independently selected from the substituents listed for R$^1$a above;
R$^1$d is selected from —CH$_2$R$^1$a, and —C(O)R$^1$a;
R$^2$ is selected from (1-4C)alkyl, halo and cyano;

$R^3$ is selected from hydrogen, (1-4C)alkyl, halo, cyano and —CO(1-6C)alkyl;

$R^4$ is selected from hydrogen, (1-4C)alkyl, halo and cyano;

$R^5$ is selected from hydrogen and (1-4C)alkyl;

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —N[di(1-4C)alkyl], (1-4C)alkoxy and -(1-4C)alkylheterocyclyl;

$R^7$ is independently at each occurrence selected from hydrogen and (1-4C)alkyl;

or $R^6$ and $R^7$ may together with the nitrogen to which they are attached form a 5 or 6-membered heterocyclyl ring, optionally substituted with 1 or 2 substituents independently selected from (1-4C)alkyl; and p is (independently at each occurrence) 0, 1 or 2.

In one embodiment of the invention there is provided a compound of formula (1) or a pharmaceutically acceptable salt thereof, wherein:

$R^1$ is selected from $R^1a$, $R^1b$, $R^1c$ and $R^1d$; wherein $R^1a$ is pyridinyl, N-oxopyridinyl, pyrimidinyl, thiazolyl, thiadiazolyl, tetrazolyl, imidazolyl, triazinyl, pyrrolidinyl, thienyl, furanyl, oxadiazolyl, isoxazolyl, oxazolyl or pyrrolyl, wherein said $R^1a$ may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)tetrahydrofuranyl, —NHC(O)phenyl, —NHS(O)p(1-4C)alkyl, —S(O)p(1-4C)alkyl, —S(O)pNR$^6$R$^7$, —NHSO$_2$Re, —NR$^6$R$^7$, morpholino, 1,3-dioxo-1,3-dihydro-2H-isoindolyl and 1,3-dioxolanyl], cyclopropyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), tetrazolyl, 2-oxo-1,3,4-oxadiazolyl, 1,2,4-oxadiazolyl, morpholino, piperazinyl, pyrrolidinyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl and —NR$^6$R$^7$;

wherein any phenyl, tetrahydrofuranyl, morpholino, 1,3-dioxo-1,3-dihydro-2H-isoindolyl, 1,3-dioxolanyl, tetrazolyl, 2-oxo-1,3,4-oxadiazolyl, 1,2,4-oxadiazolyl, morpholino, piperazinyl, pyrrolidinyl, in any of the preceding values for substituents on $R^1a$ may optionally be substituted by 1 or 2 substituents independently selected from (1-4C)alkyl and carboxy;

$R^1b$ is $R^1b$ is quinolinyl, purinyl, benzothiazolyl, indolyl, 4-oxoquinolinyl, 2,7-naphthyridinyl or quinazolinyl, and wherein said $R^1b$ may be optionally substituted by 1, 2 or 3 substituents independently selected from the substituents listed for $R^1a$ above;

$R^1c$ is a phenyl ring, substituted by 1, 2 or 3 substituents independently selected from the substituents listed for $R^1a$ above;

$R^1d$ is selected from —CH$_2$R$^1$a, and —C(O)R$^1$a;

$R^2$ is selected from methyl, ethyl, isopropyl, chloro and cyano;

$R^3$ is selected from hydrogen, methyl, ethyl, chloro, bromo, cyano and —COMe;

$R^4$ is selected from hydrogen, chloro, methyl, ethyl and cyano;

$R^5$ is hydrogen or methyl;

$R^6$ is independently at each occurrence selected from hydrogen, (1-4C)alkyl, (3-4C)alkenyl, cyclopropyl, -(1-4C)alkylC(O)O(1-4C)alkyl, hydroxy, amino, —N[di(1-4C)alkyl], (1-4C)alkoxy and -(1-4C)alkylmorpholino;

$R^7$ is independently at each occurrence selected from hydrogen and (1-4C)alkyl;

or $R^6$ and $R^7$ may together with the nitrogen to which they are attached form piperazinyl or morpholino optionally substituted with 1 or 2 substituents independently selected from (1-4C)alkyl;

p is (independently at each occurrence) 0, 1 or 2.

Preferred compounds of the invention are the compounds of the Examples, each of which provides a further independent aspect of the invention. In further aspects, the present invention also comprises any two or more compounds of the Examples.

Particular Examples are Examples 11, 20, 109, 114, 140, 141, 151, 176, 181, 208, 225, 227, 228, 278, 285, 292, 342, 343 and 344 or a pharmaceutically acceptable salt thereof.

Process

In a further aspect the present invention provides a process for preparing a compound of formula (1) or a pharmaceutically-acceptable salt thereof.

If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the examples.

It is noted that many of the starting materials for synthetic methods as described above are commercially available and/or widely reported in the scientific literature, or could be made from commercially available compounds using adaptations of processes reported in the scientific literature. The reader is further referred to Advanced Organic Chemistry, 4$^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group, for example R$^x$ of formula (2a) herein below, is, for example, an acyl group, for example an alkanoyl group such as acetyl, an alkoxycarbonyl group, for example a methoxycarbonyl, ethoxycarbonyl or t-butoxycarbonyl group, an arylmethoxy-carbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxy-carbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

The protecting groups may be removed at any convenient stage in the synthesis using conventional techniques well known in the chemical art, or they may be removed during a later reaction step or work-up.

The skilled organic chemist will be able to use and adapt the information contained and referenced within the above references, and accompanying Examples therein and also the Examples herein, to obtain necessary starting materials, and products.

Thus, the present invention also provides that the compounds of the formula (1) and pharmaceutically-acceptable salts thereof, can be prepared by a process as follows (wherein the variables are as defined above unless otherwise stated):

Another aspect of the present invention provides a process for preparing a compound of formula (1) or a pharmaceutically acceptable salt thereof which process (wherein R$^2$, R$^3$, R$^4$ are, unless otherwise specified, as defined in formula (1)) comprises of:

a) reacting an acid of the formula (2):

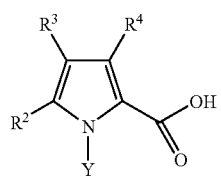

(2)

(wherein Y is H or a suitable protecting group) or an activated derivative thereof; with an amine of formula (3); or

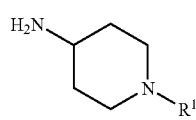

(3)

b) reacting an acid of the formula (2) or an activated derivative thereof, with an amine of formula (4) (suitably protected on the piperidine nitrogen), removal of the protecting group, followed by reaction with a compound of formula (5);

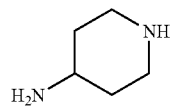

(4)

(5)

wherein X is a displaceable group; or c) reacting an acid of the formula (2) or an activated derivative thereof, with an alcohol of formula (6); or

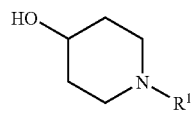

(6)

d) reacting an acid of the formula (2) or an activated derivative thereof, with an alcohol of formula (7) (suitably protected on the piperidine nitrogen), removal of the protecting group, followed by reaction with a compound of formula (8);

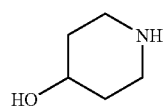

(7)

(8)

wherein X is a displaceable group; and thereafter if necessary:
i) converting a compound of the formula (1) into another compound of the formula (1);
ii) removing any protecting groups;
iii) forming a pharmaceutically acceptable salt.

X is a displaceable group, suitable values for X are for example, a chloro, bromo or iodo group.

Specific reaction conditions for the above reaction are as follows.

Acids of formula (2) and amines of formula (3) or formula (4) may be coupled together in the presence of a suitable coupling reagent. Standard peptide coupling reagents known in the art can be employed as suitable coupling reagents, or for example HATU, carbonyldiimidazole, 1-ethyl-3-(3-dimethylaminopropyl)carbodi-imide hydrochloride (EDCI) and dicyclohexyl-carbodiimide (DCCI), optionally in the presence of a catalyst such as 1-hydroxy-7-azabenzotriazole, HOAT, dimethylaminopyridine or 4-pyrrolidinopyridine, optionally in the presence of a base for example triethylamine, di-isopropylethylamine, pyridine, or 2,6-di-alkyl-pyridines such as 2,6-lutidine or 2,6-di-tert-butylpyridine. Suitable solvents include dimethylacetamide, dichloromethane, N-methylpyrrolidone, tetrahydrofuran and dimethylformamide. The coupling reaction may conveniently be performed at a temperature in the range of 0° C. to 40° C.

Suitable activated derivatives of acids of formula (2) include active esters, for example pentafluorophenyl esters, acid halides, for example acid chlorides, and acid fluorides. The reaction of these types of compounds with amines is well known in the art, for example they may be reacted in the presence of a base, such as those described above, and in a suitable solvent, such as those described above. The reaction may conveniently be performed at a temperature in the range of 0° C. to 40° C.

A compound of formula (2) may be prepared by fictionalization of a substituted pyrrole compound which are commercially available or they are known compounds or they are prepared by processes known in the art, for example by processes such as those shown in Scheme 1 for Y=H.

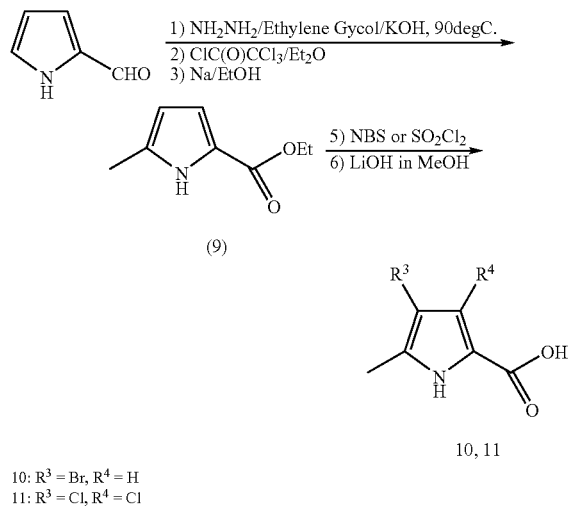

10: $R^3 = Br, R^4 = H$
11: $R^3 = Cl, R^4 = Cl$

For example, compounds of the formula (10) ($R^3$ is Br and $R^4$ is H) may be made by bromination of a compound of formula (9) with a brominating agent such as N-bromosuccinimide and other brominating reagents known in the art, in an inert organic chlorinated solvent such as dichloromethane or 1,2-dichloroethane, followed by treatment with an aqueous base, such as, aqueous sodium hydroxide.

For example, compounds of the formula (11) ($R^3$ and $R^4$ are both chloro) may be made by chlorination of a compound of formula (9) with a chlorinating agent such as sulphuryl chloride and other chlorinating reagents known in the art, in an inert organic chlorinated solvent such as carbon tetrachloride, dichloromethane or 1,2-dichloroethane followed by treatment with an aqueous base, such as, aqueous lithium hydroxide in methanol. Alternatively diethyl ether may be used instead of the chlorinated solvent. The mono chlorinated compound can be formed in a similar manner.

Conveniently, carbon tetrachloride ($CCl_4$) is used as a solvent as the compound (11) then precipitates from the reaction mixture. The process of conversion of compound (9) to compound (11) using sulphuryl chloride in carbon tetrachloride is novel and forms a further independent aspect of the invention.

Compound (9) may also be prepared in a one pot procedure by following the procedure described in Curran, T. P.; Keaney, M. T., *J Org Chem* 1996, 61 (25), 9068.

Compounds of the formula (2) containing other functional groups may be made by processes analogous to those illustrated in Scheme 1 above, or by processes known in the art (see for example Heterocyclic Chemistry, 4<sup>th</sup> Ed., J. A. Joule and K. Mills, Blackwell Science; Heterocyclic Chemistry, T. L. Gilchrist, Adison Wesley Longman, 1997) or by processes illustrated in the Examples hereinafter.

Compounds of formula (3) are prepared by processes known in the art and may be made by coupling of a compound of the formula (4) (suitably protected on the amine nitrogen as shown below, formula (4-P)) with a compound of the formula (5).

The skilled person will thus recognise that in order to form the compound of formula (1):

either suitably protected versions of the compounds of formulae (4) and (5) are reacted together to form a compound of formula (3) which is then (once deprotected where necessary) coupled to the compound of formula (2);

or a suitably protected version of the compound of formula (4) is coupled to the compound of formula (2) and then (once deprotected where necessary) reacted with the compound of formula (5).

Compounds of formula (4) are commercially available, or known in the art, or may be made by processes known in the art.

Compounds of formula (5) are commercially available, or known in the art, or may be made by processes known in the art.

For example when the compound of formula (5) (X=Cl) is a compound of formula (5a), coupling to (4) may be carried out as shown in Scheme 2 (where the protecting group P for the amine group is a Boc group).

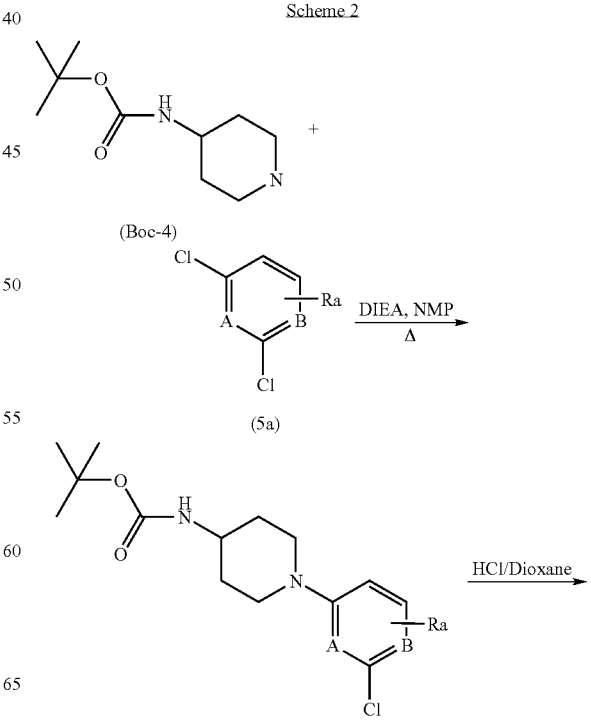

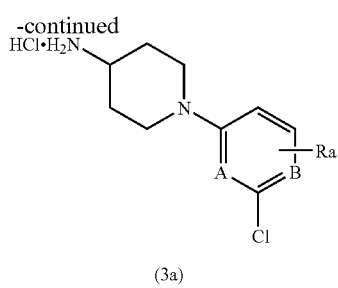

(3a)

A and B are selected from carbon and nitrogen, thus a compound of the formula (5a) may be a phenyl, pyridine or pyrimidine derivative.

Ra is a ring substituent which falls within the definition of formula (1).

Compounds of the formula (3) wherein $R^1$ is another heterocycle, for example triazine, thiazole, and thiadiazole may be made by analogous processes.

Suitable protecting groups for the coupling reaction shown above are for example carbamate protecting groups such as Boc (tert-butoxycarbonyl) or other suitable protecting groups known in the art or mentioned hereinbefore.

Compounds of formula (3) wherein $R^1$ is phenyl, or a heterocycle such as for example furan, thiophene or pyridine, may be made by coupling of a protected version of a compound of formula (4) (i.e. a compound of formula (4-P)) with a suitable compound of formula (5), for example where X is halo such as Br, using palladium catalysed amination reaction known in the art. (see for example Hartwig, J. F.; *Angew. Chem. Int. Ed,* 1998, 37, 2046-2067, *Topics in Chemistry,* 219, 2002, Alex R. Muci; Stephen L. Buchwald; Artis Klapars et al., *J. Am. Chem. Soc,* 2001, 123, 7727-7729). This process is illustrated in the scheme below.

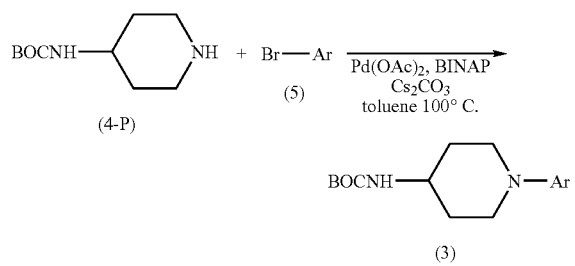

Ar = phenyl, pyridine, furan, thiophene

Alternatively, a precursor to a compound of formula (4) might be used, for example, azide or acetal derivatives such as those shown below.

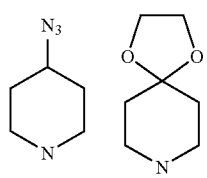

Compounds of formula (3) wherein $R^1$ is another heterocycle, for example thiazole, may also be made by a cyclisation reaction of a suitable (N-protected) derivative of a compound of formula (4). This process is illustrated in the scheme below for $R^1$ is thiazole, where a thiourea derivative of a compound of formula (12) is reacted with a halodicarbonyl derivative (13) (wherein R is an optional substituent on $R^1$ as hereinbefore defined) to give the N-protected compound of formula (14). Suitably such a reaction may be carried out in an alcohol solvent such as methanol or ethanol, suitably at elevated temperature. The N-protecting group (a BOC group in the illustrative scheme below) may then be removed under appropriate conditions known in the art.

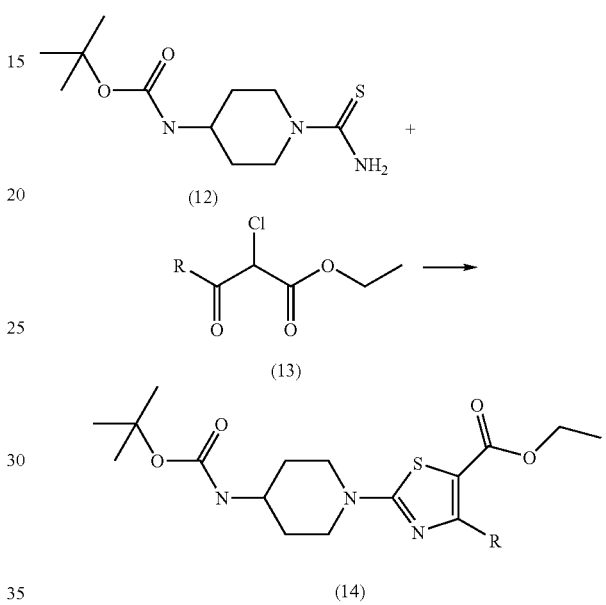

Reaction of a compound of the formula (2) with a compound of the formula (6) (process c) or a compound of the formula (7) (process d) above may be carried out for example using coupling reagents such as triphenylphosphine and diethylazodicarboxylate (DEAD), or other reagents well known in the art to promote ester bond formation.

A compound of the formula (6) may be formed by reaction of a compound of the formula (7) with a compound of the formula (8) as described above.

Where a compound of the formula (8) is X—$R^1$d, X—$R^1$e or X—$R^1$f (wherein $R^1$d to $R^1$f are as defined hereinbefore and contain a $CH_2$ group), coupling to a compound of the formula (4) or (7) (protected as necessary) may suitably be carried out using a reductive amination reaction, using a reagent such as sodium triacetoxyborohydride, for example as shown in Scheme 3 for $R^1$d:

Scheme 3

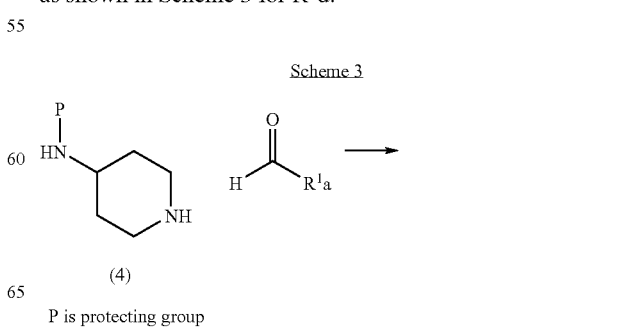

P is protecting group

-continued

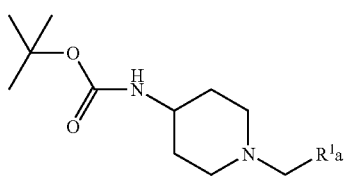

Compounds of formula (1) may be combined with nucleophiles (for example R—SH and R—OH and R—NH$_2$) according to Scheme 4 to form other compounds of the formula 1:

Scheme 4

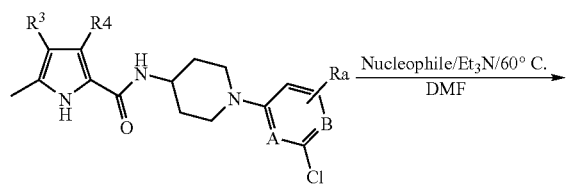

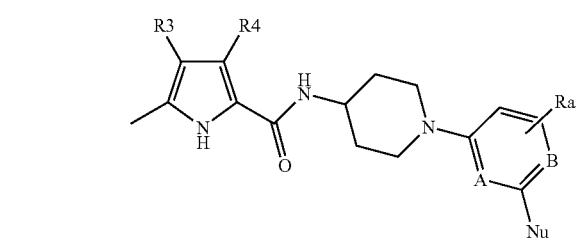

Ra is a ring substituent which falls within the definition of formula (1).

Alternatively, where B in Scheme 4 above is carbon, the equivalent reaction may be carried out where the nucleophile is ROH, in the presence of alkali metals such as sodium or potassium, under reflux conditions.

In a further aspect of the invention there is provided a process for preparing a compound of formula (1) or a pharmaceutically acceptable salt thereof which process (wherein variable groups are, unless otherwise specified, as defined in formula (1)) comprises of:

a) for compounds of formula (1) where W is NR$^5$; reacting an acid of the formula (2a):

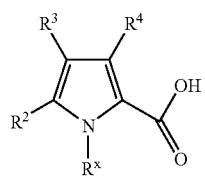

(2a)

(wherein R$^x$ is hydrogen or a suitable protecting group) or an activated derivative thereof; with an amine of formula (3a); or

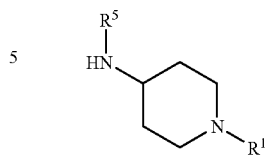

(3a)

b) reacting a compound of formula (4a):

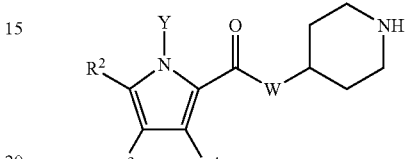

(4a)

with a compound of formula (5a):

$$X—R^1$$ (5a)

wherein X is a displaceable group;

c) for compounds of formula (1) where W is O; reacting an acid of the formula (2a) or an activated derivative thereof, with an alcohol of formula (6a); or

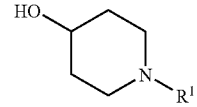 (6a)

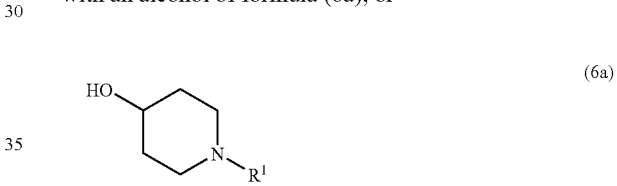

and thereafter if necessary:
i) converting a compound of the formula (1) into another compound of the formula (1);
ii) removing any protecting groups;
iii) forming a pharmaceutically acceptable salt.

X is a displaceable group, suitable values for X are for example, a chloro, bromo or iodo group.

Process conditions and generic schemes for the synthesis of intermediates are given herein above.

It will be appreciated that certain of the various ring substituents in the compounds of the present invention, for example substituents on the ring R$^1$, illustrated as Ra in the Schemes above, may be introduced by standard aromatic substitution reactions or generated by conventional functional group modifications either prior to or immediately following the processes mentioned above, and as such are included in the process aspect of the invention. The reagents used to introduce such ring substituents are either commercially available or are made by processes known in the art. Alternatively, starting materials where R$^1$ is already substituted may be commercially available.

Introduction of substituents into the ring of R$^1$ may convert one compound of the formula (1) into another compound of the formula (1). Such reactions and modifications include, for example, introduction of a substituent by means of an aromatic substitution reaction, reduction of substituents, alkylation of substituents, oxidation of substituents, esterification of substituents, amidation of substituents, formation of heteroaryl rings. The reagents and reaction conditions for such procedures are well known in the chemical art. Particular examples of aromatic substitution reactions include the introduction of alkoxides, diazotization reactions followed by introduction of thiol group, alcohol group, halogen group. Examples of modifications include; oxidation of alkylthio to alkylsulphinyl or alkylsulphonyl.

The removal of any protecting groups and the formation of a pharmaceutically-acceptable salt are within the skill of an ordinary organic chemist using standard techniques. Further information on these steps has been added above.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further feature of the invention there is provided a compound of the formula (1), or a pharmaceutically-acceptable salt thereof for use in a method of treatment of the human or animal body by therapy.

We have found that compounds of the present invention inhibit bacterial DNA gyrase and are therefore of interest for their antibacterial effects.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

According to a further feature of the invention there is provided a method for inhibition of bacterial DNA gyrase in a warm-blooded animal, such as a human being, in need of such treatment which comprises administering to said animal an effective amount of a compound of formula (1) or a pharmaceutically acceptable salt thereof as defined hereinbefore.

According to a further feature of the invention there is provided a method of treating a bacterial infection in a warm-blooded animal, such as a human being, in need of such treatment which comprises administering to said animal an effective amount of a compound of formula (1) or a pharmaceutically acceptable salt thereof as defined hereinbefore.

A further feature of the present invention is a compound of formula (1) and pharmaceutically acceptable salts thereof for use as a medicament. Suitably the medicament is an antibacterial agent.

Conveniently this is a compound of formula (1), or a pharmaceutically acceptable salt thereof, for use as a medicament for producing an antibacterial effect in a warm-blooded animal such as a human being.

Conveniently this is a compound of formula (1), or a pharmaceutically acceptable salt thereof, for use as a medicament for inhibiting bacterial DNA gyrase in a warm-blooded animal, such as a human being.

Particularly this is a compound of formula (1), or a pharmaceutically acceptable salt thereof, for use as a medicament for treating a bacterial infection in a warm-blooded animal such as a human being.

According to a further aspect of the invention there is provided the use of a compound of formula (1), or a pharmaceutically acceptable salt thereof in the manufacture of a medicament for use in the production of an anti-bacterial effect in a warm-blooded animal such as a human being.

According to a further aspect of the invention there is provided the use of a compound of formula (1), or a pharmaceutically acceptable salt thereof in the manufacture of a medicament for use in inhibition of bacterial DNA gyrase in a warm-blooded animal such as a human being.

Thus according to a further aspect of the invention there is provided the use of a compound of formula (1), or a pharmaceutically acceptable salt thereof in the manufacture of a medicament for use in the treatment of a bacterial infection in a warm-blooded animal such as a human being.

According to a further aspect of the invention there is provided a compound of formula (1), or a pharmaceutically acceptable salt thereof for use in the production of an anti-bacterial effect in a warm-blooded animal such as a human being.

According to a further aspect of the invention there is provided a compound of formula (1), or a pharmaceutically acceptable salt thereof for use in inhibition of bacterial DNA gyrase in a warm-blooded animal such as a human being.

Thus according to a further aspect of the invention there is provided a compound of formula (1), or a pharmaceutically acceptable salt thereof for use in the treatment of a bacterial infection in a warm-blooded animal such as a human being.

In order to use a compound of the formula (1) or a pharmaceutically-acceptable salt thereof, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (1) or a pharmaceutically-acceptable salt thereof, and a pharmaceutically-acceptable diluent or carrier.

According to a further aspect of the invention there is provided a pharmaceutical composition which comprises a compound of formula (1) as defined hereinbefore or a pharmaceutically acceptable salt thereof, in association with a pharmaceutically acceptable excipient or carrier for use in inhibition of bacterial DNA gyrase in an warm-blooded animal, such as a human being.

According to a further aspect of the invention there is provided a pharmaceutical composition which comprises a compound of formula (1) as defined hereinbefore or a pharmaceutically acceptable salt thereof, in association with a pharmaceutically acceptable excipient or carrier for use in the treatment of a bacterial infection in an warm-blooded animal, such as a human being.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In addition to the compounds of the present invention the pharmaceutical composition of this invention may also contain or be co-administered (simultaneously, sequentially or separately) with one or more known drugs selected from other clinically useful antibacterial agents (for example, macrolides, quinolones, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

In addition to its use in therapeutic medicine, compounds of formula (1) and their pharmaceutically acceptable salts are also useful as pharmacological tools in the development and standardization of in-vitro and in-vivo test systems for the evaluation of the effects of inhibitors of DNA gyrase in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

Enzyme Potency Testing Methods

Compounds were tested for inhibition of GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays were performed in multiwell plates in 100 µl reactions containing: 50 mM TRIS buffer pH 7.5, 75 mM ammonium acetate, 5.5 mM magnesium chloride, 0.5 mM ethylenediaminetetraacetic acid, 5% glycerol, 1 mM 1,4-Dithio-DL-threitol, 200 nM bovine serum albumin, 16 µg/ml sheared salmon sperm DNA, 4 nM *E. coli* GyrA, 4 nM *E. coli* GyrB, 250 µM ATP, and compound in dimethylsulfoxide. Reactions were quenched with 150 µL of ammonium molybdate/malachite green detection reagent containing 1.2 mM malachite green hydrochloride, 8.5 mM ammonium molybdate tetrahydrate, and 1 M hydrochloric acid. Plates were read in an absorbance plate reader at 625 nm and percent inhibition values were calculated using dimethylsulfoxide (2%)-containing reactions as 0% inhibition and novobiocin-containing (2 µM) reactions as 100% inhibition controls. Compound potency was based on $IC_{50}$ measurements determined from reactions performed in the presence of 10 different compound concentrations.

Compounds of the Examples generally have an $IC_{50}$ of <20 µg/ml.

Bacterial Susceptibility Testing Methods

Compounds were tested for antimicrobial activity by susceptibility testing in liquid media. Compounds were dissolved in dimethylsulfoxide and tested in 10 doubling dilutions in the susceptibility assays. The organisms used in the assay were grown overnight on suitable agar media and then suspended in a liquid medium appropriate for the growth of the organism. The suspension was a 0.5 McFarland and a further 1 in 10 dilution was made into the same liquid medium to prepare the final organism suspension in 100 µL. Plates were incubated under appropriate conditions at 37 degrees C. for 24 hrs prior to reading. The Minimum Inhibitory Concentration was determined as the lowest drug concentration able to reduce growth by 80% or more.

Example 130 had an MIC of 2 µg/ml against *Streptococcus pneumoniae*.

The invention is now illustrated but not limited by the following Examples in which unless otherwise stated:—

(i) evaporations were carried out by rotary evaporation in-vacuo and work-up procedures were carried out after removal of residual solids by filtration;

(ii) operations were carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques [proton magnetic resonance spectra were generally determined in DMSO-$d_6$ unless otherwise stated using a Bruker DRX-300 spectrometer operating at a field strength of 300 MHz. Chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected]or using Agilent 1100 series LC/MSD equipped with Sedex 75ELSD, run in APCI mode and, where appropriate, either positive ion data or negative ion data were collected; optical rotations were determined at 589 nm at 20° C. for 7.6 mM solutions in methanol using a Perkin Elmer Polarimeter 341; REVERSE PHASE HPLC carried out using YMC Pack ODS-AQ (100×20 mmID, S-5µ particle size, 12 nm pore size)

(vi) each intermediate was purified to the standard required for the subsequent stage and was characterized in sufficient detail to confirm that the assigned structure was correct; purity was assessed by HPLC, TLC, or NMR and identity was determined by infra-red spectroscopy (IR), mass spectroscopy or NMR spectroscopy as appropriate;

(vii) in which the following abbreviations may be used:—

DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP (or ES) is electrospray; EI is electron impact; CI is chemical ionization; APCI is atmospheric pressure chemical ionization; EtOAc is ethyl acetate; MeOH is methanol; DEAD is diethylazodicarboxylate; DIEA is diisopropylethylamine; mCPBA is meta-chloroperoxybenzoic acid; TFA is trifluoroacetic acid; HATU is N-[(dimethylamino)-1H,2,3-triazolo[4,5-b-]pyridin-1-ylmethylene]-N-methylmethanaminium hexafluorophosphate N-oxide; HOAT is 1-hydroxy-7-azabenzotriazole; EDC is 1-(3-dimethylaminopropyl)-3-ethylcarbodiimide hydrochloride; TEA is triethylamine; NMP is N-methylpyrrolidinone; Pd(dba) is bis(dibenzylidineacetone)palladium; Dppf is 1,1'bis(diphenylphosphine)ferrocene; THF is tetrahydrofuran; EtOH is ethanol; LCMS is liquid chromatography/mass spectrometry; DBU is 1,8-diazabicyclo[5.4.0]undec-7-ene; DCM is dichloromethane;

(viii) temperatures are quoted as ° C.;

(ix) Smith Microwave Synthesizer refers to an equipment that uses microwave energy to heat organic reactions in a short period of time; it was used according to the manufacturers instruction and was obtained from Personal Chemistry Uppsala AB; and (x) Kugelrohr distillation refers to a piece of equipment that distils liquids and heats sensitive compounds using air-bath oven temperature; it was used according to the manufacturers instruction and was obtained from Buchi, Switzerland or Aldrich, Milwaukee, USA.

Intermediate 1: 3,4-Dichloro-5-methyl-N-piperidin-4-yl-1H-pyrrole-2-carboxamide hydrochloride tert-Butyl 4-{[(3,4-dichloro-5-methyl-1H-pyrrol-2-yl)carbonyl]amino}piperidine-1-carboxylate (Intermediate 2, 1.978 g, 5.257 mol) was treated with 4 M HCl in dioxane (20 ml), and the reaction was stirred at room temperature for 1.5 h. The reaction mixture was concentrated under reduced pressure to give the desired material as a pink solid (1.61 g, 98% yield).

MS (ES$^-$): 274.08, 276.08 for $C_{11}H_5Cl_2N_3O$
$^1$H NMR δ: 1.71 (m, 2H); 1.95 (m, 2H); 2.18 (s, 3H); 2.99 (m, 2H); 3.27 (m, 2H); 3.99 (m, 1H); 7.64 (d, 1H); 8.67 (brs, 1H); 12.16 (s, 1H)

Intermediate 2: tert-Butyl 4-{[(3,4-dichloro-5-methyl-1H-pyrrol-2-yl)carbonyl]amino}piperidine-1-carboxylate 3,4-Dichloro-5-methyl-1H-pyrrole-2-carboxylic acid (Intermediate 3, 3.0 g, 0.016 mol), tert-butyl 4-aminopiperidine-1-carboxylate (3.1 g, 0.016 mol), and Et$_3$N (2.2 ml, 0.032 mol) were combined in DMF (20 ml) and stirred under N$_2$ for 5 minutes. HATU (6.47 g, 0.017 mol) was added in one portion, and the reaction was stirred at room temperature for 5 h. The reaction mixture was diluted with EtOAc and H$_2$O. The organic phase was washed with 1 N HCl, and the combined aqueous portions were extracted once with EtOAc. The combined organic portions were washed sequentially with saturated NaHCO$_3$ and saturated NaCl, dried over MgSO$_4$, filtered, and concentrated under reduced pressure to give a brown solid. Most of the crude material was isolated by trituration with EtOAc/hexanes to give an off-white solid. The remaining material was chromatographed on silica, eluting with 3:1, 2:1, and 1:1 EtOAc/hexanes to give a light brown solid that was triturated with EtOAc, collected and combined with the other triturated material to give a total of 1.978 g of the desired product.

MS (ES$^-$): 374.33, 376.34 for $C_{16}H_{23}Cl_2N_3O_3$
$^1$H NMR δ: 1.16 (s, 9H); 1.20 (m, 2H); 1.53 (m, 2H); 1.93 (s, 3H); 2.65 (m, 2H); 3.65 (m, 3H); 6.97 (d, 1H); 11.72 (s, 1H)

Intermediate 3: 3,4-Dichloro-5-methyl-1H-pyrrole-2-carboxylic acid

Ethyl 3,4-dichloro-5-methyl-1H-pyrrole-2-carboxylate (Intermediate 4, 7.765 g, 0.03496 mol) was dissolved in MeOH (80 ml) and DCM (10 ml) and slowly added to a 70° C. solution of 2 N LiOH (105 ml, 0.21 mol). After 2 h, the reaction mixture was cooled to room temperature and then in an ice bath, followed by acidification with 2 N HCl. The mixture was stirred at 0° C. for 1 h, and a purple solid was filtered, washed with water and lyophilized overnight to give 4.314 g (0.0222 mol, 64% yield) of the desired product.

MS (ES$^-$): 192.13, 194.13 for $CH_5Cl_2NO_2$
$^1$H NMR δ: 2.17 (s, 3H)

Intermediate 4: Ethyl 3,4-dichloro-5-methyl-1H-pyrrole-2-carboxylate

A solution of ethyl 5-methyl-1H-pyrrole-2-carboxylate (Intermediate 20) (7.00 g, 0.0457 mol) in tetrachloromethane (30 ml) was cooled to 0° C. under nitrogen. The rubber septum used in the apparatus was pierced with a needle, and SO$_2$Cl$_2$ (7.8 ml, 0.096 mol) was then added dropwise over 25 minutes. Within 1 hr, the reaction mixture had formed a slurry. The solid was collected by suction filtration, washed with cold tetrachloromethane, and dried under vacuum overnight to give the title product as a peach colored solid (7.84 g, 0.0353 mol, 77% yield).

MS (ES$^-$): 222.00, 224.00 for $C_8H_9Cl_2NO_2$
$^1$H NMR δ: 1.34-1.40 (t, 3H); 2.28 (s, 3H); 4.32-4.38 (m, 2H)

Intermediate 5: Ethyl 4-methoxy-3-oxobutanoate

The title compound was prepared in a manner analogous to Intermediate 123 starting from 2,2-dimethyl-1,3-dioxane-4,6-dione and methoxyacetyl chloride.

MS (APCI) MH+: 161, 162 for $C_7H_{12}O_4$
$^1$H NMR(CDCl$_3$) δ: 1.12-1.26 (t, 3H); 3.26 (s, 3H); 3.51 (s, 2H); 4.03-4.16 (brs, 4H).

Intermediate 6: Ethyl 2-chloro-4-methoxy-3-oxobutanoate

The title compound was prepared in a manner analogous to Intermediate 124 starting from ethyl 4-methoxy-3-oxobutanoate (Intermediate 5) and sulfuryl chloride.

MS (APCI) MH$^+$: 193, 195 for $C_7H_{11}ClO_4$
$^1$H NMR (CDCl$_3$) δ:1.10-1.12 (t, 3H); 3.22 (s, 3H); 3.22 (s, 3H); 4.22-4.25 (s, 2H); 4.08-4.19 (q, 2H); 4.48 (s, 1H)

Intermediate 7: N-(2,6-Dichloropyrimidin-4-yl)acetamide

4-Amino-2,6-dichloropyrimidine (500 mg, 3.05 mmol) was refluxed in acetic anhydride (10 ml) for 3 h. Upon cooling to room temperature, the reaction mixture was cooled in an ice bath and basified to pH 8 with 10% aqueous NaHCO$_3$. The phases were separated, and the aqueous portion was extracted twice with EtOAc. The combined organic portions were dried over Na$_2$SO$_4$, filtered, and concentrated to give an off-white solid (503.7 mg, 2.44 mmol, 80% yield).

MS (ES$^-$): 204.08, 206.08 for $C_6H_5Cl_2N_3O$
$^1$H NMR δ: 2.15 (s, 3H); 8.07 (s, 1H); 11.56 (brs, 1H)

Intermediate 8: 4-Chloro-5-methyl-1H-pyrrole-2-carboxylic acid

Lithium hydroxide (2 M, 4 ml) was warmed to 50° C. and a solution of ethyl 4-chloro-5-methyl-1H-pyrrole-2-carboxylate (Intermediate 9, 0.30 g, 1.60 mmol) in MeOH was added to it. The reaction was heated to 80° C. and stirred for two hours. The MeOH was removed and the aqueous solution was cooled to 0° C. and acidified with 30% HCl. The precipitated product (0.23 g, 92%) was filtered and dried.

MS (ES): 160 (M+1) for $C_6H_6ClNO_2$
$^1$H NMR (CDCl$_3$) δ: 2.25 (s, 3H); 6.85 (s, 1H); 8.98 (brs, 1H)

Intermediate 9: Ethyl 4-chloro-5-methyl-1H-pyrrole-2-carboxylate

N-Chlorosuccinimide (0.67 g, 5.08 mmol) was added to a solution of ethyl 5-methyl-1H-pyrrole-2-carboxylate (Intermediate 20) (0.65 g, 4.23 mmol) in chloroform (20 ml). The reaction was warmed to 40° C. and stirred for 4 hours, then poured to a beaker containing 2 N NaOH (20 ml) at 0° C. The layers were separated and the aqueous layer was extracted with chloroform (×3). The combined organic extracts were dried over magnesium sulfate and concentrated. The resultant off-white solid was purified by flash chromatography (hexanes/EtOAc, 16:1) to give the title product as a white solid (0.3 g, 38%).

MS (ES): 188 (M+1) for $C_8H_{10}ClNO_2$
$^1$H NMR (CDCl$_3$) δ: 1.34 (t, 3H); 2.27 (s, 3H); 4.30 (q, 2H); 6.76 (s, 1H); 9.07 (brs, 1H)

Intermediate 10:
4-Bromo-5-ethyl-1H-pyrrole-2-carboxylic acid

This intermediate was synthesized from ethyl 4-bromo-5-ethyl-1H-pyrrole-2-carboxylate (Intermediate 11) by an analogous method to Intermediate 8.

MS (ES): 218 (M+1) for $C_7H_8BrN_2$
$^1$H NMR (CDCl$_3$) δ: 1.11 (t, 3H); 2.54 (q, 2H); 6.67 (s, 1H); 11.94 (brs, 1H); 12.38 (s, 1H)

Intermediate 11: Ethyl
4-bromo-5-ethyl-1H-pyrrole-2-carboxylate

N-Bromosuccinimide (5.86 g, 0.033 mol) was added to a solution of ethyl 5-ethyl-1H-pyrrole-2-carboxylate (Intermediate 12, 5.0 g, 0.03 mol) in DCM (85 ml) at 0° C., and the reaction was stirred for 30 minutes then poured to a chilled beaker containing 2 N NaOH (50 ml). The layers were separated and the aqueous layer was extracted with DCM (×3). The combined organic extracts were washed with water and brine, dried over magnesium sulfate and concentrated. The resultant dark brown solid was purified by flash chromatography (hexanes/EtOAc, 10:1) to give the title product as a white solid (5.0 g, 68%).

MS (ES): 247 (M+1) for $C_9H_{12}BrNO_2$
$^1$H NMR (CDCl$_3$) δ: 1.04 (t, 3H); 1.14 (t, 3H); 2.46 (q, 2H); 4.10 (q, 2H); 6.64 (s, 1H); 8.68 (brs, 1H)

Intermediate 12: Ethyl
5-ethyl-1H-pyrrole-2-carboxylate

Absolute EtOH (6 ml) was added to a 21 wt % solution of sodium ethoxide in EtOH (0.33 ml, 1.05 mmol) followed by the portion-wise addition of 2,2,2-trichloro-1-(5-ethyl-1H-pyrrol-2-yl)ethanone (*J. Chem. Soc. Perkin Trans* 1, 1996, 03) (2.1 g, 8.75 mmol) under nitrogen. The resulting yellow solution was stirred at room temperature for 30 minutes. Then the reaction was concentrated to give light orange oil. Hydrochloric acid (3 M, 2.5 ml) and diethyl ether (8 ml) were added to the oil and layers separated. The aqueous layer was extracted with diethyl ether (×2) and the combined organic extracts were washed with saturated sodium bicarbonate solution and brine, dried over magnesium sulfate and concentrated to give the desired product as a white solid (1.27 g, 86%).

MS (ES): 168 (M+1) for $C_9H_{13}NO_2$
$^1$H NMR (CDCl$_3$) δ: 1.18 (t, 3H); 1.27 (t, 3H); 2.59 (q, 2H); 4.23 (q, 2H); 5.89 (s, 1H); 6.64 (s, 1H); 8.68 (brs, 1H)

Intermediate 13:
4-Cyano-5-methyl-1H-pyrrole-2-carboxylic acid

Lithium hydroxide (2 N, 2 ml) was warmed to 40° C. and a solution of ethyl 4-cyano-5-methyl-1H-pyrrole-2-carboxylate (Intermediate 14, 0.16 g) in 2 ml of MeOH was added. The reaction temperature was gradually increased to 90° C. and the reaction was stirred at that temperature for 2 hours. Then MeOH was removed and the remaining aqueous solution was cooled to 0° C. and acidified with 3 M HCl (pH ~2). The acidic solution was extracted with EtOAc, the combined organic extracts were dried over magnesium sulfate and concentrated to give brown solid (0.07 g, crude).

MS (ES): 151 (M+1) for $C_7H_6N_2O_2$
$^1$H NMR δ: 2.33 (s, 3H); 7.01 (s, 1H); 12.47 (s, 1H)

Intermediate 14: Ethyl
4-cyano-5-methyl-1H-pyrrole-2-carboxylate

Ethyl 4-formyl-5-methyl-1H-pyrrole-2-carboxylate (Intermediate 15, 0.2 g, 1.1 mmol) and hydroxylamine hydrochloride (0.08 g, 1.1 mmol) were dissolved in EtOH (10 ml) and refluxed for 1.5 hours. The mixture was concentrated under vacuum to give yellow solid, which was dissolved in DMF (5 ml) before addition of SOCl$_2$ (0.35 ml) at 0° C. The solvent was removed under vacuum after the completion of the reaction and the residue was partitioned between water and EtOAc. The layers were separated and the aqueous layer was extracted with EtOAc twice. The combined organic extracts were dried over MgSO$_4$ and concentrated to give brown solid (0.16 g, crude).

MS (ES): 179 (M+1) for $C_9H_{10}N_2O_2$

Intermediate 15: Ethyl
4-formyl-5-methyl-1H-pyrrole-2-carboxylate

Trimethoxymethane (1.18 ml, 10.78 mmol) was added to a solution of ethyl 5-methyl-1H-pyrrole-2-carboxylate (Intermediate 20) (0.5 g, 3.26 mmol) in TFA (2.5 ml) at 0° C. The reaction was stirred at that temperature for 10 mins then quenched with cold water (20 ml). The layers were separated and the aqueous layer was extracted with EtOAc. The combined organic extracts were dried over magnesium sulfate and concentrated to give yellow solid which was purified by flash chromatography (10% to 20% EtOAc in hexanes, 0.25 g).

MS (ES): 182 (M+1) for $C_9H_{11}NO_3$
$^1$H NMR (CDCl$_3$) δ: 1.37 (t, 3H); 2.61 (s, 3H); 4.34 (q, 2H); 7.24 (s, 1H); 9.51 (brs, 1H); 9.88 (s, 1H).

Intermediate 16: tert-Butyl 1-[4-(aminocarbonyl)-6-chloropyridin-2-yl]piperidin-4-ylcarbamate tert-Butyl piperidin-4-ylcarbamate (500 mg, 2.62 mmol), was dissolved in anhydrous N,N'-dimethyl acetamide (4 ml). 2,6-Dichloroisonicotinamide (522 mg, 2.62 mmol) was added, followed by N,N-dimethyl isopropylethylamine (465 μl, 2.62 mmol). Using a Smith Microwave Synthesizer, the mixture was subjected to single-mode microwave at 150° C. for 20 minutes. H$_2$O (50 ml) and EtOAc (100 ml) were added, the EtOAc layer was washed (4×50 ml), dried over Na$_2$SO$_4$ and concentrated in vacuo to give the title product as a brown solid. (760 mg).

MS (ES, M+H): 355 for $C_{16}H_{23}ClN_4O_3$
$^1$H NMR δ:1.42 (m, 2H); 1.53 (s, 9H); 1.94 (m, 2H); 3.12 (m, 2H); 3.45 (s, 1H); 3.70 (m, 1H); 4.34 (m, 2H); 7.07 (s, 1H); 7.26 (s, 1H); 7.81 (s, 1H); 8.49 (s, 1H).

Intermediate 17: Pentafluorophenyl
4-bromo-5-methyl-1H-pyrrole-2-carboxylate

4-Bromo-5-methyl-1H-pyrrole-2-carboxylic acid (Intermediate 18, 2.16 g, 10.59 mmol) was dissolved an THF (10 ml). Pentafluorophenol and EDC (2.03 g, 10.59 mmol) were added and the mixture was stirred at room temperature for 6 h. The solvent was removed under vacuum and EtOAc (50 ml) was added. The organic phase was washed with water, 10%

Na$_2$CO$_3$ (2×25 ml), water (50 ml) and brine (50 ml), dried over Na$_2$SO$_4$ and concentrated in vacuo to give the title compound as an off white solid (2.23 g).

MS (ESI, M+H): 368, 371 for C$_{12}$H$_5$BrF$_5$NO$_2$ $^1$H NMR δ: 2.39 (s, 3H); 7.46 (d, 1H); 12.06 (s, 1H)

$^{19}$F NMR δ: −151.5 to −192.7 ppm

Intermediate 18:
4-Bromo-5-methyl-1H-pyrrole-2-carboxylic acid

Ethyl 4-bromo-5-methyl-1H-pyrrole-2-carboxylate (Intermediate 19, 16.5 g, 71.09 mmol) was dissolved anhydrous THF (100 ml) and was added to a preheated solution of 2 N lithium hydroxide (500 ml) at 70° C. The mixture was heated at 70° C. for 4 h and the solvent was removed in vacuo and the crude aqueous solution was cooled in an ice-bath and slowly acidified with 3 N HCl. The precipitate was extracted with EtOAc (3×100 ml), the organic extracts were washed with water, brine and dried with Na$_2$SO$_4$, treated with decolorizing charcoal for 1 h, filtered over celite and concentrated in vacuo. The brown solid was filtered and washed well with n-hexanes and dried in vacuo. (13 g).

MS (APCI, M+H): 205 for C$_6$H$_6$BrNO$_2$ $^1$H NMR δ: 2.27 (s, 3H); 6.74 (d, 1H); 12.06 (s, 1H); 12.57 (s, 1H).

Intermediate 19: Ethyl 4-bromo-5-methyl-1H-pyrrole-2-carboxylate

Ethyl 5-methyl-1H-pyrrole-2-carboxylate (Intermediate 20, 12.3 g, 0.803 mmol) was dissolved in anhydrous DCM and cooled to −5° C. N-bromosuccinimide (14.23 g; 0.0803 mmol) was added and the reaction stirred for 10 min and then poured into ice-cold 2 N sodium hydroxide (500 ml). The brown solution was extracted with EtOAc (2×150 ml), the combined organic extracts were washed with water, brine and dried over Na$_2$SO$_4$, then concentrated in vacuo to give a brown solid which was dried under vacuum. (16.5 g).

MS (ES, M+H): 233 for C$_8$H$_{10}$BrNO$_2$ $^1$H NMR δ: 1.32 (t, 3H); 2.1 (s, 3H); 4.371 (q, 2H); 6.23 (d, 1H); 11.54 (s, 1H).

Intermediate 20: Ethyl 5-methyl-1H-pyrrole-2-carboxylate

Sodium (2.79 g, 0.121 mmol) was dissolved in anhydrous EtOH (100 ml), then 2,2,2-trichloro-1-(5-methyl-1H-pyrrol-2-yl)ethanone (Intermediate 21, 22.5 g, 0.099 mmol) was added in small portions. The dark brown solution was stirred at room temperature for 30 minutes then concentrated under vacuum to a small volume. The mixture was cooled in an ice bath and 3 N HCl was added slowly then extracted with diethyl ether (3×100 ml). The ether extracts were washed with 10% NaHCO$_3$, water and brine, dried over Na$_2$SO$_4$ and concentrated in vacuo to give the title compound as a brown solid. (15.04 g).

$^1$H NMR δ: 1.32 (t, 3H); 2.1 (s, 3H); 4.371 (q, 2H); 5.96 (dd, 1H); 6.78 (dd, 1H); 11.67 (s, 1H).

In an alternative procedure, Ethyl 5-methyl-1H-pyrrole-2-carboxylate (Intermediate 20) was synthesized in one pot according to Curran, T. P.; Keaney, M. T., *J Org Chem* 1996, 61 (25), 9068.

Intermediate 21: 2,2,2-Trichloro-1-(5-methyl-1H-pyrrol-2-yl)ethanone

2-Methyl-1H-pyrrole (Intermediate 22, 10 g, 0.123 mmol) in anhydrous diethyl ether (30 ml) was added dropwise over 1 h to a stirred solution of triacetyl chloride (29 g, 0.16 mmol) in anhydrous Et$_2$O (100 ml). The mixture was stirred for a further 1 h then K$_2$CO$_3$ (10 g/30 ml) was added slowly through a dropping funnel. The organic phase was dried over Na$_2$SO$_4$ and treated with decolorizing charcoal (3 g) for 30 minutes at room temperature. The resulting purple solution was concentrated and triturated with n-hexanes to give the title compound as a purple solid. (16.72 g).

$^1$H NMR (CDCl$_3$) δ: 2.36 (s, 3H); 6.04 (dd, 1H); 7.45 (dd, 1H); 10.344 (s, 1H).

Intermediate 22: 2-Methyl-1H-pyrrole

Potassium hydroxide (50 g, 0.89 mmol) was added to a solution of ethylene glycol (750 ml) and 1H-pyrrole-2-carbaldehyde (50 g, 0.53 mmol). Hydrazine hydrate (37 ml, 0.745 mmol) was added slowly over 15 minutes. The reaction mixture was refluxed at 90° C. for 90 minutes. The mixture was cooled to room temperature and cold water (250 ml) was added. The aqueous mixture was extracted with DCM (250 ml). The organic phase was washed with water (250 ml), dried over Na$_2$SO$_4$ and concentrated in vacuo. Kugelrohr distillation gave the title compound as a clear colorless liquid (29.75 g).

$^1$H NMR δ: 2.1 (s, 3H); 5.77 (s, 1H); 5.9 (dd, 1H); 6.25 (dd, 1H); 10.54 (s, 1H).

Intermediate 23: Methyl 2-{4-[(tert-butoxycarbonyl)amino]piperidin-1-yl}-6-chloroisonicotinate tert-Butyl piperidin-4-ylcarbamate (972 mg, 4.85 mmol), was dissolved in anhydrous NMP (5 ml). Methyl 2,6-dichloroisonicotinate (Intermediate 24, 1 g, 4.85 mmol) was added followed by TEA (675 μl, 4.85 mmol). The mixture was heated under microwave conditions at 150° C. for 10 minutes. Water (50 ml) and EtOAc (100 ml) were added, the aqueous phase was treated with solid NaCl and extracted with EtOAc (4×100 ml). The EtOAc layer was dried, concentrated in vacuo and purified by flash chromatography eluting with hexane:EtOAc (4:1) to give the title product as an off-white solid. (1.4 g).

MS (ES, M+H): 370 for C$_{17}$H$_{24}$ClN$_3$O$_4$ $^1$H NMR δ:1.38 (m, 2H); 1.49 (s, 9H); 1.93 (m, 2H); 2.29 (m, 1H); 3.17 (m, 1H); 3.48 (s, 1H); 3.94 (s, 3H); 4.38 (m, 2H); 7.02 (s, 1H); 7.31 (s, 1H); 7.81 (s, 1H); 8.49 (s, 1H)

Intermediate 24: Methyl 2,6-dichloroisonicotinate 2,6-Dichloroisonicotinic acid was (5 g, 26.04 mmol) was suspended in anhydrous toluene (75 ml). Thionyl chloride (19 ml, 260.4 mmol) was added and the mixture was heated to reflux for 4 h. The excess thionyl chloride was removed and solvent was removed in vacuo. Anhydrous MeOH (25 ml) was added and reaction was stirred for a further 4 h. Solvents were removed in vacuo to give a white colored solid which was dried under vacuum (4.8 g).

MS (APCI, M+H): 206 for C$_7$H$_5$Cl$_2$NO$_2$ $^1$H NMR δ: 4.10 (s, 3H); 8.15 (s, 2H).

Intermediate 25: Ethyl 4-(1,3-dioxo-1,3-dihydro-2H-isoindol-2-yl)-3-oxobutanoate The title compound was prepared in a manner analogous to Intermediate 123 starting from 2,2-dimethyl-1,3-dioxane-4,6-dione and (1,3-dioxo-1,3-dihydro-2H-isoindol-2-yl)acetyl chloride.

MS (APCI) MH$^+$: 276, 277 for $C_{14}H_{13}NO_5$
$^1$H NMR (CDCl$_3$) δ: 1.18-1.22 (t, 3H); 3.85 (s, 2H); 4.10-4.13 (q, 2H); 4.71 (s, 2H); 7.89-7.93 (brs, 4H).

Intermediate 26: 2-Chloro-6-(4-hydroxypiperidin-1-yl)isonicotinonitrile 2,6-Dichloroisoniconitrile (200 mg, 1.15 mmol) and 4-hydroxypiperidine (117 mg, 1.15 mmol) were dissolved in NMP (3 ml). TEA (160 μl, 1.15 mmol) was added. Using a Smith Microwave Synthesizer, the mixture was subjected to single-mode microwave at 150° C. for 20 minutes. The brown mixture was extracted with EtOAc and was washed with water (3×15 ml). The organic phase was dried over Na$_2$SO$_4$ and concentrated in vacuo. (250 mg).

MS (ES, M+H): 238 for $C_{11}H_{12}ClN_3O$

Intermediate 27: 3-Cyano-5-ethyl-1H-pyrrole-2-carboxylic acid methyl ester

3-Cyano-5-ethyl-1H-pyrrole-2-carboxylic acid (Intermediate 31) (500 mg) was dissolved in anhydrous THF (5 ml) and cooled to 0° C. (Trimethylsilyl)diazomethane/ether (2 ml) was added. The mixture was stirred at room temperature under nitrogen gas for 1 h. The solvent was removed in vacuo and MeOH was added. The mixture was stirred for a further 15 min, the solvent was removed in vacuo and the solid was dried under vacuum to give the title compound (580 mg).

MS (ES) MH$^+$: 177 for $C_9H_{10}N_2O_2$

Intermediate 28: 3-Cyano-5-methyl-1H-pyrrole-2-carboxylic acid methyl ester

The title compound was prepared by a procedure analogous to Intermediate 27 starting from 3-cyano-5-methyl-1H-pyrrole-2-carboxylic acid (Intermediate 32).

MS (ES) MH$^+$: 164 for $C_8H_8N_2O_2$

Intermediate 29: 5-Methyl-1H-pyrrole-2-carboxylic acid

The title compound was synthesized by an analogous method to Intermediate 18 starting from ethyl 5-methyl-1H-pyrrole-2-carboxylate (Intermediate 20).

MS (ES): 250 (MH) dimer for $C_6H_7NO_2$
$^1$H NMR δ: 2.24 (s, 3H); 5.92 (s, 1H); 6.68 (s, 1H); 11.55 (s, 1H); 12.05 (s, 1H)

Intermediate 30: 5-Ethyl-1H-pyrrole-3-carbonitrile

Iodoethane (3.99 g, 25.61 mmol) was added to a solution of 1-isocyanomethanesulfonyl-4-methyl-benzene (5 g, 25.61 mmol) in anhydrous THF (20 ml). The mixture was cooled to −78° C. and potassium tert-butoxide (31 ml of a 1 M solution in THF, 31 mmol) was added dropwise over 15 minutes. The mixture was warmed to room temperature over 1 h. Water (50 ml) was added and the solution was extracted with diethyl-ether and dried over Na$_2$SO$_4$ and evaporated to dryness. The resulting brown oily material was used without purification. The resulting 1-(1-Isocyano-propane-1-sulfonyl)-4-methylbenzene (4.29 g, 19.05 mmol) and acrylonitrile (1.26 ml, 19.05 mmol) were stirred in anhydrous THF (20 ml). The mixture was cooled to 0° C. and potassium tert-butoxide in THF (38.1 ml, 38.1 mmol) was added dropwise. The mixture was heated to reflux for 2 h then left at room temperature overnight, and then concentrated in vacuo. EtOAc (30 ml) was added to the brown solid and the mixture was stirred at room temperature for a few hours, filtered and the solid washed well with EtOAc. The EtOAc solution was concentrated in vacuo and purified by flash chromatography eluting with EtOAc/n-hexanes mixture: 3:2 to afford the title compound. (0.856 g).

MS (APCI, M+): 119, 121 for $C_7H_8N_2$
$^1$H NMR (CDCl$_3$) δ 1.43 (m, 3H); 2.79 (m, 2H); 6.24 (s, 1H); 7.35 (s, 1H); 8.91 (s, 1H).

Intermediate 31: 3-Cyano-5-ethyl-1H-pyrrole-2-carboxylic acid

Silver nitrate (1.41 g, 8.3 mmol) in water (100 ml) was added to a solution of 5-ethyl-2-formyl-1H-pyrrole-3-carbonitrile (Intermediate 58) (819 mg, 5.53 mmol) in 1 N sodium hydroxide (100 ml) in the dark. The mixture was heated at 100° C. in the dark for 1 h. The reaction mixture was cooled to room temperature and acidified with 65% aqueous nitric acid. The yellow/brown solution was extracted with EtOAc, dried over sodium sulfate and concentrated in vacuo to give the title compound (600 mg).

$^1$H NMR δ: 1.03 (m, 3H); 2.37 (m, 2H); 6.39 (d, 1H); 8.03 (brs, 1H); 12.45 (s, 1H).

Intermediate 32: 3-Cyano-5-methyl-1H-pyrrole-2-carboxylic acid

The title compound was prepared by a procedure analogous to Intermediate 31 starting from 5-methyl-2-formyl-1H-pyrrole-3-carbonitrile (preparation: *J. Med. Chem.* 1998, 41(6) 808-820).

$^1$H NMR δ: 2.26 (s, 3H); 6.46 (d, 1H); 12.58 (s, 1H); 13.47 (brs, 1H).

Intermediate 33: 4-Bromo-3-cyano-5-ethyl-1H-pyrrole-2-carboxylic acid

N-Bromosuccinimide (289 mg, 1.63 mmol) was added to a cooled solution of 3-cyano-5-ethyl-1H-pyrrole-2-carboxylic acid methyl ester (Intermediate 27; 290 mg, 1.63 mmol) in anhydrous DCM at 0° C. The mixture was stirred at 0° C. for 30 minutes. The mixture was poured into a cold solution of 2 N sodium hydroxide (15 ml) and extracted with DCM. The combined extracts were washed with water (2×15 ml), dried over sodium sulphate and concentrated in vacuo to give small amounts of title compound. The aqueous phase was acidified, extracted with EtOAc, concentrated in vacuo to give the title compound as a creamy brown solid (240 mg).

$^1$H NMR δ: 1.03 (m, 3H); 3.46 (m, 2H); 13.16 (s, 1H); 13.82 (brs, 1H).

Intermediate 34: 4-Bromo-3-cyano-5-methyl-1H-pyrrole-2-carboxylic acid

The title compound was prepared by a procedure analogous to Intermediate 33 starting from 3-cyano-5-methyl-1H-pyrrole-2-carboxylic acid methyl ester (Intermediate 28).

$^1$H NMR δ: 2.03 (m, 3H); 13.05 (s, 1H).

Intermediate 35: Ethyl 2-chloro-4-(1,3-dioxo-1,3-dihydro-2H-isoindol-2-yl)-3-oxobutanoate The title compound was prepared in a manner analogous to Intermediate 124 starting from ethyl 4-(1,3-dioxo-1,3-dihydro-2H-isoindol-2-yl)-3-oxobutanoate (Intermediate 25) and sulfuryl chloride.

MS (APCI) MH$^+$: 313 for $C_{14}H_{12}ClNO_5$ $^1$H NMR (CDCl$_3$) δ: 1.24-1.33 (t, 3H); 4.20-4.28 (q, 2H); 4.43 (q, 2H); 4.88 (s, 2H); 5.07 (s, 1H); 5.76 (s, 1H); 6.0 (s, 1H); 7.88-7.96 (brs, 6H).

Intermediate 36: Ethyl 2-(4-aminopiperidin-1-yl)-4-(methoxymethyl)-1,3-thiazole-5-carboxylate hydrochloride The title compound was prepared in a manner analogous to Intermediate 126 starting from tert-butyl [1-(aminocarbonothioyl)piperidin-4-yl]carbamate (Intermediate 125) and ethyl 2-chloro-4-methoxy-3-oxobutanoate (Intermediate 6).

MS (ES) (M+H): 300, 301 for $C_{13}H_{22}ClN_3O_3S$

Intermediate 37: 4-Bromo-5-isopropyl-1H-pyrrole-2-carboxylic acid

Intermediate 37 was synthesized by according to Elder, T et al. *Synth. Commun.* 1989, 19 (5&6) 763-767 and references therein; Kelly, T R et al. *Tetrahedron.* 1984, 40 (22) 4569.

Intermediate 38: tert-Butyl [1-(3-nitropyridin-2-yl)piperidin-4-yl]carbamate Anhydrous TEA (0.76 ml, 5.49 mmol) was added to piperidin-4-yl-carbamic acid tert-butyl ester (1 g, 5 mmol) and 2-chloro-3-nitro-pyridine (0.791 g, 5 mmol) in anhydrous NMP (3 ml). Using a Smith Microwave Synthesizer, the mixture was subjected to single-mode microwave at 150° C. for 10 minutes. The brown solution was partitioned between EtOAc and water and the organic phase was washed several times with water, dried over sodium sulphate and concentrated in vacuo to give the title compound as a yellow solid (1.35 g).

MS (ES): 323 (MH$^+$) for $C_{15}H_{22}N_4O_4$ $^1$H NMR δ: 1.37 (s, 9H); 1.48 (m, 2H); 1.96 (m, 2H); 3.18 (m, 2H); 3.7 (m, 1H); 3.86 (m, 2H); 7.05 (m, 2H); 8.33 (m, 2H)

Intermediate 39: 1-(3-Nitropyridin-2-yl)piperidin-4-amine hydrochloride salt A solution of 4 N hydrochloric acid in dioxane (10 ml) was added to tert-butyl [1-(3-nitropyridin-2-yl)piperidin-4-yl]carbamate (Intermediate 38; 1.3 g, 4.2 mmol). The mixture was stirred at room temperature for 1 h under nitrogen gas. The solvent was removed in vacuo to give the title compound as a yellow powder (500 mg).

MS (APCI): MH$^+$ 222 for $C_{11}H_{15}N_3O_2$ $^1$H NMR δ:1.76 (m, 2H); 2.10 (m, 2H); 3.18 (m, 2H); 3.82 (m, 12H); 3. 3.83 (m, 2H); 7.02 (m, 1H); 8.39 (m, 1H); 8.48 (m, 1H); 9.32 (b, 2H)

Intermediate 40: 2,6-Dichloro-N-(2-morpholin-4-yl-ethyl)-isonicotinamide

HATU (989 mg, 2.6 mmol), HOAT (354 mg, 2.6 mmol) and DIEA (907 μl, 5.21 mmol) were added to a stirred solution of 2,6-dichloroisonicotinic acid (500 mg, 2.60 mmol) in anhydrous DMA (4 ml). The mixture was stirred for 10 minutes after which 2-morpholin-4-yl-ethylamine (420 μl, 2.86 mmol) was added. The mixture was stirred at room temperature for 12 h and the mixture was partitioned between EtOAc and water. The EtOAc layer was washed well with water, dried over sodium sulphate and concentrated in vacuo to give the title compound as an oil (830 mg).

MS (ES) MH$^+$: 304

Intermediate 41: 2-(2,6-Dichloro-pyridin-4-ylsulfanyl)-N-methyl-acetamide 2,6-Dichloro-pyridin-4-ylamine (1 g, 6.13 mmol) in concentrated hydrochloric acid (5 ml) was cooled to 0° C. Sodium nitrite (465 mg, 6.75 mmol) in water (10 ml) was added slowly whilst keeping the temperature at less than 5° C. The mixture was stirred at low temperature for 20 minutes. N-Methylmercaptoacetamide (645 mg, 6.13 mmol) was added slowly, stirred at low temperature for 10 minutes and heated at 90° C. for 1 h. The yellow solution was cooled and extracted with EtOAc, washed with water, dried in vacuo and purified silica chromatography eluting with EtOAc/hexane mixture to give the title compound (855 mg).

$^1$H NMR δ: 2.55 (s, 3H); 3.94 (s, 2H); 7.55 (s, 2H)

Intermediate 42: tert-Butyl {1-[4-(aminocarbonyl)-6-cyanopyridin-2-yl]piperidin-4-yl}carbamate tert-Butyl {1-[4-(aminocarbonyl)-6-chloropyridin-2-yl]piperidin-4-yl}carbamate (Intermediate 16) (100 mg, 0.282 mmol), copper cyanide (101 mg, 1.13 mmol), Pd(dba) (103 mg, 0.11 mmol) and Dppf (250 mg, 0.45 mmol) were placed in anhydrous dioxane (5 ml) under argon. The mixture was heated at 100° C. for 5 h, then diluted with EtOAc (20 ml) and filtered through celite. The mixture was washed with sodium bicarbonate (2×20 ml), brine (20 ml), dried over sodium sulphate and concentrated in vacuo. The brown residue was purified by flash chromatography eluting with DCM and MeOH mixtures to give the title compound as a brown solid (61 mg).

MS (ES): 346 (MH$^+$) for $C_{17}H_{23}N_5O_3$ $^1$H NMR δ: 1.27 (m, 2H); 1.38 (s, 9H); 1.78 (m, 2H); 3.03 (m, 2H); 3.52 (m, 1H); 4.24 (m, 2H); 7.79 (s, 1H); 8.22 (s, 1H).

Intermediate 43: Thiophene-2-carboxylic-acid-2-chloro-pyridinyl-3-yl ester

TEA (1.2 ml, 8.49 mmol) was added to 2-chloro-3-pyridinol (1 g, 7.72 mmol) and 2-thiophenecarbonyl chloride (1.13 g, 7.72 mmol) in anhydrous toluene (10 ml). The mixture was heated at 100° C. for 25 minutes. The solvent was removed in vacuo and the mixture was partitioned between EtOAc and water, washed with water (×1), dried over sodium sulphate and dried in vacuo to give an oil which was triturated with n-hexanes to give the title compound as an off-white solid (1.85 g).

$^1$H NMR δ: 7.42 (m, 1H); 7.70 (m, 1H); 8.09 (m, 1H); 8.14 (m, 1H); 8.26 (m, 1H); 8.52 (m, 1H).

Intermediate 44: N-[6-Chloro-2-(methylthio)pyrimidin-4-yl]acetamide

Acetic anhydride (10.4 ml, 0.11 mol) was added to 6-chloro-2-(methylthio)pyrimidin-4-amine (2.5 g, 0.01 mol)

and the reaction mixture was refluxed at 135° C. for 5 hr. The reaction mixture was cooled to room temperature and basified to pH 7 with saturated sodium bicarbonate solution (20 ml). The mixture was partitioned between EtOAc and water, the organic layer was washed with water and brine, dried over $MgSO_4$ and concentrated to give the title compound (2.62 g).

MS (ES): 218 (MH$^+$) for $C_7H_8ClNO_3S$

Intermediate 45: tert-Butyl 1-[6-amino-2-(methylthio)pyrimidin-4-yl]piperidin-4-ylcarbamate TEA (0.243 ml, 1.74 mmol) and 6-chloro-2-(methylthio)pyrimidin-4-amine (0.309 g, 1.74 mmol) were added to a solution of tert-butyl piperidin-4-ylcarbamate (0.35 g, 1.74 mmol) in NMP (4 ml). Using a Smith Microwave Synthesizer, the mixture was subjected to single-mode microwave at 150° C. for 90 minutes. The mixture was partitioned between water and EtOAc and washed (×2) with water. The organic phase was dried over magnesium sulphate and concentrated to give the title compound (0.294 g).

MS (ES) (MH$^+$): 340 for $C_{16}H_{26}N_4O_2S$

Intermediate 46: 6-(4-Aminopiperidin-1-yl)-2-(methylthio)pyrimidin-4-amine hydrochloride 4 N Hydrogen chloride in dioxane (3 ml) was added to tert-butyl 1-[6-amino-2-(methylthio)pyrimidin-4-yl]piperidin-4-ylcarbamate (Intermediate 45, 0.29 mg 0.86 mmol). The mixture was stirred at room temperature for 90 minutes. The solvent was removed in vacuo to afford the title compound (238 mg).

MS (ES) (M$^+$): 240 for $C_{10}H_{17}N_5S$

Intermediate 47: 2,6-Dichloro-N-methoxy-N-methylisonicotinamide

HATU (1.97 g, 5.20 mmol), HOAT (707 mg, 5.20 mmol) and DIEA (1.77 ml, 10.5 mmol) were added to 2,6-dichloroisonicotinic acid (1 g, 5.20 mmol) in anhydrous DMF (5 ml). The mixture was stirred for 5 minutes, then N-methyl methoxylamine hydrochloride (507 mg, 5.20 mmol) was added in one portion followed by DIEA (800 µl, 5.2 mmol). The reaction was stirred for 30 minutes, then the crude product was partitioned between EtOAc (50 ml) and water (50 ml) and the organic level washed with water (3×50 ml). The organic phase was dried over sodium sulphate and concentrated in vacuo. The crude product was purified by flash chromatography eluting with EtOAc:n-hexanes (2:3) to afford the title compound (1.12 g).

MS (APCI, M+H): 235 for $C_8H_8Cl_2N_2O_2$
$^1$H NMR δ: 3.29 (s, 3H); 3.61 (s, 3H); 7.77 (s, 2H)

Intermediate 48: 1-(2,6-Dichloropyridin-4-yl)ethanone 2,6-Dichloro-N-methoxy-N-methylisonicotinamide (Intermediate 47, 780 mg, 3.3 mmol) in anhydrous diethylether (13 ml) was cooled to −78° C. Methyllithium (1.6 M solution in diethyl ether (5.2 ml, 8.3 mmol) was added dropwise. The mixture was stirred at −78° C. for 1 h and quenched with ammonium chloride solution, followed by warming to room temperature. The reaction mixture was diluted with water (20 ml) and extracted with diethyl ether (2×30 ml), dried over sodium sulphate and concentrated in vacuo to give the title compound (575 mg).

MS (APCI, M+H): 191 for $C_7H_5Cl_2O$
$^1$H NMR δ: 2.66 (s, 3H); 7.96 (s, 2H)

Intermediate 49: tert-Butyl 1-[6-chloro-4-(hydrazinocarbonyl)pyridin-2-yl]piperidin-4-ylcarbamate Hydrazine (0.55 ml 17.0 mmol) was added to a solution of methyl 2-{4-[(tert-butoxycarbonyl)amino]piperidin-1-yl}-6-chloroisonicotinate (Intermediate 23, 0.15 g, 0.40 mmol) in isopropanol (3 ml). The mixture was stirred at room temperature overnight then the isopropanol was removed in vacuo to give the title product (130 mg).

MS (ES, MH): 370,368 for $C_{17}H_{25}Cl_2N_4O_3$

Intermediate 50: tert-Butyl 1-[6-chloro-4-(5-oxo-2,5-dihydro-1,3,4-oxadiazol-2-yl)pyridin-2-yl]piperidin-4-ylcarbamate N,N'-Carbonyldiimidazole (0.12 g, 0.82 mmol) was added to a solution of tert-butyl 1-[6-chloro-4-(hydrazinocarbonyl)pyridin-2-yl]piperidin-4-ylcarbamate (Intermediate 49, 0.15 g, 0.41 mmol) in DMF (3 ml). The mixture was stirred at room temperature overnight and was purified by semi-preparative HPLC eluting with $CH_3CN/H_2O$ (0.1% TFA) mixtures to afford the title compound (0.125 g).

MS (ES, MH): 396,394 for $C_{18}H_{23}ClN_4O_4$

Intermediate 51: 5-[2-(4-Aminopiperidin-1-yl)-6-chloropyridin-4-yl]-1,3,4-oxadiazol-2(5H)-one hydrochloride 4 N Hydrochloric acid in dioxane (3 ml) was added to tert-butyl 1-[6-chloro-4-(5-oxo-2,5-dihydro-1,3,4-oxadiazol-2-yl)pyridin-2-yl]piperidin-4-ylcarbamate (Intermediate 50, 0.12 mg, 0.32 mmol). The mixture was stirred at room temperature for 45 min, then concentrated in vacuo to afford the title compound (100 mg).

MS (ES, MH): 296,294 for $C_{13}H_{15}ClN_4O_2$

Intermediate 52: tert-Butyl 4-{[(4-bromo-5-methyl-1H-pyrrol-2-yl)carbonyl]amino}piperidine-1-carboxylate Title compound was synthesized by an analogous method to Intermediate 2, starting from 4-bromo-5-methyl-1H-pyrrole-2-carboxylic acid (Intermediate 18).

MS (ESP): 386.1 (M+H) for $C_{16}H_{24}BrN_3O_3$
$^1$H NMR δ: 1.34 (m, 2H); 1.41 (s, 9H); 1.74 (d, 2H); 2.13 (s, 3H); 2.84 (m, 2H); 3.92 (m, 3H); 6.81 (s, 1H); 7.75 (d, 1H); 11.67 (s, 1H).

Intermediate 53: tert-Butyl 1-(6-chloro-4-cyanopyridin-2-yl)piperidin-4-ylcarbamate TEA (0.20 ml, 1.44 mmol) and 2,6-dichloroisonicotinonitrile (0.25 g, 1.44 mmol) were added to a solution of tert-butyl piperidin-4-ylcarbamate (0.28 g, 1.44 mmol) in NMP (2 ml). Using a Smith Microwave Synthesizer, the mixture was subjected to single-mode microwave at 150° C. for 10 minutes. The crude mixture was partitioned between water and EtOAc and washed (×2) with water. The extracts were combined dried over $MgSO_4$ and concentrated to give the title compound (400 mg).

MS (ES): 337 (MH$^+$) for $C_{17}H_{22}ClN_3O_2$

Intermediate 54: tert-Butyl 1-{4-[amino(hydroxy-imino)methyl]-6-chloropyridin-2-yl}piperidin-4-ylcarbamate TEA (0.24 ml, 1.78 mmol) was added to a solution of tert-butyl 1-(6-chloro-4-cyanopyridin-2-yl)piperidin-4-ylcarbamate (Intermediate 53, 0.4 g, 1.19 mmol) in MeOH (2 ml), followed by the addition of hydroxylamine hydrochloride (0.82 g, 1.19 mmol). The mixture was refluxed for 4 h, then the solvent was removed in vacuo to give the desired product. (410 mg).
MS (ES): 370 (MH$^+$) for $C_{17}H_{25}ClN_4O_3$

Intermediate 55: tert-Butyl 1-[6-chloro-4-(1,2,4-oxadiazol-3-yl)pyridin-2-yl]piperidin-4-ylcarbamate Boron trifluoroetherate (0.1 ml) was added to a solution of tert-butyl 1-{4-[amino (hydroxyimino)methyl]-6-chloropyridin-2-yl}piperidin-4-ylcarbamate (Intermediate 54) (0.254 g, 0.69 mmol) in 1,1,1-triethoxyethane (1.5 ml) at room temperature. The mixture was refluxed for 10 minutes. The mixture was purified by flash chromatography on silica gel eluting with (n-hexanes:EtOAc; 70:30) to afford the title compound (50 mg).
MS (ES): 380 (MH$^+$) for $C_{18}H_{23}ClN_4O_3$

Intermediate 56: 1-[6-Chloro-4-(1,2,4-oxadiazol-3-yl)pyridin-2-yl]piperidin-4-amine hydrochloride Tert-butyl 1-[6-chloro-4-(1,2,4-oxadiazol-3-yl)pyridin-2-yl]piperidin-4-ylcarbamate (Intermediate 55) (50 mg 0.13 mmol) was dissolved in 4 N HCl in dioxane (2 ml). The mixture was stirred at room temperature for 2 h. The solvent was concentrated in vacuo to afford the crude title compound which was used without further purification. (74 mg).
MS (ES): 280 (MH$^+$) for $C_{13}H_{15}ClN_4O$

Intermediate 57: 4-Bromo-5-methyl-N-piperidin-4-yl-1H-pyrrole-2-carboxamide hydrochloride Title compound was synthesized by an analogous method to Intermediate 1, starting from tert-butyl 4-{[(4-bromo-5-methyl-1H-pyrrol-2-yl)carbonyl]amino}piperidine-1-carboxylate (Intermediate 52).
MS (ESP): 286.1 (M+H) for $C_{11}H_{16}BrN_3O$
$^1$H NMR δ: 1.36 (m, 2H); 1.74 (d, 2H); 2.13 (s, 3H); 2.83 (m, 2H); 3.85-4.05 (m, 3H); 6.81 (s, 1H); 7.75 (d, 1H); 11.66 (s, 1H).

Intermediate 58: 5-Ethyl-2-formyl-1H-pyrrole-3-carbonitrile

POCl$_3$ (3.3 ml, 35.67 mmol) was added to 1,2-dichloroethane (4 ml), then anhydrous DMF (2.75 ml, 35.67 mmol) was added very slowly. The mixture was stirred at room temperature for ~10 minutes. 5-Ethyl-1H-pyrrole-3-carbonitrile (Intermediate 30, 856 mg, 7.13 mmol) in 1,2-dichloroethane (2 ml) was added dropwise and the mixture was heated at 80° C. for ~30 minutes. The mixture was cooled to room temperature and sodium acetate (2.5 g/5 ml) was added and the mixture was stirred for 1 h. The brown/black emulsion was extracted with DCM (4×50 ml). The combined organic phase was washed with water (2×50 ml) dried over Na$_2$SO$_4$ and concentrated in vacuo to give the title compound. (819 mg).
$^1$H NMR (CDCl$_3$) δ: 1.52 (m, 3H); 2.81 (m, 2H); 6.46 (s, 1H); 9.65 (s, 1H); 9.96 (s, 1H).

Intermediate 59: Ethyl 4,5-dichloro-1H-pyrrole-2-carboxylate

The title compound was prepared in a manner analogous to Intermediate 20 starting from 2,2,2-trichloro-1-(4,5-dichloro-1H-pyrrol-2-yl)ethanone (Intermediate 60).
MS (ES): MH$^-$ 207, 209 for $C_7H_7Cl_2NO_2$

Intermediate 60: 2,2,2-Trichloro-1-(4,5-dichloro-1H-pyrrol-2-yl)ethanone

A solution of sulfuryl chloride (11.3 ml, 0.14 mol) in ether (5 ml) at 0° C. was added to a solution of 2,2,2-trichloro-1-(1H-pyrrol-2-yl)ethanone (15.0 g, 0.07 mol) in diethyl ether (10 ml). The mixture was left to stir at room temperature overnight. The solvent was removed under vacuum. The crude mixture was partitioned between ether and 10% aqueous K$_2$CO$_3$. The organic phase was concentrated in vacuo and was purified by flash chromatography on silica eluting gradient (2-5% EtOAc in hexane) to give the title compound (17.0 g).
$^1$H NMR (500 MHz, CDCl$_3$) δ:: 7.42 (d, 1H); 13.85 (s, 1H)

Intermediate 61: 4,5-Dichloro-1H-pyrrole-2-carboxylic acid

A solution of lithium hydroxide in water (2 N, 0.80 ml, 0.16 mol) was added to a stirred solution of a mixture of ethyl 4,5-dichloro-1H-pyrrole-2-carboxylate (Intermediate 59; 7.0 g, 0.033 mol) in THF (15 ml) at room temperature. The mixture was stirred at 50° C. for 8 h over 2 days. The reaction mixture was acidified with 10% HCl solution to a pH ~2 and partitioned between EtOAc and water. The organic layer was dried over MgSO$_4$ and concentrated in vacuo to give the title compound (4.0 g).
MS (ES): MH$^-$ 178 for $C_5H_3Cl_2NO_2$
$^1$H NMR (500 MHz) δ:: 7.06 (s, 1H); 12.43 (s, 1H); 13.43 (s, 1H)

Intermediate 62: 2-Chloro-6-(4-hydroxypiperidin-1-yl)isonicotinamide

The title compound was prepared in a manner analogous to Intermediate 26 starting from 2,6-dichloroisonicotinamide and 4-hydroxypiperidine (both commercially available).
MS (LCMS): 255

Intermediate 63: 2-Chloro-6-[4-(methylamino)piperidin-1-yl]isonicotinonitrile 2,6-Dichloroisoniconitrile (1.28 g, 7.38 mmol) and DIEA (3.85 ml) were added to piperidin-4-one (1 g, 7.38 mmol) in anhydrous DMA (8 ml) was added. Using a Smith Microwave Synthesizer, the mixture was subjected to single-mode microwave at 150° C. for 20 minutes in two batches. The batches were combined and diluted with EtOAc (100 ml) and washed with water (3×50 ml). The organic phase was dried over Na$_2$SO$_4$ and concentrated in vacuo to give a brown solid corresponding [LCMS indicated the expected mass (236)] to 2-chloro-6-(4-oxopiperidin-1-yl)isonicotinonitrile (1.58 g).

Methylamine (2.65 ml, 5.3 mmol) was added to a solution of 2-chloro-6-(4-oxopiperidin-1-yl)isonicotinonitrile (Intermediate 26; 500 mg, 2.12 mmol) in anhydrous THF (4 ml). The mixture was stirred for 30 minutes and sodium triacetoxyborohydride (674 mg, 3.18 mmol) was added. The mixture was stirred at room temperature for 18 h, then concentrated in vacuo, diluted with EtOAc and washed with 1 N NaOH, water and brine. The organic phase was dried over Na$_2$SO$_4$ then concentrated in vacuo to give a brown oil which was dried under vacuum to yield the title compound (507 mg).

MS (ES): 251 for C$_{12}$H$_{15}$ClN$_4$ $^1$H NMR δ: 1.21 (m, 2H); 1.90 (m, 2H); 2.32 (s, 3H); 2.61 (m, 1H); 3.12 (m, 2H); 4.14 (m, 2H); 7.10 (s, 1H); 7.39 (s, 1H)

Intermediate 64: 1-[6-Chloro-4-(1H-tetrazol-5-yl) pyridin-2-yl]-N-methylpiperidin-4-amine Sodium azide (131 mg, 2.02 mmol) and NH$_4$Cl (108 mg, 2.02 mmol) were added to a solution of 2-chloro-6-[4-(methylamino)piperidin-1-yl]isonicotinonitrile (Intermediate 63, 507 mg, 2.02 mmol) in anhydrous DMF (3 ml). The mixture was heated at 120° C. under nitrogen gas for 1 h where LCMS showed the expected mass. The mixture was filtered and was purified by semi-preparative HPLC eluting with acetonitrile/water (0.1% TFA) and the title compound was concentrated in vacuo to give a hygroscopic brown solid (220 mg).

MS (ES): (MH$^+$)294 for C$_{12}$H$_{16}$ClN$_7$

Intermediate 65: 1-[6-Chloro-4-(1-methyl-1H-tetrazol-5-yl)pyridin-2-yl]-N-methylpiperidin-4-amine Sodium azide (225 mg, 3.47 mmol) and ammonium chloride (186 mg, 3.47 mmol) were added to a solution of 2,6-dichloroisonicotinile (500 mg, 2.89 mmol) in anhydrous DMF (3 ml). The mixture was heated at 120° C. under nitrogen gas for 1 h. The mixture was cooled to room temperature and K$_2$CO$_3$ (798 mg, 5.78 mmol) was added. The resulting mixture was stirred for 30 minutes after which iodomethane (270 µl, 4.33 mmol) was added. The mixture was stirred at room temperature for 18 h, diluted with EtOAc and washed with water and brine. The organic phase was dried over Na$_2$SO$_4$ and concentrated in vacuo to give a brown solid 2,6-dichloro-4-(2-methyl-2H-tetrazol-5-yl)-pyridine (486 mg).

tert-Butyl piperidin-4-ylcarbamate (87 mg, 0.44 mmol) and DIEA (76 µl, 0.44 mmol) were added to a solution of 2,6-dichloro-4-(2-methyl-2H-tetrazol-5-yl)-pyridine (100 mg, 0.44 mmol) in anhydrous NMP (2 ml). Using a Smith Microwave Synthesizer, the mixture was subjected to single-mode microwave at 150° C. for 15 minutes, diluted with EtOAc (25 ml) and washed with water (4×25 ml). The organic phase was dried over Na$_2$SO$_4$ and concentrated in vacuo to give a brown solid. This sample was treated with 4 N HCl/dioxane (8 ml) for 45 minutes. The solvent was removed under reduced pressure and the material was dried in vacuo.

MS (ES): MH$^+$294, for C$_{12}$H$_{16}$ClN$_7$O

Intermediate 66: tert-Butyl [1-(6-chloropyridin-2-yl)piperidin-4-yl]carbamate

TEA (0.13 ml, 0.99 mmol) and 2,6-dichloropyridine (0.14 g, 0.99 mmol) were added to a solution of tert-butyl piperidin-4-ylcarbamate (0.20 g, 0.99 mmol) in NMP (2 ml) at room temperature. Using a Smith Microwave Synthesizer, the mixture was subjected to single-mode microwave at 150° C. for 30 minutes. The mixture was diluted with EtOAc and washed with water three times. The organic phase was dried over magnesium sulfate and concentrated to give the title compound. (300 mg).

MS (ES): 337 (MH$^+$) for C$_{17}$H$_{22}$ClN$_3$O$_2$

Intermediate 67: 2-Bromo-5-(ethylthio)-1,3,4-thiadiazole tert-Butyl nitrite (2.20 ml, 1.91 g, 18.50 mmol) was added dropwise to a mixture of copper (11) bromide (3.32 g, 14.86 mmol) in acetonitrile (30 ml). A solution of 5-(ethylthio)-1,3,4-thiadiazol-2 amine (2.00 g, 12.40 mmol) in acetonitrile (66 ml) was added and the mixture was heated at 65° C. After approximately three hours, the mixture was cooled, diluted with water, and extracted with ether. The organic phase was dried (MgSO$_4$), and concentrated under vacuum. The crude material was purified by flash chromatography using 10% EtOAc/hexanes to give 2.15 g of the title product.

MS (ESP): 226 (MH$^+$) for C$_4$H$_5$BrN$_2$S$_2$

Intermediate 68: tert-Butyl {1-[6-(acetylamino)-2-(methylthio)pyrimidin-4-yl]piperidin-4-yl}carbamate TEA (0.32 ml, 2.28 mmol) and N-[6-chloro-2-(methylthio)pyrimidin-4-yl]acetamide (Intermediate 44, 0.50 g, 2.28 mmol) were added to a solution of tert-butyl piperidin-4-ylcarbamate (0.46 g, 2.28 mmol) in NMP (2 ml) at room temperature. Using a Smith Microwave Synthesizer, the mixture was subjected to single-mode microwave at 150° C. for 10 minutes. The mixture was partitioned between water and EtOAc. The layers were separated and the organic layer was washed with water two more times. The organic phase was dried over magnesium sulfate and concentrated to give the title compound (816 mg).

MS (ES): 381 (MH$^+$) for C$_{18}$H$_{28}$N$_4$O$_3$S

Intermediate 69: N-[6-(4-Aminopiperidin-1-yl)-2-(methylthio)pyrimidin-4-yl]cetamide hydrochloride tert-Butyl {1-[6-(acetylamino)-2-(methylthio)pyrimidin-4-yl]piperidin-4-yl}carbamate (Intermediate 68) (816 mg, 2.15 mmol) was dissolved in 4 N HCl/Dioxane (10 ml). The mixture was stirred at room temperature for 2 h. Excess 4 N HCl/Dioxane was removed by concentrating under vacuo to give the title compound as a bright yellow colored solid. (790 mg).

MS (ES): 281 (MH$^+$) for C$_{13}$H$_{20}$N$_4$OS

Intermediate 70: 2-(4-Aminopiperidin-1-yl)-6-chloroisonicotinamide hydrochloride salt 4 N HCl/Dioxane solution (6 ml) was added to tert-butyl 1-[4-(aminocarbonyl)-6-chloropyridin-2-yl]piperidin-4-ylcarbamate (Intermediate 16, 100 mg, 0.282 mmol). The mixture was stirred at room temperature for 90 minutes. The solvent was removed in vacuo and the anhydrous diethylether (25 ml) was added. The solvent was removed in vacuo and light yellow solid that resulted was dried under vacuum for several hours to give the title compound as an off-white solid (87 mg).

MS (ES): 255 for C$_{11}$H$_{15}$ClN$_4$O $^1$H NMR δ: 1.56 (m, 2H); 2.08 (m, 2H); 2.35 (m, 2H); 3.27 (m, 1H); 4.35 (m, 2H); 7.00 (s, 1H); 7.21 (s, 1H); 7.68 (s, 1H); 7.90 (s, 1H); 8.20 (b, 3H).

Intermediate 71: 4-Chloro-5-ethyl-1H-pyrrole-2-carboxylic acid

Title compound was synthesized from ethyl 4-chloro-5-ethyl-1H-pyrrole-2-carboxylate (Intermediate 72) by an analogous method to Intermediate 8.

MS (ESP): 172.1 (M–H) for $C_7H_8ClNO_2$

Intermediate 72: Ethyl 4-chloro-5-ethyl-1H-pyrrole-2-carboxylate

Title compound was synthesized from ethyl 5-ethyl-1H-pyrrole-2-carboxylate (Intermediate 12) by an analogous method to Intermediate 9.

MS (ESP): 200.1 (M–H) for $C_9H_{12}ClNO_2$

Intermediate 73: 3,4-Dichloro-5-ethyl-1H-pyrrole-2-carboxylic acid

Title compound was synthesized from ethyl 3,4-dichloro-5-ethyl-1H-pyrrole-2-carboxylate (Intermediate 74) by an analogous method to Intermediate 8.

MS (ESP): 208.1 (M+H) for $C_7H_7Cl_2NO_2$

Intermediate 74: Ethyl 3,4-dichloro-5-ethyl-1H-pyrrole-2-carboxylate

Title compound was synthesized from ethyl 5-ethyl-1H-pyrrole-2-carboxylate (Intermediate 12) by an analogous method to Intermediate 4.

MS (ESP): 234.1 (M–H) for $C_9H_{11}Cl_2NO_2$

Intermediate 75: 4-Chloro-3,5-dimethyl-1H-pyrrole-2-carboxylic acid

Title compound was synthesized from ethyl 4-chloro-3,5-dimethyl-1H-pyrrole-2-carboxylate (Intermediate 76) by an analogous method to Intermediate 8.

MS (ESP): 172 (M–H) for $C_7H_8ClNO_2$

Intermediate 76: Ethyl 4-chloro-3,5-dimethyl-1H-pyrrole-2-carboxylate

Title compound was synthesized from ethyl 3,5-dimethyl-1H-pyrrole-2-carboxylate (commercially available) by an analogous method to Intermediate 9.

MS (ESP): 200 (M–H) for $C_9H_{12}ClNO_2$

Intermediate 77: Ethyl 2-(4-aminopiperidin-1-yl)-4-[(1,3-dioxo-1,3-dihydro-2H-isoindol-2-yl)methyl]-1,3-thiazole-5-carboxylate hydrochloride The title compound was prepared in a manner analogous to Intermediate 126 starting from tert-butyl [1-(aminocarbonothioyl)piperidin-4-yl]carbamate (Intermediate 125) and ethyl 2-chloro-4-(1,3-dioxo-1,3-dihydro-2H-isoindol-2-yl)-3-oxobutanoate (Intermediate 35).

MS (ES) (M+H)$^+$: 416 for $C_{20}H_{23}ClN_4O_4S$

Intermediates 78-80

The following compounds were prepared in a manner analogous to Intermediate 126 starting from tert-butyl [1-(aminocarbonothioyl)piperidin-4-yl]carbamate (Intermediate 125) and the starting materials listed.

| Intermediate | Compound | M/Z | SM |
| --- | --- | --- | --- |
| Intermediate 78 | Ethyl 2-(4-aminopiperidin-1-yl)-4-(trifluoromethyl)-1,3-thiazole-5-carboxylate hydrochloride salt | 323 | Ethyl 2-chloro-4,4,4-trifluoro-3-oxobutanoate (commercially available) |
| Intermediate 79 | Ethyl 2-(4-aminopiperidin-1-yl)-4-(methoxymethyl)-1,3-thiazole-5-carboxylate hydrochloride | 300, 301 | Ethyl 2-chloro-4-methoxy-3-oxobutanoate (Intermediate 6) |
| Intermediate 80 | Ethyl 2-(4-aminopiperidin-1-yl)-4-butyl-1,3-thiazole-5-carboxylate hydrochloride salt | 311 | Ethyl 2-bromo-3-oxoheptanoate (Intermediate 85) |

Intermediate 81: 2-(4-Aminopiperidin-1-yl)-1,3-thiazole-5-carboxamide hydrochloride Title compound was synthesized from tert-butyl 1-[5-(aminocarbonyl)-1,3-thiazol-2-yl]piperidin-4-ylcarbamate (Intermediate 82) by an analogous method to Intermediate 1.

MS (ESP): 227 (M+H) for $C_9H_{14}N_4OS$

Intermediate 82: tert-Butyl 1-[5-(aminocarbonyl)-1,3-thiazol-2-yl]piperidin-4-ylcarbamate Title compound was synthesized by an analogous method to Intermediate 38 by coupling tert-butyl piperidin-4-ylcarbamate (commercially available) with 2-bromo-1,3-thiazole-5-carboxamide (J. Am. Chem. Soc. 1952, 74, 5799).

MS (ESP): 327 (M+H) for $C_{14}H_2N_4O_3S$

Intermediate 83: Methyl 2-chloro-6-(methylthio)isonicotinate

Methyl 2,6-dichloroisonicotinate (300 mg, 1.45 mmol) was dissolved in anhydrous DMF. Sodium thiomethoxide (102 mg, 1.45 mmol) was added and the mixture was stirred at room temperature for 4 h. The mixture was diluted with EtOAc and washed with water (×3), brine (×1) and dried over sodium sulfate and concentrated in vacuo to afford title compound (294 mg).

MS (ES) (M+H): 218 for $C_8H_8ClNO_2S$ $^1$H NMR δ: 2.73 (s, 3H); 4.04 (t, 3H); 7.64 (s, 1H); 7.79 (s, 1H)

Intermediate 84: Methyl 2-chloro-6-(methylsulfinyl)isonicotinate

Methyl 2-chloro-6-(methylthio)isonicotinate (Intermediate 83; 290 mg), was dissolved in anhydrous DCM (5 ml).

mCPBA (345 mg) was added and the mixture was stirred at room temperature for 90 minutes. The mixture was diluted with EtOAc and washed with water, 10% sodium thiosulfate, water, brine and dried over sodium sulfate. The mixture was concentrated in vacuo and purified by flash chromatography eluting with EtOAc:Hexane (7:3) to afford the title compound (129 mg).

MS (ES) (M+H): 224 for $C_8H_8ClNO_3S$ $^1$H NMR δ: 2.97 (s, 3H); 4.04 (s, 3H); 8.06 (s, 1H); 8.29 (s, 1H)

Intermediate 85: Ethyl 2-bromo-3-oxoheptanoate

Ethyl 3-oxoheptanoate (Intermediate 94; 5 g, 29.03 mmol) was dissolved in anh.$CH_3CN$ (75 ml) and cooled to 0° C. $CuBr_2$ was added, followed by addition of (hydroxy(tosyloxy) iodo)benzene (Koser's reagent). The mixture was warmed to room temperature over 1 h, after which the reaction was quenched with water (100 ml). The blue solution was extracted with DCM and combined organic phase was washed well with water, brine and dried over $Na_2SO_4$ and concentrated in vacuo. The crude material was purified by flash chromatography eluting with a gradient of 10%-50% Hexane/EtOAc, followed by Kugelrohr distillation affording the title compound (3.5 g).

$^1$H NMR δ: 0.75-0.93 (m, 3H); 1.13-1.25 (m, 5H); 1.38-1.64 (m, 2H); 2.43-2.50 (m, 2H); 3.5-3.69 (s, 2H); 5.54 (s, 1H).

Intermediate 86: 4-{[(3,4-Dichloro-5-methyl-1H-pyrrol-2-yl)carbonyl]amino}piperidinium trifluoroacetate To a solution of tert-butyl 4-{[(3,4-dichloro-5-methyl-1H-pyrrol-2-yl)carbonyl]amino}piperidine-1-carboxylate (Intermediate 2, 2.9 g, 7.7 mmol) in 15 ml DCM was added 15 ml TFA. The solution was stirred at room temperature for 30 minutes before evaporating off solvent under reduced pressure. Solid dark product was obtained in quantitative yield.

$^1$H NMR δ: 1.61-1.76 (m, 2H); 1.91-2.03 (m, 2H); 2.18 (s, 3H); 2.96-3.10 (m, 2H); 3.30 (m, 2H); 4.01 (m, 1H); 11.98 (s, 1H).

Intermediate 87: 3,4-Dichloro-5-methyl-N-(1-nitrosopiperidin-4-yl)-1H-pyrrole-2-carboxamide A solution of $NaNO_2$ (1.7 g, 24.6 mmol) in 20 ml of water was added to a solution of 4-{[(3,4-dichloro-5-methyl-1H-pyrrol-2-yl)carbonyl]amino}piperidinium trifluoroacetate (Intermediate 86; 4 g, 10.3 mmol) and 400 µl acetic acid in 60 ml of 1:1 EtOH—$H_2O$. The mixture was heated to 90° C. for 1 hour. After cooling to room temperature, 200 ml of water was added. White solids were collected by filtration and dried in vacuo (2.8 g).

MS (APCI): 305 (M+H)$^+$ for $C_{11}H_{14}Cl_2N_4O_2$ $^1$H NMR δ: 1.31-1.54 (m, 1H); 1.63-1.80 (m, 1H); 1.80-1.98 (m, 1H); 1.96-2.16 (m, 1H); 2.18 (s, 3H); 2.85-3.16 (m, 1H); 3.76-4.05 (m, 1H); 4.07-4.33 (m, 1H); 4.49-4.81 (m, 2H); 7.33 (d, J=7.72 Hz, 1H); 12.00 (s, 1H).

Intermediate 88: Methyl 2-chloro-6-methoxypyrimidine-4-carboxylate

A 0.5 M solution of sodium methoxide in MeOH was added slowly to a solution of methyl 2,6-dichloropyrimidine-4-carboxylate (0.30 g, 1.45 mmol) in MeOH (2 ml). A white precipitate formed which was stirred for further 15 minutes. The product was collected by filtration (0.20 g).

MS (ES) MH$^+$: 203 for $C_7H_7ClN_2O_3$ $^1$H NMR δ: 3.90 (s, 3H); 4.01 (s, 3H); 7.44 (s, 1H)

Intermediate 89: N-(1-Aminopiperidin-4-yl)-3,4-dichloro-5-methyl-1H-pyrrole-2-carboxamide A 20% solution of $TiCl_3$ (36 ml, 27 mmol) in water was added to a solution of 3,4-dichloro-5-methyl-N-(1-nitrosopiperidin-4-yl)-1H-pyrrole-2-carboxamide (Intermediate 87, 2.8 g, 9.2 mmol) in 60 ml of MeOH. The mixture was heated to 70° C. for 1 hour. Aqueous $Na_2CO_3$ was added to basify the mixture, which was filtered through Celite rinsing through with MeOH until no more material eluted. The filtrate was concentrated and the residual aqueous solution was saturated with NaCl before being extracted 6 times with DCM. The combined organic layers were dried ($MgSO_4$) and solvent was removed to give product as a beige solid.

MS (ES): 291 (M+H)$^+$.

$^1$H NMR δ: 1.43-1.70 (m, 2H); 1.76 (s, 2H); 2.03-2.36 (m, 5H); 2.83 (s, 2H); 3.18-3.54 (m, 2H); 3.68 (s, 1H); 7.11 (d, J=7.54 Hz, 1H); 11.95 (s, 1H).

Intermediate 90: 3,4-Dichloro-5-methyl-N-piperidin-4-yl-1H-pyrrole-2-carboxamide 4-{[(3,4-dichloro-5-methyl-1H-pyrrol-2-yl)carbonyl]amino}piperidinium trifluoroacetate (Intermediate 86, 6.07 g) was suspended in water (100 ml). To this was added 100 ml of $CHCl_3$:isopropanol (3:1) and sat. $Na_2CO_3$ (50 ml). The organic portion was separated and the aqueous portion was washed with 100 ml portions of $CHCl_3$:isopropanol (3:1) five times. The organic portions were combined, dried with $MgSO_4$ and concentrated to a yellow solid (2.73 g, 64%).

$^1$H NMR δ: 1.22-1.53 (m, 2H); 1.76 (dd, J=12.34, 3.11 Hz, 2H); 2.17 (s, 3H); 2.50-2.62 (m, 2H); 2.81-3.02 (m, 2H); 3.62-3.97 (m, 1H); 7.11 (d, J=7.72 Hz, 1H).

Intermediate 91: Methyl N-cyano-4-{[(3,4-dichloro-5-methyl-1H-pyrrol-2-yl)carbonyl]amino}piperidine-1-carbimidothioate A solution of 3,4-dichloro-5-methyl-N-piperidin-4-yl-1H-pyrrole-2-carboxamide (Intermediate 90, 2.73 g, 10 mmol) and dimethyl cyanodithioimidocarbonate (1.61 g, 10 mmol) in dichloroethane was heated to reflux for 5 hours. The reaction mixture was concentrated to an orange oil which was purified by flash chromatography on silica gel (gradient elution from 100% DCM to 5% MeOH in DCM). Pure fractions were combined to yield the title compound in 2.25 g (61%).

MS (ES): 374 (M+H)$^+$ $^1$H NMR δ: 1.53-1.67 (m, 2H); 1.93 (dd, J=13.56, 3.01 Hz, 2H); 2.18 (s, 3H); 2.67-2.75 (m, 3H); 3.31-3.44 (m, 2H); 4.03-4.16 (m, 1H); 4.33 (d, J=113.75 Hz, 2H); 7.32 (d, J=7.72 Hz, 1H); 12.06 (s, 1H).

Intermediate 92: 2,6-Dioxo-1,2,3,6-tetrahydropyrimidine-4-carbaldehyde monohydrate The title compound (9.53 g) was prepared according to the procedure of Johnson et al (Johnson, Treat B.; Schroeder, Elmer F. *J. Am. Chem. Soc.* 1931, 53, 1989-1994).

$^1$H NMR δ: 6.75 (brs, 2H); 9.60 (s, 1H); 10.61 (s, 1H); 10.99 (s, 1H)

Intermediate 93: Methyl 2-(4-aminopiperidin-1-yl)-6-chloroisonicotinate hydrochloride salt Methyl 2-{4-[(tert-butoxycarbonyl)amino]piperidin-1-yl}-6-chloroisonicotinate (Intermediate 23, 1.81 g, 4.9 mmol) was dissolved in 4 N HCl/dioxane (200 ml). The mixture was stirred at room temperature for 2 h. The solvent was removed under vacuum to give the title compound (1.5 g).

MS (LCMS): 269

Intermediate 94: Ethyl 3-oxoheptanoate

The title compound was prepared in a manner analogous to Intermediate 123 from valeryl chloride and 2,2-dimethyl-1,3-dioxane-4,6-dione (both commercially available).

$^1$H NMR δ: 0.7-0.96 (m, 3H); 1.06-1.31 (m, 5H); 1.36-1.58 (m, 2H); 2.43-2.50 (m, 2H); 3.5-3.69 (s, 2H); 3.99-4.22 (m, 2H).

Intermediate 95: N-[1-(Aminocarbonothioyl)piperidin-4-yl]-3,4-dichloro-5-methyl-1H-pyrrole-2-carboxamide The title compound was prepared by a procedure analogous to Intermediate 125 starting from 3,4-dichloro-5-methyl-N-piperidin-4-yl-1H-pyrrole-2-carboxamide (Intermediate 90, 0.5 g, 2 mmol). The product was concentrated to a solid which was purified on a silica flash column (gradient elution from 0-5% MeOH in DCM over 30 min). Purification yielded a white solid (0.22 g).

$^1$H NMR δ: 1.41-1.56 (m, 2H); 1.80 (dd, J=12.81, 3.20 Hz, 2H); 2.17 (s, 3H); 3.08-3.22 (m, 2H); 3.96-4.11 (m, 1H); 4.43 (d, J=15.07 Hz, 2H); 7.27 (d, J=7.72 Hz, 1H); 7.32-7.47 (m, 2H); 11.96 (s, 1H).

Intermediate 96: Methyl 2-chloro-6-(ethylthio)pyrimidine-4-carboxylate

A solution of ethanethiol (0.30 g, 4.8 mmol) in THF (1 ml) was added dropwise to a solution of methyl 2,6-dichloropyrimidine-4-carboxylate (1 g, 4.8 mmol), THF (8 ml) and TEA (0.49 g, 4.8 mmol) at 0° C. under nitrogen. The mixture was stirred for 2 h and slowly warmed to room temperature. The mixture was diluted with EtOAc (50 ml) and water (10 ml). The organic layer was separated, dried over sodium sulfate, filtered and concentrated in vacuo to afford the title compound (1.1 g).

MS (ESP): 431 (M+H) for $C_8H_9ClN_2O_2S$ $^1$H NMR δ: 1.38 (t, 3H); 3.29 (q, 2H); 3.96 (s, 3H); 7.97 (s, 1H).

Intermediate 97: 4-Chloro-2-butyl-6-methylpyrimidine

Using the procedure of Papet, Anne-Lure et. al., (Synthesis 1993 (5), 478-481) the title compound (1.28 g) was prepared from 2-butyl-6-methylpyrimidin-4-ol (Intermediate 98, 4 g, 32.85 mmol).

MS (ES) (M+H): 184 for $C_9H_{13}ClN_2$ $^1$H NMR δ: 1.10 (m, 3H); 1.57 (m, 2H); 1.80 (m, 2H); 2.37 (s, 3H); 2.99 (m, 2H); 6.67 (s, 1H)

Intermediate 98: 2-Butyl-6-methylpyrimidin-4-ol

Pentanimidamide hydrochloride (3.2 g) (prepared according to Garigipati, R. S.; *Tetrahedron Lett* 1990, 31 (14), 1969) was treated with ethyl acetoacetate (3.05 g) in a modified procedure using sodium (1.62 g) in anhydrous EtOH (50 ml) as base (as described in Salimbeni, Aldo; et al. *J. Med. Chem.* (1995), 38(24), 4806-20) affording the title compound (4.04 g).

MS (ES) (M+H): 166 for $C_9H_{14}N_2O$ $^1$H NMR δ: 0.80 (m, 3H); 1.31 (m, 2H); 1.63 (m, 2H); 2.25 (s, 3H); 2.41 (m, 2H); 6.29 (s, 1H)

Intermediate 99: tert-Butyl [1-(2-butyl-6-methylpyrimidin-4-yl)piperidin-4-yl]carbamate Prepared in a manner analogous to Intermediate 38 starting from 4-chloro-2-butyl-6-methylpyrimidine (Intermediate 97) and tert-butyl piperidin-4-ylcarbamate.

MS (ES) (M+H): 349 for $C_{19}H_{32}N_4O_2$ $^1$H NMR δ: 0.93 (m, 3H); 1.33 (m, 2H); 1.45 (s, 9H); 1.70 (m, 2H); 1.82 (m, 2H); 2.02 (m, 1H); 2.25 (s, 3H); 2.61 (m, 4H); 3.03 (m, 2H); 3.39 (m, 2H); 3.66 (m, 1H); 4.20 (m, 2H); 6.58 (s, 1H); 6.93 (d, 1H); 6.29.

Intermediate 100: 6-{4-[(tert-Butoxycarbonyl)amino]piperidin-1-yl}-2-butylpyrimidine-4-carboxylic acid tert-Butyl [1-(2-butyl-6-methylpyrimidin-4-yl)piperidin-4-yl]carbamate (1.08 g) (Intermediate 99) was dissolved in anhydrous pyridine (25 ml). Selenium dioxide (1.72 g) was added and the mixture was heated at 120° C. for 4 h. The black solution was diluted with water (40 ml), filtered through a bed of celite. The filtrate was acidified with 1 N HCl and extracted with EtOAc, washed well with water, dried over sodium sulfate and concentrated in vacuo. The crude material was purified by flash chromatography eluting with trichloromethane/MeOH/ammonium hydroxide (9:1:1) to afford the title compound (241 mg).

MS (ES) (M+H): 378 for $C_{19}H_{30}N_4O_4$ $^1$H NMR δ: 0.74 (t, 3H); 1.12 (m, 4H); 1.20 (s, 9H); 1.49 (m, 2H); 1.65 (m, 2H); 2.54 (m, 1H); 2.9 (m, 2H); 3.45 (m, 2H); 4.18 (m, 2H); 6.69 (d, 1H); 6.82 (s, 1H)

Intermediates 101 to 109 were Prepared by the Following General Method

The 4-(N-BOC amino)-piperidine (1.00 equivalent, 5.00 mmol), palladium (II) acetate (0.10 equiv), BINAP (rac-2,2'-bis(diphenylphosphinio)-1,1'-binaphthyl, 0.10 equiv), caesium carbonate (1.40 equiv) and aryl halide starting material shown in the following table (1.00 equiv) were combined. The solids were degassed and placed under argon. Toluene (10 ml) was added and the mixture was stirred at 100° C. for approximately 16 h. The mixture was filtered, and the filtrate was concentrated under vacuum. The crude product was purified by silica gel flash column chromatography.

The Aryl halide starting materials shown in the table below for Intermediates 101 to 109 are commercially available, except for methyl 6-bromopyridine-2-carboxylate (Intermediate 158) and methyl 5-bromothiophene-2-carboxylate (Intermediate 159) which were formed by esterification of commercially available acids.

Intermediate 101: Methyl 5-{4-[(tert-butoxycarbonyl)amino]piperidin-1-yl}thiophene-2-carboxylate Intermediate 102: Methyl 5-{4-[(tert-butoxycarbonyl)amino]piperidin-1-yl}-2-furoate Intermediate 103: Methyl 3-{4-[(tert-butoxycarbonyl)amino]piperidin-1-yl}benzoate Intermediate 104: Methyl 3-bromo-5-{4-[(tert-butoxycarbonyl)amino]piperidin-1-yl}benzoate Intermediate 105: Ethyl 5-{4-[(tert-butoxycarbonyl)amino]piperidin-1-yl}nicotinate Intermediate 106: Methyl 5-{4-[(tert-butoxycarbonyl)amino]piperidin-1-yl}nicotinate Intermediate 107: Methyl 6-{4-[(tert-butoxycarbonyl)amino]piperidin-1-yl}pyridine-2-carboxylate Intermediate 108: Methyl 3-{4-[(tert-butoxycarbonyl)amino]piperidin-1-yl}-5-morpholin-4-ylbenzoate Intermediate 109: Methyl 3-{4-[(tert-butoxycarbonyl)amino]piperidin-1-yl}-5-(4-methylpiperazin-1-yl)benzoate

| Intermediate | Aryl Halide Starting Material | $^1$H NMR δ | m/z |
|---|---|---|---|
| 101 | Methyl 5-bromothiophene-2-carboxylate (Intermediate 159) | 1.38(s, 9H); 1.43-1.53(m, 2H); 1.78-1.81(m, 2H); 3.00(t, 2H); 3.45(m, 1H); 3.55-3.60(m, 2H); 3.70(s, 3H); 6.17(d, 1H); 6.90(d, 1H); 7.49(d, 1H). | 341 |
| 102 | Methyl 5-bromo-2-furoate | 1.32-1.43(m, 11H); 1.75-1.77(m, 2H); 2.91(t, 2H); 3.42(m, 1H); 3.61-3.65(m, 2H); 3.68(s, 3H); 5.43(d, 1H); 6.89(d, 1H); 7.21(d, 1H). | 325 |
| 103 | Methyl 3-bromobenzoate | 1.38(s, 9H); 1.42-1.51(m, 2H); 1.78-1.82(m, 2H); 2.77(t, 2H); 3.40(m, overlapping with water, 1H); 3.65-3.70(m, 2H); 3.82(s, 3H); 6.86(d, 1H); 7.22(m, 1H); 7.33(d, 2H); 7.43(br s, 1H). | 335 |
| 104 | Methyl 3,5-dibromobenzoate | 1.38(s, 9H); 1.43-1.48(m, 2H); 1.76-1.79(m, 2H); 2.84(t, 2H); 3.43(m, 1H); 3.70-3.74(m, 2H); 3.83(s, 3H); 6.85(d, 1H); 7.35(br s, 2H); 7.39(s, 1H). | 413, 415 |
| 105 | Ethyl 5-bromonicotinate | 1.33(t, 3H); 1.39(s, 9H); 1.43-1.52(m, 2H); 1.79-1.83(m, 2H); 2.86(t, 2H); 3.39(m, 1H); 3.75-3.79(m, 2H); 4.33(q, 2H); 6.88(d, 1H); 7.65(m, 1H); 8.45(m, 1H); 8.53(m, 1H). | 350 |
| 106 | Methyl 5-bromonicotinate | 1.26-1.34(m, 2H); 1.38(s, 9H); 1.76-1.80(m, 2H); 2.91(t, 2H); 3.49(m, 1H); 3.82(s, 3H); 4.25-4.30(m, 2H); 6.84(d, 1H); 7.07(d, 1H); 7.26(d, 1H); 7.65(t, 1H). | 336 |
| 107 | Methyl 6-bromopyridine-2-carboxylate (Intermediate 158) | 1.26-1.34(m, 2H); 1.39(s, 9H); 1.76-1.80(m, 2H); 2.91(t, 2H); 3.50(m, 1H); 3.82(s, 3H); 4.26-4.30(m, 2H); 6.85(d, 1H); 7.08(d, 1H); 7.26(d, 1H); 7.65(t, 1H). | 336 |
| 108 | Methyl 3-bromo-5-{4-[(tert-butoxycarbonyl)amino]piperidin-1-yl}benzoate (Intermediate 104) | 1.32-1.52(m, 11H); 1.77(d, 2H); 2.72(t, 2H); 3.02-3.15(m, 4H); 3.31(s, 3H); 3.34-3.47(m, 1H); 3.64(d, 2H); 3.58-3.74(m, 4H); 3.79(s, 3H); 6.70(s, 1H); 6.84(d, 1H); 6.89(s, 1H); 6.93(s, 1H). | 420 |
| 109 | Methyl 3-bromo-5-{4-[(tert-butoxycarbonyl)amino]piperidin-1-yl}benzoate (Intermediate 104) | 1.32-1.53(m, 11H); 1.77(d, 2H); 2.21(s, 3H); 2.37-2.47(m, 4H); 2.72(t, 2H); 3.07-3.20(m, 4H); 3.35-3.41(m, 1H); 3.64(d, 2H); 3.79(s, 3H); 6.69(s, 1H); 6.85(d, 1H); 6.91(d, 2H). | 433 |

Intermediates 110 to 118 were made by deprotection of Intermediates 101 to 109 by treatment with an excess of 4 N HCl in THF, a procedure analogous to that used in Intermediate 46. The resulting crude material was used without further purification.

Intermediate 110: Methyl 5-(4-aminopiperidin-1-yl)thiophene-2-carboxylate hydrochloride MS (APCI) (MH$^+$): 241 for $C_{11}H_{16}N_2O_2S$; SM: Intermediate 101

Intermediate 111: Methyl 5-(4-aminopiperidin-1-yl)-2-furoate hydrochloride

MS (ES) (MH$^+$): 225 for $C_{11}H_{16}N_2O_3$; SM: Intermediate 102

Intermediate 112: Methyl 3-(4-aminopiperidin-1-yl)benzoate hydrochloride

MS (ES) (MH$^+$): 235 for $C_{13}H_{18}N_2O_2$; SM: Intermediate 103

Intermediate 113: Methyl 3-(4-aminopiperidin-1-yl)-5-bromobenzoate hydrochloride MS (ESP) (M, MH$^{+2}$): 313, 315 for $C_{13}H_{17}BrN_2O_2$; SM: Intermediate 104

Intermediate 114: Ethyl 5-(4-aminopiperidin-1-yl)nocotinate hydrochloride

MS (ESP) (MH$^+$): 250 for $C_{13}H_{19}N_3O_2$; SM: Intermediate 105

Intermediate 115: Methyl 5-(4-aminopiperidin-1-yl)nocotinate hydrochloride

MS (ESP) (MH$^+$): 236 for $C_{12}H_{17}N_3O_2$; SM: Intermediate 106

Intermediate 116: Methyl 6-(4-aminopiperidin-1-yl)pyridine-2-carboxylate hydrochloride MS (ESP) (MH$^+$): 236 for $C_{12}H_{17}N_3O_2$; SM: Intermediate 107

Intermediate 117: Methyl 3-(4-aminopiperidin-1-yl)-5-morpholin-4-ylbenzoate hydrochloride MS (ESP): 320 (MH$^+$) for $C_{17}H_{25}N_3O_3$; SM: Intermediate 108

Intermediate 118: Methyl 3-(4-aminopiperidin-1-yl)-5-(4-methylpiperazin-1-yl)benzoate hydrochloride MS (ESP): 333 (MH$^+$) for $C_{18}H_{28}N_4O_2$; SM: Intermediate 109

Intermediate 119: Ethyl 3-bromoisoxazole-5-carboxylate

Dibromoformaldoxime (407 mg, 2.07 mmol) (prepared via the procedure of J C Rohloff, et. al., Tetrahedron Lett 1992, 33:3113-6), and ethyl propiolate (311 mg, 3.17 mmol) were dissolved in 10 ml of 50% aqueous EtOH. While stirring, a solution of 243 mg (2.43 mmol) of potassium bicarbonate in 5 ml of water was added dropwise over 1 h. The resulting solution was stirred for an additional 4 h, diluted with 25 ml of water, and extracted with chloroform (3×25 ml). The combined organic extract was dried over sodium sulfate and concentrated in vacuo to a colourless oil, 345 mg (78% yield) as a 7:1 mixture of the 5- and 4-carboxylates.

$^1$H NMR (CDCl$_3$) δ: 1.34 (t, 3H, J=7.16 Hz), 4.30 & 4.37 (2q, 2H, J=7.16 Hz), 6.92 & 8.81 (2s, 1H, ratio 7:1).

Intermediate 120: 3-Bromoisoxazole-5-carboxylic acid

A solution of 442 mg (2.0 mmol) of ethyl 3-bromoisoxazole-5-carboxylate (Intermediate 119) and 5.0 ml of 1 N sodium hydroxide in 10 ml of MeOH was stirred at ambient temperature for 5 h, then acidified with 6.0 ml of 1 N hydrochloric acid, diluted with 25 ml of water and extracted with EtOAc (3×25 ml). The combined organic extract was dried over magnesium sulfate and concentrated in vacuo to give the title compound as a white solid (310 mg).

MS. 0.30 (ES$^-$) 189.99/191.99/193.17; $C_4H_2BrNO_3$ 191.97

$^1$H NMR δ: 7.46 (s, 1H)

Intermediate 121: Methyl 6-aminopyridine-2-carboxylate

6-Aminopyridine-2-carboxylic acid (5.0 g, 36 mmol) was dissolved in 50 ml of MeOH. To this was added acetyl chloride (9.0 ml, 126 mmol) in 50 ml of MeOH. The reaction was heated to reflux overnight. Concentrate to an orange oil and partition with EtOAc and water. The organic portions were washed with brine, dried (MgSO$_4$) and concentrated to a yellow solid.

$^1$H NMR δ: 3.79 (s, 3H); 6.32 (s, 2H); 6.64 (d, J=8.29 Hz, 1H); 7.18 (d, J=7.35 Hz, 1H); 7.51 (dd, J=8.29, 7.35 Hz, 1H).

Intermediate 122: Methyl 6-aminopyridine-2-carboxylate 1-oxide hydrochloride Methyl 6-aminopyridine-2-carboxylate (Intermediate 121, 3.3 g, 22 mmol) was dissolved in acetone and to this was added a solution of mCPBA (5.9 g, 23.5 mmol) in acetone. After stirring overnight, the acetone was removed and the residue was suspended in 3 N HCl. The precipitate was filtered off to give the HCl salt (3.57 g, 87%).

MS (ES): 169 (M+H)$^+$.

$^1$H NMR δ: 3.91 (s, 3H); 7.20 (dd, J=7.25, 1.60 Hz, 1H); 7.39 (dd, J=8.85, 1.70 Hz, 1H); 7.82 (dd, J=8.95, 7.25 Hz, 1H).

Intermediate 123: Ethyl 4-(2-methoxyethoxy)-3-oxobutanoate 2,2-Dimethyl-1,3-dioxane-4,6-dione (1.72 g) was suspended in anhydrous pyridine (20 ml) and cooled to 0° C. (2-methoxyethoxy)acetyl chloride (2 g) was added slowly. The mixture was stirred at room temperature for 3 h. The mixture was poured into 2 N HCl (30 ml) and extracted with DCM (×3). The combined organic phase was washed with water, brine, dried over sodium sulfate and concentrated in vacuo. The orange oil was dissolved in EtOH (20 ml) and was refluxed for 7 h. The solvent was removed in vacuo and the brown oil was Kugelrohr distilled affording the title compound as a colourless oil (1.55 g).

MS (ES) (M+H): 204 for $C_9H_{16}O_5$

¹H NMR (CDCl₃) δ: 1.58 (m, 2H); 1.92 (m, 2H); 2.18 (s, 3H); 2.80 (s, 3H); 3.18 (m, 2H); 3.76 (s, 3H); 4.12 (m, 1H); 4.29 (m, 2H); 7.08 (s, 1H); 7.22 (d, 1H); 7.34 (s, 1H); 11.96 (s, 1H); 12.17 (s, 1H)

Intermediate 124: Ethyl 2-chloro-4-(2-methoxyethoxy)-3-oxobutanoate

Ethyl 4-(2-methoxyethoxy)-3-oxobutanoate (Intermediate 123) (0.5 g) was dissolved in anhydrous DCM (5 ml). Sulfuryl chloride (430 mg) was added dropwise at room temperature. The mixture was stirred for 6 h. The crude mixture was diluted with EtOAc (50 ml) and washed well with water and brine, dried over sodium sulfate and concentrated in vacuo to afford the title compound as a light orange oil (414 mg).

MS (ES) (M+H): 238 for $C_9H_{15}ClO_5$
¹H NMR (CDCl₃) δ: 1.70 (m, 3H); 3.70 (s, 3H); 4.18 (m, 4H); 4.62 (m, 2H); 4.71 (s, 1H)

Intermediate 125: tert-Butyl [1-(aminocarbonothioyl)piperidin-4-yl]carbamate tert-Butyl piperidin-4-ylcarbamate (5.5 g) was dissolved in anhydrous DCM (75 ml). H-Fluoren-9-ylmethyl isothiocyanatidocarbonate (Fmoc isothiocyanate; 7.75 g) was added in small portions at room temperature after which time a white precipitate formed. The mixture was stirred at room temperature for 90 min. The solvent was removed in vacuo and the crude mixture was treated with 10% piperidine in MeOH (100 ml) for 12 h. The mixture was concentrated in vacuo and triturated with n-hexanes. The white crystalline material was filtered and washed well with n-hexanes and dried in vacuo to afford the title compound (6.55 g).

MS (ES) (M+H): 260 for $C_{12}H_{21}N_3O_2S$
¹H NMR δ: 1.24 (m, 2H); 1.38 (s, 9H); 1.67 (m, 2H); 2.99 (m, 2H); 3.33 (m, 1H); 4.15 (m, 2H); 6.52 (d, 1H); 7.72 (s, 2H).

Intermediate 126: Ethyl 2-(4-aminopiperidin-1-yl)-4-[(2-methoxyethoxy)methyl]-1,3-thiazole-5-carboxylate hydrochloride tert-Butyl [1-(aminocarbonothioyl)piperidin-4-yl]carbamate (Intermediate 125, 400 mg) was dissolved in anhydrous EtOH (5 ml). Ethyl 2-chloro-4-(2-methoxyethoxy)-3-oxobutanoate (Intermediate 124, 368 mg) was added and the mixture was heated at 90° C. for 18 h. Partial removal of Boc group was detected. Solvent was removed in vacuo and the dried material was treated with 4 N HCl/dioxane for 2 h. Solvent was removed in vacuo to give a brown/yellow solid which was dried to afford the title compound which was used without further purification (508 mg).

MS (ES) (M+H): 343 for $C_{15}H_{24}ClN_3O_4S$

Intermediate 127: Methyl 6-azidopyridine-2-carboxylate 1-oxide

Methyl 6-aminopyridine-2-carboxylate 1-oxide hydrochloride (Intermediate 122, 3.34 g, 16 mmol) was dissolved in 10% HCl (aqueous) and cooled to 5° C. An aqueous solution of NaNO₂ (1.5 g, 21 mmol) was added dropwise maintaining temperature below 5° C. After 15 minutes of stirring, an aqueous solution of NaN₃ (1.4 g, 21 mmol) was added dropwise maintaining temperature below 5° C. The reaction was stirred at 5° C. for 30 minutes and slowly warmed to room temperature. The product was extracted with DCM and then the aqueous layer was basified (with 50% NaOH to pH 13) and then extracted again with DCM. Drying (MgSO₄) and removal of solvent yielded a yellow oil (2.6 g, 82%).

¹H NMR δ: 3.89 (s, 3H); 7.61 (dd, 1H); 7.78 (dd, J=8.85, 1.70 Hz, 1H); 8.02 (dd, J=8.95, 7.25 Hz, 1H).

Intermediate 128: Methyl 5-cyano-1-hydroxy-1H-pyrrole-2-carboxylate

A solution of methyl 6-azidopyridine-2-carboxylate 1-oxide (Intermediate 127, 2.6 g, 13 mmol) in isopropanol was bubbled with nitrogen for 20 minutes followed heating to reflux for 16 hours. The solution was concentrated to a red oil (2.55 g, 99%).

¹H NMR δ: 3.81 (s, 3H); 6.75 (d, J=4.90 Hz, 1H); 6.87 (d, J=4.90 Hz, 1H).

Intermediate 129: Methyl 5-cyano-1H-pyrrole-2-carboxylate

A 20% solution of TiCl₃ (25 ml, 32 mmol) in water was added to a solution of methyl 5-cyano-1-hydroxy-1H-pyrrole-2-carboxylate (Intermediate 128, 2.55 g, 15 mmol) in MeOH. The reaction was heated to an external temperature of 70° C. for 3 hours. The reaction mixture was concentrated to remove MeOH and the residue was partitioned with EtOAc and water. The organic portion was dried with MgSO₄ and concentrated to an orange oil.

¹H NMR δ: 3.79-3.87 (m, 3H); 6.88 (dd, J=3.86, 2.35 Hz, 1H); 7.02 (dd, J=3.77, 2.07 Hz, 1H); 13.42 (s, 1H).

Intermediate 130: Methyl 3,4-dichloro-5-cyano-1H-pyrrole-2-carboxylate

Methyl 5-cyano-1H-pyrrole-2-carboxylate (Intermediate 129, 0.95 g, 6.3 mmol) was dissolved in anhydrous DCM and cooled to 0° C. TEA was added dropwise and stirred for several minutes followed by the dropwise addition of SO₂Cl₂. The reaction was stirred for 20 minutes at 0° C. before warming to room temperature. The reaction mixture was diluted with water and extracted. The organic portion was dried with MgSO₄ and concentrated to a yellow solid (1.32 g, 96%).

¹H NMR δ: 3.80-3.91 (m, 3H); 14.25 (s, 1H).

Intermediate 131: 3,4-Dichloro-5-cyano-1H-pyrrole-2-carboxylic acid

The title compound was prepared by a procedure analogous to Intermediate 3 starting from methyl 3,4-dichloro-5-cyano-1H-pyrrole-2-carboxylate (Intermediate 130).

¹H NMR δ: 14.02 (s, 1H).

Intermediate 132: 3,4-Dichloro-5-cyano-1H-pyrrole-2-carbonyl chloride 3,4-Dichloro-5-cyano-1H-pyrrole-2-carboxylic acid (Intermediate 131, 0.9 g, 0.2 mmol) was dissolved in excess thionyl chloride (5 ml) and heated to reflux for 30 minutes. The reaction mixture was concentrated and the residue was dissolved in THF and concentrated (×2). The solid (0.82 g, 89%) was pumped to dryness and stored under argon.

¹H NMR (CDCl₃) δ: 12.39 (s, 1H).

Intermediate 133: Methyl 2-{4-[(tert-butoxycarbonyl)amino]piperidin-1-yl}-1,3-thiazole-5-carboxylate tert-Butyl piperidin-4-ylcarbamate (4.5 g, 22 mmol), methyl 2-bromo-1,3-thiazole-5-carboxylate (5.0 g, 22 mmol), and diisopropylethylamine (3.8 ml, 22 mmol) were suspended in anhydrous DMF and heated to an external temperature of 130° C. for 1.5 hours. The DMF was removed and the solid was partitioned with EtOAc and water. The combined organic extracts were washed with brine, dried with MgSO$_4$ and concentrated to a yellow solid (7.05 g, 94%).

$^1$H NMR δ: 1.34-1.41 (m, 9H); 1.41-1.47 (m, 2H); 1.82 (dd, J=12.81, 2.83 Hz, 2H); 3.15-3.28 (m, 2H); 3.54 (s, 1H); 3.74 (s, 3H); 3.83-3.95 (m, 2H); 6.93 (d, J=7.72 Hz, 1H); 7.85 (s, 1H).

Intermediate 134: Methyl 2-(4-aminopiperidin-1-yl)-1,3-thiazole-5-carboxylate Methyl 2-{4-[(tert-butoxycarbonyl)amino]piperidin-1-yl}-1,3-thiazole-5-carboxylate (Intermediate 133, 6.92 g, 20 mmol) was dissolved in excess 4 M HCl in dioxane. After several minutes a white precipitate formed and after 1 hour the reaction was complete. The precipitate was filtered off, washed with ether and dried, yielding the di-HCl salt, monohydrate 6.03 g, 96%). The solid was then dissolved in sat. NaHCO$_3$ put in the continuous extractor with DCM overnight. The organic portion was dried with MgSO$_4$ and concentrated to a white solid (3.84 g, 83%).

$^1$H NMR δ: 1.19-1.33 (m, 2H); 1.57 (s, 2H); 1.70-1.83 (m, 2H); 2.76-2.89 (m, 1H); 3.12-3.25 (m, 2H); 3.74 (s, 3H); 3.87 (dt, J=13.09, 3.72 Hz, 2H); 7.84 (s, 1H).

Intermediate 135: Methyl 4-{4-[(tert-butoxycarbonyl)amino]piperidin-1-yl}quinoline-2-carboxylate The title compound was prepared by a procedure analogous to Intermediate 133 starting with methyl 4-chloroquinoline-2-carboxylate (WO 9505378). The product was purified on a silica gel flash column (0→5% MeOH in DCM) followed by recrystallization from EtOAc.

$^1$H NMR δ: 1.37-1.44 (m, 9H); 1.63-1.78 (m, 2H); 1.93 (s, 1H); 1.98 (d, J=7.54 Hz, 1H); 2.96 (t, J=11.1 Hz, 2H); 3.56 (d, J=12.25 Hz, 3H); 3.93 (s, 3H); 7.03 (d, J=7.54 Hz, 1H); 7.52 (s, 1H); 7.64-7.74 (m, 1H); 7.80 (td, J=7.63, 1.32 Hz, 1H); 7.99 (d, J=7.91 Hz, 1H); 8.07 (d, J=7.54 Hz, 1H).

Intermediate 136: Methyl 4-(4-aminopiperidin-1-yl)quinoline-2-carboxylate hydrochloride The title compound was prepared by a procedure analogous to Intermediate 134 starting from methyl 4-{4-[(tert-butoxycarbonyl)amino]piperidin-1-yl}quinoline-2-carboxylate (Intermediate 135). The product was obtained as the monohydrochloride salt.

$^1$H NMR δ: 1.89 (d, J=10.17 Hz, 2H); 2.19 (s, 2H); 3.45-3.60 (m, 3H); 4.05 (s, 3H); 4.24 (d, J=13.00 Hz, 2H); 7.59 (s, 1H); 7.75 (t, J=7.63 Hz, 1H); 7.97-8.05 (m, 1H); 8.12 (d, J=8.48 Hz, 1H); 8.34 (d, J=8.48 Hz, 1H); 8.60 (s, 2H).

Intermediates 137-142

The following quinolines were prepared via the method of F R Alexandre, et. al., Tetrahedron 2003, 59: 1413

Intermediate 137: Ethyl 4-chloro-8-methoxyquinoline-2-carboxylate

Intermediate 138: Methyl 4-chloro-8-fluoroquinoline-2-carboxylate

Intermediate 139: Methyl 4-chloro-8-methylquinoline-2-carboxylate

Intermediate 140: Methyl 4-chloro-6-fluoroquinoline-2-carboxylate

Intermediate 141: Methyl 4,8-dichloroquinoline-2-carboxylate

Intermediate 142: Ethyl 2-chloro-oxazole-4-carboxylate

Under a nitrogen atmosphere, 1.70 ml (14.3 mmol) of tert-butyl nitrite was added to a suspension of 1.65 g (12.3 mmol) of copper(II) chloride in 50 ml of acetonitrile. The resulting suspension was heated to 75° C., then 1.60 g (10.2 mmol) of ethyl 2-aminooxazole-4-carboxylate (G Crank & M J Foulis, J Med Chem 1971, 14:1075-1077) was added in portions over 20 min (gas evolution). After stirring for an additional 30 min, the reaction was allowed to cool to ambient temperature, diluted with 50 ml of EtOAc, and extracted with water (2×25 ml). The organic layer was dried over MgSO$_4$ and concentrated in vacuo to a dark oily solid. Flash chromatography through neutral silica gel using a 3:1 mixture of hexane and EtOAc gave 1.27 g (71%) of the title compound, which crystallized from hexane as white needles.

m/z (ES+): 176/177.

$^1$H NMR (CDCl$_3$) δ: 1.47 (t, 3H, J=7.16); 4.48 (q, 2H, J=7.16); 6.92 & 8.28 (s, 1H).

Intermediates 143 to 148

The following compounds in the below table were made by deprotection of Intermediates 149 to 154 by treatment with an excess of 4 N HCl in THF, a procedure analogous to that used in Intermediate 46. The resulting crude material was used without further purification.

| Intermediate | Compound | MS (ESP)(MH$^+$) | SM |
| --- | --- | --- | --- |
| Intermediate 143 | Methyl 3-allyl-5-(4-aminopiperidin-1-yl)benzoate hydrochloride | 275 for C$_{16}$H$_{22}$N$_2$O$_2$ | Intermediate 149 |
| intermediate 144 | Methyl 3-(4-aminopiperidin-1-yl)-5-(2,3-dihydroxypropyl)-benzoate hydrochloride | 309 for C$_{16}$H$_{24}$N$_2$O$_4$ | Intermediate 150 |
| Intermediate 145 | Dimethyl 5-(4-aminopiperidin-1-yl)isophthalate hydrochloride | 293 for C$_{15}$H$_{20}$N$_2$O$_4$ | Intermediate 151 |

-continued

| Intermediate | Compound | MS (ESP)(MH+) | SM |
|---|---|---|---|
| Intermediate 146 | Dimethyl 2-(4-aminopiperidin-1-yl)terephthalate hydrochloride | 293 for $C_{15}H_{20}N_2O_4$ | Intermediate 152 |
| Intermediate 147 | Methyl 4-(4-aminopiperidin-1-yl)pyridine-2-carboxylate hydrochloride | 236 for $C_{12}H_{17}N_3O_2$ | Intermediate 153 |
| Intermediate 148 | Methyl 5-(4-aminopiperidin-1-yl)nicotinate 1-oxide hydrochloride | 252 for $C_{12}H_{17}N_3O_3$ | Intermediate 154 |

Intermediate 149: Methyl 3-allyl-5-{4-[(tert-butoxycarbonyl)amino]piperidin-1-yl}benzoate Methyl 3-bromo-5-{4-[(tert-butoxycarbonyl)amino]piperidin-1-yl}benzoate (Intermediate 104, 300 mg, 0.73 mmol), tris(dibenzylidineacetone)dipalladium (0) (26 mg, 0.03 mmol), trifurylphosphine (14 mg, 0.06 mmol) were weighed into a flask and placed under argon. NMP (3 ml) was added, followed by the dropwise addition of allyltributyl tin (0.25 ml, 0.80 mmol). The mixture was stirred at 100° C. After 64 h, the mixture was diluted with EtOAc and washed sequentially with water followed by brine. The organic phase was dried over MgSO₄ and concentrated to dryness. The crude material was purified by chromatography on silica gel using 25% EtOAc/hexanes to give 174 mg of the title product.

MS (ESP) (MH+): 375 for $C_{21}H_{30}N_2O_4$ $^1$H NMR δ: 1.38 (s, 9H); 1.42-1.51 (m, 2H); 1.78-1.81 (m, 2H); 2.76 (t, 2H); 3.34-3.40 (m overlapping water, 3H); 3.64-3.68 (m, 2H); 3.81 (S, 3H); 5.04-5.13 (m, 2H); 5.94 (m, 1H); 6.86 (d, 1H); 7.05 (s, 1H); 7.17 (s, 1H); 7.28 (s, 1H).

Intermediate 150: Methyl 3-{4-[(tert-butoxycarbonyl)amino]piperidin-1-yl}-5-(2,3-dihydroxypropyl)benzoate The title compound was prepared from methyl 3-allyl-5-{4-[(tert-butoxycarbonyl)amino]piperidin-1-yl}benzoate (Intermediate 149) and AD-mix β using the method described in J. Org. Chem. 1992, 57, 2768.

MS (ESP) (MH+): 409 for $C_{21}H_{32}N_2O_6$ $^1$H NMR (CDCl₃) δ: 1.47 (s, 9H); 1.51-1.55 (m overlapping water, 2H); 1.89 (t, 1H); 2.05-2.09 (m, 3H); 2.71-2.80 (m, 2H); 2.82-2.92 (m, 2H); 3.53 (m, 1H); 3.65-3.75 (m, 4H); 3.90 (s, 3H); 3.97 (m, 1H); 4.48 (m, 1H); 6.98 (s, 1H); 7.38 (s, 1H); 7.48 (s, 1H).

Intermediates 151 to 154

The following compounds were prepared by the following general method: The 4-(N-BOC amino)-piperidine (1.00 equivalent, 5.00 mmol), palladium (II) acetate (0.10 equiv), BINAP (rac-2,2'-bis(diphenylphosphinio)-1,1'-binaphthyl, 0.10 equiv), caesium carbonate (1.40 equiv) and aryl halide (1.00 equiv) were combined. The solids were degassed and placed under argon. Toluene (10 ml) was added and the mixture was stirred at 100° C. for approximately 16 h. The mixture was filtered, and the filtrate was concentrated under vacuum. The crude product was purified by silica gel flash column chromatography.

| Intermediate | Compound | $^1$H NMR δ | M+1 | SM |
|---|---|---|---|---|
| Intermediate 151 | Dimethyl 5-(4-tert-butoxycarbonylamino piperidin-1-yl)isophthalate | 1.37(s, 9H); 1.42-1.50(m, 2H); 1.76-1.87(m, 2H); 2.85(t, 2H); 3.45(br s, 1H overlapping with water peak); 3.66-3.79(m, 2H); 3.85(s, 6H); 6.84(m, 1H); 7.66(s, 2H); 7.85(s, 1H). | 393 | Dimethyl 5-bromo isophthalate |
| Intermediate 152 | Dimethyl 2-(4-tert-butoxycarbonylamino piperidin-1-yl)terephthalate | 1.46(s, 9H); 1.54-1.67(m, 2H); 2.03-2.07(m, 2H); 2.88(t, 2H); 3.28-3.33(m, 2H); 3.61(m, 1H); 3.91(s, 3H); 3.93(s, 3H); 4.50(m, 1H); 7.60-7.74(m, 3H). | 393 | Dimethyl 2-bromo terephthalate |
| Intermediate 153 | Methyl 4-(4-tert-butoxycarbonylamino piperidin-1-yl) pyridine-2-carboxylate | 1.45(s, 9H); 1.89(br s, 1H); 2.00-2.04(m, 3H); 3.07(t, 2H); 3.72(m, 1H); 3.76-3.92(m, 2H); 3.97(s, 3H); 4.51(br s, 1H); 6.76(m, 1H); 7.55(d, 1H); 8.34(d, 1H). | 336 | Intermediate 155 |
| Intermediate 154 | Methyl 5-(4-tert-butoxycarbonylamino piperidin-1-yl) nicotinate 1-oxide | 1.46(s, 9H); 1.51-1.56(m, 2H); 2.05-2.10(m, 2H); 2.99(t, 2H); 3.65-3.69(m, 2H); 3.95(s, 3H); 4.48(m, 1H); 7.42(s, 1H); 8.00(s, 1H); 8.35(s, 1H). | 352 | Intermediate 156 |

Intermediate 155: Methyl 4-iodopyridine-2-carboxylate

This was prepared from the corresponding carboxylic acid as described under Intermediates 101-109.
MS (ESP) (MH$^+$): 264 for $C_7H_6INO_2$

Intermediate 156: Methyl 5-bromonicotinate-1-oxide

A solution of mCPBA (70%, 4.46 g, 18.11 mmol) in DCM (100 ml) was added to a solution of methyl 5-bromonicotinate (3.11 g, 15.09 mmol) in DCM (100 ml). After stirring at room temperature for several hours, additional mCPBA (6.6 g, 26.77 mmol) was added (in portions) to drive the reaction to completion. After 4 days, the reaction mixture was sequentially washed with a saturated solution of sodium bicarbonate followed by water. The organic phase was dried over MgSO$_4$, and concentrated to dryness. The crude material was purified by chromatography on silica gel using 50% EtOAc/hexanes to 100% EtOAc to give 1.16 g of the title product.
MS (ESP) (M$^+$, MH$^{2+}$): 232, 234 for $C_7H_6BrNO_3$
$^1$H NMR δ: 3.89 (s, 3H); 7.95 (s, 1H); 8.52 (s, 1H); 8.85 (s, 1H).

Intermediate 157: Methyl [2-({4-[(tert-butoxycarbonyl)amino]piperidin-1-yl}carbonyl)hydrazino](oxo)acetate A solution of tert-butyl piperidin-4-ylcarbamate (comm. available) (1.0 g, 5.0 mmol), TEA (2.0 g, 20 mmol) and DCM (30 ml) was added dropwise to phosgene (20%) in toluene (comm. available) (10 ml, ~20 mmol) at 0° C. The resultant mixture was allowed to slowly warm to room temperature while stirring overnight. The mixture was filtered to remove solid material and the filtrate was concentrated under reduced pressure to yield the carbamoyl chloride (1.2 g). The crude carbamoyl chloride (1.2 g, 5.0 mmol), TEA (0.70 ml, 5.0 mmol), methyl hydrazino(oxo)acetate (0.59 g, 5 mmol, reference: J. Med. Pharm. Chem. 1961, vol. 4,(2), p. 259) and THF (20 ml) were combined and heated at 60° C. for 24 h. The mixture was cooled to room temperature and concentrated under reduced pressure. The crude residue was purified by flash column chromatography (DCM/acetone, 5:1 ratio with 1% MeOH) to yield 462 mg of the title compound.
MS (ESP): 345.1 (M+H) for $C_{14}H_{24}N_4O_6$
$^1$H NMR δ: 1.03 (m, 2H); 1.44 (s, 9H); 1.73 (d, 2H); 2.85 (t, 2H); 3.45 (m, 1H); 3.85 (s, 3H); 3.92 (d, 2H); 6.94 (d, 1H); 8.72 (s, 1H); 10.48 (s, 1H).

Intermediate 158: Methyl 6-bromopyridine-2-carboxylate

6-Bromopicolinic acid (411 mg, 2.03 mmol) was slurried in anhydrous MeOH (6 ml). Concentrated sulfuric acid (0.3 ml) was added and the resulting solution was stirred at room temperature for approximately 3 h. EtOAc was added, followed by a saturated solution of sodium bicarbonate. The phases were separated, and the organic phase was washed with water, dried over MgSO$_4$, and concentrated to dryness. The crude ester (313 mg) was used without further purification.
MS (ESP) (M, MH$^{+2}$) 216, 218 for $C_7H_6NO_2$

Intermediate 159: Methyl 5-bromothiophene-2-carboxylate

This was made from the corresponding carboxylic acid as described in Intermediate 158.
MS (APCI) (M, MH$^{+2}$) 221, 223 for $C_6H_5BrO_2S$

Intermediate 160: Methyl 5-{4-[(tert-butoxycarbonyl)amino]piperidin-1-yl}-1,3,4-oxadiazole-2-carboxylate TEA (0.20 ml, 1.34 mmol), para-toluenesulfonyl chloride (255 mg, 1.34 mmol), methyl [2-({4-[(tert-butoxycarbonyl)amino]piperidin-1-yl}carbonyl)hydrazino](oxo)acetate (Intermediate 157) (460 mg, 1.34 mmol) and DCM (8 ml) were combined and stirred overnight. The mixture was diluted with DCM (150 ml) and washed with water (10 ml). The organic phase was separated, dried over sodium sulfate, filtered and concentrated. The crude residue was purified by flash column chromatography (DCM/acetone, 8:1 ratio with 1% MeOH) to yield 342 mg of the title compound.
MS (ESP): 326.9 (M+H) for $C_{14}H_{22}N_4O_5$
$^1$H NMR δ: 1.46 (s, 9H); 1.50 (m, 2H); 1.89 (d, 2H); 3.29 (t, 2H); 3.57 (m, 1H); 3.92 (d, 2H); 3.95 (s, 3H); 7.02 (d, 1H).

Intermediates 161 and 162

The following compounds were prepared in a manner analogous to Intermediate 98 starting from ethyl acetoacetate and the SMs listed. The resulting crude material was used without further purification.

| Intermediate | Compound | M/Z | SM |
| --- | --- | --- | --- |
| Intermediate 161 | 2-Cyclopropyl-6-methylpyrimidin-4-ol | 151 | cyclopropane carboximidamide hydrochloride |
| Intermediate 162 | 2-tert-Butyl-6-methylpyrimidin-4-ol | 167 | 2,2-dimethylpropanimidamide hydrochloride |

Intermediates 163-165

The following compounds were prepared in a manner analogous to Intermediate 97 starting from pyrimidinols listed. The resulting crude material was used without further purification.

| Intermediate | Compound | M/Z | 1H NMR | SM |
| --- | --- | --- | --- | --- |
| Intermediate 163 | 4-Chloro-2-cyclopropyl-6-methylpyrimidine | 168 | 0.83(m, 2H); 0.93(m, 2H); 2.03(m, 1H); 2.29(s, 3H); 7.21(s, 1H) | 2-Cyclopropyl-6-methylpyrimidin-4-ol (Intermediate 161) |

-continued

| Intermediate | Compound | M/Z | 1H NMR | SM |
|---|---|---|---|---|
| Intermediate 164 | 4-Chloro-2-isopropyl-6-methylpyrimidine | 170 | 1.27(d, 6H); 2.49(s, 3H); 3.17(q, 1H); 7.50(s, 1H) | 2-Isopropyl-6-methylpyrimidin-4-ol (commercially available) |
| Intermediate 165 | 2-tert-Butyl-4-chloro-6-methyl pyrimidine | 184 | 1.48(s, 9H); 2.49(s, 3H); 6.98(s, 1H) | 2-tert-Butyl-6-methylpyrimidin-4-ol (Intermediate 162) |

Intermediates 166-168

The following compounds were prepared in a manner analogous to Intermediate 99 starting from tert-butyl piperidin-4-ylcarbamate and the SMs listed.

| Intermediate | Compound | M/Z | 1H NMR | SM |
|---|---|---|---|---|
| Intermediate 166 | tert-Butyl [1-(2-cyclopropyl-6-methylpyrimidin-4-yl)piperidin-4-yl]carbamate | 332 |  | 4-Chloro-2-cyclopropyl-6-methylpyrimidine (Intermediate 163) |
| Intermediate 167 | tert-Butyl [1-(2-isopropyl-6-methylpyrimidin-4-yl)piperidin-4-yl]carbamate | 334 | 1.23(d, 6H); 1.4(s, 9H); 2.26(s, 3H); 3.20(q, 1H); 3.09(m, 2H); 3.43(m, 2H); 3.67(m, 3H); 4.46(m, 2H); 6.56(s, 1H); 7.1(d, 1H) | 4-Chloro-2-isopropyl-6-methylpyrimidine (Intermediate 164) |
| Intermediate 168 | tert-Butyl [1-(2-tert-butyl-6-methylpyrimidin-4-yl)piperidin-4-yl]carbamate | 349 | 1.33(s, 9H); 1.44-1.51(s, 9H); 1.89(m, 2H); 2.35(s, 3H); 3.09(m, 2H); 3.43(s, 2H); 3.67(m, 1H); 4.46(m, 2H); 6.64(s, 1H); 6.9(d, 1H) | 2-tert-Butyl-4-chloro-6-methylpyrimidine (Intermediate 165) |

Intermediates 169-171

The following compounds were prepared in a manner analogous to Intermediate 100 starting from the SMs listed.

| Intermediate | Compound | M/Z | SM |
|---|---|---|---|
| Intermediate 169 | 6-{4-[(tert-Butoxycarbonyl)amino]piperidin-1-yl}-2-cyclopropylpyrimidine-4-carboxylic acid | 363 | tert-butyl [1-(2-cyclopropyl-6-methylpyrimidin-4-yl)piperidin-4-yl]carbamate (Intermediate 166) |
| Intermediate 170 | 6-{4-[(tert-Butoxycarbonyl)amino]piperidin-1-yl}-2-isopropylpyrimidine-4-carboxylic acid | 364 | tert-butyl [1-(2-isopropyl-6-methylpyrimidin-4-yl)piperidin-4-yl]carbamate (Intermediate 167) |
| Intermediate 171 | 6-{4-[(tert-Butoxycarbonyl)amino]piperidin-1-yl}-2-tert-butylpyrimidine-4-carboxylic acid | 378 | tert-butyl [1-(2-tert-butyl-6-methylpyrimidin-4-yl)piperidin-4-yl]carbamate (Intermediate 168) |

Intermediates 172-174

The following compounds were prepared in a manner analogous to Intermediate 70 starting from the SMs listed.

| Intermediate | Compound | M/Z | SM |
| --- | --- | --- | --- |
| Intermediate 172 | 6-(4-Aminopiperidin-1-yl)-2-cyclopropylpyrimidine-4-carboxylic acid hydrochloride salt | 263 | 6-{4-[(tert-butoxycarbonyl)amino]piperidin-1-yl}-2-cyclopropylpyrimidine-4-carboxylic acid (Intermediate 169) |
| Intermediate 173 | 6-(4-Aminopiperidin-1-yl)-2-isopropylpyrimidine-4-carboxylic acid hydrochloride salt | 264 | 6-{4-[(tert-butoxycarbonyl)amino]piperidin-1-yl}-2-isopropylpyrimidine-4-carboxylic acid (Intermediate 170) |
| Intermediate 174 | 6-(4-Aminopiperidin-1-yl)-2-tert-butylpyrimidine-4-carboxylic acid hydrochloride salt | 278 | 6-{4-[(tert-butoxycarbonyl)amino]piperidin-1-yl}-2-tert-butylpyrimidine-4-carboxylic acid (Intermediate 171) |

Intermediates 175-195

The following compounds were prepared in a manner analogous to Intermediate 16 starting from tert-butyl piperidin-4-ylcarbamate and the haloheteroaryl starting materials listed below (commercially available unless otherwise stated).

| Intermediate | Compound | M/Z | SM |
| --- | --- | --- | --- |
| Intermediate 175 | Ethyl 2-{4-[(tert-butoxycarbonyl)amino] piperidin-1-yl}-3-cyano-6-methylisonicotinate | 409 | ethyl 2-chloro-3-cyano-6-methylisonicotinate |
| Intermediate 176 | tert-Butyl [1-(3-cyanopyridin-2-yl)piperidin-4-yl]carbamate | 303 | 2-chloronicotinonitrile |
| Intermediate 177 | tert-Butyl (1-quinolin-2-ylpiperidin-4-yl)carbamate | 328 | 2-chloroquinoline |
| Intermediate 178 | tert-Butyl [1-(6-methoxy-3-nitro pyridin-2-yl)piperidin-4-yl]carbamate | 353 | 2-chloro-6-methoxy-3-nitropyridine |
| Intermediate 179 | tert-Butyl [1-(4-acetyl-6-chloropyridin-2-yl)piperidin-4-yl]carbamate | 353 | 1-(2,6-Dichloropyridin-4-yl)ethanone (Intermediate 48) |
| Intermediate 180 | tert-Butyl {1-[6-(trifluoromethyl) pyridin-2-yl]piperidin-4-yl}carbamate | 346 | 2-chloro-6-(trifluoromethyl) pyridine |
| Intermediate 181 | tert-Butyl {1-[3-(aminocarbonyl)-6-(trifluoromethyl)pyridin-2-yl]piperidin-4-yl}carbamate | 391 | 2-chloro-6-(trifluoromethyl) nicotinamide |
| Intermediate 182 | tert-Butyl {1-[3-cyano-6-(trifluoromethyl)pyridin-2-yl]piperidin-4-yl}carbamate | 371 | 2-chloro-6-(trifluoromethyl) nicotinonitrile |
| Intermediate 183 | tert-Butyl [1-(3-chloropyridin-2-yl)piperidin-4-yl]carbamate | 313 | 2,3-dichloropyridine |
| Intermediate 184 | tert-Butyl [1-(4-cyanopyridin-2-yl)piperidin-4-yl]carbamate | 303 | 2-chloroisonicotino nitrile |
| Intermediate 185 | tert-Butyl {1-[5-(trifluoromethyl) pyridin-2-yl]piperidin-4-yl}carbamate | 347 | 2-chloro-5-(trifluoromethyl) pyridine |
| Intermediate 186 | tert-Butyl {1-[5-(aminocarbonyl) pyridin-2-yl]piperidin-4-yl}carbamate | 321 | 6-chloronicotinamide |
| Intermediate 187 | tert-Butyl [1-(6-bromopyridin-2-yl)piperidin-4-yl]carbamate | 357 | 2,6-dibromopyridine |
| Intermediate 188 | 6-{4-[(tert-Butoxycarbonyl)amino] piperidin-1-yl}-2-chloronicotinic acid | 357 | 2,6-dichloronicotinic acid |
| Intermediate 189 | tert-Butyl (1-pyrimidin-2-ylpiperidin-4-yl)carbamate | 278 | 2-chloropyrimidine |
| Intermediate 190 | Methyl 2-{4-[(tert-butoxycarbonyl)amino]piperidin-1-yl}-6-methylpyrimidine-4-carboxylate | 349 | methyl 2-chloro-6-methylpyrimidine-4-carboxylate |
| Intermediate 191 | tert-Butyl [1-(7H-purin-6-yl)piperidin-4-yl]carbamate | 318 | 6-chloro-7H-purine |

-continued

| Intermediate | Compound | M/Z | SM |
|---|---|---|---|
| Intermediate 192 | Methyl 6-{4-[(tert-butoxycarbonyl)amino]piperidin-1-yl}-2-chloropyrimidine-4-carboxylate | 270 | methyl 2,6-dichloropyrimidine-4-carboxylate |
| Intermediate 193 | tert-Butyl [1-(6-chloro-4-{[(2-morpholin-4-ylethyl)amino]carbonyl}pyridin-2-yl)piperidin-4-yl]carbamate | 468 | 2,6-Dichloro-N-(2-morpholin-4-yl-ethyl)-isonicotinamide (Intermediate 40) |
| Intermediate 194 | tert-Butyl [1-(6-chloro-4-{[(3-morpholin-4-ylpropyl)amino]carbonyl}pyridin-2-yl)piperidin-4-yl]carbamate | 481 | 2,6-Dichloro-N-(3-morpholin-4-yl-propyl)-isonicotinamide (Intermediate 196) |
| Intermediate 195 | tert-Butyl [1-(6-chloro-4-{[2-(methylamino)-2-oxoethyl]thio}pyridin-2-yl)piperidin-4-yl]carbamate | 415 | 2-(2,6-Dichloro-pyridin-4-ylsulfanyl)-N-methyl-acetamide (Intermediate 41) |

Intermediate 196: 2,6-Dichloro-N-(3-morpholin-4-yl-prolyl)-isonicotinamide

The title compound was prepared by the procedure of Intermediate 40 from 3-morpholin-4-yl-propan-1-amine and 2,6-dichloroisonicotinic acid (both commercially available). MS (ES) (M+H): 318 for $C_{13}H_{17}Cl_2N_3O_2$ Intermediates 197-220

The following compounds were prepared in a manner analogous to Intermediate 70 from SMs listed below. The resulting crude material was used without further purification.

| Intermediate | Compound | M/Z | SM |
|---|---|---|---|
| Intermediate 197 | 1-[2-(4-Aminopiperidin-1-yl)-6-chloropyridin-4-yl]ethanone hydrochloride salt | 253 | tert-butyl [1-(4-acetyl-6-chloropyridin-2-yl)piperidin-4-yl]carbamate (Intermediate 179) |
| Intermediate 198 | 2-(4-Aminopiperidin-1-yl)-6-cyanoisonicotinamide hydrochloride salt | 246 | tert-Butyl {1-[4-(aminocarbonyl)-6-cyanopyridin-2-yl]piperidin-4-yl}carbamate (Intermediate 42) |
| Intermediate 199 | Ethyl 2-(4-aminopiperidin-1-yl)-3-cyano-6-methylisonicotinate hydrochloride salt | 308 | ethyl 2-{4-[(tert-butoxycarbonyl)amino]piperidin-1-yl}-3-cyano-6-methylisonicotinate (Intermediate 175) |
| Intermediate 200 | 2-(4-Aminopiperidin-1-yl)nicotinonitrile hydrochloride salt | 202 | tert-butyl [1-(3-cyanopyridin-2-yl)piperidin-4-yl]carbamate (Intermediate 176) |
| Intermediate 201 | 1-Quinolin-2-ylpiperidin-4-amine hydrochloride salt | 228 | tert-butyl (1-quinolin-2-ylpiperidin-4-yl)carbamate (Intermediate 177) |
| Intermediate 202 | 1-(6-Methoxy-3-nitropyridin-2-yl)piperidin-4-amine hydrochloride salt | 253 | tert-butyl [1-(6-methoxy-3-nitropyridin-2-yl)piperidin-4-yl]carbamate (Intermediate 178) |
| Intermediate 203 | 2-(4-Aminopiperidin-1-yl)-6-chloroisonicotinonitrile hydrochloride salt | 237 | tert-Butyl 1-(6-chloro-4-cyanopyridin-2-yl)piperidin-4-ylcarbamate (Intermediate 53) |
| Intermediate 204 | 1-[6-(Trifluoromethyl)pyridin-2-yl]piperidin-4-amine hydrochloride salt | 246 | tert-butyl {1-[6-(trifluoromethyl)pyridin-2-yl]piperidin-4-yl}carbamate (Intermediate 180) |
| Intermediate 205 | 2-(4-Aminopiperidin-1-yl)-6-(trifluoromethyl)nicotinamide hydrochloride salt | 291 | tert-butyl {1-[3-(aminocarbonyl)-6-(trifluoromethyl)pyridin-2-yl]piperidin-4-yl}carbamate (Intermediate 181) |
| Intermediate 206 | 2-(4-Aminopiperidin-1-yl)-6-(trifluoromethyl)nicotinonitrile hydrochloride salt | 271 | tert-butyl {1-[3-cyano-6-(trifluoromethyl)pyridin-2-yl]piperidin-4-yl}carbamate (Intermediate 182) |
| Intermediate 207 | 1-(3-Chloropyridin-2-yl)piperidin-4-amine hydrochloride salt | 213 | tert-butyl [1-(3-chloropyridin-2-yl)piperidin-4-yl]carbamate (Intermediate 183) |
| Intermediate 208 | 2-(4-Aminopiperidin-1-yl)isonicotinonitrile hydrochloride salt | 202 | tert-butyl [1-(4-cyanopyridin-2-yl)piperidin-4-yl]carbamate (Intermediate 184) |

-continued

| Intermediate | Compound | M/Z | SM |
|---|---|---|---|
| Intermediate 209 | 1-[5-(Trifluoromethyl)pyridin-2-yl]piperidin-4-amine hydrochloride salt | 247 | tert-butyl {1-[5-(trifluoromethyl)pyridin-2-yl]piperidin-4-yl}carbamate (Intermediate 185) |
| Intermediate 210 | 6-(4-Aminopiperidin-1-yl)nicotinamide hydrochloride salt | 221 | tert-butyl {1-[5-(aminocarbonyl)pyridin-2-yl]piperidin-4-yl}carbamate (Intermediate 186) |
| Intermediate 211 | 1-(6-Bromopyridin-2-yl)piperidin-4-amine hydrochloride salt | 257 | tert-butyl [1-(6-bromopyridin-2-yl)piperidin-4-yl]carbamate (Intermediate 187) |
| Intermediate 212 | [1-(6-Chloropyridin-2-yl)piperidin-4-yl]amine hydrochloride salt | 213 | tert-butyl [1-(6-chloropyridin-2-yl)piperidin-4-yl]carbamate (Intermediate 66) |
| Intermediate 213 | 6-(4-Aminopiperidin-1-yl)-2-chloronicotinic acid hydrochloride salt | 257 | 6-{4-[(tert-butoxycarbonyl)amino]piperidin-1-yl}-2-chloronicotinic acid (Intermediate 188) |
| Intermediate 214 | 1-Pyrimidin-2-ylpiperidin-4-amine hydrochloride salt | 278 | tert-butyl(1-pyrimidin-2-ylpiperidin-4-yl)carbamate (Intermediate 189) |
| Intermediate 215 | Methyl 2-(4-aminopiperidin-1-yl)-6-methylpyrimidine-4-carboxylate hydrochloride salt | 249 | methyl 2-{4-[(tert-butoxycarbonyl)amino]piperidin-1-yl}-6-methylpyrimidine-4-carboxylate (Intermediate 190) |
| Intermediate 216 | 1-(7H-Purin-6-yl)piperidin-4-amine hydrochloride salt | 218 | tert-butyl [1-(7H-purin-6-yl)piperidin-4-yl]carbamate (Intermediate 191) |
| Intermediate 217 | Methyl 6-(4-aminopiperidin-1-yl)-2-chloropyrimidine-4-carboxylate hydrochloride salt | 270 | methyl 6-{4-[(tert-butoxycarbonyl)amino]piperidin-1-yl}-2-chloropyrimidine-4-carboxylate (Intermediate 192) |
| Intermediate 218 | 2-(4-Aminopiperidin-1-yl)-6-chloro-N-(2-morpholin-4-ylethyl)isonicotinamide hydrochloride salt | 368 | tert-butyl [1-(6-chloro-4-{1-[(2-morpholin-4-ylethyl)amino]carbonyl}pyridin-2-yl)piperidin-4-yl]carbamate (Intermediate 193) |
| Intermediate 219 | 2-(4-Aminopiperidin-1-yl)-6-chloro-N-(3-morpholin-4-ylpropyl)isonicotinamide hydrochloride salt | 381 | tert-butyl [1-(6-chloro-4-{[(3-morpholin-4-ylpropyl)amino]carbonyl}pyridin-2-yl)piperidin-4-yl]carbamate (Intermediate 194) |
| Intermediate 220 | 2-{[2-(4-Aminopiperidin-1-yl)-6-chloropyridin-4-yl]thio}-N-methylacetamide hydrochloride salt | 315 | tert-butyl [1-(6-chloro-4-{[2-(methylamino)-2-oxoethyl]thio}pyridin-2-yl)piperidin-4-yl]carbamate (Intermediate 195) |

Intermediate 221: Ethyl 2,4-dibromo-1,3-thiazole-5-carboxylate

A solution of 14 ml of 1.6 N n-butyllithium in hexane was added slowly to a solution of diisopropylamine (3.1 ml, 22 mmol) in 80 ml THF cooled in a dry ice/acetone bath under an inert atmosphere. The solution was warmed to 0° C. and re-cooled to −70° C. A solution of 2,5-dibromothiazole in 20 ml THF was added and the mixture was stirred for 30 min before adding ethyl chloroformate (2.1 ml, 22 mmol). After warming to room temperature, the mixture was quenched with aqueous $NaHCO_3$ and diluted with EtOAc. The EtOAc was separated and washed with water and brine. Drying ($MgSO_4$) and removal of solvent gave an oil that was purified by chromatography (1:1 hexanes-DCM followed by gradient elution to 100% DCM) to give 4.5 g of product as an oil that slowly solidified.

MS (ES): 316 (M+H)

$^1$H NMR $CDCl_3$) δ: 1.4 (t, 3H); 4.4 (q, 2H).

Intermediate 222: Ethyl 4-bromo-2-{4-[(tert-butoxycarbonyl)amino]piperidin-1-yl}-1,3-thiazole-5-carboxylate A solution of ethyl 2,4-dibromo-1,3-thiazole-5-carboxylate (Intermediate 221) (4.5 g, 14.3 mmol), carbamic acid, 4-piperidinyl-, 1,1-dimethylethyl ester (2.86 g, 14.3 mmol), and diisopropylethylamine (2.6 ml, 14.5 mmol) in 45 ml dioxane was heated at 100° C. for 4 hours. The mixture was partitioned between EtOAc and water. The EtOAc was separated and washed with brine. Drying ($MgSO_4$) and removal of solvent gave an oil that was chromatographed on silica gel (1:1 hexanes-DCM followed by gradient elution to 100% DCM and then to 8% MeOH in DCM) to give 2.1 gm of product.

MS (ES): 378, 380 (M+H)

$^1$H NMR δ: 1.24 (t, J=7.06 Hz, 3H); 1.33-1.47 (m, 11H); 1.80 (s, 2H); 3.13-3.31 (m, 2H); 3.54 (s, 1H); 3.83 (s, 2H); 4.19 (q, J=7.10 Hz, 2H); 6.95 (d, J=7.91 Hz, 1H)

Intermediate 223: Ethyl 2-{4-[(tert-butoxycarbonyl) amino]piperidin-1-yl}-4-cyano-1,3-thiazole-5-carboxylate A solution of ethyl 4-bromo-2-{4-[(tert-butoxycarbonyl) amino]piperidin-1-yl}-1,3-thiazole-5-carboxylate (Intermediate 222) (1.3 g, 2.9 mmol), Zn(CN)$_2$ (250 mg, 2.2 mmol), tris(dibenzylidineaceetone)dipalladium(0) (125 mg, 0.13 mmol) and 1,1'-bis(diphenylphosphino) ferrocene (151 mg, 13 mmol) in 20 ml DMF under argon was heated at 130° C. for 1 hour in a microwave reactor. Solvent was removed and the residue was taken up in EtOAc and washed with water and brine. Drying (MgSO$_4$) and removal of solvent gave an oil that was chromatographed on silica gel (DCM followed by gradient elution to 5% MeOH in DCM) to give 1.9 g of product as a yellow solid.

$^1$H NMR δ: 1.28 (t, J=7.06 Hz, 3H); 1.31-1.52 (m, 11H); 1.72-1.95 (m, 2H); 3.19-3.33 (m, 2H); 3.54 (s, 1H); 3.89 (d, J=13.19 Hz, 2H); 4.29 (q, J=7.16 Hz, 2H); 6.95 (s, 1H).

Intermediate 224
3,4-Dichloro-5-methyl-1H-pyrrole-2-carbonyl chloride

A solution of 3,4-dichloro-5-methyl-1H-pyrrole-2-carboxylic acid (Intermediate 3) in 50 ml SOCl$_2$ was heated at reflux for 30 min. Solvent was removed and the residue was dried in vacuo.

$^1$H NMR(CDCl$_3$) δ: 9.0 (s, 1H); 2.4 (s, 3H).

EXAMPLES

Example 1 tert-Butyl 2-[(4-{[(3,4-dichloro-5-methyl-1H-pyrrol-2-yl)carbonyl]amino}piperidin-1-yl)methyl]-1-methyl-1H-imidazol-4-ylcarbamate A mixture of 3,4-dichloro-5-methyl-N-piperidin-4-yl-1H-pyrrole-2-carboxamide hydrochloride (Intermediate 1, 243 mg, 0.777 mmol) and tert-butyl 2-formyl-1-methyl-1H-imidazol-4-ylcarbamate (WO03/002567) (175 mg, 0.777 mmol) in THF (15 ml) was stirred at room temperature for 10 minutes. Sodium triacetoxyborohydride (494 mg, 2.33 mmol) was then added in two portions, and the reaction mixture was stirred at room temperature for 16 hours. The reaction mixture was diluted with EtOAc and 10% aqueous Na$_2$CO$_3$. The aqueous layer was extracted with EtOAc, the combined organic portions were washed with brine, dried over Na$_2$SO$_4$, filtered, and concentrated under reduced pressure to give 398 mg of a pale yellow solid, 100 mg of which was dissolved in DMSO and purified by preparatory HPLC using a gradient of 20-95% CH$_3$CN/H$_2$O (0.1% TFA) to give the TFA salt of the title compound.

MS (ES$^-$): 483.30, 485.37 for C$_{21}$H$_{30}$Cl$_2$N$_6$O$_3$ $^1$H NMR δ: 1.55 (s, 9H); 1.95 (m, 2H); 2.09 (s, 3H); 2.32 (s, 3H); 3.18 (m, 2H); 3.43 (m, 2H); 3.67 (s, 3H); 3.93 (m, 1H); 4.38 (s, 2H); 7.36 (d, 1H); 7.99 (s, 1H); 11.89 (brs, 1H).

Example 2

3,4-Dichloro-5-methyl-N-{1-[2-(methylsulfonyl) pyrimidin-4-yl]piperidin-4-yl}-1H-pyrrole-2-carboxamide A suspension of 3,4-dichloro-5-methyl-N-{1-[2-(methylthio)pyrimidin-4-yl]piperidin-4-yl}-1H-pyrrole-2-carboxamide (Example 306, 200 mg, 0.5 mmol) in anhydrous DCM (8 ml) was treated with 70% mCPBA (250 mg, 1 mmol). The resulting solution was stirred under nitrogen for 1 h then diluted with DCM and washed with 10% aqueous NaHCO$_3$ solution. The aqueous portion was extracted once with DCM, and the combined organic portions were washed with brine, dried over Na$_2$SO$_4$, filtered, and concentrated under reduced pressure to give 215 mg of an off-white solid. The crude material was purified by preparatory HPLC using a gradient of 20-60% acetonitrile/water (0.1% TFA) to give the TFA salt of the title compound (103.1 mg).

MS (ES$^-$): 430.11, 432.11 for C$_{16}$H$_{19}$Cl$_2$N$_5$O$_3$S $^1$H NMR δ: 1.29 (m, 2H); 1.66 (m, 2H); 1.92 (s, 3H); 2.94 (m, 2H); 3.04 (s, 3H); 3.21 (m, 2H); 3.84 (m, 1H); 6.87 (d, 1H); 7.02 (d, 1H); 8.07 (d, 1H); 11.73 (s, 1H).

Example 3

3,4-Dichloro-5-methyl-N-{1-[2-(methylsulfinyl) pyrimidin-4-yl]piperidin-4-yl}-1H-pyrrole-2-carboxamide A suspension of 3,4-dichloro-5-methyl-N-{1-[2-(methylthio)pyrimidin-4-yl]piperidin-4-yl}-1H-pyrrole-2-carboxamide (Example 306, 114.6 mg, 0.2863 mmol) in anhydrous DCM (5 ml) at 0° C. was treated with 70% mCPBA (77.6 mg, 0.314 mmol). The reaction was stirred at 0° C. for 30 minutes and was then quenched with 10% aqueous Na$_2$SO$_3$ solution. The phases were separated, and the aqueous portion was extracted with DCM. The combined organic portions were washed with dilute aqueous Na$_2$CO$_3$ solution and brine, dried over Na$_2$SO$_4$, filtered, and concentrated under reduced pressure to give a pale yellow oil that was purified by preparatory HPLC using a gradient of 20-60% CH$_3$CN/H$_2$O (0.1% TFA) to give the TFA salt of the title compound (67.0 mg).

MS (ES$^-$): 414.15, 416.15 for C$_{16}$H$_{19}$Cl$_2$N$_5$O$_2$S $^1$H NMR δ: 1.43 (m, 2H); 1.81 (m, 2H); 2.07 (s, 3H); 2.69 (s, 3H); 3.06 (m, 2H); 4.02 (m, 2H); 4.22 (m, 1H); 6.85 (d, 1H); 7.16 (d, 1H); 7.81 (d, 1H); 11.87 (s, 1H).

Example 4

N-[1-(6-Amino-2-chloropyrimidin-4-yl)piperidin-4-yl]-3,4-dichloro-5-methyl-1H-pyrrole-2-carboxamide 3,4-Dichloro-5-methyl-N-piperidin-4-yl-1H-pyrrole-2-carboxamide hydrochloride (Intermediate 1, 500 mg, 1.6 mmol), 4-amino-2,6-dichloropyrimidine (262 mg, 1.6 mmol), and Et$_3$N (0.45 ml, 3.2 mmol) were combined in DMF (15 ml) and heated at 100° C. under nitrogen for 1 h. Upon cooling to room temperature, the reaction was diluted with EtOAc and water. The aqueous phase was extracted twice with EtOAc, and the combined organic portions were washed with brine, dried over Na$_2$SO$_4$, filtered, and concentrated under reduced pressure to give a brown oil. Approximately 1 ml DMF was added to the oil, followed by the slow addition of water. Trituration resulted in a light brown solid (212 mg) that was collected by filtration. 66 mg of this crude material was purified by preparatory HPLC using a gradient of 20-60% CH$_3$CN/H$_2$O (0.1% TFA) to give the TFA salt of the title compound (21 mg).

MS (ES$^-$): 401.12, 403.13, 405.13 for C$_{15}$H$_{17}$Cl$_3$N$_6$O $^1$H NMR δ: 1.38 (m, 2H); 1.76 (m, 2H); 2.10 (s, 3H); 2.97 (m, 2H); 3.94 (m, 1H); 4.35 (m, 2H); 5.66 (s, 2H); 6.68 (m, 1H); 7.12 (d, 1H); 11.89 (s, 1H).

Example 5

N-{1-[6-(Acetylamino)-2-chloropyrimidin-4-yl]piperidin-4-yl}-3,4-dichloro-5-methyl-1H-pyrrole-2-carboxamide 3,4-Dichloro-5-methyl-N-piperidin-4-yl-1H-pyrrole-2-carboxamide hydrochloride (Intermediate 1, 280 mg, 0.896 mmol), N-(2,6-dichloropyrimidin-4-yl)acetamide (Intermediate 7, 184.5 mg, 0.896 mmol), and TEA (0.25 ml, 1.79 mmol) were combined in DMF (6 ml) and heated at 100° C. under nitrogen for 1 h. Upon cooling to room temperature, the reaction was diluted with EtOAc and water. The phases were separated, and the aqueous portion was extracted twice with EtOAc. The combined organic portions were washed with brine, dried over $Na_2SO_4$, filtered, and concentrated under reduced pressure to give a brown liquid (some DMF still present), which was triturated with water. The resulting light brown solid (76 mg) was purified by preparatory HPLC using a gradient of 20-60% $CH_3CN/H_2O$ (0.1% TFA) to give the TFA salt of the title compound (20 mg).

MS (ES−): 445.14, 447.14, 448.14 for $C_{17}H_{19}Cl_3N_6O_2$ $^1$H NMR δ: 1.45 (m, 2H); 1.82 (m, 2H); 2.01 (s, 3H); 2.11 (s, 3H); 3.09 (m, 2H); 4.04 (m, 2H); 4.22 (m, 1H); 7.15 (d, 1H); 7.30 (s, 1H); 10.67 (s, 1H); 11.90 (s, 1H)

Example 6

Methyl 2-chloro-4-(4-{[(3,4-dichloro-5-methyl-1H-pyrrol-2-yl)carbonyl]amino}piperidin-1-yl)pyrimidine-4-carboxylate A solution of methyl 2,4-dichloropyrimidine-6-carboxylate (commercially available) (0.95 g, 4.6 mmol) in DMF (5 ml) was added dropwise to a solution of 3,4-dichloro-5-methyl-N-piperidin-4-yl-1H-pyrrole-2-carboxamide hydrochloride (Intermediate 1, 0.43 g, 4.6 mmol) and TEA (0.92 g, 9.2 mmol) in DMF (10 ml) under nitrogen. The resultant mixture was stirred for 1 h at room temperature. Water (50 ml) was added to the stirred reaction mixture and the material that precipitated was collected and washed with water/acetonitrile (1:1, 15 ml) to give 1.9 g of the title compound. An analytical sample was purified by reversed-phase HPLC (water/acetonitrile gradient, 20-95%).

MS (ESP): 446.3 (M+H) for $C_{17}H_{18}Cl_3N_5O_3$ $^1$H NMR δ: 1.73-1.83 (m, 2H); 2.14 (d, 2H); 2.39 (s, 3H); 3.40-3.52 (m, 2H); 4.09 (s, 3H); 4.30-4.45 (m, 2H); 4.60-4.80 (m, 1H); 7.46 (d, 1H); 7.60 (s, 1H); 12.2 (s, 1H).

Example 7

6-(4-{[(3,4-Dichloro-5-methyl-1H-pyrrol-2-yl)carbonyl]amino}piperidin-1-yl)-2-(methylthio)pyrimidine-4-carboxylic acid Sodium thiomethoxide (0.275 g, 3.94 mmol) was added to a solution of methyl 2-chloro-6-(4-{[(3,4-dichloro-5-methyl-1H-pyrrol-2-yl)carbonyl]amino}piperidin-1-yl)pyrimidine-4-carboxylate (Example 6, 0.44 g, 0.99 mmol) in DMF (3 ml) under nitrogen. The resultant mixture was stirred at room temperature for 18 h. The reaction was quenched by addition of water (5 ml) and 1 N HCl (5 ml), then diluted with EtOAc (100 ml) and the organic phase was separated. The aqueous phase was extracted with EtOAc (30 ml) and the combined organic layers were washed with brine, dried over $Na_2SO_4$, filtered and concentrated under vacuum. The crude residue was purified by preparative reversed-phase HPLC (water/acetonitrile gradient, 10-95%) to yield 275 mg of the title compound.

MS (ESP): 444.3 (M+H) for $C_{17}H_{19}Cl_2N_5O_3S$ $^1$H NMR δ: 1.40-1.60 (m, 2H); 1.80 (d, 2H); 2.06 (s, 3H); 2.39 (s, 3H); 3.09 (t, 2H); 4.0-4.15 (m, 1H); 4.10-4.50 (m, 2H); 5.50-6.50 (br s, 1H); 6.90 (s, 1H); 7.11 (d, 1H); 11.85 (s, 1H).

Example 8

6-(4-{[(3,4-Dichloro-5-methyl-1H-pyrrol-2-yl)carbonyl]amino}piperidin-1-yl)-N-methoxy-2-(methylthio)pyrimidine-4-carboxamide HATU (197 mg, 0.52 mmol) was added to a solution of TEA (0.14 ml, 1.0 mmol), 6-(4-{[(3,4-dichloro-5-methyl-1H-pyrrol-2-yl)carbonyl]amino}piperidin-1-yl)-2-(methylthio)pyrimidine-4-carboxylic acid (Example 7, 230 mg, 0.52 mmol) and methoxylamine hydrochloride (43 mg, 0.52 mmol) in DMF (3 ml) under nitrogen. The resultant mixture was stirred overnight at room temperature, then diluted with EtOAc (50 ml) and water (10 ml) and the organic phase was separated. The organic phase was washed with 1 N HCl (5 ml), saturated $NaHCO_3$ solution (5 ml) and brine (5 ml). The aqueous layers were back extracted with EtOAc (25 ml). The combined organic layers were dried over $Na_2SO_4$, filtered and concentrated under vacuum to give 400 mg of crude product. which was purified by preparative reversed-phase HPLC (water/acetonitrile gradient, 20-95%) to give 200 mg of the title compound.

MS (ESP): 473.3 (M+H) for $C_{18}H_{22}Cl_2N_6O_3S$ $^1$H NMR δ: 1.42-1.52 (m, 2H); 1.80-1.88 (m, 2H); 2.10 (s, 3H); 2.44 (s, 3H); 3.16 (t, 2H); 3.61 (s, 3H); 4.00-4.14 (m, 1H); 4.20-4.50 (m, 2H); 6.94 (s, 1H); 7.16 (d, 1H); 11.70 (s, 1H); 11.90 (s, 1H).

Example 9

Methyl 6-(4-{[(3,4-dichloro-5-methyl-1H-pyrrol-2-yl)carbonyl]amino}piperidin-1-yl)-2-morpholin-4-ylpyrimidine-4-carboxylate A solution of methyl 2-chloro-6-(4-{[(3,4-dichloro-5-methyl-1H-pyrrol-2-yl)carbonyl]amino}piperidin-1-yl)pyrimidine-4-carboxylate (Example 6, 300 mg, 0.67 mmol), morpholine (58 mg, 0.67 mmol) and TEA (0.09 ml, 0.67 mmol) in DMF (3 ml) were stirred at 60° C. under nitrogen for 4 hours. The mixture was cooled to room temperature and diluted with EtOAc (75 ml) and water (10 ml). The organic layer was separated, dried over $Na_2SO_4$, filtered and concentrated in vacuo to yield 320 mg of the title compound. An analytical sample was purified by reversed-phase HPLC (water/acetonitrile gradient, 20-95%).

MS (ESP): 497.4 (M+H) for $C_{21}H_{26}Cl_2N_6O_4$ $^1$H NMR δ: 1.40-1.58 (m, 2H); 1.81 (d, 2H); 2.10 (s, 3H); 3.06 (t, 2H); 3.58 (br s, 8H); 3.75 (s, 3H); 3.95-4.10 (m, 1H); 4.15-4.40 (m, 2H); 6.65 (s, 1H); 7.16 (d, 1H); 11.90 (s, 1H).

Example 10

6-(4-{[(3,4-Dichloro-5-methyl-1H-pyrrol-2-yl)carbonyl]amino}piperidin-1-yl)-N-methoxy-2-(methylsulfonyl)pyrimidine-4-carboxamide mCPBA (70%, 104 mg, 0.42 mmol) was added to a suspension of 6-(4-{[(3,4-dichloro-5-methyl-1H-pyrrol-2-yl)

carbonyl]amino}piperidin-1-yl)-N-methoxy-2-(methylthio)pyrimidine-4-carboxamide (Example 8, 100 mg, 0.21 mmol) in DCM (15 ml) and the resultant mixture was stirred for 3 h. The reaction mixture was diluted with DCM (50 ml), washed with saturated $Na_2CO_3$ solution (10 ml), dried over $Na_2SO_4$, filtered and concentrated under vacuum. The residue was purified by reversed-phase HPLC (water/acetonitrile gradient, 15-95%).

MS (ESP): 505.3 (M+H) for $C_{18}H_{22}Cl_2N_6O_5S$ $^1$H NMR δ: 1.45-1.62 (m, 2H); 1.88 (d, 2H); 2.11 (s, 3H); 3.15-3.35 (m, 2H); 3.33 (s, 3H); 3.66 (s, 3H); 4.02-4.18 (m, 2H); 4.45-4.70 (m, 1H); 7.18 (d, 1H); 7.40 (s, 1H); 11.91 (s, 1H); 11.98 (s, 1H).

Example 11

2-Chloro-6-(4-{[(3,4-dichloro-5-methyl-1H-pyrrol-2-yl)carbonyl]amino}piperidin-1-yl)-N-methoxypyrimidine-4-carboxamide The title compound was synthesised by an analogous method to Example 8 starting from 2-chloro-6-(4-{[(3,4-dichloro-5-methyl-1H-pyrrol-2-yl)carbonyl]amino}piperidin-1-yl)pyrimidine-4-carboxylic acid (Example 32) and methoxylamine hydrochloride.

MS (ESP): 461.2 (M+H) for $C_{17}H_{19}Cl_3N_6O_3$ $^1$H NMR δ: 1.45-1.59 (m, 2H); 1.89 (d, 2H); 2.15 (s, 3H); 3.12-3.30 (m, 2H); 3.65 (s, 3H); 4.04-4.17 (m, 2H); 4.35-4.62 (m, 1H); 7.20 (d, 1H); 7.26 (s, 1H); 11.95 (s, 2H).

Example 12

6-(4-{[(3,4-Dichloro-5-methyl-1H-pyrrol-2-yl)carbonyl]amino}piperidin-1-yl)-N-methoxy-2-morpholin-4-ylpyrimidine-4-carboxamide The title compound was synthesised by an analogous method to Example 8 starting from 6-(4-{[(3,4-dichloro-5-methyl-1H-pyrrol-2-yl)carbonyl]amino}piperidin-1-yl)-2-morpholin-4-ylpyrimidine-4-carboxylic acid (Example 310) and methoxylamine hydrochloride.

MS (ESP): 512.4 (M+H) for $C_{21}H_{27}Cl_2N_7O_4$ $^1$H NMR δ: 1.40-1.65 (m, 2H); 1.81 (d, 2H); 2.10 (s, 3H); 3.03 (t, 2H); 3.50-3.70 (m, 8H); 3.62 (s, 3H); 3.90-4.10 (m, 1H); 4.15-4.32 (m, 2H); 6.57 (s, 1H); 7.15 (d, 1H); 11.61 (s, 1H); 11.90 (s, 1H).

Example 13

2-Chloro-6-(4-{[(3,4-dichloro-5-methyl-1H-pyrrol-2-yl)carbonyl]amino}piperidin-1-yl)-N-(2-morpholin-4-ylethyl)pyrimidine-4-carboxamide A solution of methyl 2-chloro-6-(4-{[(3,4-dichloro-5-methyl-1H-pyrrol-2-yl)carbonyl]amino}piperidin-1-yl)pyrimidine-4-carboxylate (Example 6: 380 mg, 0.85 mmol), 2-morpholin-4-ylethanamine (222 mg, 1.70 mmol) and TEA (0.12 ml, 0.85 mmol) in DMF (3 ml) were stirred at 60° C. under nitrogen for 18 hours. The mixture was cooled to room temperature and diluted with EtOAc (75 ml) and water (10 ml). The organic layer was separated, dried over $Na_2SO_4$, filtered and concentrated under vacuum. Purification by reversed-phase HPLC (water/acetonitrile gradient, 5-95%) provided 110 mg of the title compound.

MS (ESP): 544.5 (M+H) for $C_{22}H_{28}Cl_3N_7O_3$ $^1$H NMR δ: 1.40-1.55 (m, 2H); 1.88 (d, 2H); 2.11 (s, 3H); 2.95-3.30 (m, 6H); 3.40-3.65 (m, 6H); 3.70-4.50 (m, 5H); 7.18 (d, 1H); 7.26 (s, 1H); 8.86 (t, 1H); 11.94 (s, 1H).

Example 14

6-(4-{[(3,4-Dichloro-5-methyl-1H-pyrrol-2-yl)carbonyl]amino}piperidin-1-yl)-2-(methylsulfonyl)pyrimidine-4-carboxylic acid mCPBA (70%, 164 mg, 0.67 mmol) was added to a suspension of 6-(4-{[(3,4-dichloro-5-methyl-1H-pyrrol-2-yl)carbonyl]amino}piperidin-1-yl)-2-(methylthio)pyrimidine-4-carboxylic acid (Example 7, 151 mg, 0.34 mmol) in DCM (15 ml) at 0° C. and the resultant mixture was stirred for 3 h. The mixture was allowed to slowly warm to room temperature over the 3 h period. The reaction mixture was diluted with DCM (50 ml), dried over $Na_2SO_4$, filtered and concentrated under vacuum. The residue was purified by reversed phase HPLC (water/acetonitrile gradient, 5-95%) to yield 32 mg of the title compound.

MS (ESP): 476.1 (M+H) for $C_{17}H_{19}Cl_2N_5O_5S$ $^1$H NMR δ: 1.45-1.59 (m, 2H); 1.89 (d, 2H); 2.11 (s, 3H); 3.10-3.30 (m, 2H); 3.27 (s, 3H); 4.00-4.15 (m, 2H); 4.48-4.70 (m, 1H); 7.18 (d, 1H); 7.46 (s, 1H); 11.92 (s, 1H); 13.80 (s, 1H).

Example 15

6-(4-{[(3,4-Dichloro-5-methyl-1H-pyrrol-2-yl)carbonyl]amino}piperidin-1-yl)-N-methoxy-2-(methylsulfinyl)pyrimidine-4-carboxamide mCPBA (70%, 86 mg, 0.35 mmol) was added to a suspension of 6-(4-{[(3,4-dichloro-5-methyl-1H-pyrrol-2-yl)carbonyl]amino}piperidin-1-yl)-N-methoxy-2-(methylthio)pyrimidine-4-carboxamide (Example 8, 166 mg, 0.35 mmol) in DCM (12 ml) at 0° C. and the resultant mixture was stirred for 2 h. The reaction mixture was diluted with DCM (50 ml), washed with $Na_2SO_3$ solution (5%, 10 ml), dried over $Na_2SO_4$, filtered and concentrated under vacuum. Purification by reversed-phase HPLC (water/acetonitrile gradient, 10-95%) gave 45 mg of the title product.

MS (ESP): 489.1 (M+H) for $C_{18}H_{22}Cl_2N_6O_4S$ $^1$H NMR δ: 1.40-1.60 (m, 2H); 1.88 (d, 2H); 2.11 (s, 3H); 2.84 (s, 3H); 3.21 (t, 2H); 3.64 (s, 3H); 4.00-4.15 (m, 2H); 4.40-4.80 (m, 1H); 7.18 (d, 1H); 7.25 (s, 1H); 11.91 (s, 2H).

Example 16

6-(4-{[(3,4-Dichloro-5-methyl-1H-pyrrol-2-yl)carbonyl]amino}piperidin-1-yl)-2-[(2-hydroxyethyl)thio]pyrimidine-4-carboxylic acid A suspension of methyl 2-chloro-6-(4-{[(3,4-dichloro-5-methyl-1H-pyrrol-2-yl)carbonyl]amino}piperidin-1-yl)pyrimidine-4-carboxylate (Example 6, 150 mg, 0.34 mmol), 2-mercaptoethanol (31 mg, 0.40 mmol) and potassium carbonate (139 mg, 1.01 mmol) in DMF (3 ml) were stirred at 65° C. under nitrogen for 3 hours. The mixture was cooled to room temperature and diluted with EtOAc (75 ml) and 1 N HCl (3 ml). The organic layer was separated, dried over $Na_2SO_4$, filtered and concentrated under vacuum. Purification of the residue by reversed-phase HPLC (water/acetonitrile gradient, 10-95%) gave 39 mg of the title compound.

MS (ESP): 474.2 (M+H) for $C_{18}H_{21}Cl_2N_5O_4S$ $^1$H NMR δ: 1.40-1.55 (m, 2H); 1.83 (d, 2H); 2.11 (s, 3H); 3.07-3.20 (m, 4H); 3.52-3.62 (m, 2H); 4.00-4.40 (m, 5H); 7.00 (s, 1H); 7.16 (d, 1H); 11.90 (s, 1H).

Example 17

Methyl 6-(4-{[(3,4-dichloro-5-methyl-1H-pyrrol-2-yl)carbonyl]amino}piperidin-1-yl)-2-[(2-hydroxyethyl)thio]pyrimidine-4-carboxylate The title compound was also isolated from Example 16.
MS (ESP): 488.2 (M+H) for $C_{19}H_{23}Cl_2N_5O_4S$
$^1$H NMR δ: 1.40-1.55 (m, 2H); 1.84 (d, 2H); 2.11 (s, 3H); 3.05-3.22 (m, 4H); 3.56 (t, 2H); 4.00-4.40 (m, 4H); 7.00 (s, 1H); 7.16 (d, 1H); 11.91 (s, 1H).

Example 18

2-Chloro-6-(4-{[(4-chloro-5-methyl-1H-pyrrol-2-yl)carbonyl]amino}piperidin-1-yl)isonicotinamide Diisopropylethylamine (0.34 ml, 2.0 mmol), EDC (0.121 g, 0.63 mmol) and HOAT (0.086 g, 0.63 mmol) were added to a stirred solution of 4-chloro-5-methyl-1H-pyrrole-2-carboxylic acid (Intermediate 8, 0.1 g, 0.63 mmol) in DMF (2 ml) at room temperature. The resultant solution was stirred for 15 mins then a solution of 2-(4-aminopiperidin-1-yl)-6-chloroisonicotinamide hydrochloride (Intermediate 70, 0.19 g, 0.75 mmol) in 3 ml of DMF was added. The reaction was concentrated after 2 hours and the residue was partitioned between water and EtOAc. The aqueous layer was extracted with EtOAc (×2), the combined organic layers were washed with 1 N HCl, water and brine, then dried over magnesium sulfate and concentrated under vacuum. The residue was purified by reverse phase chromatography (water/acetonitrile gradient, 20-95%) to give the title product as a white solid.
MS (ES): 396 (M+1) for $C_{17}H_{19}Cl_2N_5O_2$
$^1$H NMR δ: 1.46 (m, 2H); 1.82 (m, 2H); 2.13 (s, 3H); 3.04 (t, 2H); 4.03 (m, 1H); 4.25 (m, 2H); 6.74 (s, 1H); 6.97 (s, 1H); 7.19 (s, 1H); 7.69 (m, 2H); 8.15 (s, 1H); 11.59 (brs, 1H)

Example 19

2-(4-{[(4-Bromo-5-ethyl-1H-pyrrol-2-yl)carbonyl]amino}piperidin-1-yl)-6-chloroisonicotinamide Diisopropylethylamine (0.28 ml, 1.64 mmol), EDC (0.088 g, 0.46 mmol) and HOAT (0.063 g, 0.46 mmol) were added to a stirred solution of 4-bromo-5-ethyl-1H-pyrrole-2-carboxylic acid (Intermediate 10, 0.1 g, 0.46 mmol) in DMF (1.5 ml) at room temperature. The resultant solution was stirred for 30 mins and a solution of 2-(4-aminopiperidin-1-yl)-6-chloroisonicotinamide hydrochloride (Intermediate 70, 0.14 g, 0.55 mmol) in 3 ml of DMF was added. The reaction was stirred overnight, then concentrated under vacuum and the residue was partitioned between water and EtOAc. The aqueous layer was extracted with EtOAc (×2) and the combined organic extracts were washed with 1 N HCl, water and brine, dried over $MgSO_4$ and concentrated under vacuum. The residue was purified by reverse phase chromatography to give the desired product as a white solid.
MS (ES): 456 (M+1) for $C_{18}H_{21}BrClN_5O_2$
$^1$H NMR δ: 1.09 (t, 3H); 1.47 (m, 2H); 1.82 (m, 2H); 3.04 (t, 2H); 3.30 (q, 2H); 4.03 (m, 1H); 4.25 (m, 2H); 6.79 (s, 1H); 6.97 (s, 1H); 7.19 (s, 1H); 7.69 (s, 1H); 7.76 (d, 1H); 8.15 (s, 1H); 11.64 (brs, 1H)

Example 20

2-Chloro-6-(4-{[(3,4-dichloro-5-methyl-1H-pyrrol-2-yl)carbonyl]amino}piperidin-1-yl)isonicotinamide Diisopropylethylamine (0.063 ml, 0.37 mmol), EDC (0.095 g, 0.31 mmol) and HOAT (0.042 g, 0.31 mmol) were added to a stirred solution of 3,4-dichloro-5-methyl-1H-pyrrole-2-carboxylic acid (Intermediate 3, 0.060 g, 0.31 mmol) in DMF (1.0 ml) at room temperature. The resultant solution was stirred for 30 mins and a solution of 2-(4-aminopiperidin-1-yl)-6-chloroisonicotinamide hydrochloride (Intermediate 70, 0.096 g, 0.37 mmol) in 1 ml of DMF was added. The reaction was stirred overnight, then concentrated under vacuum and the residue was partitioned between water and EtOAc. The aqueous layer was extracted with EtOAc (×2) and the combined organic extracts were washed with 1 N HCl, water and brine, dried over $MgSO_4$ and concentrated under vacuum. The residue was purified by reverse phase chromatography to give the desired product as a white solid (40 mg).
MS (ES): 431 (M+1) for $C_{17}H_{18}Cl_3N_5O_2$
$^1$H NMR δ: 1.56 (m, 2H); 1.88 (m, 2H); 2.17 (s, 3H); 3.11 (t, 2H); 4.10 (m, 1H); 4.25 (m, 2H); 6.97 (s, 1H); 7.18 (s, 1H); 7.23 (d, 1H); 7.69 (s, 1H); 8.14 (s, 1H); 11.95 (s, 1H)

Example 21

2-Chloro-6-(4-{[(4-cyano-5-methyl-1H-pyrrol-2-yl)carbonyl]amino}piperidin-1-yl)isonicotinamide Diisopropylethylamine (0.1 ml, 0.56 mmol), EDC (0.09 g, 0.46 mmol) and HOAT (0.064 g, 0.46 mmol) were added to a stirred solution of 4-cyano-5-methyl-1H-pyrrole-2-carboxylic acid (Intermediate 13, 0.07 g, 0.47 mmol) in DMF (1.5 ml) at room temperature. The resultant solution was stirred for 30 mins and a solution of 2-(4-aminopiperidin-1-yl)-6-chloroisonicotinamide hydrochloride (Intermediate 70, 0.16 g, 0.56 mmol) in 1 ml of DMF was added. The reaction was stirred overnight, then concentrated under vacuum and the residue was partitioned between water and EtOAc. The aqueous layer was extracted with EtOAc (×2) and the combined organic extracts were washed with 1 N HCl, water and brine, dried over $MgSO_4$ and concentrated under vacuum. The residue was purified by reverse phase chromatography to give the desired product as a white solid (13 mg).
MS (ES): 387 (M+1) for $C_{18}H_{19}ClN_6O_2$
$^1$H NMR δ: 1.48 (m, 2H); 1.84 (m, 2H); 2.31 (s, 3H); 3.05 (t, 2H); 4.04 (m, 1H); 4.26 (m, 2H); 6.98 (s, 1H); 7.03 (s, 1H); 7.19 (s, 1H); 7.69 (s, 1H); 7.98 (d, 1H); 8.15 (s, 1H); 12.23 (s, 1H)

Example 22

2-Chloro-6-(4-{[(4-chloro-5-ethyl-1H-pyrrol-2-yl)carbonyl]amino}piperidin-1-yl)isonicotinamide Title compound was synthesized by an analogous method to Example 18 by coupling 2-(4-aminopiperidin-1-yl)-6-chloroisonicotinamide hydrochloride (Intermediate 70) with 4-chloro-5-ethyl-1H-pyrrole-2-carboxylic acid (Intermediate 71).
MS (ES): 410 (M+1) for $C_{18}H_{21}Cl_2N_5O_2$
$^1$H NMR δ: 1.10 (t, 3H); 1.45 (m, 2H); 1.83 (m, 2H); 2.54 (q, 2H); 3.04 (t, 2H); 4.03 (m, 1H); 4.27 (m, 2H); 6.73 (d, 1H); 6.97 (s, 1H); 7.19 (s, 1H); 7.69 (s, 1H); 7.76 (d, 1H); 8.15 (s, 1H); 11.57 (s, 1H)

Example 23

2-Chloro-6-(4-{[(3,5-dimethyl-1H-pyrrol-2-yl)carbonyl]amino}piperidin-1-yl)isonicotinamide Title compound was synthesized by an analogous method to Example 18 using 2-(4-aminopiperidin-1-yl)-6-chloroisonicotinamide hydrochloride (Intermediate 70) and 3,5-dimethyl-1H-pyrrole-2-carboxylic acid (commercially available).

MS (ES): 476 (M+1) for $C_{18}H_{22}ClN_5O_2$
$^1$H NMR δ: 1.46 (m, 2H); 1.87 (m, 2H); 2.13 (s, 3H); 2.19 (s, 3H); 3.09 (t, 2H); 4.03 (m, 1H); 4.23 (m, 2H); 5.63 (s, 1H); 6.97 (s, 1H); 7.00 (d, 1H); 7.19 (s, 1H); 7.69 (s, 1H); 8.15 (s, 1H); 10.69 (s, 1H)

Example 24

2-Chloro-6-(4-{[(3,4-dichloro-5-ethyl-1H-pyrrol-2-yl)carbonyl]amino}piperidin-1-yl)isonicotinamide Title compound was synthesized by an analogous method to Example 18 by coupling 2-(4-aminopiperidin-1-yl)-6-chloroisonicotinamide hydrochloride (Intermediate 70) with 3,4-dichloro-5-ethyl-1H-pyrrole-2-carboxylic acid (Intermediate 73).

MS (ES): 446 (M+1) for $C_{18}H_{20}Cl_2N_5O_2$
$^1$H NMR δ: 1.12 (t, 3H); 1.56 (m, 2H); 1.87 (m, 2H); 2.56 (q, 2H); 3.11 (t, 2H); 4.06 (m, 1H); 4.24 (m, 2H); 6.97 (s, 1H); 7.18 (s, 1H); 7.25 (d, 1H); 7.69 (s, 1H); 8.14 (s, 1H); 11.92 (s, 1H)

Example 25

2-Chloro-6-(4-{[(3-ethyl-4,5-dimethyl-1H-pyrrol-2-yl)carbonyl]amino}piperidin-1-yl)isonicotinamide Title compound was synthesized by an analogous method to Example 18 by coupling 2-(4-aminopiperidin-1-yl)-6-chloroisonicotinamide hydrochloride (Intermediate 70) with 3-ethyl-4,5-dimethyl-1H-pyrrole-2-carboxylic acid (commercially available).

MS (ES): 404 (M+1) for $C_{20}H_{26}Cl_3N_5O_2$
$^1$H NMR δ: 0.97 (t, 3H); 1.43 (m, 2H); 1.82 (s, 3H); 1.90 (m, 2H); 2.08 (s, 3H); 2.65 (q, 2H); 3.07 (t, 2H); 3.99 (m, 1H); 4.22 (m, 2H); 6.96 (s, 1H); 7.06 (d, 1H); 7.18 (s, 1H); 7.68 (s, 1H); 8.14 (s, 1H); 10.48 (s, 1H)

Example 26

2-Chloro-6-(4-{[(3,4-diethyl-5-methyl-1H-pyrrol-2-yl)carbonyl]amino}piperidin-1-yl)isonicotinamide Title compound was synthesized by an analogous method to Example 18 by coupling 2-(4-aminopiperidin-1-yl)-6-chloroisonicotinamide hydrochloride (Intermediate 70) with 3,4-diethyl-5-methyl-1H-pyrrole-2-carboxylic acid (commercially available).

MS (ES): 418 (M+1) for $C_{21}H_{28}ClN_5O_2$
$^1$H NMR δ: 0.94-1.04 (m, 6H); 1.43 (m, 2H); 1.90 (m, 2H); 2.08 (s, 3H); 2.28 (q, 2H); 2.63 (q, 2H); 3.07 (t, 2H); 4.08 (m, 1H); 4.20 (m, 2H); 6.96 (s, 1H); 7.07 (d, 1H); 7.18 (s, 1H); 7.66 (s, 1H); 8.14 (s, 1H); 10.51 (s, 1H)

Example 27

2-Chloro-6-(4-{[(4-chloro-3,5-dimethyl-1H-pyrrol-2-yl)carbonyl]amino}piperidin-1-yl)isonicotinamide Title compound was synthesized by an analogous method to Example 18 by coupling 2-(4-aminopiperidin-1-yl)-6-chloroisonicotinamide hydrochloride (Intermediate 70) with 4-chloro-3,5-dimethyl-1H-pyrrole-2-carboxylic acid (Intermediate 75).

MS (ES): 408 (M−1) for $C_{18}H_{21}Cl_2N_5O_2$
$^1$H NMR δ: 1.47 (m, 2H); 1.87 (m, 2H); 2.13 (s, 3H); 2.16 (s, 3H); 3.10 (t, 2H); 4.00 (m, 1H); 4.21 (m, 2H); 6.96 (s, 1H); 7.18 (s, 1H); 7.20 (d, 1H); 7.68 (s, 1H); 8.14 (s, 1H); 1.1.17 (s, 1H)

Example 28

2-Chloro-6-(4-{[(4-cyano-3,5-dimethyl-1H-pyrrol-2-yl)carbonyl]amino}piperidin-1-yl)isonicotinamide Title compound was synthesized by an analogous method to Example 18 by coupling 2-(4-aminopiperidin-1-yl)-6-chloroisonicotinamide hydrochloride (Intermediate 70) with 4-cyano-3,5-dimethyl-1H-pyrrole-2-carboxylic acid (commercially available).

MS (ES): 399 (M−1) for $C_{19}H_{21}ClN_6O_2$
$^1$H NMR δ: 1.48 (m, 2H); 1.86 (m, 2H); 2.25 (s, 3H); 2.28 (s, 3H); 3.08 (t, 2H); 4.01 (m, 1H); 4.21 (m, 2H); 6.96 (s, 1H); 7.18 (s, 1H); 7.40 (d, 1H); 7.68 (s, 1H); 8.13 (s, 1H); 11.77 (s, 1H)

Example 29

2-(4-{[(3,4-Dichloro-5-methyl-1H-pyrrol-2-yl)carbonyl]amino}piperidin-1-yl)-1,3-thiazole-5-carboxamide Diisopropylethylamine (0.19 ml, 1.12 mmol), EDC (0.098 g, 0.51 mmol) and HOAT (0.070 g, 0.51 mmol) were added to a stirred solution of 3,4-dichloro-5-methyl-1H-pyrrole-2-carboxylic acid (Intermediate 3, 0.1 g, 0.51 mmol) in DMF (1.5 ml) at room temperature. The resultant solution was stirred for 30 mins and 2-(4-aminopiperidin-1-yl)-1,3-thiazole-5-carboxamide hydrochloride (Intermediate 81; 0.163 g, 0.62 mmol) was added. The reaction was stirred at room temperature overnight under nitrogen. The reaction was stirred overnight, then concentrated under vacuum and the residue was partitioned between water and EtOAc. The aqueous layer was extracted with EtOAc and the combined organic extracts were washed with 1 N HCl, water and brine, dried over MgSO$_4$ and concentrated under vacuum. The residue was purified by reverse phase chromatography (water/acetonitrile gradient, 20-95%) to give the desired product as a white solid (50 mg).

MS (ES): 402 (M+1) for $C_{15}H_{17}Cl_2N_5O_2S$
$^1$H NMR δ: 1.58 (m, 2H); 1.82 (m, 2H); 2.11 (s, 3H); 3.17 (t, 2H); 3.81 (m, 2H); 3.97 (m, 1H); 7.07 (brs, 1H); 7.20 (d, 1H); 7.61 (brs, 1H); 7.71 (s, 1H); 11.90 (s, 1H)

Example 30

2-(4-{[(3,4-Dichloro-5-ethyl-1H-pyrrol-2-yl)carbonyl]amino}piperidin-1-yl)-1,3-thiazole-5-carboxamide Title compound was synthesized by an analogous method to Example 29 by coupling 3,4-dichloro-5-ethyl-1H-pyrrole-2-carboxylic acid (Intermediate 73) with 2-(4-aminopiperidin-1-yl)-1,3-thiazole-5-carboxamide hydrochloride (Intermediate 81).

MS (ES): 416 (M+1) for $C_{16}H_{19}Cl_2N_5O_2S$
$^1$H NMR δ: 1.11 (t, 3H); 1.66 (m, 2H); 1.89 (m, 2H); 2.56 (q, 2H); 3.24 (t, 2H); 3.81 (m, 2H); 4.06 (m, 1H); 7.14 (brs, 1H); 7.31 (d, 1H); 7.71 (brs, 1H); 7.78 (s, 1H); 11.94 (s, 1H)

Example 31

6-(4-{[(4-Bromo-5-methyl-1H-pyrrol-2-yl)carbonyl]amino}piperidin-1-yl)-2-chloropyrimidine-4-carboxylic acid Lithium hydroxide (2 M, 4 ml) was warmed to 40° C. and a solution of methyl 6-(4-{[(4-bromo-5-methyl-1H-pyrrol-2-yl)carbonyl]amino}piperidin-1-yl)-2-chloropyrimidine-4-carboxylate (Example 73, 0.180 g, 0.394 mmol) in MeOH was added. The reaction was stirred at 40° C. for 30 mins. The MeOH was removed and the aqueous solution was cooled to 0° C. and it was acidified with 6 M HCl. The acidic solution was extracted with EtOAc, dried over MgSO$_4$ and concentrated to give pink solid (0.15 g, 86%). An analytical sample was purified by reversed phase HPLC (acetonitrile/water (0.1% TFA), 20-95%).

MS (ES): 443 (M+1) for $C_{16}H_{17}BrClN_5O_3$
$^1$H NMR δ: 1.45 (m, 2H); 1.88 (m, 2H); 2.12 (s, 3H); 3.17 (m, 2H); 3.81 (m, 2H); 4.06 (m, 1H); 6.79 (s, 1H); 7.37 (s, 1H); 7.76 (d, 1H); 11.67 (s, 1H)

Example 32

2-Chloro-6-(4-{[(3,4-dichloro-5-methyl-1H-pyrrol-2-yl)carbonyl]amino}piperidin-1-yl)pyrimidine-4-carboxylic acid Title compound was synthesized from methyl 2-chloro-6-(4-{[(3,4-dichloro-5-methyl-1H-pyrrol-2-yl)carbonyl]amino}piperidin-1-yl)pyrimidine-4-carboxylate (Example 6) by an analogous method to Example 31.

MS (ES): 432 (M+1) for $C_{16}H_{16}Cl_3N_5O_3$
$^1$H NMR δ: 1.57 (m, 2H); 1.91 (m, 2H); 2.17 (s, 3H); 3.21 (m, 2H); 4.11 (m, 1H); 4.36 (m, 2H); 7.22 (d, 1H); 7.33 (s, 1H); 11.96 (s, 1H)

Example 33

6-(4-{[(4-Bromo-5-methyl-1H-pyrrol-2-yl)carbonyl]amino}piperidin-1-yl)-2-chloro-N-methoxypyrimidine-4-carboxamide Title compound was synthesized by an analogous method to Example 8 by coupling 6-(4-{[(4-bromo-5-methyl-1H-pyrrol-2-yl)carbonyl]amino}piperidin-1-yl)-2-chloropyrimidine-4-carboxylic acid (Example 31) with methoxylamine hydrochloride (commercially available).

MS (ES): 473 (M+1) for $C_{17}H_{20}BrClN_6O_3$
$^1$H NMR δ: 1.43 (m, 2H); 1.85 (m, 2H); 2.10 (s, 3H); 3.24 (m, 2H); 3.16 (t, 3H); 4.06 (m, 1H); 4.71 (m, 2H); 6.79 (s, 1H); 7.26 (s, 1H); 7.74 (d, 1H); 11.65 (s, 1H); 11.94 (s, 1H)

Example 34

6-(4-{[(4-Bromo-5-methyl-1H-pyrrol-2-yl)carbonyl]amino}piperidin-1-yl)-N-methoxy-2-(methylthio)pyrimidine-4-carboxamide Title compound was synthesized by an analogous method to Example 8 by coupling 6-(4-{[(4-bromo-5-methyl-1H-pyrrol-2-yl)carbonyl]amino}piperidin-1-yl)-2-(methylthio)pyrimidine-4-carboxylic acid (Example 35) with methoxylamine hydrochloride (commercially available).

MS (ES): 484 (M+1) for $C_{18}H_{23}BrN_6O_3S$
$^1$H NMR δ: 1.38 (m, 2H); 1.84 (m, 2H); 2.11 (s, 3H); 2.50 (s, 3H); 3.10 (t, 2H); 3.67 (s, 3H); 4.03 (m, 1H); 4.37 (m, 2H); 6.78 (s, 1H); 6.95 (s, 1H); 7.74 (d, 1H); 11.66 (s, 1H); 11.75 (s, 1H)

Example 35

6-(4-{[(4-Bromo-5-methyl-1H-pyrrol-2-yl)carbonyl]amino}piperidin-1-yl)-2-(methylthio)pyrimidine-4-carboxylic acid Title compound was synthesized from methyl 6-(4-{[(4-bromo-5-methyl-1H-pyrrol-2-yl)carbonyl]amino}piperidin-1-yl)-2-chloropyrimidine-4-carboxylate (Example 73) by an analogous method to Example 7.

MS (ES): 455 (M+1) for $C_{17}H_{20}BrN_5O_3S$
$^1$H NMR δ: 1.44 (m, 2H); 1.86 (m, 2H); 2.12 (s, 3H); 2.46 (s, 3H); 3.12 (t, 2H); 4.06 (m, 1H); 4.36 (m, 2H); 6.79 (s, 1H); 7.06 (s, 1H); 7.75 (d, 1H); 11.67 (s, 1H); 11.66 (s, 1H)

Example 36

6-(4-{[(4-Bromo-5-methyl-1H-pyrrol-2-yl)carbonyl]amino}piperidin-1-yl)-2-chloropyrimidine-4-carboxamide Title compound was synthesized by an analogous method to Example 8 by coupling 6-(4-{[(4-bromo-5-methyl-1H-pyrrol-2-yl)carbonyl]amino}piperidin-1-yl)-2-chloropyrimidine-4-carboxylic acid (Example 31) with 2 M ammonia in MeOH.

MS (ES): 443 (M+1) for $C_{16}H_{18}BrClN_6O_2$
$^1$H NMR δ: 1.45 (m, 2H); 1.90 (m, 2H); 2.12 (s, 3H); 3.18 (t, 2H); 4.06 (m, 1H); 4.39 (m, 2H); 6.79 (s, 1H); 7.30 (s, 1H); 7.79 (d, 1H); 7.83 (s, 1H); 7.95 (s, 1H); 11.68 (s, 1H)

Example 37

2-Chloro-6-(4-{[(3,4-dichloro-5-methyl-1H-pyrrol-2-yl)carbonyl]amino}piperidin-1-yl)pyrimidine-4-carboxamide Title compound was synthesized by an analogous method to Example 8 by coupling 2-chloro-6-(4-{[(3,4-dichloro-5-methyl-1H-pyrrol-2-yl)carbonyl]amino}piperidin-1-yl)pyrimidine-4-carboxylic acid (Example 32) with 2 M ammonia in MeOH.

MS (ES): 431 (M+1) for $C_{16}H_{17}Cl_3N_6O_2$
$^1$H NMR δ: 1.56 (m, 2H); 1.90 (m, 2H); 2.16 (s, 3H); 3.30 (t, 2H); 4.12 (m, 1H); 4.36 (m, 2H); 7.23 (d, 1H); 7.30 (s, 1H); 7.82 (s, 1H); 7.94 (s, 1H); 11.97 (s, 1H)

Example 38

6-(4-{[(4-Bromo-5-methyl-1H-pyrrol-2-yl)carbonyl]amino}piperidin-1-yl)-2-(methylthio)pyrimidine-4-carboxamide Title compound was synthesized by an analogous method to Example 8 by coupling 6-(4-{[(4-bromo-5-methyl-1H-pyrrol-2-yl)carbonyl]amino}piperidin-1-yl)-2-(methylthio)pyrimidine-4-carboxylic acid (Example 35) with 2 M ammonia in MeOH (commercially available).

MS (ES): 454 (M+1) for $C_{17}H_{21}BrN_6O_2S$
$^1$H NMR δ: 1.43 (m, 2H); 1.88 (m, 2H); 2.12 (s, 3H); 2.46 (s, 3H); 3.11 (t, 2H); 4.04 (m, 1H); 4.45 (brs, 2H); 6.78 (s, 1H); 7.04 (s, 1H); 7.74 (s, 2H); 7.93 (s, 1H); 11.67 (s, 1H).

Example 39

6-(4-{[(3,4-Dichloro-5-methyl-1H-pyrrol-2-yl)carbonyl]amino}piperidin-1-yl)-N,2-dimethoxypyrimidine-4-carboxamide The title compound was synthesised by an analogous method to Example 8 starting from 6-(4-{[(3,4-dichloro-5-methyl-1H-pyrrol-2-yl)carbonyl]amino}piperidin-1-yl)-2-methoxypyrimidine-4-carboxylic acid (Example 311) and methoxylamine hydrochloride.

MS (ES): 457 (M+1) for $C_{18}H_{22}Cl_2N_6O_4$
$^1$H NMR δ: 1.52 (m, 2H); 1.88 (m, 2H); 2.16 (s, 3H); 3.17 (t, 2H); 3.67 (s, 3H); 3.87 (s, 3H); 4.09 (m, 1H); 4.32 (m, 2H); 6.96 (s, 1H); 7.22 (d, 1H); 11.81 (s, 1H); 11.96 (s, 1H)

Example 40

6-(4-{[(3,4-Dichloro-5-methyl-1H-pyrrol-2-yl)carbonyl]amino}piperidin-1-yl)-2-ethoxy-N-methoxy-pyrimidine-4-carboxamide The title compound was synthesised by an analogous method to Example 8 starting from 6-(4-{[(3,4-dichloro-5-methyl-1H-pyrrol-2-yl)carbonyl]amino}piperidin-1-yl)-2-ethoxypyrimidine-4-carboxylic acid (Example 312) and methoxylamine hydrochloride.

MS (ES): 471 (M+1) for $C_{19}H_{24}Cl_2N_6O_4$
$^1$H NMR δ: 1.28 (t, 3H); 1.52 (m, 2H); 1.88 (m, 2H); 2.16 (s, 3H); 3.16 (t, 2H); 3.66 (s, 3H); 4.09 (m, 1H); 4.32 (m, 2H); 4.32 (q, 2H); 6.95 (s, 1H); 7.22 (d, 1H); 11.80 (s, 1H); 11.96 (s, 1H)

Example 41

3,4-Dichloro-N-[1-(4-chloro-6-methoxy-1,3,5-triazin-2-yl)piperidin-4-yl]-5-methyl-1H-pyrrole-2-carboxamide A solution of 2,4-dichloro-6-methoxy-1,3,5-triazine (commercially available) (0.05 g, 0.32 mmol) in DMF (0.5 ml) was added to a solution of 3,4-dichloro-5-methyl-N-piperidin-4-yl-1H-pyrrole-2-carboxamide hydrochloride (Intermediate 1, 0.1 g, 0.32 mmol) and TEA (0.06 g, 0.64 mmol) in DMF (1.5 ml). The resultant mixture was stirred for 1 h at room temperature, then was diluted with water and extracted with EtOAc. During the aqueous workup, some of the product precipitated and was collected by suction filtration. The organic extract was dried over magnesium sulphate, filtered and concentrated to give the desired product with small amount of impurities.

MS (ESP): 419 (M+1) for $C_{15}H_{17}Cl_3N_6O_2$
$^1$H NMR δ: 1.54 (m, 2H); 1.90 (m, 2H); 2.16 (s, 3H); 3.10 (t, 2H); 3.88 (t, 3H); 4.08 (m, 1H); 4.45 (t, 2H); 7.25 (d, 1H); 12.01 (s, 1H).

Example 42

2-(4-{[(4-Bromo-5-methyl-1H-pyrrol-2-yl)carbonyl]amino}piperidin-1-yl)-6-chloroisonicotinamide 4 N HCl/dioxane solution (10 ml) was added to tert-butyl 1-[4-(aminocarbonyl)-6-chloropyridin-2-yl]piperidin-4-yl-carbamate (Intermediate 16, 100 mg, 0.282 mmol). The mixture was stirred at room temperature for 90 minutes. The solvent was removed in vacuo and the anhydrous diethylether (25 ml) was added. The solvent was removed in vacuo and the light brown solid that resulted was dried under vacuum for several hours. LCMS indicated a pure product 2-(4-aminopiperidin-1-yl)-6-chloroisonicotinamide hydrochloride salt (MS M+H:255). Pentafluorophenyl 4-bromo-5-methyl-1H-pyrrole-2-carboxylate (Intermediate 17) (104 mg, 0.282 mmol), and N,N-diisopropyl ethylamine (98 μl, 0.564 mmol) were added to 2-(4-aminopiperidin-1-yl)-6-chloroisonicotinamide hydrochloride salt (82 mg, 0.282 mmol) in anhydrous DMA (4 ml). The mixture was stirred at room temperature 18 h and was filtered and purified by semi-preparative HPLC using $CH_3CN/H_2O$ (0.1% TFA) to give the title compound (28 mg).

MS (ES, M+H): 442 for $C_{17}H_{19}ClN_5O_2$
$^1$H NMR δ: 1.25 (m, 2H); 1.62 (m, 2H); 1.93 (s, 3H); 2.83 (m, 2H); 3.88 (m, 1H); 4.29 (m, 2H); 6.64 (d, 1H); 6.8 (s, 1H); 6.99 (s, 1H); 7.47 (s, 1H); 7.78 (s, 1H); 7.96 (s, 1H); 11.54 (s, 1H).

Example 43

Methyl 2-(4-{[(4-bromo-5-methyl-1H-pyrrol-2-yl)carbonyl]amino}piperidin-1-yl)-6-chloroisonicotinate Pentafluorophenyl 4-bromo-5-methyl-1H-pyrrole-2-carboxylate (intermediate 17, 1.81 g, 4.90 mmol) and TEA (682 μl, 4.9 mmol) were added to methyl 2-(4-aminopiperidin-1-yl)-6-chloroisonicotinate hydrochloride salt (Intermediate 93; 1.5 g, 4.90 mmol) in anhydrous DMA (10 ml). The mixture was stirred at room temperature 18 h then partitioned between EtOAc and water. The organic layer was washed with water, dried over $Na_2SO_4$ and concentrated under vacuum. The solid material was purified by flash chromatography eluting with EtOAc/n-hexanes mixture (7:3) to give the title compound as a brown solid (1.7 g).

MS (ES, M+H): 456 for $C_{18}H_{20}BrClN_4O_3$
$^1$H NMR δ:1.39 (m, 2H); 1.82 (m, 2H); 2.11 (s, 3H); 3.00 (m, 2H); 3.86 (s, 3H); 3.99 (m, 1H); 4.23 (d, 2H); 6.80 (d, 1H); 6.96 (s, 1H); 7.21 (s, 1H); 7.73 (d, 1H); 11.26 (s, 1H)

Example 44

2-(4-{[(4-Bromo-5-methyl-1H-pyrrol-2-yl)carbonyl]amino}piperidin-1-yl)-6-chloroisonicotinic acid Methyl 2-(4-{[(4-bromo-5-methyl-1H-pyrrol-2-yl)carbonyl]amino}piperidin-1-yl)-6-chloroisonicotinate (Example 43, 1.7 g, 3.72 mmol) was dissolved in THF (10 ml). 2 N lithium hydroxide (10 ml) was added and the reaction was stirred at room temperature for 3 h. The mixture was acidified with 1 N HCl and was extracted with EtOAc (3×50 ml), dried over $Na_2SO_4$ and concentrated in vacuo.

MS (ES, M+H): 442 for $C_{17}H_{18}BrN_4O_3$
$^1$H NMR δ:1.29 (m, 2H); 1.72 (m, 2H); 2.04 (s, 3H); 2.91 (m, 2H); 3.89 (m, 1H); 4.13 (d, 2H); 6.70 (d, 1H); 6.84 (s, 1H); 7.10 (s, 1H); 7.65 (d, 1H); 11.26 (s, 1H)

Example 45

2-(4-{[(4-Bromo-5-methyl-1H-pyrrol-2-yl)carbonyl]amino}piperidin-1-yl)-6-chloro-N-methoxyisonicotinamide 2-(4-{[(4-Bromo-5-methyl-1H-pyrrol-2-yl)carbonyl]amino}piperidin-1-yl)-6-chloroisonicotinic acid (Example 44, 150 mg, 0.34 mmol); HATU, (129 mg, 0.34 mmol); HOAT (46.25 mg; 0.34 mmol); N,N-diisopropyl ethylamine (116 µl, 0.68 mmol) were stirred in anhydrous DMF (3 ml) for 30 minutes. Methoxylamine hydrochloride (28.4 mg, 0.340 mmol), N,N-diisopropyl ethylamine (58 µl, 0.340 mmol) were added. The mixture was stirred at room temperature for 18 h and the crude mixture was filtered, then purified by semi-prep reverse phase HPLC eluting with $CH_3CN/H_2O$ (0.1% TFA). (23 mg).

MS (ES, M+H): 472 for $C_{18}H_{21}BrClN_5O_3$ $^1$H NMR δ: 1.36 (m, 2H); 1.78 (m, 2H); 2.08 (s, 3H); 2.96 (m, 2H); 3.66 (s, 3H); 3.96 (m, 1H); 4.17 (d, 2H); 6.76 (d, 1H); 6.82 (s, 1H); 7.02 (s, 1H); 7.71 (d, 1H); 11.63 (s, 1H); 11.92 (s, 1H)

Example 46

3,4-Dichloro-N-(1-{6-chloro-4-[(1E)-N-hydroxy-ethanimidoyl]pyridin-2-yl}piperidin-4-yl)-5-methyl-1H-pyrrole-2-carboxamide N-[1-(4-Acetyl-6-chloropyridin-2-yl)piperidin-4-yl]-3,4-dichloro-5-methyl-1H-pyrrole-2-carboxamide (Example 115) (49 mg, 0.114 mmol) was dissolved in EtOH (2 ml). Pyridine (74 µl, 0.913 mmol) was added followed by hydroxylamine hydrochloride (63.4 mg, 0.913 mmol). The mixture was stirred at room temperature overnight. The product was purified by semi-prep reverse phase HPLC eluting with $CH_3CN/H_2O$ (0.1% TFA). (28 mg).

MS (ES, M+H): 446 for $C_{18}H_{20}Cl_3N_5O_2$ $^1$H NMR δ: 146 (m, 2H); 1.83 (s, 3H); 2.10 (s, 3H); 2.15 (s, 3H); 3.02 (m, 2H); 3.99 (m, 1H); 4.17 (d, 2H); 6.83 (s, 1H); 6.91 (s, 1H); 7.20 (s, 1H); 11.65 (s, 1H); 11.93 (s, 1H)

Example 47

N-(1-{4-[Amino(hydroxyimino)methyl]-6-chloro-2-pyridinyl}-4-piperidinyl)-3,4-dichloro-5-methyl-1H-pyrrole-2-carboxamide 3,4-Dichloro-N-[1-(6-chloro-4-cyanopyridin-2-yl)piperidin-4-yl]-5-methyl-1H-pyrrole-2-carboxamide (Example 95; 150 mg, 0.362 mmol) was dissolved in MeOH (5 ml) and TEA (100 µl, 0.724 mmol) was added. Hydroxylamine hydrochloride (25.2 mg, 0.362 mmol) was added and the mixture was refluxed for 1 h. The solvent was removed in vacuo and the resulting precipitate was dissolved in DMSO and purified by semi preparative reverse phase HPLC eluting with $CH_3CN/H_2O$ (0.1% TFA). (80 mg).

MS (ES, M+H): 447 for $C_{17}H_{19}Cl_3N_6O_2$ $^1$H NMR δ: 1.35 (m, 2H); 1.73 (m, 2H); 2.06 (s, 3H); 2.94 (m, 2H); 3.89 (m, 1H); 4.07 (d, 2H); 6.04 (brm, 2H); 6.78 (s, 1H); 6.95 (s, 1H); 7.13 (d, 1H); 9.98 (s, 1H); 11.85 (s, 1H)

Example 48

1-[6-Chloro-4-(1H-tetrazol-5-yl)pyridin-2-yl]piperidin-4-yl 3,4-dichloro-5-methyl-1H-pyrrole-2-carboxylate 1-(6-Chloro-4-cyanopyridin-2-yl)piperidin-4-yl 3,4-dichloro-5-methyl-1H-pyrrole-2-carboxylate (Example 308, 64 mg, 0.154 mmol), sodium azide (12 mg, 0.185 mmol) and ammonium chloride (8.3 mg, 0.154 mmol) were dissolved in anhydrous DMF (2 ml) and the mixture was heated at 120° C. for 8 h. The mixture was filtered and purified my semi-preparative reverse phase HPLC eluting with $CH_3CN/H_2O$ (0.1% TFA) (48 mg).

MS (ES, M+H): 456 for $C_{17}H_{16}Cl_3N_7O_2$ $^1$H NMR δ: 1.67 (m, 2H); 1.91 (m, 2H); 2.16 (s, 3H); 3.66 (m, 2H); 3.79 (m, 2H); 5.19 (m, 1H); 7.17 (s, 1H); 7.39 (s, 1H); 12.24 (s, 1H)

Example 49

3,4-Dichloro-5-methyl-N-[1-(1-methyl-5-nitro-1H-imidazol-2-yl)piperidin-4-yl]-1H-pyrrole-2-carboxamide TEA (0.26 ml, 1.86 mmol) was added to a mixture of 2-bromo-1-methyl-5-nitro-1H-imidazole (G. B. Barlin, J. Chem. Soc. B, 1967, 641; 126 mg, 0.61 mmol,) and 3,4-dichloro-5-methyl-N-piperidin-4-yl-1H-pyrrole-2-carboxamide hydrochloride (Intermediate 1), 191 mg, 0.61 mmol) in 1-methyl-2-pyrrolidinone (1.5 ml). Using a Smith Microwave Synthesizer, the mixture was subjected to single-mode microwave at 150° C. for 30 min. EtOAc was added and the solution was washed with water (2×). The organic phase was separated, dried over $MgSO_4$, and concentrated under vacuum. The crude material was purified by chromatography on silica gel using 50% EtOAc/hexanes to give 158 mg of the title product.

MS (ESP): 401 (MH$^+$) for $C_{15}H_{18}Cl_2N_6O_3$ $^1$H-NMR δ: 1.73-1.86 (m, 2H); 1.97-2.01 (m, 2H); 2.25 (s, 3H); 3.18 (t, 2H); 3.56-3.64 (m, 2H); 3.71 (s, 3H); 4.08 (m, 1H); 7.34 (d, 1H); 8.02 (s, 1H); 12.19 (s, 1H).

Example 50

3,4-Dichloro-5-methyl-N-[1-(1-methyl-4-nitro-1H-imidazol-2-yl)piperidin-4-yl]-1H-pyrrole-2-carboxamide Using a procedure similar to that used in Example 52, 30 mg of the title product was obtained starting from 2-bromo-1-methyl-4-nitro-1H-imidazole (G. B. Barlin, J. Chem. Soc. B, 1967, 641).

MS (ESP): 401 (MH$^+$) for $C_{15}H_{18}Cl_2N_6O_3$ $^1$H-NMR δ: 1.76-1.86 (m, 2H); 1.98-2.01 (m, 2H); 2.26 (s, 3H); 3.02 (t, 2H); 3.42-3.52 (m overlapping water, 2H); 3.65 (s, 3H); 4.03 (m, 1H); 7.35 (d, 1H); 8.28 (s, 1H); 12.06 (s, 1H).

Example 51

1-tert-Butyl 2-methyl (2S)-4-(4-{[(3,4-dichloro-5-methyl-1H-pyrrol-2-yl)carbonyl]amino}piperidin-1-yl)pyrrolidine-1,2-dicarboxylate N-BOC-trans-4-Hydroxy-L-proline methylester (0.20 g, 0.81 mM) and 3,4-dichloro-5-methyl-N-piperidin-4-yl-1H-pyrrole-2-carboxamide (free base of Intermediate 1), 0.16 g, 0.81 mM) were stirred in 1,2-dichloroethane (3.5 ml). Sodium triacetoxyborohydride (0.24 g, 1.1 mM) was added followed by acetic acid (0.05 ml). The reaction was stirred under nitrogen at room temperature overnight then diluted with ether and washed with 1 N sodium hydroxide. The organic phase was washed with brine, dried over $MgSO_4$ and concentrated to give an orange oil. The oil was chromatographed using EtOAc to give the desired product as a light yellow solid.

MS (ESP): 503 (MH$^+$) for $C_{22}H_{32}Cl_2N_4O_5$ $^1$H-NMR (CDCl$_3$) δ: 1.39 and 1.45 (2s, 9H, rotamers); 1.71-1.92 (m, 1H); 1.92-2.10 (m, 2H); 2.10-2.34 (m, 5H); 2.41-2.61 (m, 1H); 2.67-2.94 (m, 3H); 3.21 (t, 1H); 3.71 (s, 3H); 3.81-4.01 (m, 2H); 4.19-4.31 (m, 1H); 6.58 (d, 1H); 9.59 (brs, 1H).

Example 52

Methyl 4-(4-{[(3,4-dichloro-5-methyl-1H-pyrrol-2-yl)carbonyl]amino}piperidin-1-yl)-L-prolinate 1-tert-Butyl 2-methyl (2S)-4-(4-{[(3,4-dichloro-5-methyl-1H-pyrrol-2-yl)carbonyl]amino}piperidin-1-yl)pyrrolidine-1,2-dicarboxylate (Example 51, 0.16 g, 0.32 mM) was stirred in 4 N hydrogen chloride in dioxane (4.0 ml) at room temperature for twenty minutes. The orange mixture was concentrated then dissolved in a small amount of MeOH/DCM, diluted with DCM, and washed with sodium bicarbonate. The organic layer was dried over $MgSO_4$, filtered and concentrated to give an orange solid (0.130 g).

MS (ESP): 403 ($MH^+$) for $C_{17}H_{24}Cl_2N_4O_3$ $^1$H-NMR ($CDCl_3$): 1.51-1.70 (m, 2H); 1.70-1.82 (m, 1H); 1.89-2.04 (m, 2H); 2.18-2.34 (m, 5H); 2.36-2.48 (m, 1H); 2.77-3.01 (m, 4H); 3.07-3.20 (m, 1H); 3.72 (s, 3H); 3.77-3.95 (m, 2H).

Example 53

4-(4-{[(3,4-Dichloro-5-methyl-1H-pyrrol-2-yl)carbonyl]amino}piperidin-1-yl)-L-proline A 2 N solution of lithium hydroxide was heated to 70° C. Methyl 4-(4-{[(3,4-dichloro-5-methyl-1H-pyrrol-2-yl)carbonyl]amino}piperidin-1-yl)-L-prolinate (Example 52, 0.081 g, 0.20 mM) in acetonitrile (1.1 ml) and water (0.4 ml) was added to the solution and stirred at 70° C. for ten minutes then ambient temperature for twenty minutes. 1 N Hydrogen chloride was added and a minor impurity was extracted using EtOAc. The aqueous layer was lyophilized to give an orange solid that was purified by HPLC eluting $CH_3CN/H_2O$ (0.1% TFA). Relevant fractions were collected, concentrated and lyophilized to give the desired product as a light orange solid (0.039 g).

MS (ESP): 389 ($MH^+$) for $C_{16}H_{22}Cl_2N_4O_3$ $^1$H-NMR ($D_2O$) δ: 1.80-2.02 (m, 2H); 2.11-2.33 (m, 6H); 2.85-3.04 (m, 1H); 3.15-3.41 (m, 2H); 3.48-3.73 (m, 3H); 3.92 (t, 1H); 4.04-4.20 (m, 2H); 4.27 (t, 1H).

Example 54

4-Bromo-5-methyl-N-[1-(3-nitro-2-pyridinyl)-4-piperidinyl]-1H-pyrrole-2-carboxamide 1-(3-Nitropyridin-2-yl)piperidin-4-amine hydrochloride salt (Intermediate 39) (41 mg, 1.35 mmol) and TEA (37 μl, 1.35 mmol) were added to pentafluorophenyl 4-bromo-5-methyl-1H-pyrrole-2-carboxylate (Intermediate 17): (50 mg, 1.35 mmol) in anhydrous DMA (1 ml). The mixture was stirred at room temperature overnight. The crude mixture was filtered and purified by semi-preparative HPLC using $CH_3CN/H_2O$ (0.1% TFA) to yield the title compound as a yellow solid (26 mg).

MS (ES) $MH^+$: 410 for $C_{16}H_{18}BrN_5O_3$ $^1$H NMR δ: 1.25 (m, 2H); 1.53 (m, 2H); 1.79 (s, 3H); 2.82 (m, 2H); 3.43 (m, 2H); 3.74 (m, 1H); 6.4 (d, 1H); 6.83 (m, 1H); 7.58 (d, 1H); 7.96 (d, 1H); 8.16 (d, 1H); 11.39 (s, 1H).

Examples 55-69

The following compounds were synthesized by an analogous method to Example 54 starting from pentafluorophenyl 4-bromo-5-methyl-1H-pyrrole-2-carboxylate (Intermediate 17) and the starting materials given in the table below.

Examples 55-69

Example 55

Ethyl 2-(4-{[(4-bromo-5-methyl-1H-pyrrol-2-yl)carbonyl]amino}-1-piperidinyl)-3-cyano-6-methyl-isonicotinate

Example 56

4-Bromo-N-[1-(3-cyano-2-pyridinyl)-4-piperidinyl]-5-methyl-1H-pyrrole-2-carboxamide

Example 57

4-Bromo-5-methyl-N-[1-(2-quinolinyl)-4-piperidinyl]-1H-pyrrole-2-carboxamide

Example 58

4-Bromo-N-[1-(6-methoxy-3-nitro-2-pyridinyl)-4-piperidinyl]-5-methyl-1H-pyrrole-2-carboxamide

Example 59

4-Bromo-N-[1-(6-chloro-4-cyano-2-pyridinyl)-4-piperidinyl]-5-methyl-1H-pyrrole-2-carboxamide

Example 60

4-Bromo-5-methyl-N-{1-[6-(trifluoromethyl)-2-pyridinyl]-4-piperidinyl}-1H-pyrrole-2-carboxamide

Example 61

2-(4-{[(4-Bromo-5-methyl-1H-pyrrol-2-yl)carbonyl]amino}-1-piperidinyl)-6-(trifluoromethyl)nocotinamide

Example 62

4-Bromo-N-{1-[3-cyano-6-(trifluoromethyl)-2-pyridinyl]-4-piperidinyl}-5-methyl-1H-pyrrole-2-carboxamide

Example 63

4-Bromo-N-[1-(3-chloro-2-pyridinyl)-4-piperidinyl]-5-methyl-1H-pyrrole-2-carboxamide

Example 64

4-Bromo-N-[1-(4-cyano-2-pyridinyl)-4-piperidinyl]-5-methyl-1H-pyrrole-2-carboxamide

Example 65

4-Bromo-5-methyl-N-{1-[5-(trifluoromethyl)pyridin-2-yl]piperidin-4-yl}-1H-pyrrole-2-carboxamide

Example 66

6-(4-{[(4-Bromo-5-methyl-1H-pyrrol-2-yl)carbonyl]amino}-1-piperidinyl)nocotinamide

Example 67

4-Bromo-N-[1-(6-bromopyridin-2-yl)piperidin-4-yl]-5-methyl-1H-pyrrole-2-carboxamide

Example 68

4-Bromo-N-[1-(6-chloro-2-pyridinyl)-4-piperidinyl]-5-methyl-1H-pyrrole-2-carboxamide

Example 69

6-(4-{[(4-Bromo-5-methyl-1H-pyrrol-2-yl)carbonyl]amino}-1-piperidinyl)-2-chloronicotinic acid

| Example | $^1$H NMR δ | m/z | SM |
|---|---|---|---|
| 55 | 1.5(t, 3H); 1.8(m, 2H); 2.1(m, 2H); 2.3(s, 3H); 2.6(s, 3H); 3.3(m, 2H); 4.2(m, 1H); 4.4(m, 2H); 4.6(m, 2H); 7.0(d, 1H); 7.4(s, 1H); 11.6(s, 1H). | 474 | Ethyl 2-(4-aminopiperidin-1-yl)-3-cyano-6-methylisonicotinate hydrochloride salt (Intermediate 199) |
| 56 | 1.5(m, 2H); 1.8(m, 2H); 2.1(s, 3H); 3.1(m, 2H); 3.3(m, 2H); 3.9(m, 1H); 4.41(m, 2H); 6.8(d, 1H); 6.9(d, 1H); 7.8(d, 1H); 8.0(d, 1H); 8.4(d, 1H); 11.6(s, 1H). | 388 | 2-(4-Aminopiperidin-1-yl)nicotinonitrile hydrochloride salt (Intermediate 200) |
| 57 | 1.4(m, 2H); 1.8(m, 2H); 2.0(s, 3H); 3.1(m, 2H); 2.9(m, 2H); 4.0(m, 1H); 4.4(m, 2H); 6.6(d, 1H); 7.3(m, 1H); 7.8(brm, 4H); 8.2(m, 1H); 8.4(d, 1H); 11.6(s, 1H). | 415 | 1-Quinolin-2-ylpiperidin-4-amine hydrochloride salt (Intermediate 201) |
| 58 | 1.5(m, 2H); 1.8(m, 2H); 2.0(s, 3H); 3.0(m, 2H); 3.7(m, 2H); 3.8(s, 3H); 3.9(m, 1H); 6.2(d, 1H); 6.7(s, 1H); 6.9(d, 1H); 8.2(d, 1H); 11.6(s, 1H). | 440 | 1-(6-Methoxy-3-nitropyridin-2-yl)piperidin-4-amine hydrochloride salt (Intermediate 202) |
| 59 | 1.30(m, 2H); 1.7(m, 2H); 1.93(s, 3H); 2.83(m, 2H); 3.88(m, 1H); 4.29(m, 2H); 6.64(d, 1H); 6.8(s, 1H); 6.99(s, 1H); 7.27(s, 1H); 7.7(d, 1H); 11.54(s, 1H). | 420 | 2-(4-Aminopiperidin-1-yl)-6-chloroisonicotinonitrile hydrochloride salt (Intermediate 203) |
| 60 | 1.29(m, 2H); 1.70(m, 2H); 1.97(s, 3H); 2.86(m, 2H); 3.89(m, 1H); 4.13(m, 2H); 6.92(s, 1H); 7.09(d, 1H); 7.61(m, 2H); 11.58(s, 1H). | 433 | 1-[6-(Trifluoromethyl)pyridin-2-yl]piperidin-4-amine hydrochloride salt (Intermediate 204) |
| 61 | 1.43(m, 2H); 1.72(m, 2H); 2.03(s, 3H); 2.91(m, 2H); 3.75(m, 3H); 6.70(s, 1H); 7.08(s, 1H); 7.61(d, 1H); 7.75(d, 2H); 7.91(m, 1H); 11.54(s, 1H). | 476 | 2-(4-Aminopiperidin-1-yl)-6-(trifluoromethyl)nicotinamide hydrochloride salt (Intermediate 205) |
| 62 | 1.43(m, 2H); 1.78(m, 2H); 1.99(s, 3H); 2.96(m, 2H); 3.91(m, 1H); 4.22(m, 1H); 6.63(s, 1H); 7.16(d, 1H); 7.66(d, 1H); 8.24(d, 1H); 11.50(s, 1H). | 458 | 2-(4-Aminopiperidin-1-yl)-6-(trifluoromethyl)nicotinonitrile hydrochloride salt (Intermediate 206) |
| 63 | 1.58(m, 2H); 1.76(m, 2H); 2.00(s, 3H); 2.2.71(m, 2H); 3.61(d, 2H); 3.84(m, 1H); 6.75(s, 1H); 6.91(s, 1H); 7.66(m, 1H); 8.03(m, 1H); 11.55(s, 1H). | 399 | 1-(3-Chloropyridin-2-yl)piperidin-4-amine hydrochloride salt (Intermediate 207) |
| 64 | 1.17(m, 2H); 1.62(m, 2H); 1.97(s, 3H); 2.95(m, 2H); 3.84(m, 1H); 4.19(d, 2H); 6.64(d, 1H); 7.09(d, 1H); 7.4(s, 1H); 7.8(d, 1H); 8.34(d, 1H); 11.68(s, 1H). | 389 | 2-(4-Aminopiperidin-1-yl)isonicotinonitrile hydrochloride salt (Intermediate 208) |
| 65 | 1.45(m, 2H); 1.85(m, 2H); 2.10(s, 3H); 2.35(s, 3H); 2.97(m, 2H); 3.82(s, 3H); 4.10(m, 1H); 4.7(d, 2H); 6.85(s, 1H); 7.56(s, 1H); 7.85(d, 1H); 11.68(s, 1H). | | 1-[5-(Trifluoromethyl)pyridin-2-yl]piperidin-4-amine hydrochloride salt (Intermediate 209) |

-continued

| Example | ¹H NMR δ | m/z | SM |
|---|---|---|---|
| 66 | 1.35(m, 2H); 1.77(m, 2H); 2.10(s, 3H); 3.10(m, 2H); 4.12(m, 1H); 4.45(d, 2H); 6.82(brs, 1H); 7.18(d, 1H); 7.71(s, 1H); 7.92(s, 1H); 7.99(dd 1H); 8.58(d, 1H); 11.69(s, 1H). | 406 | 6-(4-Aminopiperidin-1-yl)nicotinamide hydrochloride salt (Intermediate 210) |
| 67 | 1.13(m, 2H); 1.53(m, 2H); 1.87(s, 3H); 2.67(m, 2H); 3.70(m, 1H); 3.92(d, 2H); 6.50(d, 1H); 6.60(d 1H); 6.67(d, 1H); 7.17(dd, 1H); 7.49(d 1H); 11.40(s, 1H). | 443 | 1-(6-Bromopyridin-2-yl)piperidin-4-amine hydrochloride salt (Intermediate 211) |
| 68 | 1.28(m, 2H); 1.68(m, 2H); 2.02(s, 3H); 2.83(m, 2H); 3.87(m, 1H); 4.09(d, 2H); 6.52(d, 1H); 6.70(m, 2H); 7.41(m, 1H); 7.63(d, 1H); 11.52(s, 1H) | 399 | [1-(6-Chloropyridin-2-yl)piperidin-4-yl]amine hydrochloride salt (Intermediate 212) |
| 69 | 1.27(m, 2H); 1.72(m, 2H); 2.01(s, 3H); 2.94(m, 2H); 3.90(m, 1H); 4.18(d, 2H); 6.69(s, 1H); 6.76(d, 1H); 7.65(d, 1H); 7.88(d, 1H); 11.55(s, 1H); 12.53(s, 1H). | 443 | 6-(4-Aminopiperidin-1-yl)-2-chloronicotinic acid hydrochloride salt (Intermediate 213) |

Examples 70-73

The following compounds were synthesized by an analogous method to Example 54 using pentafluorophenyl 4-bromo-5-methyl-1H-pyrrole-2-carboxylate (Intermediate 17) and the starting materials given in the table below.

Example 70

4-Bromo-5-methyl-N-[1-(2-pyrimidinyl)-4-piperidinyl]-1H-pyrrole-2-carboxamide

Example 71

Methyl 2-(4-{[(1-bromo-5-methyl-1H-pyrrol-2-yl)carbonyl]amino}-1-piperidinyl)-6-methyl-4-pyrimidinecarboxylate Example 72

4-Bromo-5-methyl-N-[1-(7H-purin-6-yl)piperidin-4-yl]-1H-pyrrole-2-carboxamide

Example 73

Methyl 6-(4-{[(4-bromo-5-methyl-1H-pyrrol-2-yl)carbonyl]amino}-1-piperidinyl)-2-chloro-4-pyrimidinecarboxylate

| Example | ¹H NMR δ | m/z | SM |
|---|---|---|---|
| 70 | 1.17(m, 2H); 1.62(m, 2H); 1.97(s, 3H); 2.95(m, 2H); 3.84(m, 1H); 4.19(d, 2H); 6.64(d, 1H); 7.09(d, 1H); 7.4(s, 1H); 7.8(d, 1H); 8.34(d, 1H); 11.68(s, 1H). | 365 | 1-Pyrimidin-2-ylpiperidin-4-amine hydrochloride salt (Intermediate 214) |
| 71 | 1.45(m, 2H); 1.85(m, 2H); 2.10(s, 3H); 2.35(s, 3H); 2.97(m, 2H); 3.82(s, 3H); 4.10(m, 1H); 4.7(d, 2H); 6.85(s, 1H); 7.56(s, 1H); 7.85(d, 1H); 11.68(s, 1H). | 438 | Methyl 2-(4-aminopiperidin-1-yl)-6-methylpyrimidine-4-carboxylate hydrochloride salt (Intermediate 215) |
| 72 | 1.29(m, 2H); 1.77(m, 2H); 2.05(s, 3H); 3.99(m, 1H); 4.96(m, 2H); 6.60(d, 1H); 7.55(s, 1H); 7.96(d, 1H); 8.13(d, 1H); 8.86(brs, 2H); 11.46(s, 1H); 12.76(brs, 1H) | 406 | 1-(7H-Purin-6-yl)piperidin-4-amine hydrochloride salt (Intermediate 216) |
| 73 | 1.21(m, 2H); 1.71(m, 2H); 1.91(s, 3H); 2.97(m, 2H); 3.30(m, 2H); 3.67(s, 3H); 3.92(m, 1H); 6.49(s, 1H); 7.16(s, 1H); 7.53(d, 1H); 11.46(s, 1H) | 458 | Methyl 6-(4-aminopiperidin-1-yl)-2-chloropyrimidine-4-carboxylate hydrochloride salt (Intermediate 217) |

Examples 74-85

The following compounds were synthesized by an analogous method to Example 45, starting from 2-(4-{[(4-bromo-5-methyl-1H-pyrrol-2-yl)carbonyl]amino}piperidin-1-yl)-6-chloroisonicotinic acid (Example 44) and the commercially available amines given in the table below.

Example 74

2-(4-{[(4-Bromo-5-methyl-1H-pyrrol-2-yl)carbonyl]amino}-1-piperidinyl)-6-chloro-N-cyclopropylisonicotinamide

Example 75

2-(4-{[(4-Bromo-5-methyl-1H-pyrrol-2-yl)carbonyl]amino}-1-piperidinyl)-6-chloro-N-methylisonicotinamide

Example 76

Methyl 2-{[2-(4-{[(4-bromo-5-methyl-1H-pyrrol-2-yl)carbonyl]amino}-1-piperidinyl)-6-chloroisonicotinoyl]amino}acetate

Example 77

2-(4-{[(4-Bromo-5-methyl-1H-pyrrol-2-yl)carbonyl]amino}-1-piperidinyl)-6-chloro-N-hydroxyisonicotinamide

Example 78

4-Bromo-N-{1-[6-chloro-4-(hydrazinocarbonyl)-2-pyridinyl]-4-piperidinyl}-5-methyl-1H-pyrrole-2-carboxamide

Example 79

4-Bromo-N-(1-{6-chloro-4-[(4-methyl-1-piperazinyl)carbonyl]-2-pyridinyl}-4-piperidinyl)-5-methyl-1H-pyrrole-2-carboxamide

Example 80

4-Bromo-N-(1-{6-chloro-4-[(2,2-dimethylhydrazino)carbonyl]-2-pyridinyl}-4-piperidinyl)-5-methyl-1H-pyrrole-2-carboxamide

Example 81

4-Bromo-N-{1-[6-chloro-4-(4-morpholinylcarbonyl)-2-pyridinyl]-4-piperidinyl}-5-methyl-1H-pyrrole-2-carboxamide

Example 82

2-(4-{[(4-Bromo-5-methyl-1H-pyrrol-2-yl)carbonyl]amino}-1-piperidinyl)-6-chloro-N,N-dimethylisonicotinamide

Example 83

2-(4-{[(4-Bromo-5-methyl-1H-pyrrol-2-yl)carbonyl]amino}-1-piperidinyl)-6-chloro-N-methoxy-N-methylisonicotinamide

Example 84

2-(4-{[(4-Bromo-5-methyl-1H-pyrrol-2-yl)carbonyl]amino}-1-piperidinyl)-6-chloro-N-[3-(4-morpholinyl)propyl]isonicotinamide

Example 85

2-(4-{[(4-Bromo-5-methyl-1H-pyrrol-2-yl)carbonyl]amino}-1-piperidinyl)-6-chloro-N-[2-(4-morpholinyl)ethyl]isonicotinamide

| Example | Amine | $^1$H NMR δ | m/z |
|---|---|---|---|
| 74 | Cyclopropylamine | 0.28(m, 2H); 0.40(m, 2H); 0.97(m, 2H); 1.6(m, 2H); 1.87(s, 3H); 2.51(m, 1H); 2.69(m, 2H); 3.60(m, 1H); 4.18(d, 2H); 3.69(s, 1H); 3.91(d, 2H); 6.43(s, 1H); 6.58(s, 1H); 6.78(s, 1H); 7.36(d, 1H); 8.21(d, 1H); 11.26(s, 1H) | 482 |
| 75 | Methylamine | 1.59(m, 2H); 2.01(m, 2H); 2.32(s, 3H); 2.96(m, 1H); 3.27(m, 2H); 4.18(m, 1H); 4.41(d, 2H); 6.99(d, 1H); 7.12(s, 2H); 7.33(s, 1H); 7.92(d, 1H); 8.79(d, 1H); 11.81(s, 1H) | 456 |
| 76 | Amino-acetic acid methyl ester.HCl | 1.56(m, 2H); 1.91(m, 2H); 2.15(s, 3H); 3.14(m, 2H); 3.41(s, 3H); 3.69(m, 1H); 4.08(m, 2H); 4.4(m, 2H); 6.85(m, 1H); 7.07(s, 1H); 7.94(d, 1H); 11.81(s, 1H) | 512 |
| 77 | Hydroxylamine.HCl | 1.27(m, 2H); 1.7(m, 2H); 2.03(s, 3H); 2.84(m, 2H); 3.88(m, 1H); 4.07(d, 2H); 6.68(d, 1H); 6.76(s, 1H); 6.93(s, 1H); 7.60(d, 1H); 9.12(d, 1H); 11.27(s, 1H); 11.47(s; 1H). | 457 |
| 78 | Hydrazine | 1.29(m, 2H); 1.71(m, 2H); 2.03(s, 3H); 2.89(m, 2H); 2.69(m, 2H); 3.87(m, 1H); 4.13(d, 2H); 5.48(brm, 2H); 6.69(d, 1H); 6.84(s, 1H); 7.05(s, 1H); 7.64(d, 1H); 9.95(d, 1H); 11.55(s, 1H) | 456 |

-continued

| Example | Amine | ¹H NMR δ | m/z |
|---|---|---|---|
| 79 | 1-methyl-piperazine | 1.35(m, 2H); 1.78(m, 2H); 2.09(s, 3H); 2.75(s, 3H); 2.96(m, 4H); 3.95(m, 1H); 4.17(d, 2H); 4.41(m, 1H); 6.61(d, 1H); 6.76(m, 2H); 7.72(d, 1H); 11.60(s, 1H) | 525 |
| 80 | N,N-dimethyl hydrazine | 1.36(m, 2H); 1.78(m, 2H); 2.09(s, 3H); 2.54(s, 6H); 2.94(m, 2H); 3.31(m, 2H); 4.10(m, 1H); 4.33(d, 2H); 6.76(d, 1H); 6.85(s, 1H); 7.03(s, 1H); 7.71(d, 1H); 9.55, (s, 1H); 11.62(s, 1H) | 485 |
| 81 | morpholine | 1.32(m, 2H); 1.75(m, 2H); 2.07(s, 3H); 2.92(m, 2H); 3.12(m, 2H); 3.22(m, 2H); 3.30(m, 2H); 3.47(m, 4H); 3.94(m, 1H); 4.05(m, 1H); 4.16(m, 2H); 6.57(s, 1H); 6.74(m, 2H); 7.67(d, 1H); 11.60(s, 1H) | 512 |
| 82 | dimethylamine | 1.51(m, 2H); 1.92(m, 2H); 2.26(s, 3H); 3.01(s, 3H); 3.09(s, 3H); (m, 2H); 3.15(m, 21H); 3.44(d, 4H); 4.10(m, 1H); 4.36(d, 2H); 6.73(s, 1H); 6.93(d, 2H); 7.87(d, 1H); 11.78(s, 1H) | 468 |
| 83 | O,N-Dimethyl-hydroxylamine | 1.35(m, 2H); 1.76(m, 2H); 2.11(s, 3H); 2.95(m, 2H); 3.20(s, 3H); 3.56(s, 3H); 3.95(m, 1H); 4.19(d, 2H); 6.67(s, 1H); 6.77(s, 1H); 6.88(s, 1H); 7.71(d, 1H); 11.64(s, 1H) | 486 |
| 84 | 3-Morpholin-4-yl-propylamine | 1.33(m, 2H); 1.70(m, 4H); 2.08(s, 3H); 2.94(m, 4H); 3.24(m, 2H); 3.38(m, 2H); 3.51(m, 6H); 3.87(m, 2H); 4.12(m, 1H); 6.74(s, 1H); 6.91(s, 1H); 7.04(s 1H); 7.61(s 1H); 8.66(d, 1H); 11.51(s, 1H). | 569 |
| 85 | 2-Morpholin-4-yl-ethylamine | 1.24(m, 2H); 1.66(m, 2H); 2.05(s, 3H); 2.93(m, 4H); 3.24(m, 2H); 3.4(m, 8H); 3.79(m, 2H); 4.13(m, 1H); 6.71(s, 1H); 6.88(s, 1H); 7.04(s 1H); 7.66(d, 1H); 8.78(m, 1H); 11.58(s, 1H). | 555 |

Examples 86-88

The following examples were synthesised by an analogous method to Example 48 from the starting materials given in the table below.

Example 86

4-Bromo-5-methyl-N-{1-[4-(1H-1,2,3,4-tetrazol-5-yl)-2-pyridinyl]-4-piperidinyl}-1H-pyrrole-2-carboxamide

Example 87

4-Bromo-N-{1-[6-chloro-4-(1H-1,2,3,4-tetrazol-5-yl)-2-pyridinyl]-4-piperidinyl}-5-methyl-1H-pyrrole-2-carboxamide

Example 88

3,4-Dichloro-N-{1-[6-chloro-4-(1H-1,2,3,4-tetrazol-5-yl)-2-pyridinyl]-4-piperidinyl}-5-methyl-1H-pyrrole-2-carboxamide

| Example | ¹H NMR δ | m/z | SM |
|---|---|---|---|
| 86 | 1.30(m, 2H); 1.7(m, 2H); 1.93(s, 3H); 2.83(m, 2H); 3.88(m, 1H); 4.29(m, 2H); 6.64(d, 1H); 6.8(s, 1H); 6.99(s, 1H); 7.27(s, 1H); 7.7(d, 1H); 11.54(s, 1H). | 433 | 4-Bromo-N-[1-(4-cyano-2-pyridinyl)-4-piperidinyl]-5-methyl-1H-pyrrole-2-carboxamide (Example 64) |
| 87 | 1.24(m, 2H); 1.66(m, 2H); 1.99(s, 3H); 2.88(m, 2H); 3.84(m, 1H); 4.08(d, 1H); 6.55(s, 1H); 6.96(s, 1H); 7.16(s, 1H); 7.53(d, 1H); 11.28(s, 1H). | 467 | 4-Bromo-N-[1-(6-chloro-4-cyano-2-pyridinyl)-4-piperidinyl]-5-methyl-1H-pyrrole-2-carboxamide (Example 59) |
| 88 | 1.32(m, 2H); 1.71(m, 2H); 2.04(s, 3H); 2.97(m, 2H); 3.88(m, 1H); 4.13(d, 2H); 6.97(s, 1H); 7.15(d, 1H); 7.29(s, 1H); 11.58(s, 1H). | 457 | 3,4-Dichloro-N-[1-(6-chloro-4-cyanopyridin-2-yl)piperidin-4-yl]-5-methyl-1H-pyrrole-2-carboxamide (Example 95) |

Examples 89-95

The following compounds were made according to the method of Example 18, by coupling the amine derivative of tert-butyl 1-[4-(aminocarbonyl)-6-chloropyridin-2-yl]piperidin-4-ylcarbamate (Intermediate 16) with the relevant carboxylic acid given in the table below.

Example 89

2-(4-{[(4-Acetyl-3-cyano-5-methyl-1H-pyrrol-2-yl)carbonyl]amino}-1-piperidinyl)-6-chloroisonicotinamide

Example 90

2-Chloro-6-(4-{[(3-cyano-5-ethyl-1H-pyrrol-2-yl)carbonyl]amino}-1-piperidinyl)isonicotinamide

Example 91

2-(4-{[(4-Bromo-3-cyano-5-ethyl-1H-pyrrol-2-yl)carbonyl]amino}-1-piperidinyl)-6-chloroisonicotinamide

Example 92

2-(4-{[(4-Bromo-3-cyano-5-methyl-1H-pyrrol-2-yl)carbonyl]amino}-1-piperidinyl)-6-chloroisonicotinamide

Example 93

2-Chloro-6-(4-{[(3-cyano-5-methyl-1H-pyrrol-2-yl)carbonyl]amino}-1-piperidinyl)isonicotinamide

Example 94

2-Chloro-6-(4-{[(5-methyl-1H-pyrrol-2-yl)carbonyl]amino}-1-piperidinyl)isonicotinamide

| Example | Acid | $^1$H NMR δ | m/z |
|---|---|---|---|
| 89 | 4-Acetyl-3-cyano-5-methyl-1H-pyrrole-2-carboxylic acid (commercially available) | 1.36(m, 2H); 1.79(m, 2H); 2.32(s, 6H); 2.89(m, 2H); 3.88(m, 1H); 4.12(m, 2H); 6.86(s, 1H); 7.07(s, 1H); 7.47(s, 1H); 7.92(m, 2H); 12.36(s, 1H) | 429 |
| 90 | 3-Cyano-5-ethyl-1H-pyrrole-2-carboxylic acid (Intermediate 31) | 0.96(t, 3H); 1.29(m, 2H); 1.70(m, 2H); 2.90(m, 2H); 3.14(m, 2H); 3.81(m, 1H); 4.02(d, 2H); 6.14(s, 1H); 6.77(s, 1H); 6.96(s, 1H); 7.50(s, 1H); 7.65(m, 1H); 11.70(s, 1H). | 401 |
| 91 | 4-Bromo-3-cyano-5-ethyl-1H-pyrrole-2-carboxylic acid (Intermediate 33) | 1.14(t, 3H); 1.51(m, 2H); 1.89(m, 2H); 2.61(m, 2H); 3.12(m, 2H); 4.22(m, 3H); 6.93(s, 1H); 7.17(s, 1H); 7.69(s, 1H); 8.05(s, 1H); 8.17(m, 1H); 12.39(s, 1H). | 481 |
| 92 | 4-Bromo-3-cyano-5-methyl-1H-pyrrole-2-carboxylic acid (Intermediate 34) | 1.15(m, 2H); 1.60(m, 2H); 1.88(m, 3H); 2.72(m, 2H); 3.70(m, 1H); 3.91(m, 2H); 6.59(s, 1H); 6.89(s, 1H); 7.33(s, 1H); 7.65(d, 1H); 7.85(m, 1H); 12.06(s, 1H). | 467 |
| 93 | 3-Cyano-5-methyl-1H-pyrrole-2-carboxylic acid (Intermediate 32) | 1.31(m, 2H); 1.74(m, 2H); 2.07(s, 3H); 2.96(m, 2H); 3.89(m, 1H); 4.07(d, 2H); 6.09(s, 1H); 6.78(d, 1H); 7.00(s, 1H); 7.58(s, 1H); 7.71(s, 1H); 7.99(s, 1H); 11.88(s, 1H). | 389 |
| 94 | 5-Methyl-1H-pyrrole-2-carboxylic acid (Intermediate 29) | 1.33(m, 2H); 1.70(m, 2H); 2.09(s, 3H); 2.88(m, 2H); 3.95(m, 1H); 4.18(m, 2H); 5.70(s, 1H); 6.49(d, 1H); 6.88(s, 1H); 7.14(s, 1H); 7.49(m, 2H); 8.05(s, 1H); 11.03(s, 1H). | 362 |

Example 95

3,4-Dichloro-N-[1-(6-chloro-4-cyanopyridin-2-yl)piperidin-4-yl]-5-methyl-1H-pyrrole-2-carboxamide The title compound was prepared from 3,4-dichloro-5-methyl-1H-pyrrole-2-carboxylic acid (Intermediate 3) and 2-(4-aminopiperidin-1-yl)-6-chloroisonicotinonitrile hydrochloride salt (Intermediate 203) in a manner analogous to Example 18.

MS (ES, M+H): 411,413 for $C_{17}H_{16}Cl_3N_5O$

Examples 96 and 97

The following compounds were made by an analogous method to Example 18 using 1-(3-nitropyridin-2-yl)piperidin-4-amine hydrochloride salt (Intermediate 39) as a starting material.

Example 96

4,5-Dichloro-N-[1-(3-nitro-2-pyridinyl)-4-piperidinyl]-1H-pyrrole-2-carboxamide

Example 97

4-Bromo-5-isopropyl-N-[1-(3-nitro-2-pyridinyl)-4-piperidinyl]-1H-pyrrole 2-carboxamide

| Example | Acid | $^1$H NMR δ | m/z |
|---|---|---|---|
| 96 | 4,5, Dichloro-1H-pyrrole-2-carboxylic acid (Intermediate 61) | 1.55(m, 2H); 1.92(m, 2H); 3.2(m, 2H); 3.82(m, 2H); 4.1(m, 1H); 6.8(d, 1H); 6.95(m, 1H); 8.1(d, 1H); 8.3(d, 1H); 8.5(d, 1H); 11.39(s, 1H). | 386 |
| 97 | 4-Bromo-5-isopropyl-1H-pyrrole-2-carboxylic acid (Intermediate 37) | 1.33(m, 6H); 1.71(m, 2H); 2.03(m, 2H); 3.26(m, 3H); 3.89(m, 2H); 4.18(m, 1H); 6.9(d, 1H); 7.01(q, 1H); 8.09(d, 1H); 8.40(dd, 1H); 8.63(dd, 1H); 11.77(s, 1H) | 435 |

Example 98

3,4-Dichloro-N-[1-(6-chloro-2-pyridinyl)-4-piperidinyl]-5-methyl-1H-pyrrole-2-carboxamide The title compound was synthesised by an analogous method to Example 42 starting from [1-(6-chloropyridin-2-yl)piperidin-4-yl]amine hydrochloride salt (Intermediate 212; 1 mmol) and 3,4-dichloro-5-methyl-1H-pyrrole-2-carboxylic acid (Intermediate 3, 1 mmol).

MS (ES): 410 (MH$^+$) for $C_{16}H_{17}Cl_3N_4O$ $^1$H NMR δ: 1.38 (m, 2H); 1.76 (m, 2H); 2.10 (s, 3H); 2.94 (m, 2H); 3.92 (m, 1H); 4.10 (m, 2H); 6.57 (d, 1H); 6.71 (d, 1H); 7.08 (d, 1H); 7.42 (m, 1H); 11.71 (s, 1H).

Example 99

2-Chloro-6-(4-{[(3,4-dichloro-5-methyl-1H-pyrrol-2-yl)carbonyl]amino}-1-piperidinyl)-N-[2-(4-morpholinyl)ethyl]isonicotinamide The title compound was synthesised by an analogous method to Example 18 from 2-(4-aminopiperidin-1-yl)-6-chloro-N-(2-morpholin-4-ylethyl)isonicotinamide hydrochloride salt (Intermediate 218) and 3,4-dichloro-5-methyl-1H-pyrrole-2-carboxylic acid (Intermediate 3).

MS (ES): 543 (MH$^+$) for $C_{23}H_{29}Cl_3N_6O_3$ $^1$H NMR δ: 1.42 (m, 2H); 1.86 (m, 2H); 2.13 (s, 3H); 3.04 (m, 4H); 3.22 (m, 2H); 3.40 (m, 8H); 3.93 (m, 3H); 4.13 (m, 2H); 3.96 (m, 2H); 6.89 (s, 1H); 7.09 (s, 1H); 7.21 (d, 1H); 8.76 (d, 1H); 11.84 (s, 1H).

Example 100

2-Chloro-6-(4-{[(3,4-dichloro-5-methyl-1H-pyrrol-2-yl)carbonyl]amino}-1-piperidinyl)-N-[3-(4-morpholinyl)propyl]isonicotinamide The title compound was synthesised by an analogous method to Example 99 starting from 2-(4-aminopiperidin-1-yl)-6-chloro-N-(3-morpholin-4-ylpropyl)isonicotinamide hydrochloride salt (Intermediate 219) and 3,4-dichloro-5-methyl-1H-pyrrole-2-carboxylic acid (Intermediate 3).

MS (ES): 559 (MH$^+$) for $C_{24}H_{31}Cl_3N_6O_3$ $^1$H NMR δ: 1.28 (m, 2H); 1.69 (m, 4H); 1.92 (s, 3H); 2.76 (m, 6H); 3.05 (m, 2H); 3.21 (m, 2H); 3.37 (d, 2H); 3.72 (m, 3H); 3.96 (m, 2H); 6.61 (s, 1H); 6.87 (s, 1H); 7.00 (s, 1H); 8.49 (d, 1H); 11.63 (s, 1H).

Example 101

3,4-Dichloro-N-[1-(6-chloro-4-{[2-(methylamino)-2-oxoethyl]sulfanyl}-2-pyridinyl)-4-piperidinyl]-5-methyl-1H-pyrrole-2-carboxamide The title compound was synthesised by an analogous method to Example 18 starting from 2-{[2-(4-aminopiperidin-1-yl)-6-chloropyridin-4-yl]thio}-N-methylacetamide hydrochloride salt (Intermediate 220) and 3,4-dichloro-5-methyl-1H-pyrrole-2-carboxylic acid (Intermediate 3).

MS (ES): 492 (MH$^+$) for $C_{19}H_{22}Cl_3N_5O_2S$ $^1$H NMR δ: 1.41 (m, 2H); 1.79 (m, 2H); 2.11 (s, 3H); 2.54 (s, 3H); 2.92 (m, 2H); 3.64 (s, 2H); 3.89 (m, 2H); 4.12 (m, 1H); 6.51 (s, 1H); 6.59 (s, 1H); 7.11 (s 1H); 8.08 (m, 1H); 11.90 (s, 1H).

Example 102

4-Bromo-N-[1-(6-chloro-4-{[2-(methylamino)-2-oxoethyl]sulfanyl}-2-pyridinyl)-4-piperidinyl]-5-methyl-1H-pyrrole-2-carboxamide The title compound was prepared by analogous method to Example 18 starting from 2-{[2-(4-aminopiperidin-1-yl)-6-chloropyridin-4-yl]thio}-N-methylacetamide hydrochloride salt (Intermediate 220) and 4-bromo-5-methyl-1H-pyrrole-2-carboxylic acid (Intermediate 18).

MS (ES): 502 (MH$^+$) for $C_{19}H_{23}BrClN_5O_2S$ $^1$H NMR δ: 1.33 (m, 2H); 1.70 (m, 2H); 2.07 (s, 3H); 2.41 (s, 3H); 2.58 (m, 2H); 3.64 (s, 2H); 3.89 (m, 2H); 4.17 (m, 1H); 6.42 (s, 1H); 6.62 (s, 1H); 6.71 (s, 1H); 7.67 (s 1H); 7.97 (m, 1H); 11.51 (s, 1H).

Example 103

2-Cyano-6-(4-{[(3,4-dichloro-5-methyl-1H-pyrrol-2-yl)carbonyl]amino}-1-piperidinyl)isonicotinamide The title compound was synthesised by an analogous method to Example 18 starting from 2-(4-aminopiperidin-1-yl)-6-cyanoisonicotinamide hydrochloride salt (Intermediate 198) and 3,4-dichloro-5-methyl-1H-pyrrole-2-carboxylic acid (Intermediate 3).

MS (ES): 423 (MH$^+$) for $C_{18}H_{18}Cl_2N_5O_2$ $^1$H NMR δ: 1.36 (m, 2H); 1.64 (m, 2H); 2.01 (s, 3H); 2.17 (m, 2H); 2.90 (m, 2H); 4.08 (m, 2H); 4.32 (m, 3H); 7.05 (d, 1H); 7.67 (s, 1H); 8.06 (s, 1H); 11.73 (s, 1H).

Example 104

2-(4-{[(4-Bromo-5-methyl-1H-pyrrol-2-yl)carbonyl]amino}-1-piperidinyl)-3-hydroxy-1-pyridiniumolate Anhydrous TEA (0.23 ml, 1.65 mmol) was added to piperidin-4-yl-carbamic acid tert-butyl ester (300 mg, 1.65 mmol) and thiophene-2-carboxylic acid-2-chloro-pyridinyl-3-yl ester (Intermediate 43, 119 mg, 0.5 mmol) in anhydrous NMP (2 ml). The mixture was heated in a pressure bottle at 165° C. for 18 h. The brown solution was partitioned between EtOAc and water and the organic phase was washed several times with water, dried over sodium sulphate and concentrated in vacuo to give 2-{4-[(tert-butoxycarbonyl)amino]piperidin-1-yl}pyridin-3-yl thiophene-2-carboxylate (170 mg, LCMS:420). This compound was treated with 4 N hydrochloric acid in dioxane for 45 minutes, solvent removed in vacuo and dried to give 2-(4-aminopiperidin-1-yl)pyridin-3-yl thiophene-2-carboxylate as a white solid. The white solid (0.421 mmol) was dissolved in anhydrous NMP (3 ml), and pentafluorophenyl 4-bromo-5-methyl-1H-pyrrole-2-carboxylate (Intermediate 17) (75 mg, 0.21 mmol) was added followed by TEA (64 µl, 0.46 mmol). The mixture was stirred at room temperature for 18 h and the crude mixture was filtered and purified by semi-preparative HPLC eluting with $CH_3CN/H_2O$ (0.1% TFA) to give the title compound (30 mg) (spontaneous oxidation and hydrolysis to give the title compound occurred).

MS (ES): 398 (MH$^+$) for $C_{16}H_{19}BrN_4O_3$ $^1$H NMR δ: 1.29 (m, 2H); 1.47 (m, 2H); 1.82 (s, 3H); 3.72 (m, 1H); 3.90 (m, 2H); 6.47 (d, 1H); 6.78 (m, 1H); 7.07 (m, 1H); 7.42 (d, 1H); 7.57 (d, 1H); 9.16 (m, 3H); 11.32 (s, 1H).

Example 105

4-Bromo-N-[1-(6-methoxy-2-pyridinyl)-4-piperidinyl]-5-methyl-1H-pyrrole-2-carboxamide tert-Butyl [1-(6-chloropyridin-2-yl)piperidin-4-yl]carbamate (Intermediate 66) (300 mg, 0.99 mmol) was dissolved in 0.5 M solution of sodium methoxide in MeOH (9 ml, 4.45 mmol) at room temperature and the mixture was refluxed for 72 h. The solvent was removed in vacuo, extracted with EtOAc then washed with water. The organic phase was concentrated in vacuo and treated with 4 N hydrochloric acid in dioxane (10 ml) for 2 h. The solvent was removed in vacuo and dried to remove excess hydrochloric acid. The solid was dissolved in NMP (3 ml) and pentafluorophenyl 4-bromo-5-methyl-1H-pyrrole-2-carboxylate (Intermediate 17) (80 mg, 0.216 mmol) and TEA (137 µl, 0.9 mmol) were added. The mixture was stirred at room temperature for 2 h and the mixture was purified by semi-preparative HPLC using a gradient of 15-95% $CH_3CN/H_2O$ (0.1% TFA) to give the title compound (23 mg).

MS (ES): 395 (MH$^+$) for $C_{17}H_{21}BrN_4O_2$ $^1$H NMR δ: 1.31 (m, 2H); 1.67 (m, 2H); 2.03 (s, 3H); 2.78 (m, 2H); 3.67 (s, 3H); 3.87 (m, 1H); 4.10 (d, 2H); 5.97 (d, 1H); 6.24 (d, 1H); 6.77 (d, 1H); 7.32 (t, 1H); 7.63 (d, 1H); 11.54 (s, 1H)

Example 106

4-Bromo-N-{1-[6-chloro-4-(5-oxo-2,5-dihydro-1,3,4-oxadiazol-2-yl)pyridin-2-yl]piperidin-4-yl}-5-methyl-1H-pyrrole-2-carboxamide TEA (0.10 ml, 0.70 mmol) and 5-[2-(4-aminopiperidin-1-yl)-6-chloropyridin-4-yl]-1,3,4-oxadiazol-2(5H)-one hydrochloride (Intermediate 51, 0.10 g, 0.33 mmol) were added to a solution of pentafluorophenyl 4-bromo-5-methyl-1H-pyrrole-2-carboxylate (Intermediate 17) (0.12 g, 0.33 mmol) in DMA (2 ml). The mixture was stirred at room temperature overnight and was purified by semi-preparative HPLC eluting with water/acetonitrile and TFA mixtures to give the title compound (18 mg).

MS (ES): 480 (MH$^+$) for $C_{18}H_{18}ClBrN_6O_3$ $^1$H NMR δ: 1.42 (m, 2H); 1.84 (m, 2H); 2.16 (s, 3H); 3.05 (m, 2H); 4.02 (m, 1H); 4.29 (d, 2H); 6.84 (d, 1H); 6.93 (s, 1H); 7.11 (s, 1H); 7.79 (d, 1H); 11.70 (s, 1H); 12.96 (s, 1H)

Example 107

4-Bromo-N-{1-[(4-bromo-5-methyl-1H-pyrrol-2-yl)carbonyl]-4-piperidinyl}-5-methyl-1H-pyrrole-2-carboxamide The title compound was obtained as a by-product during the synthesis of Example 44 (69 mg).

MS (ES): 471 (MH$^+$) for $C_{17}H_{20}Br_2N_4O_2$ $^1$H NMR δ: 1.34 (m, 2H); 1.74 (m, 2H); 1.93 (s, 3H); 2.02 (s, 3H); 2.84 (m, 2H); 3.93 (m, 1H); 4.26 (d, 2H); 6.40 (d, 1H); 6.78 (d, 1H); 7.73 (d, 1H); 11.48 (s, 1H)

Example 108

3,4-Dichloro-N-{1-[6-chloro-4-(5-oxo-4,5-dihydro-1,3,4-oxadiazol-2-yl)-2-pyridinyl]-4-piperidinyl}-5-methyl-1H-pyrrole-2-carboxamide N,N'-Carbonyldiimidazole (0.021 g, 0.13 mmol) was added to a stirred solution of 3,4-dichloro-N-{1-[6-chloro-4-(hydrazinocarbonyl)pyridin-2-yl]piperidin-4-yl}-5-methyl-1H-pyrrole-2-carboxamide (Example 309) (30 mg, 0.06 mmol) in DMF (2 ml). The mixture was stirred at room temperature for 6 h. The mixture was filtered and purified by semi-preparative HPLC eluting with $CH_3CN/H_2O$ (0.1% TFA) mixtures to give the title compound (15 mg).

MS (ES): 471 (MH$^+$) for $C_{18}H_{17}Cl_3N_6O_3$ $^1$H NMR δ: 1.47 (m, 2H); 1.84 (m, 2H); 2.15 (m, 3H); 3.06 (m, 2H); 4.01 (m, 1H); 4.18 (d, 2H); 6.87 (s, 1H); 7.02 (s, 1H); 7.20 (d, 1H); 11.91 (s, 1H); 12.87 (s, 1H).

Example 109

1-[4-(Aminocarbonyl)-6-chloro-2-pyridinyl]-4-piperidinyl 4-bromo-5-methyl-1H-pyrrole-2-carboxylate 2-chloro-6-(4-hydroxypiperidin-1-yl)isonicotinamide (Intermediate 62; 123 mg, 0.48 mmol), 4-bromo-5-methyl-1H-pyrrole-2-carboxylic acid (Intermediate 18) (98 mg, 0.48 mmol) and triphenylphosphine (138 mg, 0.53 mmol) were stirred in anhydrous THF and cooled to 0° C. DEAD (83 μl, 0.53 mmol) was added and the mixture was stirred at room temperature for 18 h. The mixture was filtered, diluted with EtOAc and washed with water and dried over sodium sulphate and concentrated in vacuo. The crude product was purified by flash chromatography eluting with EtOAc/hexane (4:1) to afford the title compound (11 mg).

MS (ES):441 (MH$^+$) for $C_{17}H_{18}BrClN_4O_3$
$^1$H NMR δ: 1.69 (m, 2H); 1.97 (m, 2H); 2.24 (s, 3H); 3.58 (m, 2H); 3.91 (m, 2H); 5.18 (m, 1H); 6.86 (d, 1H); 7.03 (s, 1H); 7.25 (s, 1H); 7.73 (d, 1H); 8.17 (s, 1H); 12.08 (s, 1H)

Example 110

1-[6-Chloro-4-(1H-tetrazol-5-yl)pyridin-2-yl]piperidin-4-yl 4-bromo-5-methyl-1H-pyrrole-2-carboxylate The title compound was synthesised by an analogous method to Example 48 starting from 1-(6-chloro-4-cyanopyridin-2-yl)piperidin-4-yl-4-bromo-5-methyl-1H-pyrrole-2-carboxylate (Example 330).

MS (ES): 468 (MH$^+$) for $C_{17}H_{17}BrClN_7O_2$
$^1$H NMR δ: 1.69 (m, 2H); 1.97 (m, 2H); 2.24 (s, 3H); 3.58 (m, 2H); 3.91 (m, 2H); 5.18 (m, 1H); 6.86 (d, 1H); 7.03 (s, 1H); 7.25 (s, 1H); 7.73 (d, 1H); 8.17 (s, 1H); 12.08 (s, 1H.)

Example 111

3,4-Dichloro-N-{1-[6-chloro-4-(1,2,4-oxadiazol-3-yl)-2-pyridinyl]-4-piperidinyl}-5-methyl-1H-pyrrole-2-carboxamide Diisopropylethylamine (0.04 ml, 0.46 mmol), HOAT (0.03 g, 0.23 mmol) and HATU (0.08 g, 0.23 mmol) were added to a stirred solution of 3,4-dichloro-5-methyl-1H-pyrrole-2-carboxylic acid (Intermediate 3, 0.04 g, 0.23 mmol) in DMF (2 ml) at room temperature. The resulting solution was stirred for 5 minutes and 1-[6-chloro-4-(1,2,4-oxadiazol-3-yl)pyridin-2-yl]piperidin-4-amine hydrochloride (Intermediate 56) (0.074 g, 0.23 mmol) was added. The mixture was stirred at room temperature for 1 h and was filtered and purified by semi-preparative HPLC eluting with CH$_3$CN/H$_2$O (0.1% TFA) mixtures to give the title compound (100 mg).

MS (ES): 457 (MH$^+$) for $C_{18}H_{17}Cl_3N_6O_2$
$^1$H NMR δ: 1.50 (m, 2H); 1.84 (m, 2H); 2.13 (s, 3H); 3.09 (m, 2H); 4.04 (m, 1H); 4.20 (d, 2H); 7.08 (s, 1H); 7.20 (d, 1H); 7.28 (s, 1H); 9.80 (s, 1H); 11.91 (s, 1H)

Example 112

1-[6-Chloro-4-(1,2,4-oxadiazol-3-yl)-2-pyridinyl]-4-piperidinyl 3,4-dichloro-5-methyl-1H-pyrrole-2-carboxylate BF$_3$.Et$_2$O (0.1 ml) was added to a solution of 1-{4-[amino(hydroxyimino)methyl]-6-chloropyridin-2-yl}piperidin-4-yl 3,4-dichloro-5-methyl-1H-pyrrole-2-carboxylate (Example 114) (0.07 g, 0.15 mmol) in 1,1,1-triethoxyethane (1.0 ml) at room temperature. The mixture was stirred at room temperature for 1 h. The mixture was purified by semi-preparative HPLC eluting with CH$_3$CN/H$_2$O (0.1% TFA) mixtures to give the title compound (21 mg).

MS (ES): 458 (MH$^+$) for $C_{18}H_{16}Cl_3N_5O_3$
$^1$H NMR δ: 1.66 (m, 2H); 1.90 (m, 2H); 2.17 (s, 3H); 3.67 (m, 2H); 3.79 (m, 2H); 5.18 (m, 1H); 7.09 (s, 1H); 7.31 (s, 1H); 9.80 (s, 1H); 12.23 (s, 1H)

Example 113

2-Chloro-6-(4-{[(3,4-dichloro-5-methyl-1H-pyrrol-2-yl)carbonyl]amino}-1-piperidinyl)-N-methoxy-isonicotinamide The title compound was synthesised by an analogous method to Example 45 starting from 2-chloro-6-(4-{[(3,4-dichloro-5-methyl-1H-pyrrol-2-yl)carbonyl]amino}piperidin-1-yl)isonicotinic acid (Example 153) and methoxylamine hydrochloride.

MS (ES): 462 (MH$^+$) for $C_{18}H_{20}Cl_3N_5O_3$
$^1$H NMR δ: 1.46 (m, 2H); 1.84 (m, 2H); 2.15 (s, 3H); 3.05 (m, 2H); 3.68 (s, 3H); 4.00 (m, 1H); 4.16 (d, 2H); 6.82 (s, 1H); 7.04 (s, 1H); 7.19 (d, 1H); 11.91 (s, 1H)

Example 114

1-{4-[Amino(hydroxyimino)methyl]-6-chloro-2-pyridinyl}-4-piperidinyl 3,4-dichloro-5-methyl-1H-pyrrole-2-carboxylate The title compound was synthesized by an analogous method to Example 47 from 1-(6-chloro-4-cyanopyridin-2-yl)piperidin-4-yl 3,4-dichloro-5-methyl-1H-pyrrole-2-carboxylate (Example 308).

MS (ES): 446 (MH$^+$) for $C_{17}H_{18}Cl_3N_5O_3$
$^1$H NMR δ: 1.48 (m, 2H); 1.72 (m, 2H); 2.04 (s, 3H); 3.43 (m, 2H); 3.60 (d, 2H); 5.01 (m, 1H); 6.72 (s, 1H); 6.90 (s, 1H); 7.35 (s, 2H); 9.91 (s, 1H); 12.09 (s, 1H)

Example 115

N-[1-(4-Acetyl-6-chloro-2-pyridinyl)-4-piperidinyl]-3,4-dichloro-5-methyl-1H-pyrrole-2-carboxamide The title compound was synthesized by an analogous method to Example 18 starting from 1-[2-(4-aminopiperidin-1-yl)-6-chloropyridin-4-yl]ethanone hydrochloride salt (Intermediate 197) and 3,4-dichloro-5-methyl-1H-pyrrole-2-carboxylic acid (Intermediate 3).

MS (ES): 431 (MH$^+$) for $C_{18}H_{19}Cl_3N_4O_2$
$^1$H NMR δ: 1.46 (m, 2H); 1.84 (m, 2H); 2.14 (s, 3H); 2.55 (s, 3H); 3.05 (m, 2H); 4.00 (m, 1H); 4.21 (d, 2H); 6.94 (s, 1H); 7.18 (s, 1H); 7.21 (s, 1H); 11.91 (s, 1H)

Example 116

N-[1-(4-Acetyl-6-chloro-2-pyridinyl)-4-piperidinyl]-4-bromo-5-methyl-1H-pyrrole-2-carboxamide The title compound was synthesized by an analogous method to Example 42 starting from 1-1-[2-(4-aminopiperidin-1-yl)-6-chloropyridin-4-yl]ethanone hydrochloride salt (Intermediate 197) and 4-Bromo-5-methyl-1H-pyrrole-2-carboxylic acid (Intermediate 18).

MS (ES): 441 (MH$^+$) for $C_{18}H_{20}BrClN_5O_2$

¹H NMR δ: 1.38 (m, 2H); 1.80 (m, 2H); 2.11 (s, 3H); 2.57 (s, 3H); 2.99 (m, 2H); 3.97 (m, 1H); 4.26 (d, 2H); 6.78 (s, 1H); 6.94 (s, 1H); 7.18 (s, 1H); 7.73 (d. 1H); 11.64 (s, 1H)

Example 117

2-Chloro-N-methoxy-6-(4-{[(5-methyl-1H-pyrrol-2-yl)carbonyl]amino}-1-piperidinyl)isonicotinamide The title compound was synthesised by an analogous method to Example 45 starting from 2-chloro-6-(4-{[(5-methyl-1H-pyrrol-2-yl)carbonyl]amino}piperidin-1-yl)isonicotinic acid (Example 332) and methoxylamine hydrochloride.

MS (ES): 392 (MH⁺) for $C_{18}H_{22}BrClN_5O_3$

¹H NMR δ: 1.36 (m, 2H); 1.76 (m, 2H); 2.12 (s, 3H); 2.96 (m, 2H); 3.66 (s, 3H); 3.96 (m, 1H); 4.20 (m, 2H); 5.72 (s, 3H); 6.59 (s, 1H); 6.81 (s, 1H); 7.03 (s, 1H); 7.56 (d 1H); 11.11 (s, 1H); 11.92 (s, 1H)

Example 118

N-{1-[6-Amino-2-(methylsulfanyl)-4-pyrimidinyl]-4-piperidinyl}-3,4-dichloro-5-methyl-1H-pyrrole-2-carboxamide Diisopropylethylamine (0.21 ml, 1.25 mmol) and HATU (0.239 g, 0.63 mmol) were added to a stirred solution of 3,4-dichloro-5-methyl-1H-pyrrole-2-carboxylic acid (Intermediate 3) (0.122 g, 0.63 mmol) in DMF (2 ml). The resultant solution was stirred for 5 minutes, 6-(4-amino-piperidin-1-yl)-2-(methylthio)pyrimidin-4-amine hydrochloride (Intermediate 46) (0.2 g, 0.63 mmol) was added and the mixture was stirred at room temperature for 18 h. The crude mixture was filtered and purified by semi-preparative HPLC eluting with CH₃CN/H₂O (0.1% TFA) to give the title product (42 mg).

MS (ES): 417 (MH⁺) for $C_{16}H_{20}Cl_2N_6OS$

¹H NMR δ: 1.22 (m, 2H); 1.61 (m, 2H); 1.92 (s, 3H); 2.84 (m, 2H); 3.78 (m 4H); 5.25 (s, 1H); 5.52 (s, 1H); 6.50 (m, 2H); 11.72 (s, 1H)

Example 119

N-{1-[6-(Acetylamino)-2-(methylsulfanyl)-4-pyrimidinyl]-4-piperidinyl}-3,4-dichloro-5-methyl-1H-pyrrole-2-carboxamide The title compound was synthesised by an analogous method to Example 118 starting from N-[6-(4-aminopiperidin-1-yl)-2-(methylthio)pyrimidin-4-yl]acetamide hydrochloride (Intermediate 69) and 3,4-dichloro-5-methyl-1H-pyrrole-2-carboxylic acid (Intermediate 3).

MS (ES): 456 (MH⁺) for $C_{16}H_{20}Cl_2N_6OS$

¹H NMR δ: 1.39 (m, 2H); 1.78 (m, 2H); 1.99 (s, 3H); 2.10 (s, 3H); 2.36 (s, 3H); 2.99 (m, 2H); 3.95 (m, 1H); 4.23 (m, 2H); 7.09 (s, 1H); 7.15 (d, 1H); 7.50 (q, 1H); 8.46 (dd, 1H); 10.31 (s, 1H); 11.88 (s, 1H)

Example 120

N-{1-[6-(Acetylamino)-2-methylsulfanyl)-4-pyrimidinyl]-4-piperidinyl}-3,4-dichloro-5-methyl-1H-pyrrole-2-carboxamide mCPBA (0.11 g, 0.133 mmol) was added to a stirred solution of N-{1-[6-(acetylamino)-2-(methylthio)pyrimidin-4-yl]piperidin-4-yl}-3,4-dichloro-5-methyl-1H-pyrrole-2-carboxamide (Example 119), 0.15 g, 0.33 mmol) in DCM (2 ml). The mixture was stirred at room temperature for 3 hr and was purified by semi-preparative HPLC eluting with CH₃CN/H₂O (0.1% TFA) to afford the title compound (5 mg).

MS (ES): 473 (MH⁺) for $C_{18}H_{22}Cl_2N_6O_3S$

¹H NMR δ: 1.42 (m, 2H); 1.86 (m, 2H); 2.06 (s, 3H); 2.13 (s, 3H); 2.76 (s, 3H); 4.02 (m, 4H); 7.21 (d, 1H); 7.42 (s, 1H); 10.81 (s, 1H); 11.94 (s, 1H)

Example 121

N-{1-[6-(Acetylamino)-2-(methylsulfonyl)pyrimidin-4-yl]piperidin-4-yl}-3,4-dichloro-5-methyl-1H-pyrrole-2-carboxamide The title compound was synthesised by an analogous method to Example 120 starting from N-{1-[6-(acetylamino)-2-(methylsulfinyl)-4-pyrimidinyl]-4-piperidinyl}-3,4-dichloro-5-methyl-1H-pyrrole-2-carboxamide (Example 120).

MS (ES): 489 (MH⁺) for $C_{18}H_{22}Cl_2N_6O_4S$

¹H NMR δ: 1.48 (m, 2H); 1.87 (m, 2H); 2.08 (s, 3H); 2.14 (s, 3H); 3.13-3.26 (m, 2H); 3.29 (s, 3H); 4.04 (m, 2H); 4.18 (m, 1H); 7.20 (d, 1H); 7.51 (s, 1H); 10.89 (s, 1H); 11.93 (s, 1H)

Example 122

4-Bromo-5-methyl-N-{1-[(1-methyl-1H-imidazol-2-yl)methyl]piperidin-4-yl}-1H-pyrrole-2-carboxamide Title compound was synthesized by an analogous method to Example 1 by coupling 4-bromo-5-methyl-N-piperidin-4-yl-1H-pyrrole-2-carboxamide hydrochloride (Intermediate 57) with 1-methyl-1H-imidazole-2-carbaldehyde (commercially available).

MS (ESP): 380.1 (M+H) for $C_{16}H_{22}BrN_5O$

¹H NMR δ: 1.45 (m, 2H); 1.72 (d, 2H); 2.04 (m, 2H); 2.12 (s, 3H); 2.75 (d, 2H); 3.50 (s, 2H); 3.65 (s, 3H); 3.72 (m, 1H); 6.74 (s, 1H); 6.81 (s, 1H); 7.00 (s, 1H); 7.69 (d, 1H); 11.62 (s, 1H).

Example 123

Ethyl 2-(4-{[(4-bromo-5-methyl-1H-pyrrol-2-yl)carbonyl]amino}piperidin-1-yl)-1,3-thiazole-4-carboxylate 4-Bromo-5-methyl-N-piperidin-4-yl-1H-pyrrole-2-carboxamide hydrochloride (intermediate 57, 0.41 g, 1.27 mmol), sodium bicarbonate (0.42 g, 1.78 mmol) and ethyl 2-bromo-1,3-thiazole-4-carboxylate (0.30 g, 1.27 mmol) were combined in DMF (5 ml) under nitrogen and heated at 50° C. for 18 h. The mixture was cooled to room temperature and diluted with EtOAc (75 ml) and water (10 ml). The organic layer was separated, dried over sodium sulphate, filtered and concentrated under vacuum. Purification by flash chromatography (MeOH/DCM, 10%) provided 275 mg of the title compound.

MS (ESP): 439.2 (M–H) for $C_{17}H_{21}BrN_4O_3S$

¹H NMR δ: 1.28 (t, 3H); 1.56 (m, 2H); 1.87 (d, 2H); 2.14 (s, 3H); 3.18 (t, 2H); 3.81-4.10 (m, 3H); 4.24 (q, 2H); 6.83 (s, 1H); 7.71 (s, 1H); 7.81 (d, 1H); 11.54 (s, 1H).

Example 124

4-Bromo-5-methyl-N-[1-(1,3-thiazol-2-yl)piperidin-4-yl]-1H-pyrrole-2-carboxamide Title compound was synthesized by an analogous method to Example 123 by coupling 4-bromo-5-methyl-N-piperidin-4-yl-1H-pyrrole-2-carboxamide hydrochloride (Intermediate 57) with 2-bromo-1,3-thiazole (commercially available).

MS (ESP): 369.1 (M+H) for $C_{14}H_{17}BrN_4OS$ $^1$H NMR δ: 1.57 (m, 2H); 1.86 (d, 2H); 2.14 (s, 3H); 3.16 (t, 2H); 3.87-4.10 (m, 3H); 6.82 (s, 1H); 6.86 (s, 1H); 7.19 (s, 1H); 7.81 (d, 1H); 11.68 (s, 1H).

Example 125

N-[1-(1,3-Benzothiazol-2-yl)piperidin-4-yl]-4-bromo-5-methyl-1H-pyrrole-2-carboxamide Title compound was synthesized by an analogous method to Example 123 by coupling 4-bromo-5-methyl-N-piperidin-4-yl-1H-pyrrole-2-carboxamide hydrochloride (Intermediate 57) with 2-bromo-1,3-benzothiazole (commercially available).

MS (ESP): 419.1 (M+H) for $C_{18}H_{19}BrN_4OS$ $^1$H NMR δ: 1.58 (q, 2H); 1.91 (d, 2H); 2.14 (s, 3H); 3.31 (t, 2H); 3.95-4.15 (m, 3H); 6.82 (s, 1H); 7.07 (t, 1H); 7.28 (t, 1H); 7.47 (d, 1H); 7.76-7.82 (m, 2H); 11.70 (s, 1H).

Example 126

Ethyl 5-(4-{[(4-bromo-5-methyl-1H-pyrrol-2-yl)carbonyl]amino}piperidin-1-yl)-1,3,4-thiadiazole-2-carboxylate Title compound was synthesized by an analogous method to Example 123 by coupling 4-bromo-5-methyl-N-piperidin-4-yl-1H-pyrrole-2-carboxamide hydrochloride (Intermediate 57) with 5-chloro-[1,3,4]thiadiazole-2-carboxylic acid ester (Demaree, P et. al. *Can. J. Chem* 1977, 55(2) 243-50).

MS (ESP): 442.0 (M+H) for $C_{16}H_{20}BrN_5O_3S$ $^1$H NMR δ: 1.32 (t, 3H); 1.58 (m, 2H); 1.92 (d, 2H); 2.14 (s, 3H); 3.41 (t, 2H); 3.85-4.10 (m, 3H); 4.36 (q, 2H); 6.82 (s, 1H); 7.82 (d, 1H); 11.70 (s, 1H).

Example 127

2-(4-{[(4-Bromo-5-methyl-1H-pyrrol-2-yl)carbonyl]amino}piperidin-1-yl)-1,3-thiazole-5-carboxamide Title compound was synthesized by an analogous method to Example 123 by coupling 4-bromo-5-methyl-N-piperidin-4-yl-1H-pyrrole-2-carboxamide hydrochloride (Intermediate 57) with 2-bromo-1,3-thiazole-5-carboxamide (*J. Am. Chem. Soc.* 1952, 74, 5799).

MS (ESP): 412.0 (M+H) for $C_{15}H_{18}BrN_5O_2S$ $^1$H NMR δ: 1.54 (m, 2H); 1.86 (d, 2H); 2.14 (s, 3H); 3.21 (t, 2H); 3.87-4.10 (m, 3H); 6.82 (s, 1H); 7.16 (s, 1H); 7.64 (s, 1H); 7.79 (s, 1H); 7.81 (d, 1H); 11.69 (s, 1H).

Example 128

5-(4-{[(4-Bromo-5-methyl-1H-pyrrol-2-yl)carbonyl]amino}piperidin-1-yl)-1,3,4-thiadiazole-2-carboxylic acid Title compound was synthesized from ethyl 5-(4-{[(4-bromo-5-methyl-1H-pyrrol-2-yl)carbonyl]amino}piperidin-1-yl)-1,3,4-thiadiazole-2-carboxylate (Example 126) by an analogous method to Example 31.

MS (ESP): 414.0 (M+H) for $C_{14}H_{16}BrN_5O_3S$ $^1$H NMR δ: 1.58 (m, 2H); 1.87 (d, 2H); 2.14 (s, 3H); 3.28 (t, 2H); 3.88 (d, 2H); 4.01 (m, 1H); 6.82 (s, 1H); 7.84 (d, 1H); 8.82 (s, 1H); 11.71 (s, 1H).

Example 129

2-(4-{[(4-Bromo-5-methyl-1H-pyrrol-2-yl)carbonyl]amino}piperidin-1-yl)-1,3-thiazole-4-carboxylic acid Title compound was synthesized from ethyl 2-(4-{[(4-bromo-5-methyl-1H-pyrrol-2-yl)carbonyl]amino}piperidin-1-yl)-1,3-thiazole-4-carboxylate (Example 123) by an analogous method to Example 31.

MS (ESP): 413.0 (M+H) for $C_{15}H_{17}BrN_4O_3S$ $^1$H NMR δ: 1.56 (m, 2H); 1.86 (d, 2H); 2.14 (s, 3H); 3.17 (t, 2H); 3.90 (d, 2H); 4.00 (m, 1H); 6.83 (s, 1H); 7.64 (s, 1H); 7.85 (d, 1H); 8.20 (s, 1H); 11.72 (s, 1H).

Example 130

4-Bromo-N-[1-(4-cyano-1,3-thiazol-2-yl)piperidin-4-yl]-5-methyl-1H-pyrrole-2-carboxamide Title compound was synthesized by an analogous method to Example 123 by coupling 4-bromo-5-methyl-N-piperidin-4-yl-1H-pyrrole-2-carboxamide hydrochloride (Intermediate 57) with 2-bromo-1,3-thiazole-4-carbonitrile (*Tetrahedron Lett.* 1977, 18 (21), 1813).

MS (ESP): 394.0 (M+H) for $C_{15}H_{16}BrN_5OS$ $^1$H NMR δ: 1.56 (m, 2H); 1.88 (d, 2H); 2.14 (s, 3H); 3.24 (t, 2H); 3.89 (d, 2H); 4.02 (m, 1H); 6.82 (s, 1H); 7.81 (d, 1H); 7.98 (s, 1H); 11.69 (s, 1H).

Example 131

4-Bromo-5-methyl-N-[1-(1-methyl-1H-tetrazol-5-yl)piperidin-4-yl]-1H-pyrrole-2-carboxamide Title compound was synthesized by an analogous method to Example 123 by coupling 4-bromo-5-methyl-N-piperidin-4-yl-1H-pyrrole-2-carboxamide hydrochloride (Intermediate 57) with 5-bromo-1-methyl-1H-tetrazole (*Can. J. Chem.* 1971, 49, 2139).

MS (ESP): 368.0 (M+H) for $C_{13}H_{18}BrN_7O$ $^1$H NMR δ: 1.66 (m, 2H); 1.85 (d, 2H); 2.14 (s, 3H); 3.10 (t, 2H); 3.64 (d, 2H); 3.89 (s, 3H); 3.99 (m, 1H); 6.85 (s, 1H); 7.84 (d, 1H); 11.68 (s, 1H).

Example 132

4-Bromo-N-[1-(5-cyano-1,3-thiazol-2-yl)piperidin-4-yl]-5-methyl-1H-pyrrole-2-carboxamide Title compound was synthesized by an analogous method to Example 123 by coupling 4-bromo-5-methyl-N-piperidin- 4-yl-1H-pyrrole-2-carboxamide hydrochloride (Intermediate 57) with 2-bromo-1,3-thiazole-5-carbonitrile (*Tetrahedron Lett.* 1977, 21, 1813).

MS (ESP): 394.0 (M+H) for $C_{15}H_{16}BrN_5OS$ $^1H$ NMR δ: 1.56 (m, 2H); 1.90 (d, 2H); 2.14 (s, 3H); 3.35 (t, 2H); 3.97 (d, 2H); 4.05 (m, 1H); 6.82 (s, 1H); 7.82 (d, 1H); 8.04 (s, 1H); 11.70 (s, 1H).

Example 133

2-(4-{[(4-Bromo-5-methyl-1H-pyrrol-2-yl)carbonyl]amino}piperidin-1-yl)-1,3-thiazole-4-carboxamide Title compound was synthesized by an analogous method to Example 123 by coupling 4-bromo-5-methyl-N-piperidin-4-yl-1H-pyrrole-2-carboxamide hydrochloride (Intermediate 57) with 2-bromo-1,3-thiazole-4-carboxamide (*J. Am. Chem. Soc.* 1952, 74, 5799).

MS (ESP): 412.0 (M+H) for $C_{15}H_{18}BrN_5O_2S$ $^1H$ NMR δ: 1.57 (m, 2H); 1.86 (d, 2H); 2.14 (s, 3H); 3.18 (t, 2H); 3.90-4.10 (m, 3H); 6.82 (s, 1H); 7.39 (s, 1H); 7.40 (s, 1H); 7.46 (s, 1H); 7.81 (d, 1H); 11.68 (s, 1H).

Example 134

Methyl 6-chloro-4-(4-{[(3,4-dichloro-5-methyl-1H-pyrrol-2-yl)carbonyl]amino}piperidin-1-yl)quinoline-2-carboxylate A solution of 3,4-dichloro-5-methyl-N-piperidin-4-yl-1H-pyrrole-2-carboxamide hydrochloride (Intermediate 1; 59 mg, 0.21 mmol), methyl 4,6-dichloroquinoline-2-carboxylate (F R Alexandre, et. al., Tetrahedron 2003, 59: 1413; 57 mg 0.22 mmol) and diisopropylethylamine (0.10 ml) in DMF (2.0 ml) was heated in a microwave reactor to 180° C. for 30 minutes. The reaction was diluted with 50 ml of EtOAc, then extracted with 25 ml of 1 N NaOH, 2×25 ml of water, dried over anhydrous $MgSO_4$ and concentrated in vacuo. The crude solid was flash chromatographed through neutral silica gel using EtOAc as the eluent to give 37 mg of the title compound; crystallization from MeOH gave a white solid.

MS (ES+): 494.95/496.95/498.90 for $C_{22}H_{21}Cl_3N_4O_3$ $^1H$ NMR δ: 1.85 (m, 2H); 1.954 (m, 2H); 2.10 (s, 3H); 2.98 (m, 2H); 3.49 (m, 2H); 3.85 (s, 3H); 3.97 (m, 1H); 7.24 (d, 1H, J=7.91); 7.50 (s, 1H); 7.75 (m, 1H); 7.87 (s, 1H); 8.02 (d, 1H, J=9.04); 11.93 (s, 1H).

Example 135

4-Bromo-5-methyl-N-(1-{[4-(trifluoromethyl)-1H-indol-2-yl]carbonyl}piperidin-4-yl)-1H-pyrrole-2-carboxamide Title compound was synthesized by an analogous method to Intermediate 2 by coupling 4-bromo-5-methyl-N-piperidin-4-yl-1H-pyrrole-2-carboxamide hydrochloride (Intermediate 57) with 4-(trifluoromethyl)-1H-indole-2-carboxylic acid (*J. Am. Chem. Soc.* 1957, 79, 1745).

MS (ESP): 497.0 (M+H) for $C_{21}H_{20}BrF_3N_4O_2$ $^1H$ NMR δ: 1.50 (q, 2H); 1.93 (d, 2H); 2.14 (s, 3H); 3.23 (m, 2H); 4.07 (m, 1H); 4.40 (m, 2H); 6.77 (s, 1H); 6.83 (s, 1H); 7.37 (t, 1H); 7.46 (d, 1H); 7.74 (d, 1H); 7.83 (d, 1H); 11.70 (s, 1H); 12.23 (s, 1H).

Example 136

4-Bromo-N-{1-[6-chloro-4-(1H-1,2,3,4-tetraazol-5-yl)-2-pyridinyl]-4-piperidinyl}-N,5-dimethyl-1H-pyrrole-2-carboxamide The title compound was synthesised by an analogous method to Example 18 starting from 1-[6-chloro-4-(1H-tetrazol-5-yl)pyridin-2-yl]-N-methylpiperidin-4-amine (Intermediate 64) and pentafluorophenyl 4-bromo-5-methyl-1H-pyrrole-2-carboxylate (Intermediate 17).

MS (ES): 481 (M+H) for $C_{18}H_{20}BrIN_8O$ $^1H$ NMR δ: 1.54 (m, 4H); 2.04 (s, 3H); 2.72 (s, 3H); 2.95 (t, 2H); 4.21 (d, 2H); 4.46 (t, 1H); 6.30 (s, 1H); 7.01 (s, 1H); 7.17 (s, 1H); 11.29 (s, 1H).

Example 137

4-Bromo-N-{1-[6-chloro-4-(2-methyl-2H-1,2,3,4-tetraazol-5-yl)-2-pyridinyl]-4-piperidinyl}-5-methyl-1H-pyrrole-2-carboxamide The title compound was synthesised by an analogous method to Example 42 starting from 1-[6-chloro-4-(1-methyl-1H-tetrazol-5-yl)pyridin-2-yl]-N-methylpiperidin-4-amine (Intermediate 65) and pentafluorophenyl 4-bromo-5-methyl-1H-pyrrole-2-carboxylate (Intermediate 17).

MS (ES): 481 (M+H) for $C_{18}H_{20}BrClN_8O$ $^1H$ NMR δ: 1.49 (m, 2H); 1.87 (m, 2H); 2.14 (s, 3H); 3.11 (m, 2H); 4.06 (m, 1H); 4.31 (m, 2H); 4.34 (s, 3H); 6.82 (s, 1H); 7.07 (s, 1H); 7.16 (s, 1H); 7.78 (d, 1H); 11.68 (s, 1H).

Example 138

Ethyl 2-(4-{[(3,4-dichloro-5-methyl-1H-pyrrol-2-yl)carbonyl]amino}piperidin-1-yl)-4-(hydroxymethyl)-1,3-thiazole-5-carboxylate Ethyl 2-(4-{[(3,4-dichloro-5-methyl-1H-pyrrol-2-yl)carbonyl]amino}piperidin-1-yl)-4-(methoxymethyl)-1,3-thiazole-5-carboxylate (Example 276; 50 mg; 0.105 mmol) was dissolved in anhydrous DCM and cooled to −78° C. 1 M Boron tribromide/DCM (105 μl; 0.105 mmol) was added dropwise. The mixture was stirred at −78° C. for 15 min, then at room temperature for 4 h. The mixture was diluted with DCM, washed with water and dried over $Na_2SO_4$. Organic phase was concentrated in vacuo giving the title compound (20 mg).

MS (ES) MH+: 461 for $C_{18}H_{22}Cl_2N_4O_4S$ $^1H$ NMR δ: 1.16-1.19 (t, 3H); 1.56-1.61 (brs, 2H); 1.84-1.87 (d, 2H); 2.11 (s, 3H); 3.24 (t, 2H); 3.88 (d, 2H); 4.00 (brs, 1H); 4.11-4.13 (q, 2H); 4.55 (s, 1H); 7.21-7.23 (d, 1H); 11.91 (s, 1H).

Example 139

2-(4-{[(3,4-Dichloro-5-methyl-1H-pyrrol-2-yl)carbonyl]amino}piperidin-1-yl)-6-[2-(dimethylamino)ethoxy]isonicotinic acid Sodium (155 mg, 6.74 mmol) and 2-(dimethylamino)ethanol (0.677 ml, 6.74 mmol) were stirred together in DMF (1.5 ml). Methyl 2-chloro-6-(4-{[(3,4-dichloro-5-methyl-1H-pyrrol-2-yl)carbonyl]amino}piperidin-1-yl)isonicotinate (Example 333; 200 mg, 0.449 mmol) was added. The reaction mixture was refluxed overnight, then brought to room temperature and acidified with 10% HCl. The reaction mixture was partitioned between EtOAc and water. The organic layer was washed with water, then with brine, dried over sodium sulfate and concentrated to give the desired product. The crude product was purified by reversed phase HPLC eluting with water/acetonitrile/TFA mixtures to afford the desired product (60 mg).

MS (ES): 484 (MH$^+$) for $C_{21}H_{27}Cl_2N_5O_4$ $^1$H NMR δ: 1.57 (m, 2H); 1.88 (m, 2H); 2.17 (s, 3H); 2.85 (s, 6H); 3.09 (m, 2H); 4.07 (m, 1H); 4.24 (m, 2H); 4.55 (m, 2H); 6.46 (s, 1H); 6.83 (s, 1H); 7.20 (d, 1H); 9.52 (brs, 1H); 11.98 (s, 1H); 13.41 (brs, 1H)

Examples 140-147

The following compounds were synthesized by an analogous method to Example 139, starting from methyl 2-chloro-6-(4-{[(3,4-dichloro-5-methyl-1H-pyrrol-2-yl)carbonyl]amino}piperidin-1-yl)isonicotinate (Example 333) and the commercially available alcohols given in the table below.

Example 140

2-Butoxy-6-(4-{[(3,4-dichloro-5-methyl-1H-pyrrol-2-yl)carbonyl]amino}piperidin-1-yl)isonicotinic acid

Example 141

2-(4-{[(3,4-Dichloro-5-methyl-1H-pyrrol-2-yl)carbonyl]amino}piperidin-1-yl)-6-(2-methoxyethoxy)isonicotinic acid

Example 142

2-(4-{[(3,4-Dichloro-5-methyl-1H-pyrrol-2-yl)carbonyl]amino}piperidin-1-yl)-6-(2-hydroxyethoxy)isonicotinic acid

Example 143

2-(4-{[(3,4-Dichloro-5-methyl-1H-pyrrol-2-yl)carbonyl]amino}piperidin-1-yl)-6-[2-(2-hydroxyethoxy)ethoxy]isonicotinic acid

Example 144

2-(4-{[(3,4-Dichloro-5-methyl-1H-pyrrol-2-yl)carbonyl]amino}piperidin-1-yl)-6-[2-(2-methoxyethoxy)ethoxy]isonicotinic acid

Example 145

2-(4-{[(3,4-Dichloro-5-methyl-1H-pyrrol-2-yl)carbonyl]amino}piperidin-1-yl)-6-(2-isopropoxyethoxy)isonicotinic acid

Example 146

2-[2-(Allyloxy)ethoxy]-6-(4-{[(3,4-dichloro-5-methyl-1H-pyrrol-2-yl)carbonyl]amino}piperidin-1-yl)isonicotinic acid

Example 147

2-(4-{[(3,4-Dichloro-5-methyl-1H-pyrrol-2-yl)carbonyl]amino}piperidin-1-yl)-6-(2-morpholin-4-ylethoxy)isonicotinic acid

| Examples | Alcohol | $^1$H NMR δ | m/z |
|---|---|---|---|
| 140 | butan-1-ol | 0.94(t, 3H); 1.44(m, 2H); 1.61(m, 2H); 1.76(m, 2H); 1.95(m, 2H); 2.22(s, 3H); 3.15(m, 2H); 4.05(m, 1H); 4.24(m, 2H); 6.38(s, 1H); 6.76(s, 1H); 7.23(d, 1H); 11.98(s, 1H); 13.31(brs, 1H) | 469 |
| 141 | 2-methoxy ethanol | 1.38(m, 2H); 1.67(m, 2H); 1.98(s, 3H); 2.84(m, 2H); 3.10(s, 3H); 3.45(m, 2H); 3.85(m, 2H); 3.99(m, 2H); 4.17(m, 2H); 6.19(s, 1H); 6.57(s, 1H); 7.02(d, 1H); 11.76(s, 1H); 13.12(s, 1H). | 471 |
| 142 | ethylene glycol | 1.56(m, 2H); 1.60(m, 2H); 2.17(s, 3H); 2.57(m, 2H); 3.69(m, 2H); 4.04(m, 1H); 4.24(m, 4H); 6.38(s, 1H); 6.75(s, 1H); 7.21(d, 1H); 11.96(s, 1H); 13.31(brs, 1H) | 457 |
| 143 | 2,2'-oxydiethanol | 1.63(m, 2H); 1.93(m, 2H); 2.24(s, 3H); 3.13(m, 2H); 3.53(m, 4H); 3.79(m, 2H); 4.07(m, 1H); 4.25(m, 2H); 4.39(m, 2H); 6.45(s, 1H); 6.82(s, 1H); 7.27(d, 1H); 12.02(s, 1H); 13.38(brs, 1H). | 501 |
| 144 | 2-(2-methoxy ethoxy) ethanol | 1.56(m, 2H); 1.85(m, 2H); 2.16(s, 3H); 3.06(m, 2H); 3.23(s, 3H); 3.45(m, 2H); 3.54(m, 2H); 3.71(m, 2H); 4.03(m, 1H); 4.18(m, 2H); 6.37(s, 1H); 6.75(s, 1H); 7.20(d, 1H); 11.95(s, 1H); 13.31(brs, 1H). | 499 |
| 145 | 2-isopropoxy ethanol | 1.31(m, 6H); 1.79(m, 2H); 2.08(m, 2H); 2.40(s, 3H); 3.29(m, 2H); 3.79(q, 1H); 3.90(m, 2H); 4.26(m, 1H); 4.45(m, 2H); 4.53(m, 2H); 6.60(s, 1H); 6.98(s, 1H); 7.43(d, 1H); 12.18(s, 1H); 13.54(brs, 1H). | 515 |
| 146 | 2-(allyloxy) ethanol | 1.67(m, 2H); 1.96(m, 2H); 2.28(s, 3H); 3.17(m, 2H); 3.81(t, 2H); 4.09(m, 2H); 4.11(m, 1H); 4.29(m, 2H); 4.46(m, 2H); 5.26(dd, 1H); 5.34(dd, 1H); 5.98(m, 1H); 6.49(s, 1H); 6.86(s, 1H); 7.43(d, 1H); 12.06(s, 1H); 13.41(brs, 1H). | 497 |
| 147 | 2-morpholin-4-ylethanol | 1.54(m, 2H); 1.65(m, 1H); 1.87(m, 2H); 2.19(s, 3H); 2.46(m, 4H); 2.67(m, 2H); 2.99(m, 1H); 3.05(m, 2H); 3.57(m, 4H); 4.04(m, 1H); 4.18(m, 2H); 4.33(m, 2H); 6.36(s, 1H); 6.75(s, 1H); 7.37(d, 1H). | 526 |

Example 148

2-tert-Butoxy-2-oxoethyl 2-(4-{[(3,4-dichloro-5-methyl-1H-pyrrol-2-yl)carbonyl]amino}piperidin-1-yl)-(2-methoxyethoxy)isonicotinate tert-Butyl chloroacetate (28 mg, 0.190 mmol) was added to a solution of 2-(4-{[(3,4-dichloro-5-methyl-1H-pyrrol-2-yl)carbonyl]amino}piperidin-1-yl)-6-(2-methoxyethoxy)isonicotinic acid (60 mg, 0.127 mmol) (Example 141) in DMF (2 ml), followed by the addition of caesium fluoride (47 mg, 0.313 mmol). The resulting mixture was stirred at room temperature for 24 hr. The mixture was filtered and purified by HPLC eluting with water/acetonitrile/TFA mixtures to afford the desired product (20 mg).

MS (ES): 585 (MH$^+$) for $C_{26}H_{34}Cl_2N_4O_7$ $^1$H NMR δ: 0.96 (s, 9H); 1.37 (m, 2H); 1.67 (m, 2H); 1.97 (s, 3H); 2.85 (m, 2H); 3.09 (s, 3H); 3.44 (m, 2H); 3.84 (m, 1H); 3.99 (m, 2H); 4.14 (m, 3H); 5.73 (s, 1H); 6.16 (s, 1H); 6.55 (s, 1H); 7.00 (d, 1H); 11.75 (s, 1H).

Example 149

2-(4-{[(3,4-Dichloro-5-methyl-1H-pyrrol-2-yl)carbonyl]amino}piperidin-1-yl)-6-[2-(dimethylamino)ethoxy]-N-methoxyisonicotinamide The title compound was prepared as described for Example 8 from 2-(4-{[(3,4-dichloro-5-methyl-1H-pyrrol-2-yl)carbonyl]amino}piperidin-1-yl)-6-[2-(dimethylamino)ethoxy]isonicotinic acid (Example 139) acid and O-methylhydroxylamine hydrochloride.

MS (ES): 513 (MH$^+$) for $C_{22}H_{30}Cl_2N_6O_4$ $^1$H NMR δ: 1.56 (m, 2H); 1.88 (m, 2H); 2.17 (s, 3H); 2.85 (s, 6H); 3.08 (m, 2H); 3.70 (s, 3H); 4.19 (m, 1H); 4.52 (d, 2H); 4.54 (m, 2H); 6.34 (s, 1H); 6.69 (s, 1H); 7.20 (d, 1H); 11.85 (s, 1H); 11.98 (s, 1H).

Example 150

2-(4-{[(3,4-Dichloro-5-methyl-1H-pyrrol-2-yl)carbonyl]amino}piperidin-1-yl)-[2-(propionyloxy)ethoxy]isonicotinic acid 2-(4-{[(3,4-Dichloro-5-methyl-1H-pyrrol-2-yl)carbonyl]amino}piperidin-1-yl)-6-(2-hydroxyethoxy)isonicotinic acid (Example 142) (199 mg, 0.435 mmol) was dissolved in DCM (3 ml). Propanoyl chloride (37.83 μl, 0.435 mmol) was added dropwise and the resulting mixture stirred at room temperature for 2.5 h. The mixture was diluted with EtOAc and washed with water. The aqueous phase was extracted with EtOAc, and the combined organic phase was dried over sodium sulfate and concentrated in vacuo to give the desired product. The crude product was dissolved in DMSO and purified by reversed phase HPLC, eluting with water/acetonitrile/TFA mixtures to afford the desired product (35 mg).

MS (ES): 513 (MH$^+$) for $C_{22}H_{26}Cl_2N_4O_6$ $^1$H NMR δ: 1.01 (t, 3H); 1.57 (m, 2H); 1.87 (m, 2H); 2.17 (s, 3H); 2.31 (m, 2H); 3.07 (m, 2H); 4.05 (m, 1H); 4.23 (m, 2H); 4.33 (m, 2H); 4.44 (m, 2H); 6.40 (s, 1H); 6.79 (s, 1H); 7.43 (d, 1H); 12.17 (s, 1H); 13.62 (m, 1H).

Example 151

2-(4-{[(3,4-Dichloro-5-methyl-1H-pyrrol-2-yl)carbonyl]amino}piperidin-1-yl)-N-methoxy-6-(methylsulfonyl)isonicotinamide 2-(4-{[(3,4-Dichloro-5-methyl-1H-pyrrol-2-yl)carbonyl]amino}piperidin-1-yl)-N-methoxy-6-(methylsulfinyl)isonicotinamide (Example 152) (90 mg, 0.185 mmol) was dissolved in anhydrous DCM (5 ml). mCPBA (32 mg, 0185 mmol) was added and the mixture was stirred at room temperature for 12 h. The crude mixture was diluted and washed with 10% sodium thiosulfate, water, brine and dried over sodium sulfate and concentrated in vacuo. The brown oil was purified by flash chromatography eluting with acetonitrile/water (0.1% TFA) to give the title compound (11 mg).

MS (ES) (M+H): 504 for $C_{19}H_{23}Cl_2N_5O_5S$ $^1$H NMR δ: 1.53 (m, 2H); 1.83 (m, 2H); 2.03 (s, 3H); 2.97 (m, 2H); 3.12 (s, 3H); 3.62 (s, 3H); 4.07 (m, 1H); 4.28 (m, 2H); 7.16 (d, 1H); 7.30 (s, 2H); 11.87 (s, 1H); 12.05 (s, 1H).

Example 152

2-(4-{[(3,4-Dichloro-5-methyl-1H-pyrrol-2-yl)carbonyl]amino}piperidin-1-yl)-N-methoxy-6-(methylsulfinyl)isonicotinamide Methyl 2-(4-{[(3,4-dichloro-5-methyl-1H-pyrrol-2-yl)carbonyl]amino}piperidin-1-yl)-6-(methylsulfinyl)isonicotinate (Example 334; 200 mg, 0.422 mmol) was dissolved in anhydrous THF (5 ml) and treated with 2 N lithium hydroxide (10 ml) with stirring for 45 minutes. The mixture was cooled in an ice bath and acidified with 1 N HCl. The aqueous solution was extracted with EtOAc. The organic phase was washed with water, dried over sodium sulfate and concentrated in vacuo to give the acid derivative as a brown solid (LCMS showed a peak of 459). This acid (95 mg, 0.207 mmol) was treated with methoxyamine hydrochloride (17.3 mg, 0.207 mmol) in a manner analogous to Example 8 to afford the title compound. (30 mg).

MS (ES) (M+H): 488 for $C_{19}H_{23}Cl_2N_5O_4S$ $^1$H NMR δ: 1.58 (m, 2H); 1.92 (m, 2H); 2.18 (s, 3H); 2.80 (s, 3H); 3.18 (m, 2H); 3.76 (s, 3H); 4.12 (m, 1H); 4.29 (m, 2H); 7.08 (s, 1H); 7.22 (d, 1H); 7.34 (s, 1H); 11.96 (s, 1H); 12.17 (s, 1H)

Example 153

2-Chloro-6-(4-{[(3,4-dichloro-5-methyl-1H-pyrrol-2-yl)carbonyl]amino}piperidin-1-yl)isonicotinic acid The title compound was prepared in a manner analogous to Example 44 from methyl 2-chloro-6-(4-{[(3,4-dichloro-5-methyl-1H-pyrrol-2-yl)carbonyl]amino}piperidin-1-yl)isonicotinate (Example 333).

MS (ES) (M+H): 431 for $C_{17}H_{17}Cl_3N_4O_3$ $^1$H NMR δ: 1.64 (m, 2H); 2.00 (m, 2H); 2.46 (s, 3H); 3.46 (m, 2H); 4.40 (m, 1H); 4.55 (m, 2H); 7.21 (s, 1H); 7.27 (s, 1H); 7.59 (d, 1H); 12.13 (s, 1H); 14.06 (brs, 1H).

Example 154

2-{2-[(tert-Butoxycarbonyl)amino]ethoxy}-6-(4-{[(3,4-dichloro-5-methyl-1H-pyrrol-2-yl)carbonyl]amino}piperidin-1-yl)pyrimidine-4-carboxylic acid Sodium hydride (0.097 g, 4.02 mmol) was added to a stirred solution of tert-butyl 2-hydroxyethylcarbamate (0.62 ml, 4.02 mmol) in THF at 0° C. under a nitrogen atmosphere. This mixture was stirred for 15 minutes at 0° C. and warmed to room temperature. Methyl 2-chloro-6-(4-{[(3,4-dichloro-5-methyl-1H-pyrrol-2-yl)carbonyl]amino}piperidin-1-yl)pyrimidine-4-carboxylate (Example 6, 0.30 g, 0.67 mmol) was added to the reaction mixture and the resultant mixture was stirred overnight. The reaction was quenched with water (10 ml) and the THF was removed under reduced pressure. The aqueous solution was acidified with 1 N HCl and extracted with EtOAc. The combined extract was washed with water and brine, dried over magnesium sulfate, filtered and concentrated to give a brown oil which was purified by purified by semi-preparative reverse phase HPLC eluting with acetonitrile/water (0.1% TFA).

MS (ES) MH$^+$: 557 for $C_{23}H_{30}Cl_2N_6O_6$ $^1$H NMR δ: 1.36 (s, 9H); 1.53 (m, 2H); 1.89 (m, 2H); 2.16 (s, 3H); 3.20 (m, 2H); 3.27 (m, 2H); 4.09 (m, 1H); 4.24 (t, 2H); 4.53 (brs, 2H); 7.00 (t, 1H); 7.05 (s, 1H); 7.23 (d, 1H); 11.96 (s, 1H).

Example 155-162

The following compounds were synthesized by an analogous method to Example 154 starting from commercially available alcohols and sodium hydride, and reacting the alkoxide generated in situ with methyl 2-chloro-6-(4-{[(3,4-dichloro-5-methyl-1H-pyrrol-2-yl)carbonyl]amino}piperidin-1-yl)pyrimidine-4-carboxylate (Example 6). The commercially available alcohols are given in the table below.

Example 155

6-(4-{[(3,4-Dichloro-5-methyl-1H-pyrrol-2-yl)carbonyl]amino}piperidin-1-yl)-2-(2-methoxyethoxy)pyrimidine-4-carboxylic acid

Example 156

6-(4-{[(3,4-Dichloro-5-methyl-1H-pyrrol-2-yl)carbonyl]amino}piperidin-1-yl)-2-[2-(methylthio)ethoxy]pyrimidine-4-carboxylic acid

Example 157

6-(4-{[(3,4-Dichloro-5-methyl-1H-pyrrol-2-yl)carbonyl]amino}piperidin-1-yl)-2-(2-morpholin-4-ylethoxy)pyrimidine-4-carboxylic acid

Example 158

6-(4-{[(3,4-Dichloro-5-methyl-1H-pyrrol-2-yl)carbonyl]amino}piperidin-1-yl)-2-(2-hydroxyethoxy)pyrimidine-4-carboxylic acid

Example 159

2-Butoxy-6-(4-{[(3,4-dichloro-5-methyl-1H-pyrrol-2-yl)carbonyl]amino}piperidin-1-yl)pyrimidine-4-carboxylic acid

Example 160

2-(2-Aminoethoxy)-6-(4-{[(3,4-dichloro-5-methyl-1H-pyrrol-2-yl)carbonyl]amino}piperidin-1-yl)pyrimidine-4-carboxylic acid

Example 161

6-(4-{[(3,4-Dichloro-5-methyl-1H-pyrrol-2-yl)carbonyl]amino}piperidin-1-yl)-2-[2-(dimethylamino)ethoxy]pyrimidine-4-carboxylic acid

Example 162

6-(4-{[(3,4-Dichloro-5-methyl-1H-pyrrol-2-yl)carbonyl]amino}piperidin-1-yl)-2-[3-(dimethylamino)propoxy]pyrimidine-4-carboxylic acid

| Example | Alcohol | $^1$H NMR δ | m/z |
|---|---|---|---|
| 155 | 2-methoxy ethanol | 1.54(m, 2H); 1.88(m, 2H); 2.16(s, 3H); 3.18(m, 2H); 3.28(s, 3H); 3.62(t, 2H); 4.08(brs, 1H); 4.33(m, 2H); 4.37(t, 2H); 7.03(s, 1H); 7.22(d, 1H); 11.96(s, 1H). | 472 |
| 156 | 2-(methylthio) ethanol | 1.53(m, 2H); 1.89(m, 2H); 2.13(s, 3H); 2.16(s, 3H); 2.82(t, 2H); 3.19(t, 2H); 4.09(brs, 1H); 4.35(m, 2H); 4.42(t, 2H); 7.04(s, 1H); 7.23(d, 1H); 11.96(s, 1H). | 488 |
| 157 | 2-morpholin-4-ylethanol | 1.52(m, 2H); 1.95(m, 2H); 2.16(s, 3H); 3.20(t, 2H); 3.56(brs, 2H); 3.73(brs, 2H); 3.94(brs, 2H); 4.09(brs, 2H); 4.35(brs, 3H); 4.61(brs, 4H); 7.10(s, 1H); 7.25(d, 1H); 12.01(s, 1H). | 527 |
| 158 | ethylene glycol | 1.52(m, 2H); 1.87(m, 2H); 2.15(s, 3H); 3.17(t, 2H); 3.66(t, 2H); 4.07(m, 1H); 4.26(t, 2H); 4.35(brs, 2H); 7.02(s, 1H); 7.21(d, 1H); 11.95(s, 1H). | 458 |
| 159 | butan-1-ol | 0.92(t, 3H); 1.39(m, 2H); 1.53(m, 2H); 1.67(m, 2H); 1.80(m, 2H); 2.16(s, 3H); 3.22(m, 2H); 4.10(m, 2H); 4.28(t, 2H); 4.45(brs, 1H); 7.05(s, 1H); 7.23(d, 1H); 11.97(s, 1H) | 470 |

-continued

| Example | Alcohol | ¹H NMR δ | m/z |
|---|---|---|---|
| 160 | 3-(dimethylamino)propan-1-ol | 1.52(m, 2H); 1.89(m, 2H); 2.02(m, 2H); 2.16(s, 3H); 2.80(s, 3H); 2.81(s, 3H); 3.18(m, 4H); 4.09(m, 1H); 4.31(t, 2H); 4.58(m, 2H); 7.05(s, 1H); 7.21(d, 1H); 9.36(brs, 1H); 11.98(s, 1H). | 499 |
| 161 | 2-aminoethanol | 1.53(m, 2H); 1.91(m, 2H); 2.17(s, 3H); 3.21(m, 4H); 4.13(m, 1H); 4.35(brs, 2H); 4.43(t, 2H); 7.10(s, 1H); 7.22(d, 1H); 7.96(brs, 2H); 11.98(s, 1H). | 457 |
| 162 | 2-(dimethylamino)ethanol | 1.52(m, 2H); 1.92(m, 2H); 2.16(s, 3H); 2.85(s, 6H); 3.21(t, 2H); 3.49(brs, 2H); 4.10(m, 1H); 4.33(brs, 2H); 4.58(m, 2H); 7.11(s, 1H); 7.23(d, 1H); 9.88(brs, 1H); 11.99(s, 1H). | 485 |

Example 163

6-(4-{[(3,4-Dichloro-5-methyl-1H-pyrrol-2-yl)carbonyl]amino}piperidin-1-yl)-2-[2-(methylsulfonyl)ethoxy]pyrimidine-4-carboxylic acid The title compound was synthesized by an analogous method to Example 14 starting from 6-(4-{[(3,4-dichloro-5-methyl-1H-pyrrol-2-yl)carbonyl]amino}piperidin-1-yl)-2-[2-(methylthio)ethoxy]pyrimidine-4-carboxylic acid (Example 156).

MS (ES) MH⁺: 520 for $C_{19}H_{23}Cl_2N_5O_6S$

¹H NMR δ: 1.54 (m, 2H); 1.88 (m, 2H); 2.16 (s, 3H); 3.00 (s, 3H); 3.14 (t, 2H); 3.55 (m, 2H); 4.03 (m, 1H); 4.28 (m, 2H); 4.55 (t, 2H); 7.01 (s, 1H); 7.16 (d, 1H); 11.90 (s, 1H).

Examples 164-168

The following compounds were synthesized by an analogous method to Example 8 starting from the corresponding carboxylic acid derivatives and methoxylamine hydrochloride. The starting carboxylic acid derivatives are given in the table below.

Example 164

6-(4-{[(3,4-Dichloro-5-methyl-1H-pyrrol-2-yl)carbonyl]amino}piperidin-1-yl)-N-methoxy-2-(2-methoxyethoxy)pyrimidine-4-carboxamide

Example 165

6-(4-{[(3,4-Dichloro-5-methyl-1H-pyrrol-2-yl)carbonyl]amino}piperidin-1-yl)-N-methoxy-2-[2-(methylthio)ethoxy]pyrimidine-4-carboxamide

Example 166

2-Butoxy-6-(4-{[(3,4-dichloro-5-methyl-1H-pyrrol-2-yl)carbonyl]amino}piperidin-1-yl)-N-methoxypyrimidine-4-carboxamide

Example 167

6-(4-{[(3,4-Dichloro-5-methyl-1H-pyrrol-2-yl)carbonyl]amino}piperidin-1-yl)-2-[2-(dimethylamino)ethoxy]-N-methoxypyrimidine-4-carboxamide

Example 168

6-(4-{[(3,4-Dichloro-5-methyl-1H-pyrrol-2-yl)carbonyl]amino}piperidin-1-yl)-2-(2-hydroxyethoxy)-N-methoxypyrimidine-4-carboxamide

| Example | SM | ¹H NMR δ | m/z |
|---|---|---|---|
| 164 | 6-(4-{[(3,4-dichloro-5-methyl-1H-pyrrol-2-yl)carbonyl]amino}piperidin-1-yl)-2-(2-methoxyethoxy)pyrimidine-4-carboxylic acid (Example 155) | 1.52(m, 2H); 1.88(m, 2H); 2.16(s, 3H); 3.21(t, 2H); 3.28(s, 3H); 3.61(t, 2H); 3.66(s, 3H); 4.08(m, 1H); 4.33(m, 2H); 4.41(t, 2H); 6.96(s, 1H); 7.22(d, 1H); 11.84(brs, 1H); 11.96(s, 1H). | 501 |
| 165 | 6-(4-{[(3,4-dichloro-5-methyl-1H-pyrrol-2-yl)carbonyl]amino}piperidin-1-yl)-2-[2-(methylthio)ethoxy]pyrimidine-4-carboxylic (Example 156) | 1.52(m, 2H); 1.88(m, 2H); 2.13(s, 3H); 2.16(s, 3H); 2.81(t, 2H); 3.17(t, 2H); 3.67(s, 3H); 4.08(m, 1H); 4.31(m, 2H); 4.44(t, 2H); 6.97(s, 1H); 7.22(d, 1H); 11.84(brs, 1H); 11.96(s, 1H). | 517 |
| 166 | 2-butoxy-6-(4-{[(3,4-dichloro-5-methyl-1H-pyrrol-2-yl)carbonyl]amino}piperidin-1-yl)pyrimidine-4-carboxylic acid (Example 159) | 0.92(t, 3H); 1.40(m, 2H); 1.51(m, 2H); 1.66(m, 2H); 1.88(m, 2H); 2.16(s, 3H); 3.17(t, 2H); 3.66(t, 3H); 4.08(m, 1H); 4.27(t, 2H); 4.38(brs, 2H); 6.95(s, 1H); 7.22(d, 1H); 11.81(brs, 1H); 11.96(s, 1H) | 499 |
| 167 | 6-(4-{[(3,4-dichloro-5-methyl-1H-pyrrol-2-yl)carbonyl]amino}piperidin-1-yl)-2-[2-(dimethylamino)ethoxy] | 1.50(m, 2H); 1.89(m, 2H); 2.16(s, 3H); 2.83(s, 3H); 2.85(s, 3H); 3.19(t, 2H); 3.69(s, 3H); 4.08(m, 1H); 4.31(m, 2H); 4.65(t, 2H); 7.03(s, | 514 |

-continued

| Example | SM | ¹H NMR δ | m/z |
|---|---|---|---|
| | pyrimidine-4-carboxylic acid (Example 161) | 1H); 7.20(d, 1H); 11.85(s, 1H); 11.97(s, 1H); 2H buried underneath water peak | |
| 168 | 6-(4-{[(3,4-dichloro-5-methyl-1H-pyrrol-2-yl)carbonyl]amino}piperidin-1-yl)-2-(2-hydroxyethoxy)pyrimidine-4-carboxylic acid (Example 158) | 1.52(m, 2H); 1.88(m, 2H); 2.16(s, 3H); 3.17(t, 2H); 3.67(s, 3H); 3.68(t, 2H); 4.10(m, 1H); 4.30(t, 2H); 4.35(m, 2H); 6.96(s, 1H); 7.21(d, 1H); 11.81(s, 1H); 11.95(s, 1H) | 487 |

Example 169

6-(4-{[(3,4-Dichloro-5-methyl-1H-pyrrol-2-yl)carbonyl]amino}piperidin-1-yl)-2-(2,3-dihydroxypropoxy)-N-methoxypyrimidine-4-carboxamide 6-(4-{[(3,4-Dichloro-5-methyl-1H-pyrrol-2-yl)carbonyl]amino}piperidin-1-yl)-2-[(2,2-dimethyl-1,3-dioxolan-4-yl)methoxy]-N-methoxypyrimidine-4-carboxamide (Example 313; 0.60 g, 1.08 mmol) was dissolved in THF/water (4:1; 2.5 ml) and cooled to 0° C. TFA (0.1 ml) was added to the solution which was then slowly warmed to room temperature and stirred overnight. The mixture was neutralized with concentrated ammonium hydroxide and the THF was removed in vacuo. The mixture was diluted with water (4 ml), extracted with DCM, and the organic layers dried over magnesium sulfate. The mixture was concentrated in vacuo and crude product was purified by reverse phase chromatography eluting with acetonitrile/water (0.1% TFA) (33 mg).

MS (ES) MH$^+$: 517 for $C_{20}H_{26}Cl_2N_6O_6$

¹H NMR δ: 1.52 (m, 2H); 1.88 (m, 2H); 2.16 (s, 3H); 3.18 (t, 2H); 3.43 (d, 2H); 3.67 (s, 3H); 4.08 (m, 1H); 4.17 (m, 2H); 4.30 (m, 2H); 4.35 (m, 1H); 6.96 (s, 1H); 7.22 (d, 1H); 11.81 (s, 1H); 11.96 (s, 1H).

Example 170

6-(4-{[(3,4-Dichloro-5-methyl-1H-pyrrol-2-yl)carbonyl]amino}piperidin-1-yl)-N-methoxy-2-[2-(methylsulfonyl)ethoxy]pyrimidine-4-carboxamide 6-(4-{[(3,4-Dichloro-5-methyl-1H-pyrrol-2-yl)carbonyl]amino}piperidin-1-yl)-N-methoxy-2-[2-(methylthio)ethoxy]pyrimidine-4-carboxamide (Example 165, 0.10 g, 0.19 mmol) was suspended in DCM (5 ml) and cooled to 0° C. mCPBA (0.067 g, 0.387 mmol, 70%) was added, then the reaction was warmed to room temperature and stirred for 4 h. A further equivalent of mCPBA was added and the mixture was stirred overnight. A solution of sodium sulfite (5%, 3 ml) was added and the layers separated. The aqueous phase was extracted with EtOAc and the combined organic extract was dried over magnesium sulfate and concentrated to give a white solid which was purified by reverse phase chromatography eluting with (20% to 75% acetonitrile in water, 0.1% TFA) affording the title compound (44 mg).

MS (ES) MH$^+$: 549 for $C_{20}H_{26}Cl_2N_6O_6S$

¹H NMR δ: 1.52 (m, 2H); 1.88 (m, 2H); 2.15 (s, 3H); 3.05 (s, 3H); 3.18 (t, 2H); 3.60 (t, 2H); 3.67 (s, 3H); 4.10 (m, 1H); 4.32 (m, 2H); 4.64 (t, 2H); 7.00 (s, 1H); 7.21 (d, 1H); 11.86 (s, 1H); 11.95 (s, 1H).

Example 171

6-(4-{[(3,4-Dichloro-5-methyl-1H-pyrrol-2-yl)carbonyl]amino}piperidin-1-yl)-N-methoxy-2-{2-[(methylsulfonyl)amino]ethoxy}pyrimidine-4-carboxamide Methane sulfonyl chloride (0.032 ml, 0.412 mmol) was added dropwise to a solution of 2-(2-aminoethoxy)-6-(4-{[(3,4-dichloro-5-methyl-1H-pyrrol-2-yl)carbonyl]amino}piperidin-1-yl)-N-methoxypyrimidine-4-carboxamide (Example 319, 0.20 g, 0.412 mmol), TEA (0.11 ml, 0.824 mmol) and DMF (3 ml) at 0° C. The reaction was stirred for 15 minutes at 0° C. then quenched with water. The aqueous phase was extracted with EtOAc, washed with saturated sodium bicarbonate solution, water and brine. It was dried over magnesium sulfate and concentrated to give brown solid, which was purified by reverse phase HPLC (30% to 35% acetonitrile in water, 0.1% TFA) affording the title compound (70 mg).

MS (ES) MH$^+$: 564 for $C_{20}H_{27}Cl_2N_7O_6S$

¹H NMR δ: 1.52 (m, 2H); 1.88 (m, 2H); 2.16 (s, 3H); 2.93 (s, 3H); 3.18 (t, 2H); 3.29 (m, 2H); 3.67 (s, 3H); 4.20 (m, 1H); 4.32 (m, 2H); 4.34 (t, 2H); 6.98 (s, 1H); 7.23 (m, 2H); 11.82 (s, 1H); 11.97 (s, 1H).

Example 172

6-(4-{[(3,4-Dichloro-5-methyl-1H-pyrrol-2-yl)carbonyl]amino}piperidin-1-yl)-N-methoxy-2-oxo-2,3-dihydropyrimidine-4-carboxamide The title compound was synthesized by an analogous method to Example 8 starting from 6-(4-{[(3,4-dichloro-5-methyl-1H-pyrrol-2-yl)carbonyl]amino}piperidin-1-yl)-2-oxo-2,3-dihydropyrimidine-4-carboxylic acid (Example 173) and methoxylamine hydrochloride.

MS (ES) MH$^+$: 443 for $C_{17}H_{20}Cl_2N_6O_4$

¹H NMR δ: 1.54 (m, 2H); 1.90 (m, 2H); 2.17 (s, 3H); 3.25 (m, 2H); 3.71 (s, 3H); 4.10 (m, 2H); 4.39 (brs, 1H); 6.55 (s, 1H); 7.24 (d, 1H); 11.97 (s, 1H); 12.11 (s, 1H); 1H underneath water peak.

Example 173

6-(4-{[(3,4-Dichloro-5-methyl-1H-pyrrol-2-yl)carbonyl]amino}piperidin-1-yl)-2-oxo-2,3-dihydropyrimidine-4-carboxylic acid The title compound was synthesized by an analogous method to Example 154 starting from 2-furylmethanol (commercially available) and sodium hydride, and reacting the alkoxide generated in situ with methyl 2-chloro-6-(4-{[(3,4-dichloro-5-methyl-1H-pyrrol-2-yl)carbonyl]amino}piperidin-1-yl)pyrimidine-4-carboxylate (Example 6). Purification of the crude material by reversed-phase HPLC resulted in hydrolysis of the desired product to form the title compound.

MS (ES) MH$^+$: 414 for $C_{16}H_{17}Cl_2N_5O_4$ $^1$H NMR δ: 1.54 (m, 2H); 1.90 (m, 2H); 2.16 (s, 3H); 3.26 (m, 2H); 3.71 (s, 3H); 4.09 (m, 2H); 4.49 (br s, 1H); 6.68 (s, 1H); 7.24 (d, 1H); 11.97 (s, 1H); 1H buried underneath water peak.

Example 174

2-(4-{[(3,4-Dichloro-5-methyl-1H-pyrrol-2-yl)carbonyl]amino}piperidin-1-yl)-6-methoxypyrimidine-4-carboxylic acid Lithium hydroxide (2 M, 4 ml) was warmed to 40° C. and a solution of methyl 2-(4-{[(3,4-dichloro-5-methyl-1H-pyrrol-2-yl)carbonyl]amino}piperidin-1-yl)-6-methoxypyrimidine-4-carboxylate (Example 315, 0.30 g, 0.68 mmol) in MeOH was added. The reaction temperature was increased to 60° C. and it was stirred at that temperature for 3 h. The MeOH was removed, the aqueous solution was cooled to 0° C. and then acidified with 1 N HCl. The precipitate was collected by suction filtration and washed with EtOAc to give the title compound (0.13 g).

MS (ES) MH$^+$: 428 for $C_{17}H_{19}Cl_2N_5O_4$ $^1$H NMR δ: 1.54 (m, 2H); 1.90 (m, 2H); 2.17 (s, 3H); 3.24 (t, 2H); 3.89 (s, 3H); 4.04 (m, 1H); 4.49 (d, 2H); 6.50 (s, 1H); 7.22 (d, 1H); 11.97 (s, 1H); 13.23 (s, 1H).

Example 175

2-(4-{[(3,4-Dichloro-5-methyl-1H-pyrrol-2-yl)carbonyl]amino}piperidin-1-yl)-N,6-dimethoxypyrimidine-4-carboxamide The title compound was synthesized by an analogous method to Example 8 starting from 2-(4-{[(3,4-dichloro-5-methyl-1H-pyrrol-2-yl)carbonyl]amino}piperidin-1-yl)-6-methoxypyrimidine-4-carboxylic acid (Example 174) and methoxylamine hydrochloride.

MS (ES) MH$^+$: 457 for $C_{18}H_{22}Cl_2N_6O_4$ $^1$H NMR δ: 1.51 (m, 2H); 1.87 (m, 2H); 2.16 (s, 3H); 3.11 (t, 2H); 3.69 (s, 3H); 3.86 (s, 3H); 4.06 (m, 1H); 4.67 (brs, 2H); 6.45 (s, 1H); 7.20 (d, 1H); 11.83 (s, 1H); 11.96 (s, 1H).

Example 176

2-(Butylthio)-6-(4-{[(3,4-dichloro-5-methyl-1H-pyrrol-2-yl)carbonyl]amino}piperidin-1-yl)pyrimidine-4-carboxylic acid A suspension of sodium hydride (239.5 mg, 9.98 mmol) in THF (5 ml) was cooled to 0° C. and treated with a solution of 1-butanethiol (1.0 g, 0.011 mol) in THF (5 ml). The reaction mixture was allowed to warm to room temperature slowly. Concentration under reduced pressure gave a white solid (1.02 g), which was presumed to be the sodium salt of the thiol. methyl 2-chloro-6-(4-{[(3,4-dichloro-5-methyl-1H-pyrrol-2-yl)carbonyl]amino}piperidin-1-yl)pyrimidine-4-carboxylate (Example 6) (500 mg, 1.12 mmol) and the sodium salt of the thiol (627 mg, 5.6 mmol) were combined in DMF (12 ml) and heated at 90° C. under nitrogen for 1 h. Upon cooling to room temperature, the reaction solution was diluted with EtOAc and water and then acidified with 1 N HCl. The aqueous portion was extracted with EtOAc, and the combined organic portions were dried over sodium sulfate, filtered, and concentrated under reduced pressure to give a brown oil. Some of the crude material was purified by preparatory HPLC using a gradient of 20-60% acetonitrile/water (0.1% TFA) to give the TFA salt of the title compound (50 mg).

MS (ES$^+$): 486.22, 488.22

$^1$H NMR δ: 0.83 (t, 3H); 1.32 (m, 2H); 1.4 (m, 2H); 1.58 (m, 2H); 1.81 (m, 2H); 2.10 (s, 3H); 3.0 (t, 2H); 3.14 (m, 2H); 4.04 (m, 2H); 4.27 (m, 1H); 6.98 (s, 1H); 7.16 (d, 1H); 11.90 (s, 1H); carboxylic acid proton not visible

Examples 177-181

The following compounds were synthesized by an analogous method to Example 176 from commercially available thiols and sodium hydride by reacting the sodium salt generated in situ with methyl 2-chloro-6-(4-{[(3,4-dichloro-5-methyl-1H-pyrrol-2-yl)carbonyl]amino}piperidin-1-yl)pyrimidine-4-carboxylate (Example 6). The relevant thiols are given in the table below.

Example 177

2-({2-[(tert-Butoxycarbonyl)amino]ethyl}thio)-6-(4-{[(3,4-dichloro-5-methyl-1H-pyrrol-2-yl)carbonyl]amino}piperidin-1-yl)pyrimidine-4-carboxylic acid

Example 178

6-(4-{[(3,4-Dichloro-5-methyl-1H-pyrrol-2-yl)carbonyl]amino}piperidin-1-yl)-2-[(2,3-dihydroxypropyl)thio]pyrimidine-4-carboxylic acid

Example 179

6-(4-{[(3,4-Dichloro-5-methyl-1H-pyrrol-2-yl)carbonyl]amino}piperidin-1-yl)-2-(isobutylthio)pyrimidine-4-carboxylic acid

Example 180

6-(4-{[(3,4-Dichloro-5-methyl-1H-pyrrol-2-yl)carbonyl]amino}piperidin-1-yl)-2-(isopropylthio)pyrimidine-4-carboxylic acid

Example 181

2-(tert-Butylthio)-6-(4-{[(3,4-dichloro-5-methyl-1H-pyrrol-2-yl)carbonyl]amino}piperidin-1-yl)pyrimidine-4-carboxylic acid

| Example | Starting Material | $^1$H NMR δ | m/z |
|---|---|---|---|
| 177 | tert-butyl N-(2-mercaptoethyl) carbamate | 1.25(m, 2H); 1.30(s, 9H); 1.49(m, 2H); 1.83(m, 2H); 2.11(s, 3H); 3.03(m, 2H); 3.18(m, 2H); 4.05(m, 2H); 4.27(m, 1H); 6.99(s, 1H); 7.0(t, 1H); 7.15(d, 1H); 11.91(s, 1H); carboxylic acid proton not visible | 571 |
| 178 | 3-mercapto-1,2-propanediol | 1.48(m, 2H); 1.82(m, 2H); 2.10(s, 3H); 2.91(d, 2H); 2.96(d, 2H); 3.14(m, 2H); 3.6(m, 1H); 4.03(m, 2H); 4.29(m, 1H); 7.00(s, 1H); 7.15(d, 1H); 11.90(s, 1H); carboxylic acid proton not visible | 504 |
| 179 | 2-methyl-1-propanethiol | 0.90(d, 6H); 1.46(m, 2H); 1.84(m, 2H); 2.11(s, 3H); 2.91(d, 2H); 3.15(m, 2H); 3.7-4.3(overlapping multiplets, 4H); 7.00(s, 1H); 7.17(d, 1H); 11.90(s, 1H); carboxylic acid proton not visible | 484 |
| 180 | 2-propanethiol | 1.28(d, 6H); 1.49(m, 2H); 1.82(m, 2H); 2.10(s, 3H); 3.14(m, 2H); 3.77(m, 1H); 4.04(m, 2H); 4.28(m, 1H); 6.99(s, 1H); 7.18(d, 1H); 11.93(s, 1H); carboxylic acid proton not visible | 472 |
| 181 | tert-butyl mercaptan | 1.43(m, 4H); 1.50(s, 9H); 1.82(m, 2H); 2.10(s, 3H); 3.11(m, 2H); 4.05(m, 2H); 4.24(m, 1H); 6.98(s, 1H); 7.16(d, 1H); 11.90(s, 1H); carboxylic acid proton not visible. | 484 |

Examples 182-185

The following compounds were synthesized by an analogous method to Example 8 by coupling the acids in the table below with methoxylamine hydrochloride.

Example 182 tert-Butyl 2-({4-(4-{[(3,4-dichloro-5-methyl-1H-pyrrol-2-yl)carbonyl]amino}piperidin-1-yl)-6-[(methoxyamino)carbonyl]pyrimidin-2-yl}thio)ethylcarbamate

Example 183

2-(Butylthio)-6-(4-{[(3,4-dichloro-5-methyl-1H-pyrrol-2-yl)carbonyl]amino}piperidin-1-yl)-N-methoxypyrimidine-4-carboxamide

Example 184

6-(4-{[(3,4-Dichloro-5-methyl-1H-pyrrol-2-yl)carbonyl]amino}piperidin-1-yl)-2-(isopropylthio)-N-methoxypyrimidine-4-carboxamide

Example 185

6-(4-{[(3,4-Dichloro-5-methyl-1H-pyrrol-2-yl)carbonyl]amino}piperidin-1-yl)-2-[(2-hydroxyethyl)thio]-N-methoxypyrimidine-4-carboxamide

| Example | Acid | $^1$H NMR δ | m/z |
|---|---|---|---|
| 182 | 2-({2-[(tert-butoxycarbonyl)amino]ethyl}thio)-6-(4-{[(3,4-dichloro-5-methyl-1H-pyrrol-2-yl)carbonyl]amino} piperidin-1-yl)pyrimidine-4-carboxylic acid (Example 177) | 1.38(m, 2H); 1.46(s, 9H); 1.60(m, 2H); 1.94(m, 2H); 2.23(s, 3H); 3.1(m, 2H); 3.24(m, 2H); 4.15(m, 2H); 4.39(m, 1H); 7.11(s, 1H); 7.3(overlapping triplet and doublet, 2H); 11.85(s, 1H); 12.03(s, 1H) | 600 |
| 183 | 2-(butylthio)-6-(4-{[(3,4-dichloro-5-methyl-1H-pyrrol-2-yl)carbonyl]amino} piperidin-1-yl)pyrimidine-4-carboxylic acid (Example 176) | 0.81(t, 3H); 1.33(m, 2H); 1.5(m, 2H); 1.57(m, 2H); 1.81(m, 2H); 2.10(s, 3H); 3.01(t, 2H); 3.15(m, 2H); 3.61(s, 3H); 4.05(m, 2H); 4.21(m, 1H); 6.92(s, 1H); 7.18(d, 1H); 11.68(s, 1H); 11.90(s, 1H) | 513 |
| 184 | 6-(4-{[(3,4-dichloro-5-methyl-1H-pyrrol-2-yl)carbonyl]amino}piperidin-1-yl)-2-(isopropylthio)pyrimidine-4-carboxylic acid(Example 180) | 1.27(d, 6H); 1.48(m, 2H); 1.81(m, 2H); 2.10(s, 3H); 3.12(m, 2H); 3.88(m, 1H); 4.03(m, 2H); 4.27(m, 1H); 6.92(s, 1H); 7.15(d, 1H); 11.68(brs, 1H); 11.90(s, 1H) | 501 |

-continued

| Example | Acid | ¹H NMR δ | m/z |
|---|---|---|---|
| 185 | 6-(4-{[(3,4-dichloro-5-methyl-1H-pyrrol-2-yl)carbonyl]amino}piperidin-1-yl)-2-[(2-hydroxyethyl)thio]pyrimidine-4-carboxylic acid(Example 16) | 1.44(m, 2H); 1.82(m, 2H); 2.11(s, 3H); 3.1-3.16(overlapping triplet and multiplet, 4H); 3.55(t, 2H); 4.02(m, 2H); 4.26(m, 1H); 6.94(s, 1H); 7.15(d, 1H); 11.67(s, 1H); 11.90(s, 1H) | 501 |

Examples 186-189

The following compounds were synthesized by an analogous method to Example 10 by oxidizing the thioethers in the table above with mCPBA.

Example 186 tert-Butyl 2-({4-(4-{[(3,4-dichloro-5-methyl-1H-pyrrol-2-yl)carbonyl]amino}piperidin-1-yl)-6-[(methoxyamino)carbonyl]pyrimidin-2-yl}sulfonyl)ethylcarbamate

Example 187

2-(Butylsulfonyl)-6-(4-{[(3,4-dichloro-5-methyl-1H-pyrrol-2-yl)carbonyl]amino}piperidin-1-yl)-N-methoxypyrimidine-4-carboxamide

Example 188

6-(4-{[(3,4-Dichloro-5-methyl-1H-pyrrol-2-yl)carbonyl]amino}piperidin-1-yl)-2-(isopropylsulfonyl)-N-methoxypyrimidine-4-carboxamide

Example 189

6-(4-{[(3,4-Dichloro-5-methyl-1H-pyrrol-2-yl)carbonyl]amino}piperidin-1-yl)-2-[(2-hydroxyethyl)sulfonyl]-N-methoxypyrimidine-4-carboxamide

Example 190

6-(4-{[(3,4-Dichloro-5-methyl-1H-pyrrol-2-yl)carbonyl]amino}piperidin-1-yl)-2-(isopropylthio)pyrimidine-4-carboxamide 6-(4-{[(3,4-Dichloro-5-methyl-1H-pyrrol-2-yl)carbonyl]amino}piperidin-1-yl)-2-(isopropylthio)pyrimidine-4-carboxylic acid (Example 180; 200 mg, 0.423 mmol), ammonia solution (2 M in MeOH, 0.43 ml, 0.846 mmol), TEA (0.06 ml, 0.423 mmol), and HATU (161 mg, 0.42 mmol) were combined in DMF (3 ml) and stirred at room temperature for 1 h. The reaction was diluted with EtOAc and water, and the organic portion was washed sequentially with 1 N HCl, saturated sodium bicarbonate, and brine. The organic portion was dried over sodium sulfate, filtered and concentrated to give an off-white solid (312 mg). The crude material was purified by preparatory HPLC using a gradient of 40-70% acetonitrile/water (0.1% TFA) over 14 minutes to give the title compound as a white solid.

MS (ES⁻): 469.06, 471.18

¹H NMR δ: 1.27 (d, 6H); 1.49 (m, 2H); 1.82 (m, 2H); 2.10 (s, 3H); 3.12 (m, 2H); 3.86 (m, 3H); 4.04 (m, 2H); 4.25 (m, 1H); 6.97 (s, 1H); 7.15 (d, 1H); 7.68 (s, 1H); 7.78 (s, 1H); 11.90 (s, 1H).

| Example | Starting material | ¹H NMR δ | m/z |
|---|---|---|---|
| 186 | Example 182 | 1.11(t, 2H); 1.30(s, 9H); 1.53(m, 2H); 1.88(m, 2H); 2.11(s, 3H); 3.22(m, 2H); 3.71(m, 2H); 4.08(m, 2H); 4.58(m, 1H); 6.97(t, 1H); 7.17(d, 1H); 7.41(s, 1H); 11.89(s, 1H); 11.92(s, 1H) | 634 |
| 187 | Example 183 | 0.81(t, 3H); 1.37(m, 2H); 1.55(m, 2H); 1.86(m, 2H); 2.11(s, 3H); 3.2(m, 2H); 3.6(m, 2H); 3.66(s, 3H); 4.08(m, 2H); 4.55(m, 1H); 7.17(d, 1H); 7.39(s, 1H); 11.91(s, 1H); 11.97(s, 1H) | 545 |
| 188 | Example 184 | 1.16(d, 6H); 1.53(m, 2H); 1.87(m, 2H); 2.11(s, 3H); 3.24(m, 2H); 3.66(s, 3H); 4.08(m, 2H); 4.25(m, 1H); 4.55(m, 1H); 7.17(d, 1H); 7.39(s, 1H); 11.91(s, 1H); 11.95(s, 1H) | 531 |
| 189 | Example 185 | 1.49(m, 2H); 1.87(m, 2H); 2.11(s, 3H); 3.23(m, 2H); 3.66(s, 3H); 3.76(t, 2H); 4.08(m, 2H); 4.60(m, 1H); 7.17(d, 1H); 7.38(s, 1H); 11.67(s, 1H); 11.91(s, 1H); 11.96(s, 1H) | 535 |

Example 191

6-(4-{[(3,4-Dichloro-5-methyl-1H-pyrrol-2-yl)carbonyl]amino}piperidin-1-yl)-N-methoxy-2-pyrrolidin-1-ylpyrimidine-4-carboxamide The title compound was synthesized by an analogous method to Example 8 starting from 6-(4-{[(3,4-dichloro-5-methyl-1H-pyrrol-2-yl)carbonyl]amino)}piperidin-1-yl)-2-pyrrolidin-1-ylpyrimidine-4-carboxylic acid (Example 335) and methoxylamine hydrochloride.

MS (ES$^-$): 494.67, 496.66

$^1$H NMR δ: 1.49 (m, 2H); 1.85 (m, 6H); 2.11 (s, 3H); 3.17 (m, 2H); 3.67 (s, 3H); 3.7 (m, 4H); 4.04 (m, 2H); 4.28 (m, 1H); 6.67 (s, 1H); 7.17 (d, 1H); 11.86 (s, 1H); 11.91 (s, 1H)

Example 192

3,4-Dichloro-N-{1-[2-chloro-6-(hydrazinocarbonyl)pyrimidin-4-yl]piperidin-4-yl}-5-methyl-1H-pyrrole-2-carboxamide Methyl 2-chloro-6-(4-{[(3,4-dichloro-5-methyl-1H-pyrrol-2-yl)carbonyl]amino}piperidin-1-yl)pyrimidine-4-carboxylate (Example 6) (500 mg, 1.12 mmol), hydrazine (0.035 ml, 1.12 mmol), and TEA (0.16 ml, 1.12 mmol) were combined in DMF (3 ml) and stirred at room temperature. Within 1.5 h, a white precipitate had formed. The reaction was stirred for another 30 minutes, and then the precipitate was collected by suction filtration to give 377 mg of the title compound. 100 mg of the crude material was purified by preparatory HPLC, using a gradient of 40-70% acetonitrile/water (0.1% TFA) over 14 minutes to give 23 mg of the title compound.

MS (ES$^-$): 446.21, 448.20

$^1$H NMR δ: 1.47 (m, 2H); 1.84 (m, 2H); 2.11 (s, 3H); 3.1 (m, 2H); 4.06 (m, 2H); 4.35 (m, 2H); 4.77 (m, 1H); 7.16 (d, 1H); 7.18 (s, 1H); 9.85 (m, 1H); 11.91 (s, 1H)

Example 193

N-Allyl-2-chloro-6-(4-{[(3,4-dichloro-5-methyl-1H-pyrrol-2-yl)carbonyl]amino}piperidin-1-yl)pyrimidine-4-carboxamide Methyl 2-chloro-6-(4-{[(3,4-dichloro-5-methyl-1H-pyrrol-2-yl)carbonyl]amino}piperidin-1-yl)pyrimidine-4-carboxylate (Example 6) (100 mg, 0.224 mmol) in anhydrous THF (3 ml) was treated with allylamine (0.025 ml, 0.336 mmol), sodium tert-butoxide (32.29 mg, 0.336 mmol), Pd(Dppf)$_2$Cl$_2$-DCM complex (9.14 mg, 0.0112 mmol) and Dppf (18.61 mg, 0.0336 mmol). The reaction was heated at 80° C. for 2 h. The reaction mixture was filtered through Celite, and the filtrate was concentrated to give a rust-coloured solid. The crude material was purified by preparatory HPLC, using a gradient of 35-75% acetonitrile/water (0.1% TFA) to give 12 mg pale brown solid.

MS (ES$^-$): 471.47

$^1$H NMR δ: 1.47 (m, 2H); 1.84 (m, 2H); 2.11 (s, 3H); 3.18 (m, 2H); 3.79 (t, 2H); 4.02 (m, 2H); 4.3 (m, 1H); 5.02 (t, 2H); 5.8 (m, 1H); 7.16 (d, 1H); 7.24 (s, 1H); 8.7 (t, 1H); 11.91 (s, 1H)

Example 194

6-(4-{[(3,4-Dichloro-5-methyl-1H-pyrrol-2-yl)carbonyl]amino}piperidin-1-yl)-2-piperazin-1-ylpyrimidine-4-carboxylic acid The title compound was synthesized by an analogous method to Example 310 starting from methyl 6-(4-{[(3,4-dichloro-5-methyl-1H-pyrrol-2-yl)carbonyl]amino}piperidin-1-yl)-2-piperazin-1-ylpyrimidine-4-carboxylate (Example 317) and 2 N lithium hydroxide.

MS (ES$^-$): 480.29, 482.28

$^1$H NMR δ: 1.41 (m, 2H); 1.81 (m, 2H); 2.11 (s, 3H); 3.08 (m, 4H); 3.75 (m, 4H); 4.01 (m, 2H); 4.23 (m, 2H); 4.48 (m, 1H); 6.68 (s, 1H); 7.14 (d, 1H); 8.71 (m, 1H); 11.92 (s, 1H); carboxylic acid proton not visible

Example 195

6-(4-{[(3,4-Dichloro-5-methyl-1H-pyrrol-2-yl)carbonyl]amino}piperidin-1-yl)-N-methoxy-2-piperazin-1-ylpyrimidine-4-carboxamide The title compound was synthesized by an analogous method to Example 8 starting from 6-(4-{[(3,4-dichloro-5-methyl-1H-pyrrol-2-yl)carbonyl]amino}piperidin-1-yl)-2-piperazin-1-ylpyrimidine-4-carboxylic acid (Example 194) and methoxylamine hydrochloride.

MS (ES$^-$): 509.70, 511.67

$^1$H NMR δ: 1.41 (m, 2H); 1.81 (m, 2H); 2.11 (s, 3H); 3.06 (m, 4H); 3.63 (s, 3H); 3.75-4.0 (overlapping multiplets, 6H); 4.23 (m, 2H); 4.55 (m, 1H); 6.62 (s, 1H); 7.15 (d, 1H); 8.75 (m, 1H); 11.69 (s, 1H); 11.93 (s, 1H)

Example 196

6-(4-{[(3,4-Dichloro-5-methyl-1H-pyrrol-2-yl)carbonyl]amino}piperidin-1-yl)-2-(4-methylpiperazin-1-yl)pyrimidine-4-carboxylic acid The title compound was synthesized by an analogous method to Example 310 starting from methyl 6-(4-{[(3,4-dichloro-5-methyl-1H-pyrrol-2-yl)carbonyl]amino}piperidin-1-yl)-2-(4-methylpiperazin-1-yl)pyrimidine-4-carboxylate (Example 318) and 2 N lithium hydroxide.

MS (ES$^-$): 494.31, 496.3

$^1$H NMR δ: 1.44 (m, 2H); 1.83 (m, 2H); 2.11 (s, 3H); ~2.4 (s, 3H); 3.17 (m, 4H); 3.6-4.1 (overlapping multiplets, 8H); 4.38 (m, 1H); 7.15 (d, 1H); 7.27 (s, 1H); 11.91 (s, 1H)

Example 197

6-(4-{[(3,4-Dichloro-5-methyl-1H-pyrrol-2-yl)carbonyl]amino}piperidin-1-yl)-N-methoxy-2-(4-methylpiperazin-1-yl)pyrimidine-4-carboxamide The title compound was synthesized by an analogous method to Example 8 starting from 6-(4-{[(3,4-dichloro-5-methyl-1H-pyrrol-2-yl)carbonyl]amino}piperidin-1-yl)-2-(4-methylpiperazin-1-yl)pyrimidine-4-carboxylic acid (Example 196) and methoxylamine hydrochloride.

MS (ES$^-$): 523.72, 525.65

$^1$H NMR δ: 1.44 (m, 2H); 1.81 (m, 2H); 2.11 (s, 3H); 2.76 (s, 3H); 2.94 (m, 2H); 3.06 (m, 2H); 3.39 (m, 2H); 3.63 (s, 3H); 3.9 (m, 2H); 4.23 (m, 2H); 4.55 (m, 1H); 4.77 (m, 2H); 6.64 (s, 1H); 7.13 (d, 1H); 7.27 (s, 1H); 11.71 (s, 1H); 11.92 (s, 1H)

Example 198

2-(4-{[(3,4-Dichloro-5-methyl-1H-pyrrol-2-yl)carbonyl]amino}piperidin-1-yl)-6-(ethylsulfonyl)-N-methoxypyrimidine-4-carboxamide The title compound was synthesized by an analogous method to Example 10 starting from 2-(4-{[(3,4-dichloro-5-methyl-1H-pyrrol-2-yl)carbonyl]amino}piperidin-1-yl)-6-(ethylthio)-N-methoxypyrimidine-4-carboxamide (Example 203) and mCPBA.

MS (ES$^-$): 517.62, 519.61

$^1$H NMR δ: 1.13 (t, 3H); 1.44 (m, 2H); 1.85 (m, 2H); 2.11 (s, 3H); 3.14 (m, 2H); 3.41 (q, 2H); 3.67 (s, 3H); 4.05 (m, 2H); 4.77 (m, 1H); 7.15 (d, 1H); 7.34 (s, 1H); 11.92 (s, 1H); 12.16 (s, 1H)

Example 199

3,4-Dichloro-N-[1-(2-chloro-6-cyanopyrimidin-4-yl)piperidin-4-yl]-5-methyl-1H-pyrrole-2-carboxamide A stock solution of trimethylsilyl polyphosphate (prepared according to Yokoyama, Masataka; Yoshida, Sayaka; Imamoto, Tsuneo. *Synthesis*, 1982, 7, 591-592) was prepared by combining P$_2$O$_5$ (10 g) and hexamethyldisiloxane (25 ml) in anhydrous toluene (50 ml) and heating the mixture at 80° C. until it became a clear solution (about 45 minutes). 2-Chloro-6-(4-{[(3,4-dichloro-5-methyl-1H-pyrrol-2-yl)carbonyl]amino}piperidin-1-yl)pyrimidine-4-carboxamide (Example 37, 2.1 g, 4.8 mmol) was treated with trimethylsilyl polyphosphate (80 ml), and the reaction was heated at 80° C. for 5 h, after which the reaction was about 50% complete. No further reaction was apparent after adding more trimethylsilyl polyphosphate and letting the reaction stir an additional 2.5 days. Upon cooling to room temperature, the reaction was concentrated under reduced pressure until most of the solvent was removed. The remaining liquid was triturated with EtOAc and water to form a brown precipitate, which was mostly the amide precursor. The mixture was filtered, and the filtrate was concentrated under reduced pressure to give the title compound as a yellow solid. About 20 mg was purified by preparatory HPLC, using a gradient of 35-75% acetonitrile/water (0.1% TFA), while the rest was carried on without further purification.

MS (ES$^-$): 436.17, 438.16

$^1$H NMR δ: 1.51 (m, 2H); 1.9 (m, 2H); 2.12 (s, 3H); 3.28 (m, 2H); 4.06 (m, 2H); 4.43 (m, 1H); 7.16 (d, 1H); 7.64 (s, 1H); 11.93 (s, 1H)

Example 200

N-(1-{6-[(Z)-Amino(hydroxyimino)methyl]-2-chloropyrimidin-4-yl}piperidin-4-yl)-3,4-dichloro-5-methyl-1H-pyrrole-2-carboxamide 3,4-Dichloro-N-[1-(2-chloro-6-cyanopyrimidin-4-yl)piperidin-4-yl]-5-methyl-1H-pyrrole-2-carboxamide (Example 199, 150 mg, 0.36 mmol), hydroxylamine hydrochloride (25 mg, 0.36 mmol) and TEA (0.05 ml, 0.36 mmol) were combined in MeOH (5 ml), and the reaction was heated at 80° C. for 2 h. The reaction was diluted with EtOAc and washed with water. The aqueous portion was extracted with EtOAc, and the combined organic portions were dried (sodium sulfate), filtered and concentrated to give a pale yellow solid. The crude material was purified by preparatory HPLC, using a gradient of 35-75% acetonitrile/water (0.1% TFA) to give 53 mg of the title compound.

MS (ES$^+$): 446.06, 448.05

$^1$H NMR δ: 1.50 (m, 2H); 1.84 (m, 2H); 2.11 (s, 3H); 3.16 (m, 2H); 4.06 (m, 2H); 4.21 (m, 1H); 7.08 (s, 1H); 7.16 (d, 1H); 10.36 (brs, 1H); 11.91 (s, 1H)

Example 201

Methyl 2-(4-{[(3,4-dichloro-5-methyl-1H-pyrrol-2-yl)carbonyl]amino}piperidin-1-yl)-6-(ethylthio)pyrimidine-4-carboxylate The title compound was synthesized by a method analogous to Example 9 by coupling methyl 2-chloro-6-(ethylthio)pyrimidine-4-carboxylate (Intermediate 96) with 3,4-dichloro-5-methyl-N-piperidin-4-yl-1H-pyrrole-2-carboxamide hydrochloride (Intermediate 1).

MS (ESP): 472.56 (M+H) for C$_{19}$H$_{23}$Cl$_2$N$_5$O$_3$S $^1$H NMR δ: 1.31 (t, 3H); 1.52 (m, 2H); 1.90 (d, 2H); 2.17 (s, 3H); 3.05-3.25 (m, 4H); 3.83 (s, 3H); 4.10 (m, 1H); 4.57 (d, 2H); 6.95 (s, 1H); 7.25 (d, 1H); 12.0 (s, 1H).

Example 202

2-(4-{[(3,4-Dichloro-5-methyl-1H-pyrrol-2-yl)carbonyl]amino}piperidin-1-yl)-6-(ethylthio)pyrimidine-4-carboxylic acid The title compound was synthesized from methyl 2-(4-{[(3,4-dichloro-5-methyl-1H-pyrrol-2-yl)carbonyl]amino}piperidin-1-yl)-6-(ethylthio)pyrimidine-4-carboxylate (Example 201) by a method analogous to Example 31.

MS (ESP): 458.2 (M+H) for C$_{18}$H$_{21}$Cl$_2$N$_5$O$_3$S $^1$H NMR δ 1.25 (t, 3H); 1.50 (m, 2H); 1.85 (d, 2H); 2.11 (s, 3H); 3.03-3.20 (m, 4H); 4.05 (m, 1H); 4.20 (br s, 1H); 4.54 (d, 2H); 6.86 (s, 1H); 7.14 (d, 1H); 11.90 (s, 1H).

Example 203

2-(4-{[(3,4-Dichloro-5-methyl-1H-pyrrol-2-yl)carbonyl]amino}piperidin-1-yl)-6-(ethylthio)-N-methoxypyrimidine-4-carboxamide The title compound was synthesized by an analogous method to Example 8 starting from 2-(4-{[(3,4-dichloro-5-methyl-1H-pyrrol-2-yl)carbonyl]amino}piperidin-1-yl)-6-(ethylthio)pyrimidine-4-carboxylic acid (Example 202) and methoxylamine hydrochloride.

MS (ESP): 487.5 (M+H) for C$_{19}$H$_{24}$Cl$_2$N$_6$O$_3$S $^1$H NMR δ: 1.24 (t, 3H); 1.46 (m, 2H); 1.82 (d, 2H); 2.11 (s, 3H); 3.02-3.11 (m, 4H); 3.62 (s, 3H); 4.05 (m, 1H); 4.60 (d, 2H); 6.83 (s, 1H); 7.14 (d, 1H); 11.83 (s, 1H); 11.90 (s, 1H).

Example 204

2-Chloro-6-(4-{[(3,4-dichloro-5-methyl-1H-pyrrol-2-yl)carbonyl]amino}piperidin-1-yl)-N-(methylsulfonyl)pyrimidine-4-carboxamide A solution of methanesulfonamide (40 mg, 0.44 mmol) and DMF (0.5 ml) was added to a suspension of sodium hydride (95%) (11 mg, 0.44 mmol) and DMF (0.5 ml) under nitrogen. The mixture was stirred for 20 minutes at room temperature. A solution of methyl 2-chloro-6-(4-{[(3,4-dichloro-5-methyl-1H-pyrrol-2-yl)carbonyl]amino}piperidin-1-yl)pyrimidine-4-carboxylate (Example 6, 47 mg, 0.11 mmol) in DMF (1 ml) was added dropwise to the mixture over 5 minutes. The mixture was stirred for 1 h at room temperature and for 3 h at 60° C. The mixture was cooled to room temperature and concentrated under reduced pressure. The crude residue was purified by preparative reversed-phase HPLC (water/acetonitrile gradient, 10-90%) to afford the title compound (14 mg).

MS (ESP): 507.3 (M−H) for $C_{17}H_{19}Cl_3N_6O_4S$ $^1$H NMR δ: 1.49 (m, 214); 1.86 (d, 2H); 2.11 (s, 3H); 3.20 (m, 2H); 3.29 (s, 3H); 4.05 (m, 2H); 4.45 (m, 1H); 4.60-4.80 (br s, 1H); 7.17 (d, 1H); 7.30 (s, 1H); 11.91 (s, 1H).

Example 205

2-Butyl-6-(4-{[(3,4-dichloro-5-methyl-1H-pyrrol-2-yl)carbonyl]amino}piperidin-1-yl)pyrimidine-4-carboxylic acid (6-{4-[(tert-Butoxycarbonyl)amino]piperidin-1-yl}-2-butylpyrimidine-4-carboxylic acid) (Intermediate 100) was treated with 4 N HCl/dioxane for as described for Intermediate 70. The resulting hydrochloride salt, 6-(4-aminopiperidin-1-yl)-2-butylpyrimidine-4-carboxylic acid hydrochloride salt was coupled to 3,4-dichloro-5-methyl-1H-pyrrole-2-carboxylic acid (Intermediate 3) in a manner analogous to Example 29 to give the title compound.

MS (ES) (M+H): 454 for $C_{20}H_{25}Cl_2N_5O_3$ $^1$H NMR δ: 0.95 (t, 3H); 1.36 (m, 2H); 1.56 (m, 2H); 1.71 (m, 2H); 1.96 (m, 2H); 2.15 (s, 3H); 2.80 (m, 2H); 3.36 (b, 2H); 4.18 (m, 1H); 4.52 (m, 2H); 7.15 (s, 1H); 7.29 (d, 1H); 12.01 (s, 1H)

Examples 206-208

The following compounds were synthesized by an analogous method to Example 29 from 3,4-dichloro-5-methyl-1H-pyrrole-2-carboxylic acid (Intermediate 3) and the starting materials indicated.

Example 206

2-Cyclopropyl-6-(4-{[(3,4-dichloro-5-methyl-1H-pyrrol-2-yl)carbonyl]amino}piperidin-1-yl)pyrimidine-4-carboxylic acid

Example 207

6-(4-{[(3,4-Dichloro-5-methyl-1H-pyrrol-2-yl)carbonyl]amino}piperidin-1-yl)-2-isopropylpyrimidine-4-carboxylic acid

Example 208

2-tert-Butyl-(4-{[(3,4-dichloro-5-methyl-1H-pyrrol-2-yl)carbonyl]amino}piperidin-1-yl)pyrimidine-4-carboxylic acid

| Example | Starting material | $^1$H NMR δ | m/z |
|---|---|---|---|
| 206 | 6-(4-aminopiperidin-1-yl)-2-cyclopropyl pyrimidine-4-carboxylic acid hydrochloride (Intermediate 172) | 1.22(m, 4H); 1.65(m, 2H); 2.00(m, 2H); 2.71(s, 3H); 3.36(m, 4H); 3.93(m, 2H); 4.12(m, 1H); 7.25(d, 1H); 7.35(s, 1H); 11.97(s, 1H) | 438 |
| 207 | 6-(4-aminopiperidin-1-yl)-2-isopropyl pyrimidine-4-carboxylic acid hydrochloride (Intermediate 173) | 1.29(d, 6H); 1.68(m, 2H); 2.02(m, 2H); 2.22(s, 3H); 3.31(m, 1H); 3.54(m, 2H); 4.26(m, 2H); 4.21(m, 1H); 7.27(d, 1H); 7.43(s, 1H); 12.12(s, 1H) | 440 |
| 208 | 6-(4-aminopiperidin-1-yl)-2-tert-butyl pyrimidine-4-carboxylic acid hydrochloride (Intermediate 174) | 1.29(s, 9H); 1.58(m, 2H); 1.93(m, 2H); 2.11(s, 3H); 3.32(m, 2H); 4.17(m, 2H); 4.21(m, 1H); 7.06(s, 1H); 7.18(d, 1H); 12.02(s, 1H) | 454 |

Example 209-217

The following compounds were prepared by an analogous method to N-{1-[6-amino-2-(methylsulfanyl)-4-pyrimidinyl]-4-piperidinyl}-3,4-dichloro-5-methyl-1H-pyrrole-2-carboxamide (Example 118) starting from 3,4-dichloro-5-methyl-1H-pyrrole-2-carboxylic acid (Intermediate 3) and the intermediates shown in the table below.

Example 209

Methyl 5-(4-{[(3,4-dichloro-5-methyl-1H-pyrrol-2-yl)carbonyl]amino}piperidin-1-yl)thiophene-2-carboxylate

Example 210

Methyl 5-(4-{[(3,4-dichloro-5-methyl-1H-pyrrol-2-yl)carbonyl]amino}piperidin-1-yl)-2-furoate

Example 211

Methyl 3-(4-{[(3,4-dichloro-5-methyl-1H-pyrrol-2-yl)carbonyl]amino}piperidin-1-yl)benzoate

Example 212

Methyl 3-bromo-5-(4-{[(3,4-dichloro-5-methyl-1H-pyrrol-2-yl)carbonyl]amino}piperidin-1-yl)benzoate

Example 213

Ethyl 5-(4-{[(3,4-dichloro-5-methyl-1H-pyrrol-2-yl)carbonyl]amino}piperidin-1-yl)nocotinate

Example 214

Methyl 5-(4-{[(3,4-dichloro-5-methyl-1H-pyrrol-2-yl)carbonyl]amino}piperidin-1-yl)nocotinate

Example 215

Methyl 6-(4-{[(3,4-dichloro-5-methyl-1H-pyrrol-2-yl)carbonyl]amino}piperidin-1-yl)pyridine-2-carboxylate

Example 216

Methyl 3-(4-{[(3,4-dichloro-methyl-1H-pyrrol-2-yl)carbonyl]amino}piperidin-1-yl)-5-morpholin-4-yl-benzoate

Example 217

Methyl 3-(4-{[(3,4-dichloro-5-methyl-1H-pyrrol-2-yl)carbonyl]amino}piperidin-1-yl)-5-(4-methylpiperazin-1-yl)benzoate

| Example | Starting material | $^1$H NMR δ | m/z |
|---|---|---|---|
| 209 | Intermediate 110 | 1.65-1.78(m, 2H); 1.91-1.95(m, 2H); 2.20(s, 3H); 3.11-3.19(m, 2H); 3.62-3.67(m, 2H); 3.74(s, 3H); 4.01(m, 1H); 6.24(d, 1H); 7.30(d, 1H); 7.54(d, 1H); 11.98(s, 1H). | 416 |
| 210 | Intermediate 111 | 1.56-1.67(m, 2H); 1.87-1.96(m, 2H); 2.18(s, 3H); 3.04(t, 2H); 3.67-3.71(m, 5H); 3.98(m, 1H); 5.5(d, 1H); 7.25-7.29(m, 2H); 11.96 s, 1H). | 400 |
| 211 | Intermediate 112 | 1.61-1.71(m, 2H); 1.90-1.94(m, 2H); 2.18(s, 3H); 2.94(t, 2H); 3.70-3.75(m, 2H); 3.84(s, 3H); 3.96(m, 1H); 7.23-7.70(m, 5H); 11.96(s, 1H). | 410 |
| 212 | Intermediate 113 | 1.57-1.68(m, 2H); 1.87-1.91(m, 2H); 2.18(s, 3H); 2.99(t, 2H); 3.76-3.80(m, 2H); 3.85(s, 3H); 3.98(m, 1H); 7.25(d, 1H); 7.38-7.43(m, 3H); 11.9(s, 1H). | 489 |
| 213 | Intermediate 114 | 1.33(t, 3H); 1.57-1.73(m, 2H); 2.08-2.12(m, 2H); 2.20(s, 3H); 2.94-3.03(m, 2H); 3.62-3.66(m, 2H); 4.09(m, 1H); 4.32(q, 2H); 6.52(d, 1H); 7.70(s, 1H); 8.39(s, 1H); 8.60(s, 1H); 9.26(s, 1H). | 425 |
| 214 | Intermediate 115 | 1.59-1.72(m, 2H); 1.90-1.93(m, 2H); 2.18(s, 3H); 3.00(t, 2H); 3.80-3.85(m, 2H); 3.87(s, 3H); 3.99(m, 1H); 7.25(d, 1H); 7.70(s, 1H); 8.46(S, 1H); 8.57(s, 1H); 11.96(s, 1H). | 411 |
| 215 | Intermediate 116 | 1.48-1.59(m, 2H); 1.87-1.90(m, 2H); 2.17(s, 3H); 3.05(t, 2H); 3.83(s, 3H); 4.05(m, 1H); 4.27-4.32(m, 2H); 7.12(d, 1H); 7.22(d, 1H); 7.28(d, 1H); 7.68(t, 1H); 12.09(s, 1H). | 411 |
| 216 | Intermediate 117 | 1.63(m, 2H); 1.88(d, 2H); 2.16(s, 3H); 2.88(t, 2H); 3.04-3.19(m, 4H); 3.62-3.76(m, 6H); 3.80(s, 3H); 3.86-3.99(m, 1H); 6.74(s, 1H); 6.91(s, 1H); 6.98(s, 1H); 7.22(d, 1H); 11.94(s, 1H). | 495 |
| 217 | Intermediate 118 | 1.53-1.73(q, 2H); 1.89(d, 2H); 2.17(s, 3H); 2.30-2.47(m, 2H); 2.57-2.80(m, 4H); 2.88(t, 3H); 3.04-3.25(m, 4H); 3.69(d, 2H); 3.80(s, 3H); 3.85-4.03(m, 1H); 6.74(s, 1H); 6.92(s, 1H); 6.97(s, 1H); 7.22(d, 1H); 11.94(s, 1H). | 508 |

Example 218

Ethyl 2-(4-{[(3,4-dichloro-5-methyl-1H-pyrrol-2-yl)carbonyl]amino}piperidin-1-yl)-4-methyl-1,3-thiazole-5-carboxylate 3,4-Dichloro-5-methyl-N-piperidin-4-yl-1H-pyrrole-2-carboxamide hydrochloride (Intermediate 1; 0.500 g, 2.00 mmol), ethyl 2-bromo-4-methyl-1,3-thiazole-5-carboxylate (0.625 g, 2.00 mmol) and sodium bicarbonate (0.336 g, 2.00 mmol) were stirred in DMF (5 ml). The reaction was heated to 50° C. overnight. The solution was diluted by the addition of water and the resulting layers were separated. The aqueous layer was extracted with EtOAc (3×), and the organic layers were combined, dried over anhydrous magnesium sulfate, filtered and concentrated. Hexanes were added to the crude material, and the precipitate was filtered and rinsed with EtOAc to give the title compound as a beige solid (0.273 g).

MS (ESP): 445 (MH$^+$) for $C_{18}H_{22}Cl_2N_4O_3S$ $^1$H NMR (CDCl$_3$) δ: 1.32 (t, 3H); 1.62-1.72 (m, 2H); 2.12 (dd, 2H); 2.27 (s, 3H); 2.55 (s, 3H); 3.27 (dt, 2H); 4.11 (d, 2H); 4.13-4.33 (m, 3H); 6.57 (d, 1H); 9.41 (brs, 1H).

Examples 219 and 220

The following example was prepared by the general procedure of Example 218 using 3,4-dichloro-5-methyl-N-piperidin-4-yl-1H-pyrrole-2-carboxamide hydrochloride (Intermediate 1) and the appropriate halide.

Example 219

Ethyl 5-(4-{[(3,4-dichloro-5-methyl-1H-pyrrol-2-yl)carbonyl]amino}piperidin-1-yl)-1,3,4-thiadiazole-2-carboxylate

Example 220

3,4-Dichloro-N-{1-[5-(ethylthio)-1,3,4-thiadiazol-2-yl]piperidin-4-yl}-5-methyl-1H-pyrrole-2-carboxamide and cooled to −15° C. mCPBA (2.51 g, 10.2 mmol) was added, and the reaction mixture was stirred at −15° C. for one hour, then warmed to room temperature. The yellow mixture was washed with 5% sodium thiosulfate (3×), 50% sodium bicarbonate (1×) and brine (1×), dried over anhydrous magnesium sulfate, filtered, and concentrated to give a mixture of products. The yellow solid was further purified by semi-preparative HPLC (acetonitrile/water buffer (20:80→95:5)) to give peak 1 as the sulfoxide (0.040 g) and peak 2 as the sulphone (0.025 g).

Example 221

3,4-Dichloro-N-{1-[5-(ethylsulphinyl)-1,3,4-thiadiazol-2-yl]piperidin-4-yl}-5-methyl-1H-pyrrole-2-carboxamide MS (ESP): 436 (MH$^+$) for $C_{15}H_{19}Cl_2N_5O_2S_2$ $^1$H NMR δ: 1.17 (t, 3H); 1.69 (m, 2H); 1.92 (dd, 2H); 2.17 (s, 3H); 3.07-3.25 (m, 2H); 3.36-3.54 (m, 2H); 3.82-3.98 (m, 2H); 3.98-4.14 (m, 1H); 7.28 (d, 1H); 11.96 (s, 1H).

Example 222

3,4-Dichloro-N-{1-[5-(ethylsulphonyl)-1,3,4-thiadiazol-2-yl]piperidin-4-yl}-5-methyl-1H-pyrrole-2-carboxamide MS (ESP): 452 (MH$^+$) for $C_{15}H_{19}Cl_2N_5O_3S_2$ $^1$H NMR δ: 1.23 (t, 3H); 1.70 (m, 2H); 1.93 (dd, 2H); 2.17 (s, 3H); 3.44 (t, 2H); 3.55 (q, 2H); 3.93 (d, 2H); 4.01-4.19 (brs, 1H); 7.28 (d, 1H); 11.97 (s, 1H).

Example 223

5-(4-{[(3,4-Dichloro-5-methyl-1H-pyrrol-2-yl)carbonyl]amino}piperidin-1-yl)-1,3,4-thiadiazole-2-carboxylic acid Ethyl 5-(4-{[(3,4-dichloro-5-methyl-1H-pyrrol-2-yl)carbonyl]amino}piperidin-1-yl)-1,3,4-thiadiazole-2-carboxylate (Example 219; 0.530 g, 1.2 mmol) and lithium hydroxide

| Example | Halide | $^1$H NMR δ | m/z |
|---|---|---|---|
| 219 | ethyl 5-chloro-1,3,4-thiadiazole-2-carboxylate | 1.29(t, 3H); 1.73(m, 2H); 1.93(d, 2H); 2.16(s, 3H); 3.31-3.45(hidden by H$_2$O peak, 2H); 3.99(d, 2H); 4.00-4.16(m, 1H); 4.34(q, 2H); 7.28(d, 1H); 11.95(brs, 1H). | 418 |
| 220 | 2-bromo-5-(ethylthio)-1,3,4-thiadiazole (Intermediate 67) | 1.29(t, 3H); 1.66(m, 2H); 1.88(d, 2H); 2.16(s, 3H); 3.09-3.28(overlapping with H$_2$O peak 2H); 3.77(d, 2H); 3.91-4.14(m, 1H); 7.27(d, 1H); 11.93(brs, 1H). | 420 |

Examples 221 and 222

Sulfoxide and sulphone derivatives of 3,4-Dichloro-N-{1-[5-(ethylthio)-1,3,4-thiadiazol-2-yl]piperidin-4-yl}-5-methyl-1H-pyrrole-2-carboxamide 3,4-Dichloro-N-{1-[5-(ethylthio)-1,3,4-thiadiazol-2-yl]piperidin-4-yl}-5-methyl-1H-pyrrole-2-carboxamide (Example 220; 2.873 g, 6.80 mmol) was stirred in DCM (42 ml)

(0.117 g, 4.9 mmol) were stirred in dioxane (5 ml) and water (0.5 ml) and heated to 50° C. for thirty minutes. The solution was acidified (pH 4) using 1 N HCl resulting in a precipitate. The solids were collected and purified using semi-preparative HPLC to give the title compound (0.025 g).

MS (ESP): 404 (MH$^+$) for $C_{14}H_{15}Cl_2N_5O_3S$ $^1$H NMR δ: 1.62 (d, 2H); 1.86 (d, 2H): 2.16 (s, 3H); 3.11-3.27 (m, 2H); 3.78 (d, 2H); 3.93-4.08 (m, 1H); 7.55 (d, 1H).

Example 224

3,4-Dichloro-5-methyl-N-[1-(1,3,4-thiadiazol-2-yl)piperidin-4-yl]-1H-pyrrole-2-carboxamide 5-(4-{[(3,4-Dichloro-5-methyl-1H-pyrrol-2-yl)carbonyl]amino}piperidin-1-yl)-1,3,4-thiadiazole-2-carboxylic acid (Example 223; 0.250 g, 0.60 mmol) was stirred in 10 mM ammonium acetate (pH 8) (15 ml) and acetonitrile (15 ml) overnight. The mixture was concentrated then the residue was stirred in acetonitrile and filtered. The solid was dissolved in DMSO and purified using semi-preparative HPLC (10% ammonium acetate:water/acetonitrile (20:80-95:5)) to give the title compound as a white solid (0.092 g).

MS (ESP): 360 (MH$^+$) for $C_{13}H_{15}Cl_2N_5OS$ $^1$H NMR δ: 1.56-1.71 (m, 2H); 1.87 (d, 1H); 2.14 (s, 3H); 3.11-3.51 (overlapping with H$_2$O peak, 2H); 3.84 (d, 2H); 3.89-4.09 (m, 1H); 7.97 (brs, 1H); 8.79 (s, 1H).

Example 225

4-(4-{[(3,4-Dichloro-5-methyl-1H-pyrrol-2-yl)carbonyl]amino}piperidin-1-yl)quinoline-2-carboxylic acid tert-Butyl 4-{[(3,4-dichloro-5-methyl-1H-pyrrol-2-yl)carbonyl]amino}piperidine-1-carboxylate (Intermediate 2) (280 mg, 0.74 mmol) was suspended in 5 ml of 4.0 M HCl in dioxane and stirred for 2 h, then evaporated in vacuo to give a brown solid, which was dissolved in 20 ml of DMF. 4-Bromoquinoline-2-carboxylic acid (188 mg, 0.74 mmol) (prepared via the procedure of Y Kato, et. al., Tetrahedron Lett 2001, 42:4849-51), and sodium bicarbonate (554 mg, 6.6 mmol) were added and the resulting solution was heated under a nitrogen atmosphere with stirring for 20 h. Upon cooling to ambient temperature, the reaction was diluted with 25 ml of water, adjusted to pH 4 using concentrated HCl, filtered and the filtrate extracted with chloroform (2×25 ml). The combined organic extract was dried over sodium sulfate and concentrated in vacuo to a yellow solid, which was suspended in 10 ml of MeOH and collected by suction filtration, to afford the title compound as a yellow solid (64 mg).

m.p. 254-256° C. MS(ES): 448.10/450.10 (MH$^+$) for $C_{21}H_{20}Cl_2N_4O_3$ $^1$H NMR δ: 1.73 (m, 2H); 1.85 (m, 2H); 2.30 (s, 3H); 3.03 (m, 2H); 3.0-3.5 (br m, 1H); 3.55 (m, 2H); 3.94 (m, 1H); 7.13 (m, 1H); 7.35 (s, 1H); 7.47 (m, 1H); 7.85 (m, 1H); 7.97 (m, 1H); 11.82 (s, 1H).

Example 226

3-(4-{[(3,4-Dichloro-5-methyl-1H-pyrrol-2-yl)carbonyl]amino}piperidin-1-yl)isoxazole-5-carboxylic acid The title compound was prepared via the procedure described in Example 1 from 182 mg (0.5 mmol) of 3,4-dichloro-5-methyl-N-piperidin-4-yl-1H-pyrrole-2-carboxamide hydrochloride (Intermediate 1) and 103 mg (0.54 mmol) of 3-bromoisoxazole-5-carboxylic acid (Intermediate 120), to afford the title compound as a white solid, (65 mg).

m.p. 232-234° C. (EtOAc).

MS(ES) 343.19/345.24 (M-CO$_2$) MW 387.23 for $C_{15}H_{16}Cl_2N_4O_4$ $^1$H NMR δ: 1.52 (m, 2H); 1.88 (m, 2H); 2.22 (s, 3H); 2.91 (m, 1H); 3.20 (m, 2H); 3.68 (m, 1H); 4.06 (m, 1H); 4.11 (d, 1H, J=6.0 Hz); 4.26 (m, 1H); 7.29 (d, 1H, J=6.0 Hz); 12.03 (s, 1H).

Example 227

2-(4-{[(3,4-Dichloro-5-methyl-1H-pyrrol-2-yl)carbonyl]amino}piperidin-1-yl)-1,3-thiazole-5-carboxylic acid Methyl 2-(4-{[(3,4-dichloro-5-methyl-1H-pyrrol-2-yl)carbonyl]amino}piperidin-1-yl)-1,3-thiazole-5-carboxylate (Example 320, 250 mg, 0.60 mmol) was dissolved in THF (3 ml). 2 N lithium hydroxide solution in water (3 ml, 6.00 mmol) was added and the mixture was refluxed for 1 hr. The mixture was cooled to room temperature and acidified with 10% HCl solution. The mixture was extracted with EtOAc and organic layer was washed with water twice, dried over sodium sulfate and concentrated to give the desired product. The crude material was dissolved in DMF and purified by semi-preparative reverse phase HPLC eluting with acetonitrile/water (0.1% TFA). The desired fraction were collected and concentrated affording the title compound (28 mg).

MS (ES): 403 (MH$^+$) for $C_{15}H_{16}Cl_2N_4O_3S$ $^1$H NMR δ: 1.73 (m, 2H); 1.99 (m, 2H); 2.22 (s, 3H); 3.36 (m, 2H); 3.57 (m, 2H); 4.14 (m, 1H); 7.27 (d, 1H); 7.77 (s, 1H); 11.97 (s, 1H); 12.64 (s, 1H).

Example 228

2-(4-{[(3,4-Dichloro-5-methyl-1H-pyrrol-2-yl)carbonyl]amino}piperidin-1-yl)-1,3-thiazole-4-carboxylic acid The title compound was prepared in a manner analogous to Example 227 from ethyl 2-(4-{[(3,4-dichloro-5-methyl-1H-pyrrol-2-yl)carbonyl]amino}piperidin-1-yl)-1,3-thiazole-4-carboxylate (Example 336).

MS (ES): 403 (MH$^+$) for $C_{15}H_{16}Cl_2N_4O_3S$ $^1$H NMR δ: 1.44 (m, 2H); 1.66 (m, 2H); 1.95 (s, 3H); 2.93 (m, 2H); 3.62 (m, 2H); 3.80 (m, 1H); 7.04 (d, 1H); 7.40 (s, 1H); 11.74 (s, 1H).

Example 229

2-(4-[{(3,4-Dichloro-5-methyl-1H-pyrrol-2-yl)carbonyl]amino}piperidin-1-yl)-N-methoxy-1,3-thiazole-5-carboxamide 2-(4-{[(3,4-Dichloro-5-methyl-1H-pyrrol-2-yl)carbonyl]amino}piperidin-1-yl)-1,3-thiazole-5-carboxylic acid (Example 227, 100 mg, 0.25 mmol) was reacted with methoxylamine hydrochloride according to procedure described in Example 8 to afford the title compound (30 mg).

MS (ES): 432 (MH$^+$) for $C_{16}H_{19}Cl_2N_5O_3S$ $^1$H-NMR δ: 1.54 (m, 2H); 1.78 (m, 2H); 2.07 (s, 3H); 3.24 (m, 2H); 3.57 (brs, 4H); 3.86 (m, 2H); 4.02 (m, 1H); 7.16 (d, 1H); 7.62 (s, 1H); 11.47 (s, 1H); 11.86 (s, 1H).

Example 230

2-(4-{[(3,4-Dichloro-5-methyl-1H-pyrrol-2-yl)carbonyl]amino}piperidin-1-yl)-N-methoxy-1,3-thiazole-4-carboxamide Prepared in a manner analogous to Example 229 starting from 2-(4-{[(3,4-dichloro-5-methyl-1H-pyrrol-2-yl)carbonyl]amino}piperidin-1-yl)-1,3-thiazole-4-carboxylic acid (Example 228).

MS (ES): 432 (MH$^+$) for $C_{16}H_{19}Cl_2N_5O_3S$

¹H NMR δ: 1.54 (m, 2H); 1.76 (m, 2H); 2.05 (s, 3H); 3.04 (m, 2H); 3.54 (s, 3H); 3.79 (m, 2H); 3.93 (m, 1H); 7.15 (d, 1H); 7.32 (s, 1H); 11.24 (s, 1H); 11.84 (s, 1H).

Example 231

3,4-Dichloro-N-{1-[5-(hydrazinocarbonyl)-1,3-thiazol-2-yl]piperidin-4-yl}-5-methyl-1H-pyrrole-2-carboxamide 2-(4-{[(3,4-Dichloro-5-methyl-1H-pyrrol-2-yl)carbonyl]amino}piperidin-1-yl)-1,3-thiazole-5-carboxylic acid (Example 227, 100 mg, 0.240 mmol) was dissolved in DMF (1 ml) and hydrazine (500 μL, 16.0 mmol). The mixture was stirred at room temperature for 2 h. The mixture was filtered and purified by semi-preparative reverse phase HPLC eluting with acetonitrile/water (0.1% TFA) (36 mg).

MS (ES): 417 (MH$^+$) for $C_{15}H_{18}Cl_2N_6O_2S$

¹H NMR δ: 1.62 (m, 2H); 1.89 (m, 2H); 2.17 (s, 3H); 3.29 (m, 2H); 3.47 (m, 2H); 3.89 (m, 2H); 4.04 (m, 1H); 7.26 (d, 1H); 7.80 (s, 1H); 9.92 (brs, 1H); 11.97 (s, 1H)

Example 232

2-(4-{[(3,4-Dichloro-5-methyl-1H-pyrrol-2-yl)carbonyl]amino}piperidin-1-yl)-N-(methylsulfonyl)-1,3-thiazole-5-carboxamide 2-(4-{[(3,4-Dichloro-5-methyl-1H-pyrrol-2-yl)carbonyl]amino}piperidin-1-yl)-1,3-thiazole-5-carboxylic acid (Example 227; 0.160 g, 0.397 mmol) was suspended in toluene (3 ml) and thionyl chloride (0.288 ml, 3.97 mmol) was added dropwise at room temperature. The solution was refluxed for 1 h. Excess thionyl chloride and toluene were removed in vacuo. The precipitate formed was dissolved in dioxane and methane sulfonamide (0.075 g, 0.794 mmol) was added. The mixture was stirred at 100° C. for 0.5 h after which DBU (0.119 ml, 0.794 mmol) was added. The mixture was stirred for a further 1 h at room temperature was acidified with 10% HCl solution. The mixture was extracted with EtOAc and washed with water. The organic layer was dried over sodium sulfate and conc in vacuo. The crude mixture dissolved in DMSO, and was purified by reverse phase HPLC eluting with acetonitrile/water (0.1% TFA) to afford the desired product. (15 mg).

MS (ES): 480 (MH$^+$) for $C_{16}H_{19}Cl_2N_5O_4S_2$

¹H NMR δ: 1.58 (m, 2H); 1.90 (m, 2H); 2.18 (s, 3H); 3.32 (m, 5H); 3.94 (m, 2H); 4.09 (m, 1H); 7.30 (d, 1H); 8.13 (s, 1H); 11.92 (brs, 1H); 11.98 (s, 1H)

Example 233

3,4-Dichloro-5-methyl-N-{1-[5-(1H-tetrazol-5-yl)-1,3-thiazol-2-yl]piperidin-4-yl}-1H-pyrrole-2-carboxamide To a solution of 3,4-dichloro-N-[1-(5-cyano-1,3-thiazol-2-yl)piperidin-4-yl]-5-methyl-1H-pyrrole-2-carboxamide (Example 321, 0.100 g, 0.26 mmol) in DMF (3 ml) was added sodium azide (0.169 g, 2.60 mmol) followed by the addition of ammonium chloride (0.139 g, 2.60 mmol) at room temperature. The reaction was stirred at 120° C. for 3 hrs. The reaction mixture was cooled to room temperature, filtered and purified by reverse phase HPLC eluting with acetonitrile/water (0.1% TFA) (0.025 g).

MS (ES): 427 (MH$^+$) for $C_{15}H_{16}Cl_2N_8OS$

¹H NMR δ: 1.60 (m, 2H); 1.86 (m, 2H); 2.11 (s, 3H); 3.27 (m, 2H); 3.88 (m, 2H); 4.01 (m, 1H); 7.36 (d, 1H); 7.79 (s, 1H); 11.91 (s, 1H)

Example 234

3,4-Dichloro-5-methyl-N-{1-[5-(1H-tetrazol-5-yl)-1,3-thiazol-2-yl]piperidin-4-yl}-1H-pyrrole-2-carboxamide The title compound was prepared in a manner analogous to Example 233 from 3,4-dichloro-N-[1-(4-cyano-1,3-thiazol-2-yl)piperidin-4-yl]-5-methyl-1H-pyrrole-2-carboxamide (Example 337).

MS (ES): 427 (MH$^+$) for $C_{15}H_{16}Cl_2N_8OS$

¹H NMR δ: 1.61 (m, 2H); 1.86 (m, 2H); 2.11 (s, 3H); 3.20 (m, 2H); 3.90 (m, 2H); 4.00 (m, 1H); 7.23 (d, 1H); 7.59 (s, 1H); 11.92 (s, 1H)

Example 235

N-(1-{4-[(Z)-Amino(hydroxyimino)methyl]-1,3-thiazol-2-yl}piperidin-4-yl)-3,4-dichloro-5-methyl-1H-pyrrole-2-carboxamide To a solution of 3,4-dichloro-N-[1-(5-cyano-1,3-thiazol-2-yl)piperidin-4-yl]-5-methyl-1H-pyrrole-2-carboxamide (Example 321, 0.100 g, 0.26 mmol) in MeOH (2 ml) was added TEA (50 μL, 0.26 mmol) followed by the addition of hydroxylamine hydrochloride (0.0182 g, 0.26 mmol) and treated as described in Example 47 to afford the title compound (0.049 g).

MS (ES): 417 (MH$^+$) for $C_{15}H_{18}Cl_2N_6O_2S$

¹H NMR δ: 1.63 (m, 2H); 1.91 (m, 2H); 2.17 (s, 3H); 3.32 (m, 2H); 3.89 (m, 2H); 4.07 (m, 1H); 7.27 (d, 1H); 7.88 (s, 1H); 10.46 (s, 1H); 11.98 (s, 1H)

Example 236

N-(1-{4[(E)-Amino(hydroxyimino)methyl]-1,3-thiazol-2-yl}piperidin-4-yl)-3,4-dichloro-5-methyl-1H-pyrrole-2-carboxamide Prepared in a manner analogous to Example 235 from 3,4-dichloro-N-[1-(4-cyano-1,3-thiazol-2-yl)piperidin-4-yl]-5-methyl-1H-pyrrole-2-carboxamide (Example 337).

MS (ES): 417 (MH$^+$) for $C_{15}H_{18}Cl_2N_6O_2S$

¹H NMR δ: 1.62 (m, 2H); 1.90 (m, 2H); 2.18 (s, 3H); 3.23 (m, 2H); 3.94 (m, 2H); 4.07 (m, 1H); 7.29 (d, 1H); 7.82 (s, 1H); 8.84 (brs, 2H); 11.11 (s, 1H); 12.00 (s, 1H)

Example 237

2-(4-{[(3,4-Dichloro-5-methyl-1H-pyrrol-2-yl)carbonyl]amino}piperidin-1-yl)-4-(hydroxymethyl)-1,3-thiazole-5-carboxylic acid The title compound was prepared in a manner analogous to Example 31 from ethyl 2-(4-{[(3,4-dichloro-5-methyl-1H-pyrrol-2-yl)carbonyl]amino}piperidin-1-yl)-4-(hydroxymethyl)-1,3-thiazole-5-carboxylate (Example 138).

MS (ES) MH+: 433 for $C_{16}H_{18}Cl_2N_4O_4S$

¹H NMR δ: 1.59-1.67 (m, 1H); 1.89-1.93 (d, 2H); 2.18 (s, 3H); 3.23-3.29 (t, 2H); 2.18 (s, 3H); 3.23-3.29 (t, 2H); 3.91 (d, 2H); 4.07 (brs, 1H); 4.58 (s, 2H); 7.28-7.30 (d, 1H); 11.98 (s, 1H).

Example 238

2-(4-{[(3,4-Dichloro-5-methyl-1H-pyrrol-2-yl)carbonyl]amino}piperidin-1-yl)-4-[(2-methoxyethoxy)methyl]-1,3-thiazole-5-carboxylic acid Prepared in an analogous manner to Example 129 starting from ethyl 2-(4-aminopiperidin-1-yl)-4-[(2-methoxyethoxy)methyl]-1,3-thiazole-5-carboxylate hydrochloride (Intermediate 126) and 3,4-dichloro-5-methyl-1H-pyrrole-2-carboxylic acid (Intermediate 3). The ester product was submitted to hydrolysis using LiOH/THF at 65° C.

MS (ES) (M+H): 493 for $C_{19}H_{24}Cl_2N_4O_5S$ $^1$H NMR δ: 1.71 (m, 2H); 1.91 (m, 2H); 2.17 (s, 3H); 3.22 (s, 3H); 3.44 (b, 2H); 3.57 (m, 2H); 3.80 (m, 1H); 3.94 (m, 2H); 4.07-4.29 (m, 2H); 4.52 (m, 2H); 7.15 (s, 1H); 7.30 (d, 1H); 12.03 (s, 1H)

Examples 239-241

The following compounds were prepared in a manner analogous to Example 238 using 3,4-dichloro-5-methyl-1H-pyrrole-2-carboxylic acid (Intermediate 3) and the starting materials given in the table below.

Example 239

2-(4-{[(3,4-Dichloro-5-methyl-1H-pyrrolyl)carbonyl]amino}piperidin-1-yl)-4-(trifluoromethyl)-1,3-thiazole-5-carboxylic acid

Example 240

4-Butyl-2-(4-{[(3,4-dichloro-5-methyl-1H-pyrrol-2-yl)carbonyl]amino}piperidin-1-yl)-1,3-thiazole-5-carboxylic acid

Example 241

2-(4-{[(3,4-Dichloro-5-methyl-1H-pyrrol-2-yl)carbonyl]amino}piperidin-1-yl)-4-(methoxymethyl)-1,3-thiazole-5-carboxylic acid

Example 242

4-[(Acetyloxy)methyl]-2-(4-{[(3,4-dichloro-5-methyl-1H-pyrrol-2-yl)carbonyl]amino}piperidin-1-yl)-1,3-thiazole-5-carboxylic acid 2-(4-{[(3,4-dichloro-5-methyl-1H-pyrrol-2-yl)carbonyl]amino}piperidin-1-yl)-4-(hydroxymethyl)-1,3-thiazole-5-carboxylic acid (Example 237; 100 mg, 0.23 mmol) was dissolved in pyridine (2 ml) and cooled to 0° C. Acetic anhydride (21.8 μl, 0.230 mmol) was added and mixture was stirred at room temperature for 1 h. The mixture was diluted with EtOAc and washed with water. Organic phase was dried over $Na_2SO_4$ and concentrated in vacuo to give the title compound (40 mg).

MS (ES) MH+: 477 for $C_{18}H_{20}Cl_2N_4O_5S$ $^1$H NMR δ: 1.60-1.63 (m, 2H); 1.86-1.91 (m, 4H); 2.03 (s, 2H); 2.18 (s, 3H); 3.16-3.24 (t, 2H); 3.83-3.87 (d, 2H); 4.02-4.03 (s, 1H); 5.25 (d, 1H).

Example 243

4-[(Butyryloxy)methyl]-2-(4-{[(3,4-dichloro-5-methyl-1H-pyrrol-2-yl)carbonyl]amino}piperidin-1-yl)-1,3-thiazole-5-carboxylic acid The title compound was prepared in a manner analogous to Example 242 from 2-(4-{[(3,4-dichloro-5-methyl-1H-pyrrol-2-yl)carbonyl]amino}piperidin-1-yl)-4-(hydroxymethyl)-1,3-thiazole-5-carboxylic acid (Example 237) and butanoic anhydride.

MS (ES) MH+: 503 for $C_{20}H_{24}Cl_2N_4O_5S$ $^1$H NMR δ: 0.88-0.92 (t, 3H); 1.54-1.59 (m, 2H); 1.61-1.67 (m, 2H); 1.89-1.92 (d, 2H); 2.18 (s, 3H); 2.30-2.33 (t, 2H); 3.25-3.31 (t, 2H); 3.89-3.92 (d, 2H); 4.07 (m, 1H); 4.58 (s, 2H); 5.3 (s, 2H); 7.27-7.29 (d, 1H); 11.98 (s, 1H); 12.84 (s, 1H).

| Example | SM | $^1$H NMR δ | m/z |
|---|---|---|---|
| 239 | Ethyl 2-(4-aminopiperidin-1-yl)-4-(trifluoromethyl)-1,3-thiazole-5-carboxylate hydrochloride salt (Intermediate 78) | 1.71(m, 2H); 1.90(m, 2H); 2.15(s, 3H); 3.06(b, 2H); 3.93(m, 2H); 4.12(m, 1H); 7.40(d, 1H); 11.33(s, 1H); 13.43(b, 1H). | 471 |
| 240 | Ethyl 2-(4-aminopiperidin-1-yl)-4-(methoxymethyl)-1,3-thiazole-5-carboxylate hydrochloride (Intermediate 79) | 1.42(m, 2H); 1.67(m, 2H); 1.95(s, 3H); 3.09(m, 5H); 3.67(m, 2H); 3.82(m, 1H); 4.34(s, 2H); 7.08(d, 1H); 11.74(s, 1H); 12.54(s, 1H) | 447, 451 |
| 241 | Ethyl 2-(4-aminopiperidin-1-yl)-4-butyl-1,3-thiazole-5-carboxylate hydrochloride salt (Intermediate 80) | 1.29(s, 9H); 1.58(m, 2H); 1.93(m, 2H); 2.11(s, 3H); 3.32(m, 2H); 4.17(m, 2H); 4.21(m, 1H); 7.06(s, 1H); 7.18(d, 1H); 12.02(s, 1H) | 459 |

Example 244

4-{[(2-Carboxybenzoyl)amino]methyl}-2-(4-{[(3,4-dichloro-5-methyl-1H-pyrrol-2-yl)carbonyl]amino}piperidin-1-yl)-1,3-thiazole-5-carboxylic acid Ethyl 2-(4-{[(3,4-dichloro-5-methyl-1H-pyrrol-2-yl)carbonyl]amino}piperidin-1-yl)-4-[(1,3-dioxo-1,3-dihydro-2H-isoindol-2-yl)methyl]-1,3-thiazole-5-carboxylate (Example 277; 194 mg, 0.32 mmol) in anhydrous THF (2 ml) was added 2 N LiOH (0.82 ml). The mixture was stirred at room temperature for 4 h. The mixture was acidified to pH 3 and the precipitate that formed was diluted with water and extracted with EtOAc, dried over $Na_2SO_4$ and concentrated in vacuo to give the title compound (160 mg).

MS (ES) MH+: 580 for $C_{24}H_{23}Cl_2N_5O_6S$ $^1$H NMR δ: 1.71-1.73 (d, 2H); 1.96-1.99 (d, 2H); 2.23 (s, 3H); 3.23 (s, 1H); 3.31-3.37 (brs, 3H); 4.01-4.03 (d, 2H); 4.13 (m, 1H); 4.67 (s, 2H); 7.37-7.39 (d, 1H); 7.54-7.69 (m, 3H); 7.76-7.78 (d, 1H); 12.06 (s, 1H); 12.88 (s, 1H).

Example 245

2-(4-{[(3,4-Dichloro-5-methyl-1H-pyrrol-2-yl)carbonyl]amino}piperidin-1-yl)-4-[(1,3-dioxo-1,3-dihydro-2H-isoindol-2-yl)methyl]-1,3-thiazole-5-carboxylic acid 4-{[(2-Carboxybenzoyl)amino]methyl}-2-(4-{[(3,4-dichloro-5-methyl-1H-pyrrol-2-yl)carbonyl]amino}piperidin-1-yl)-1,3-thiazole-5-carboxylic acid (Example 244; 100 mg; 0.17 mmol) was stirred with 4 N HCl/Dioxane (3 ml) at room temperature for 8 h. The mixture was concentrated in vacuo and the resulting solid was purified by reversed phase HPLC eluting with water/acetonitrile/ammonium acetate buffer mixtures giving the title compound (31 mg).

MS (ES) MH+: 564 for $C_{24}H_{21}Cl_2N_5O_5S$ $^1$H NMR δ: 1.55-1.60 (m, 2H); 1.79-1.81 (d, 2H); 2.29 (s, 3H); 3.03-3.08 (t, 2H); 3.61-3.64 (d, 2H); 3.98-3.99 (m, 1H); 5.13 (s, 2H); 7.88-7.89 (d, 1H); 7.94-8.01 (m, 4H).

Example 246

Ethyl 4-(aminomethyl)-2-(4-{[(3,4-dichloro-5-methyl-1H-pyrrol-2-yl)carbonyl]amino}piperidin-1-yl)-1,3-thiazole-5-carboxylate Ethyl 2-(4-{[(3,4-dichloro-5-methyl-1H-pyrrol-2-yl)carbonyl]amino}piperidin-1-yl)-4-[(1,3-dioxo-1,3-dihydro-2H-isoindol-2-yl)methyl]-1,3-thiazole-5-carboxylate (Example 277; 1.43 g, 2.42 mmol) in EtOH (10 ml) was added hydrazine hydrate (0.174 ml; 3.63 mmol) and refluxed for 14 h. The reaction mixture cooled to room temperature and concentrated in vacuo, diluted with DCM and acidified with 10% HCl, washed with $H_2O$. The precipitate was filtered and dried in vacuo to give the title compound (600 mg).

MS (ES) MH+: 461 for $C_{18}H_{23}Cl_2N_5O_3S$

Example 247

4-(Aminomethyl)-2-(4-{[(3,4-dichloro-5-methyl-1H-pyrrol-2-yl)carbonyl]amino}piperidin-1-yl)-1,3-thiazole-5-carboxylic acid The title compound was prepared in a manner analogous to Example 31 from ethyl 4-(aminomethyl)-2-(4-{[(3,4-dichloro-5-methyl-1H-pyrrol-2-yl)carbonyl]amino}piperidin-1-yl)-1,3-thiazole-5-carboxylate (Example 246) and LiOH/THF.

MS (ES) MH+: 434 for $C_{16}H_{19}Cl_2N_5O_3S$ $^1$H NMR δ: 1.42-1.57 (d, 2H); 1.63 (s, 6H); 1.75-1.83 (d, 2H); 2.10 (s, 3H); 3.03-3.10 (t, 2H); 3.74-3.79 (m, 4H); 3.93 (m, 1H); 8.22 (d, 1H); 9.32 (brs, 1H)

Example 248

4-({[Amino(imino)methyl]amino}methyl)-2-(4-{[(3,4-dichloro-5-methyl-1H-pyrrol-2-yl)carbonyl]amino}piperidin-1-yl)-1,3-thiazole-5-carboxylic acid Ethyl 4-(aminomethyl)-2-(4-{[(3,4-dichloro-5-methyl-1H-pyrrol-2-yl)carbonyl]amino}piperidin-1-yl)-1,3-thiazole-5-carboxylate (Example 246) (300 mg, 0.652 mmol) was dissolved in NMP (2 ml). di-tert-butyl [(Z)-1H-pyrazol-1-ylmethylylidene]biscarbamate (1.01 g, 3.26 mmol) was added and the mixture was stirred at 50° C. for 18 h (LCMS: 702, 705). 4 N HCl/Dioxane (10 ml) was added and mixture was heated at 50° C. for 5 h. The solvent was removed in vacuo and the residual material was diluted with EtOAc, washed with sodium bicarbonate. Organic layer was filtered and dried over $Na_2SO_4$ and concentrated in vacuo to give the ethyl ester (320 mg): (LCMS:502,505). Ethyl ester (185 mg, 0.3 mmol) was dissolved in THF (3 ml) and 2 N LiOH (1.84 ml, 3.6 mmol) was heated at 50° C. for 4 h. The solvent was removed in vacuo and residual material was acidified to pH 3. The precipitate was filtered, washed with water, extracted with EtOAc, dried over $Na_2SO_4$ and concentrated in vacuo affording the title compound (47 mg).

MS (ES) MH+: 434 for $C_{17}H_{21}Cl_2N_7O_3S$ $^1$H NMR δ: 1.61 (m, 2H); 1.88 (m, 2H); 2.15 (s, 3H); 3.14 (t, 2H); 3.82-3.84 (d, 2H); 4.00 (brs, 1H); 4.40 (s, 2H); 6.60 (s, 2H); 7.33 (d, 1H); 8.12 (s, 1H); 12.09 (s, 1H).

Example 249

2-(4-{[(3,4-Dichloro-5-methyl-1H-pyrrol-2-yl)carbonyl]amino}piperidin-1-yl)-4-{[(methylsulfonyl)amino]methyl}-1,3-thiazole-5-carboxylic acid Ethyl 4-(aminomethyl)-2-(4-{[(3,4-dichloro-5-methyl-1H-pyrrol-2-yl)carbonyl]amino}piperidin-1-yl)-1,3-thiazole-5-carboxylate (Example 246; 312 mg, 0.677 mmol) was dissolved in DCM and methanesulfonyl chloride (65 μl; 0.844 mmol) was added slowly. The reaction was stirred at room temperature for 16 h, diluted with DCM, washed well with water dried over $Na_2SO_4$ and concentrated in vacuo to give the title compound as a light brown thick oil (350 mg)-(LCMS (ES) MH+: 538). The ethyl ester product was hydrolysed with lithium hydroxide/THF in a manner analogous to Example 31 to give the title compound (30 mg).

MS (ES) MH+: 512 for $C_{17}H_{21}Cl_2N_5O_5S_2$ $^1$H NMR δ: 1.51-1.60 (q, 2H); 1.82-1.85 (m, 2H); 2.11 (s, 3H); 2.79 (s, 3H); 3.14-3.21 (t, 2H); 3.83-3.86 (d, 2H); 4.00 (s, 1H); 4.40 (s, 2H); 7.29 (d, 1H); 12.00 (s, 1H).

Example 250

4-({[(tert-Butylamino)carbonyl]amino}methyl)-2-(4-{[(3,4-dichloro-5-methyl-1H-pyrrol-2-yl)carbonyl]amino}piperidin-1-yl)-1,3-thiazole-5-carboxylic acid Ethyl 4-(aminomethyl)-2-(4-{[(3,4-dichloro-5-methyl-1H-pyrrol-2-yl)carbonyl]amino}piperidin-1-yl)-1,3-thiazole-5-carboxylate (Example 246; 200 mg; 0.424 mmol) was dissolved in DCM (4 ml). tert-Butyl isocyanate (130 mg; 1.28 mmol) was added and the mixture stirred at room temperature for 1 h. The solvent was removed in vacuo and the ester (215 mg), LCMS:561 was treated with LiOH/THF in a manner analogous to Example 31 to give the title compound (290 mg).

MS (ES) MH+: 533 for $C_{21}H_{28}Cl_2N_6O_4S$
$^1$H NMR δ: 1.21 (s, 9H); 1.60-1.68 (m, 2H); 1.90-1.93 (m, 2H); 2.18 (s, 3H); 3.25-3.28 (m, 2H); 3.95-3.98 (d, 2H); 4.05-4.10 (m, 1H); 4.34 (s, 2H); 5.92 (s, 1H); 6.06 (s, 1H); 7.49-7.51 (d, 1H).

Example 251

2-(4-{[(3,4-Dichloro-5-methyl-1H-pyrrol-2-yl)carbonyl]amino}piperidin-1-yl)-4-({[(ethylamino)carbonyl]amino}methyl)-1,3-thiazole-5-carboxylic acid The title compound was prepared in a manner analogous to Example 250 from ethyl 4-(aminomethyl)-2-(4-{[(3,4-dichloro-5-methyl-1H-pyrrol-2-yl)carbonyl]amino}piperidin-1-yl)-1,3-thiazole-5-carboxylate (Example 246) and ethyl isocyanate.

MS (ES) MH+: 506 for $C_{19}H_{24}Cl_2N_6O_4S$
$^1$H NMR δ: 0.95-1.00 (t, 3H); 1.60-1.69 (m, 2H); 1.91 (m, 2H); 2.18 (s, 3H); 2.97-3.04 (q, 2H); 3.20-3.24 (t, 2H); 3.90-3.94 (d, 2H); 4.05-4.06 (m, 1H); 4.34 (s, 2H); 6.13 (brs, 1H); 6.42 (brs, 1H); 7.41-7.44 (d, 1H).

Example 252

4-[(Butyrylamino)methyl]-2-(4-{[(3,4-dichloro-5-methyl-1H-pyrrol-2-yl)carbonyl]amino}piperidin-1-yl)-1,3-thiazole-5-carboxylic acid The title compound was prepared in a manner analogous to Example 242 from 4-(aminomethyl)-2-(4-{[(3,4-dichloro-5-methyl-1H-pyrrol-2-yl)carbonyl]amino}piperidin-1-yl)-1,3-thiazole-5-carboxylic acid (Example 247) and butanoic anhydride.

MS (ES) MH+: 504 for $C_{20}H_{25}Cl_2N_5O_4S$
$^1$H NMR δ: 0.77-0.81 (t, 3H); 1.40-1.48 (m, 2H); 1.53-1.59 (m, 2H); 1.82-1.85 (d, 2H); 2.00-2.04 (t, 2H); 2.11 (s, 3H); 3.16-3.20 (t, 2H); 3.84-3.87 (d, 2H); 3.97-4.02 (m, 1H); 4.37-4.38 (d, 2H); 7.26-7.28 (d, 1H); 8.02 (s, 1H); 11.98 (brs, 1H); 12.64 (brs, 1H).

Example 253

2-(4-{[(3,4-Dichloro-5-methyl-1H-pyrrol-2-yl)carbonyl]amino}piperidin-1-yl)-4-{[(tetrahydrofuran-3-ylcarbonyl)amino]methyl}-1,3-thiazole-5-carboxylic acid Ethyl 4-(aminomethyl)-2-(4-{[(3,4-dichloro-5-methyl-1H-pyrrol-2-yl)carbonyl]amino}piperidin-1-yl)-1,3-thiazole-5-carboxylate (Example 246; 200 mg; 0.434 mmol) was dissolved in anhydrous DMF (2 ml). HATU 165 mg; 0.434 mmol) was added followed by diisopropylethylamine (149 µl, 0.868 mmol). The reaction mixture was stirred for 10 minutes and tetrahydrofuran-3-carboxylic acid (50 mg; 0.434 mmol) and reaction was stirred at room temperature for 2.5 h. The mixture was diluted with EtOAc, washed well with water, dried over $Na_2SO_4$ and concentrated in vacuo to give the title compound as an off-white solid (220 mg)-(LCMS (ES) MH+: 558, 561). The ethyl ester product was hydrolysed with lithium hydroxide/THF in a manner analogous to Example 31 to give the title compound (25 mg).

MS (ES) MH+: 533 for $C_{21}H_{25}Cl_2N_5O_5S$
$^1$H NMR δ: 1.68 (m, 2H); 1.92-1.97 (m, 3H); 2.00-2.07 (m, 2H); 2.25 (s, 3H); 2.97-3.07 (m, 1H); 3.22-3.30 (m, 2H); 3.66-3.72 (m, 2H); 3.74-3.79 (m, 1H); 3.86-3.94 (m, 2H); 4.08 (m, 1H); 4.47-4.49 (d, 1H); 7.59-7.62 (d, 1H); 9.05 (s, 1H)

Example 254

2-(4-{[(3,4-Dichloro-5-methyl-1H-pyrrol-2-yl)carbonyl]amino}piperidin-1-yl)-1,3-thiazole-5-sulfonic acid 3,4-Dichloro-5-methyl-N-[1-(1,3-thiazol-2-yl)piperidin-4-yl]-1H-pyrrole-2-carboxamide (Example 329; 692 mg, 1.93 mmol) was dissolved in anhydrous DCM. Chlorosulfonic acid (513 µl, 7.7 mmol) was added slowly and the mixture was heated at 60° C. for 2 h. The mixture was cooled to 0° C. and water was added, whereupon a brown solid separated. This was filtered and washed well with water, dried in vacuo to give the title compound (393 mg).

MS (ES) MH+: 441 for $C_{14}H_{16}Cl_2N_4O_4S_2$
$^1$H NMR δ: 1.83 (m, 2H); 2.06 (m, 2H); 2.28 (s, 3H); 3.46 (m, 2H); 3.94 (m, 3H); 7.10 (s, 1H); 7.41 (d, 1H); 12.19 (s, 1H)

Example 255

N-{1-[5-(Aminosulfonyl)-1,3-thiazol-2-yl]piperidin-4-yl}-3,4-dichloro-5-methyl-1H-pyrrole-2-carboxamide 0.5 M ammonia/dioxane (10 ml, 5 mmol) was added to 2-(4-{[(3,4-dichloro-5-methyl-1H-pyrrol-2-yl)carbonyl]amino}piperidin-1-yl)-1,3-thiazole-5-sulfonic acid (Example 254; 100 mg, 0.226 mmol) in a pressure bottle. The mixture was stirred at room temperature for 4 h. Excess solvent was removed in vacuo and the brown solid was dried in vacuo to give the title compound (56 mg).

MS (ES) MH+: 438 for $C_{14}H_{16}Cl_2N_4O_4S_2$
$^1$H NMR δ: 1.75 (m, 2H); 1.92 (m, 2H); 2.18 (s, 3H); 3.27 (m, 2H); 3.86 (m, 2H); 4.10 (m, 1H); 7.01 (s, 1H); 7.14 (d, 1H); 7.34 (s, 2H); 12.07 (s, 1H)

Example 256

3,4-Dichloro-N-{1-[5-(hydroxymethyl)-1,3,4-thiadiazol-2-yl]piperidin-4-yl}-5-methyl-1H-pyrrole-2-carboxamide A solution of ethyl 5-(4-{[(3,4-dichloro-5-methyl-1H-pyrrol-2-yl)carbonyl]amino}piperidin-1-yl)-1,3,4-thiadiazole-2-carboxylate (Example 219, 280 mg, 0.65 mmol) in THF (5 ml) was cooled to 0° C. and treated with diisobutylaluminium hydride (1.3 ml, 1.95 mmol) dropwise over 5 min. The reaction was kept in the ice bath and allowed to slowly warm to room temperature while stirring overnight. LC-MS indicated that the reaction was complete. The reaction was quenched with aqueous Rochelle salt, and the resultant mixture was diluted with EtOAc (10 ml) and stirred vigorously for 2 h. The layers were separated, and the aqueous portion was extracted with EtOAc. The combined organic portions were dried (Na$_2$SO$_4$), filtered, and concentrated to give a pale orange oil. The crude material was purified by preparatory HPLC (35-75% CH$_3$CN/H$_2$O, 0.1% TFA, 14 min.) to give 17 mg of the title compound.

MS (ES$^+$): 390.07 for C$_{14}$H$_{17}$Cl$_2$N$_5$O$_2$S $^1$H NMR δ: 1.6 (m, 2H); 1.82 (m, 2H); 2.11 (s, 3H); 3.21 (t, 2H); 3.96 (m, 3H); 7.2 (d, 1H); 11.9 (s, 1H)

Example 257

3-Quinolinecarboxylic acid, 1-[4-[[(3,4-dichloro-5-methyl-1H-pyrrol-2-yl)carbonyl]amino]-1-piperidinyl]-1,4-dihydro-4-oxo-, ethyl ester A solution of N-(1-aminopiperidin-4-yl)-3,4-dichloro-5-methyl-1H-pyrrole-2-carboxamide (Intermediate 89, 400 mg, 1.4 mmol) and ethyl (2Z)-3-ethoxy-2-(2-fluorobenzoyl) acrylate (WO 2000040561 A1, 370 mg, 1.4 mmol) in 20 ml EtOH was stirred at room temperature for 2 hours. After dilution with 100 ml water, solids were filtered and dried in vacuo. The solids were suspended in 20 ml dioxane containing DBU (300 μl) and the mixture was heated in a microwave reactor at 120° C. for 3 hours. Solvent was removed and the residue was dissolved in EtOAc before being washed wit water and brine. Drying (MgSO$_4$) and removal of solvent followed by trituration with hot EtOAc gave 160 mg of product as a white solid.

MS (ES): 491.0 (M+H)$^+$, MS (ES): 489.2 (M−H)$^−$.

$^1$H NMR δ: 1.31 (t, J=7.16 Hz, 3H); 1.78-2.12 (m, 4H); 2.14-2.30 (m, 3H); 3.12 (s, 2H); 3.34-3.50 (m, 2H); 4.05 (s, 1H); 4.14-4.37 (m, 2H); 7.26 (d, J=7.72 Hz, 1H); 7.49 (t, J=7.54 Hz, 1H); 7.71-7.95 (m, 1H); 8.07-8.31 (m, 2H); 8.97 (s, 1H); 12.04 (s, 1H).

Example 258

1-(4-{[(3,4-Dichloro-5-methyl-1H-pyrrol-2-yl)carbonyl]amino}piperidin-1-yl)-oxo-1,4-dihydroquinoline-3-carboxylic acid A suspension of 3-quinolinecarboxylic acid, 1-[4-[[(3,4-dichloro-5-methyl-1H-pyrrol-2-yl)carbonyl]amino]-1-piperidinyl]-1,4-dihydro-4-oxo-, ethyl ester (Example 257, 67 mg, 0.14 mmol) in 5 ml MeOH and 150 μl (0.15 mmol) of aqueous 1 N NaOH was heated at 80° C. for 40 min in a microwave reactor. A solution aqueous 1 N HCl (150 μl) was added affording a mass of solid precipitate. The mixture was taken up in hot water and insoluble material was filtered to afford 19 mg of product as a white solid.

MS (ES): 463 (M+H)$^+$, MS (ES): 461 (M−H)$^−$.

$^1$H NMR δ: 2.03 (s, 4H); 2.19 (s, 3H); 3.18 (s, 2H); 3.53 (s, 2H); 4.09 (s, 1H); 7.25 (s, 1H); 7.69 (s, 1H); 8.01 (s, 1H); 8.39 (s, 2H); 9.37 (s, 1H); 11.82-12.44 (m, 1H); 15.25 (s, 1H).

Example 259

3,4-Dichloro-N-[1-(3-formyl-1H-pyrrol-1-yl)piperidin-4-yl]-5-methyl-1H-pyrrole-2-carboxamide A mixture of N-(1-aminopiperidin-4-yl)-3,4-dichloro-5-methyl-1H-pyrrole-2-carboxamide (Intermediate 89; 67 mg, 0.14 mmol), 2,5-dimethoxytetrahydrofuran-3-carbaldehyde (100 μl, 4.2 mg), and sodium acetate (0.35 g, 4.1 mmol) in 30 ml acetic acid was heated at 70° C. for 2 hours. Solvent was removed and the residue was portioned between EtOAc and aqueous Na$_2$CO$_3$. Insoluble material was removed by filtering through diatomaceous earth rinsing through with EtOAc. The EtOAc from the filtrate was separated and washed with water and brine. Drying (MgSO$_4$) and removal of solvent gave a brown solid that was purified by normal phase chromatography (100% DCM with gradient elution to 2% MeOH in DCM) to give a material that was triturated with ether to afford 110 mg of a white solid.

MS (ES): 369 (M+H)$^+$, MS (ES): 367.2 (M−H)$^−$.

$^1$H NMR δ: 1.65-1.89 (m, 2H); 1.90-2.11 (m, 2H); 2.18 (s, 3H); 3.15 (dd, J=7.06, 3.30 Hz, 4H); 3.92 (s, 1H); 6.44 (dd, J=3.01, 1.88 Hz, 1H); 7.15-7.27 (m, 1H); 7.31 (d, J=7.72 Hz, 1H); 7.89 (t, J=1.88 Hz, 1H); 9.62 (s, 1H); 12.00 (s, 1H).

Example 260

3,4-Dichloro-N-(1-{3-[(E)-(hydroxyimino)methyl]-1H-pyrrol-1-yl}piperidin-4-yl)-5-methyl-1H-pyrrole-2-carboxamide A solution of 3,4-dichloro-N-[1-(3-formyl-1H-pyrrol-1-yl)piperidin-4-yl]-5-methyl-1H-pyrrole-2-carboxamide (Example 259, 151 mg, 0.41 mmol) and 50% aqueous hydroxylamine (55 μl, 0.83 mmol) in 5 ml EtOH was heated at 80° C. for 30 min. The mixture was diluted with EtOAc and washed with brine. Drying (MgSO$_4$) and removal of solvent gave a solid that was purified by reverse phase HPLC (30-55% gradient CH$_3$CN in water with 0.1% TFA) to give product as a mixture of geometrical isomers.

MS (ES): 384 (M+H)$^+$, MS (ES): 282 (M−H)$^−$.

$^1$H NMR δ: 1.78 (m, 1H); 1.94 (m, 2H); 2.2 (s, 3H); 2.95-3.24 (m, 4H); 3.91 (m, 1H); 6.1-6.3 (2d, 1H); 6.9 and 7.1 (2s, 1H); 7.16 (s, 1H); 7.22-7.41 (m, 1H); 7.6 and 7.9 (2s, 1H); 10.9 and 10.4 (2s, 1H); 12.00 (s, 1H).

Example 261

1-(4-{[(3,4-Dichloro-5-methyl-1H-pyrrol-2-yl)carbonyl]amino}piperidin-1-yl)-1H-pyrrole-3-carboxylic acid Solutions of 3,4-dichloro-N-[1-(3-formyl-1H-pyrrol-1-yl) piperidin-4-yl]-5-methyl-1H-pyrrole-2-carboxamide (Example 259, 90 mg, 0.24 mmol) in 10 ml acetone and KMNO$_4$ (39 mg, 0.24 mmol) in 3 ml water were combined and stirred at ambient temperature overnight. Due to incomplete conversion, solutions of KMnO$_4$ (15 and 20 mg) in 3 ml water were added at 5 hour intervals. The mixture was quenched with aqueous NaHSO$_3$ and partitioned between EtOAc and water. The EtOAc was separated and washed with brine. Drying (MgSO$_4$) and removal of solvent gave product as a white solid.

MS (ES): 384 (M+H)$^+$, MS (ES): 282 (M−H)$^−$.

$^1$H NMR δ: 1.79 (d, J=3.58 Hz, 2H); 1.86-2.04 (m, 2H); 2.18 (s, 3H); 3.11 (d, J=3.39 Hz, 4H); 3.77-4.05 (m, 1H); 6.22-6.42 (m, 1H); 7.05 (t, J=2.45 Hz, 1H); 7.31 (d, J=7.72 Hz, 1H); 7.58 (s, 1H); 11.96 (d, J=31.65 Hz, 2H).

Example 262

1-(4-{[(3,4-Dichloro-5-methyl-1H-pyrrol-2-yl)carbonyl]amino}piperidin-1-yl)isoquinoline-3-carboxylic acid In a mixture of 20 ml THF, 5 ml $H_2O$, and 1 ml 50 wt % NaOH (aq) was dissolved methyl 1-(4-{[(3,4-dichloro-5-methyl-1H-pyrrol-2-yl)carbonyl]amino}piperidin-1-yl)isoquinoline-3-carboxylate (Example 301; 70 mg). The solution was stirred at 80° C. for 1 hr. The solution was cooled to room temperature, diluted with EtOAc and acidified with dilute HCl (aq). The EtOAc fraction was isolated, at which time a white solid precipitated from solution. The solid was collected by filtration and washed with acetonitrile to yield 50 mg white solid product.

MS (ES): 447 (M+H)$^+$.

$^1$H NMR δ: 1.90 (s, 2H); 1.98-2.12 (m, 2H); 2.19 (s, 3H); 3.14 (m, 2H); 3.82 (m, 2H); 4.04 (s, 1H); 731 (m, 1H); 7.77 (m, 2H); 8.06-8.21 (m, 2H); 12.02 (s, 1H); 12.79 (s, 1H).

Example 263

1-(4-{[(3,4-Dichloro-5-methyl-1H-pyrrol-2-yl)carbonyl]amino}piperidin-1-yl)-4-methoxyisoquinoline-3-carboxylic acid In a sealed high pressure container with a Teflon lining was combined ethyl 1-chloro-4-methoxyisoquinoline-3-carboxylate (EP 650961 A1; 390 mg, 1.55 mmol), 4-{[(3,4-dichloro-5-methyl-1H-pyrrol-2-yl)carbonyl]amino}piperidinium trifluoroacetate (Intermediate 86; 1.7 g, 4.4 mmol), and $K_2CO_3$ (2.2 g) in 20 ml tert-butanol. The container was heated at 170° C. with stirring for 8 hours. The solution was concentrated by rotary evaporation and reconstituted with EtOAc. The organic layer was washed 4× with $H_2O$, and dried over $MgSO_4$. Crude ethyl 1-(4-{[(3,4-dichloro-5-methyl-1H-pyrrol-2-yl)carbonyl]amino}piperidin-1-yl)-4-methoxyisoquinoline-3-carboxylate was purified by reverse phase Si yielding 20 mg of the intermediate ester. The ethyl ester was then hydrolyzed as in Example 262 to yield 13.5 mg white solid final product.

MS (ES): 477 (M+H)$^+$, MS (ES): 475 (M−H)$^−$.

$^1$H NMR δ: 1.81-1.97 (m, 2H); 2.01 (s, 2H); 2.14-2.26 (m, 3H); 3.06 (t, J=11.30 Hz, 2H); 3.71 (m, 2H); 3.93 (s, 3H); 4.03 (s, 1H); 7.40 (m, 1H); 7.73-7.89 (m, 2H); 8.10-8.22 (m, 2H); 12.12 (s, 1H).

Example 264

Ethyl 1-(4-{[(3,4-dichloro-5-methyl-1H-pyrrol-2-yl)carbonyl]amino}piperidin-1-yl)-2,7-naphthyridine-3-carboxylate In a sealed high pressure container with a Teflon lining was combined ethyl 1-chloro-2,7-naphthyridine-3-carboxylate (280 mg, 1.18 mmol), 4-{[(3,4-dichloro-5-methyl-1H-pyrrol-2-yl)carbonyl]amino}piperidinium trifluoroacetate (Intermediate 86; 957 mg), and $K_2CO_3$ (1.25 g) in 15 ml tert-butanol. The container was heated at 170° C. with stirring for 8 hours. The solution was concentrated by rotary evaporation and reconstituted with EtOAc. The organic layer was washed 4× with $H_2O$, and dried over $MgSO_4$. Product was purified on reverse phase Si to yield 36 mg white solid.

MS (ES): 476 (M+H)$^+$.

$^1$H NMR δ: 1.82-1.95 (m, 2H); 1.99-2.11 (m, 2H); 2.14-2.22 (m, 3H); 3.23-3.33 (m, 2H); 3.98-4.14 (m, 2H); 4.37 (m, 1H); 7.33 (d, J=7.54 Hz, 1H); 7.97 (d, J=5.28 Hz, 1H); 8.05 (s, 1H); 8.75 (d, J=5.28 Hz, 1H); 9.41 (s, 1H); 12.01 (s, 1H).

Example 265

1-(4-{[(3,4-Dichloro-5-methyl-1H-pyrrol-2-yl)carbonyl]amino}piperidin-1-yl)-2,7-naphthyridine-3-carboxylic acid As described for the synthesis of Example 262, ethyl 1-(4-{[(3,4-dichloro-5-methyl-1H-pyrrol-2-yl)carbonyl]amino}piperidin-1-yl)-2,7-naphthyridine-3-carboxylate (Example 264; 30 mg) was hydrolyzed to yield 9.1 mg yellow solid.

MS (ES): 448 (M+H)$^+$, MS (ES): 446 (M−H)$^−$.

$^1$H NMR δ: 1.80-1.94 (m, 2H); 1.98-2.12 (m, 2H); 2.19 (s, 3H); 3.24-3.36 (m, 2H); 4.07 (d, J=13.57 Hz, 3H); 7.31 (d, J=8.29 Hz, 1H); 7.95-8.09 (m, 2H); 8.73 (d, J=5.28 Hz, 1H); 9.43 (s, 1H); 12.02 (s, 1H).

Example 266

Ethyl 4-(4-{[(3,4-dichloro-5-methyl-1H-pyrrol-2-yl)carbonyl]amino}piperidin-1-yl)quinazoline-2-carboxylate As described for the synthesis of Example 264, ethyl 4-chloroquinazoline-2-carboxylate (690 mg), 4-{[(3,4-dichloro-5-methyl-1H-pyrrol-2-yl)carbonyl]amino}piperidinium trifluoroacetate (Intermediate 86; 1.7 g), and $K_2CO_3$ (1.7 g) in 20 ml tert-butanol were combined to yield 662 mg grey solid.

MS (ES): 476 (M+H)$^+$.

$^1$H NMR δ: 1.34 (t, J=7.16 Hz, 3H); 1.79 (m, 2H); 2.01 (s, 2H); 2.18 (s, 3H); 4.17 (s, 1H); 4.33-4.46 (m, 4H); 7.33 (d, J=7.54 Hz, 1H); 7.68 (d, J=6.03 Hz, 1H); 7.88-7.98 (m, 1H); 8.06 (d, J=9.04 Hz, 1H); 12.03 (s, 1H).

Example 267

4-(4-{[(3,4-Dichloro-5-methyl-1H-pyrrol-2-yl)carbonyl]amino}piperidin-1-yl)quinazoline-2-carboxylic acid As described for the synthesis of Example 262, ethyl 4-(4-{[(3,4-dichloro-5-methyl-1H-pyrrol-2-yl)carbonyl]amino}piperidin-1-yl)quinazoline-2-carboxylate (Example 266; 100 mg) was hydrolyzed to yield 32 mg white solid.

MS (ES): 448 (M+H)$^+$, MS (ES): 446 (M−H)$^−$.

$^1$H NMR δ: 1.60-1.75 (m, 2H); 1.75-1.90 (m, 2H); 2.15-2.24 (s, 3H); 3.70-3.86 (m, 2H); 4.23 (m, 1H); 4.53 (m, 2H); 7.41 (d, J=7.54 Hz, 1H); 7.69 (t, J=7.16 Hz, 1H); 7.92-8.04 (m, 2H); 8.10 (d, J=8.29 Hz, 1H); 12.11 (s, 1H).

Example 268

Methyl 4-amino-2-(4-{[(3,4-dichloro-5-methyl-1H-pyrrol-2-yl)carbonyl]amino}piperidin-1-yl)-1,3-thiazole-5-carboxylate A suspension of methyl N-cyano-4-{[(3,4-dichloro-5-methyl-1H-pyrrol-2-yl)carbonyl]amino}piperidine-1-carbimidothioate (Intermediate 91, 1.78 g, 4.8 mmol) and methyl mercaptoacetate (0.43 ml, 4.8 mmol) with TEA (1.2 ml, 8.6 mmol) in MeOH was stirred at room temperature overnight.

Reaction mixture was concentrated to 50% volume, the precipitate was filtered off and the solid was washed with MeOH and dried.

MS (ES): 432 (M+H)+.

$^1$H NMR δ: 1.54-1.69 (m, 2H); 1.90 (dd, J=12.62, 2.83 Hz, 2H); 2.18 (s, 3H); 3.16-3.31 (m, 2H); 3.61 (s, 3H); 3.87 (d, J=14.69 Hz, 2H); 3.99-4.14 (m, 1H); 6.84 (s, 2H); 7.29 (d, J=7.91 Hz, 1H); 11.98 (s, 1H).

Example 269

3,4-Dichloro-N-[1-(5-cyano-4-methoxy-1,3-thiazol-2-yl)piperidin-4-yl]-5-methyl-1H-pyrrole-2-carboxamide A suspension of N-[1-(aminocarbonothioyl)piperidin-4-yl]-3,4-dichloro-5-methyl-1H-pyrrole-2-carboxamide (Intermediate 95, 0.22 g, 0.7 mmol) and tert-butyl chloro(cyano) acetate (0.12 g, 0.7 mmol) in MeOH was heated to 80° C. in the microwave reactor for 40 minutes. The product precipitated and was filtered off.

MS (ES): 414 (M+H)+.

$^1$H NMR δ: 1.57-1.72 (m, 2H); 1.93 (dd, J=12.81, 3.01 Hz, 2H); 2.18 (s, 3H); 3.28-3.43 (m, 2H); 3.80-3.94 (m, 2H); 3.97 (s, 3H); 4.01-4.15 (m, 1H); 7.31 (d, J=7.72 Hz, 1H); 12.00 (s, 1H).

Example 270

3,4-Dichloro-N-[1-(5-cyano-4-hydroxy-1,3-thiazol-2-yl)piperidin-4-yl]-5-methyl-1H-pyrrole-2-carboxamide Iodotrimethylsilane (0.02 ml, 0.13 mmol) was added to a suspension of 3,4-dichloro-N-[1-(5-cyano-4-methoxy-1,3-thiazol-2-yl)piperidin-4-yl]-5-methyl-1H-pyrrole-2-carboxamide (Example 269, 0.04 g, 0.1 mmol) in DCM:CHCl$_3$ (1:1). After stirring for one hour the reaction was complete. Partitioning with EtOAc and water, drying organic portion with MgSO$_4$ and concentrating yielded a yellow oil which, after triturating with ether, gave a yellow solid.

MS (ES): 400 (M+H)+.

$^1$H NMR δ: 1.65 (s, 2H); 1.84-1.95 (m, 2H); 2.08-2.20 (m, 3H); 3.77-3.90 (m, 2H); 4.09 (s, 2H); 4.41 (s, 1H); 7.25-7.39 (m, 1H); 12.00 (d, J=5.84 Hz, 1H); 12.48 (s, 1H).

Example 271

Methyl 2-(4-{[(3,4-dichloro-5-cyano-1H-pyrrol-2-yl) carbonyl]amino}piperidin-1-yl)-1,3-thiazole-5-carboxylate TEA (0.06 ml, 0.5 mmol) was added to a solution of methyl 2-(4-aminopiperidin-1-yl)-1,3-thiazole-5-carboxylate (Intermediate 134, 0.1 g, 0.5 mmol)) in anhydrous THF. To this was added 3,4-dichloro-5-cyano-1H-pyrrole-2-carbonyl chloride (Intermediate 132, 0.1 g, 0.5 mmol) as a solution in anhydrous THF. After stirring 15 minutes, THF was removed. The product was partitioned with EtOAc and water. The organic portion was dried with MgSO$_4$ and concentrated to a yellow oil. Trituration with ether followed by filtration yielded a tan solid.

MS (ES): 428 (M+H)+

$^1$H NMR δ: 1.65 (s, 2H); 1.87 (s, 2H); 3.09 (s, 1H); 3.25-3.40 (m, 2H); 3.75 (s, 3H); 3.95 (d, J=13.75 Hz, 2H); 7.87 (s, 2H).

Example 272

2-(4-{[(3,4-Dichloro-5-cyano-1H-pyrrol-2-yl)carbonyl]amino}piperidin-1-yl)-1,3-thiazole-5-carboxylic acid The title compound was prepared by a procedure analogous to Intermediate 3 starting from methyl 2-(4-{[(3,4-dichloro-5-cyano-1H-pyrrol-2-yl)carbonyl] amino}piperidin-1-yl)-1,3-thiazole-5-carboxylate (Example 271). The reaction mixture was concentrated to remove MeOH. Water was added and the pH was adjusted to pH 4 with NaHCO$_3$. The product was extracted with CHCl$_3$:isopropanol (3:1). Drying (MgSO4) and removal of solvent yielded a white solid. The was dried in drying pistol at 75° C. under vacuum.

MS (ES): 414 (M+H)+.

$^1$H NMR δ: 1.66 (s, 2H); 1.91 (s, 2H); 3.36 (s, 2H); 3.94 (d, J=13.38 Hz, 2H); 4.09 (s, 1H); 7.76-7.91 (m, 1H); 8.04 (d, J=7.72 Hz, 1H); 12.64 (s, 1H); 13.86 (s, 1H).

Example 273

Methyl 4-(4-{[(3,4-dichloro-5-cyano-1H-pyrrol-2-yl) carbonyl]amino}piperidin-1-yl)quinoline-2-carboxylate The title compound was prepared by an analogous procedure to Example 271 starting from 3,4-dichloro-5-cyano-1H-pyrrole-2-carbonyl chloride (Intermediate 132) and methyl 4-(4-aminopiperidin-1-yl)quinoline-2-carboxylate hydrochloride (Intermediate 136).

$^1$H NMR δ: 1.95 (d, J=15.82 Hz, 2H); 2.99-3.14 (m, 2H); 3.38 (q, J=6.97 Hz, 2H); 3.54-3.69 (m, 2H); 3.94 (s, 4H); 7.55 (s, 1H); 7.69 (t, J=7.63 Hz, 1H); 7.76-7.86 (m, 1H); 7.96-8.11 (m, 2H).

Example 274

4-(4-[{(3,4-Dichloro-5-cyano-1H-pyrrol-2-yl)carbonyl]amino}piperidin-1-yl)quinoline-2-carboxylic acid The title compound was prepared by an analogous procedure to Intermediate 3 starting with methyl 4-(4-{[(3,4-dichloro-5-cyano-1H-pyrrol-2-yl)carbonyl] amino}piperidin-1-yl)quinoline-2-carboxylate (Example 273) and following the work-up procedure of Example 272.

MS (ES) (M+H)+: 458

$^1$H NMR δ: 1.93 (s, 2H); 2.05 (s, 2H); 3.27 (s, 2H); 3.77 (s, 2H); 4.12 (s, 1H); 7.56 (s, 1H); 7.69 (s, 1H); 7.85 (s, 1H); 8.05 (s, 1H); 8.18 (d, J=8.67 Hz, 2H).

Example 275

N-Methoxy 8-fluoro-4-(4-{[(3,4-dichloro-5-methyl-1H-pyrrol-2-yl)carbonyl]amino}piperidin-1-yl) quinoline-2-carboxamide The title compound was prepared from 8-fluoro-4-(4-{[(3,4-dichloro-5-methyl-1H-pyrrol-2-yl)carbonyl] amino}piperidin-1-yl)quinoline-2-carboxylic acid (Example 280) and O-methylhydroxylamine hydrochloride via the procedure described for Example 8.

MS(ES+): 494/496 for $C_{22}H_{22}Cl_2FN_5O_3$
$^1$H NMR δ:1.88 (m, 2H); 2.06 (m, 2H); 2.17 (s, 3H); 2.98 (m, 2H); 3.50 (m, 2H); 3.69 (s, 3H); 4.04 (m, 1H); 7.42 (m, 2H); 7.59 (s, 1H); 7.72 (m, 1H); 8.13 (s, 2H)

Example 276

Ethyl 2-(4-{[(3,4-dichloro-5-methyl-1H-pyrrol-2-yl)carbonyl]amino}piperidin-1-yl)-4-(methoxymethyl)-1,3-thiazole-5-carboxylate The title compound was prepared from 3,4-dichloro-5-methyl-1H-pyrrole-2-carboxylic acid (Intermediate 3) and ethyl 2-(4-aminopiperidin-1-yl)-4-(methoxymethyl)-1,3-thiazole-5-carboxylate hydrochloride (Intermediate 36) in a manner analogous to Example 29.

MS (ES) (M+H): 474 for $C_{19}H_{24}Cl_2N_4O_4S$

Example 277

Ethyl 2-(4-{[(3,4-dichloro-5-methyl-1H-pyrrol-2-yl)carbonyl]amino}piperidin-1-yl)-4-[(1,3-dioxo-1,3-dihydro-2H-isoindol-2-yl)methyl]-1,3-thiazole-5-carboxylate The title compound was prepared from 3,4-dichloro-5-methyl-1H-pyrrole-2-carboxylic acid (Intermediate 3) and ethyl 2-(4-aminopiperidin-1-yl)-4-[(1,3-dioxo-1,3-dihydro-2H-isoindol-2-yl)methyl]-1,3-thiazole-5-carboxylate hydrochloride (Intermediate 77) in a manner analogous to Example 29.

MS (ES) (M+H): 593 for $C_{26}H_{25}Cl_2N_5O_5S$

Example 278

6-Chloro-4-(4-{[(3,4-dichloro-5-methyl-1H-pyrrol-2-yl)carbonyl]amino}piperidin-1-yl)quinoline-2-carboxylic acid Methyl 6-chloro-4-(4-{[(3,4-dichloro-5-methyl-1H-pyrrol-2-yl)carbonyl]amino}piperidin-1-yl)quinoline-2-carboxylate (Example 134; 20 mg) was dissolved in 6 ml of 2:1 THF/MeOH, 0.20 ml of 1 N NaOH was added and the resulting solution was stirred at ambient temperature for 20 h. Following neutralization with 0.25 ml of 1 N HCl, the reaction was diluted with 5 ml of water and filtered. The solid was washed with water and dried under vacuum, giving 18.4 mg of a light yellow granular solid.

MS(ES+): 480.94/482,94/484.94 for $C_{21}H_{19}Cl_3N_4O_3$
$^1$H NMR δ: 1.81 (m, 2H); 1.94 (m, 2H); 2.09 (s, 3H); 3.07 (m, 2H); 3.25 (s, 1H); 3.50 (m, 2H); 4.00 (m, 1H); 7.23 (d, 1H, J=7.54); 7.48 (s, 1H); 7.74 (d, 1H, J=9.04); 7.88 (s, 1H); 8.02 (d, 1H, J=9.04); 11.93 (s, 1H).

Examples 279-283

The following compounds were prepared by an analogous method to Example 278.

| Example | Compound | $^1$H NMR δ | m/z (ES$^+$) | SM |
|---|---|---|---|---|
| 279 | 8-Methoxy-4-(4-{[(3,4-dichloro-5-methyl-1H-pyrrol-2-yl)carbonyl]amino}piperidin-1-yl)quinoline-2-carboxylic acid | 1.86(m, 2H); 1.99(m, 2H); 2.14(s, 3H); 3.05(m, 2H); 3.56(m, 2H); 3.94(s, 3H); 4.00(m, 1H); 3.9-4.5(v br s, 1H); 7.21(m, 1H); 7.29(m, 1H); 7.52(m, 3H); 11.97(s, 1H) | 477/ 479 | Example 323 |
| 280 | 8-Fluoro-4-(4-{[(3,4-dichloro-5-methyl-1H-pyrrol-2-yl)carbonyl]amino}piperidin-1-yl)quinoline-2-carboxylic acid | 1.86(m, 2H); 2.03(m, 2H); 2.14(s, 3H); 3.06(m, 2H); 3.59(m, 2H); 3.87(s, 3H); 4.01(m, 1H); 7.56(m, 3H); 7.80(m, 1H) | 465/ 467 | Example 324 |
| 281 | 6-Fluoro-4-(4-{[(3,4-dichloro-5-methyl-1H-pyrrol-2-yl)carbonyl]amino}piperidin-1-yl)quinoline-2-carboxylic acid | 1.91(m, 2H); 2.03(m, 2H); 2.18(s, 3H); 3.14(m, 2H); 3.61(m, 2H); 4.05(m, 1H); 7.31(d, 1H, J=7.5); 7.58(s, 1H); 7.68(m, 1H); 7.80(m, 1H); 8.20(m, 1H); 12.03(s, 1H) | 465/ 467 | Example 325 |
| 282 | 8-Chloro-4-(4-{[(3,4-dichloro-5-methyl-1H-pyrrol-2-yl)carbonyl]amino}piperidin-1-yl)quinoline-2-carboxylic acid | 1.85(m, 2H); 2.02(m, 2H); 2.14(s, 3H); 3.06(m, 2H); 3.57(m, 2H); 3.93(s, 3H); 3.99(m, 1H); 7.36(d, 1H, J=7.5); 7.55(s, 1H); 7.58(m, 1H); 7.93(m, 2H) | 481/ 483 | Example 326 |
| 283 | 2-(4-{[(3,4-Dichloro-5-methyl-1H-pyrrol-2-yl)carbonyl]amino}piperidin-1-yl)oxazole-4-carboxylic acid | 1.60(m, 2H); 1.86(m, 2H); 2.18(s, 3H); 3.16(m, 2H); 3.89(m, 2H); 4.02(m, 1H); 7.27(d, 1H, J=7.7); 8.22(s, 1H); 11.99(s, 1H); 12.72(br s, 1H) | 387/ 389 | Example 328 |

Example 284

5-(4-{[(3,4-Dichloro-5-methyl-1H-pyrrol-2-yl)carbonyl]amino}piperidin-1-yl)nocotinamide The title compound was synthesized by an analogous method to Example 8 starting from 5-(4-{[(3,4-dichloro-5-methyl-1H-pyrrol-2-yl)carbonyl]amino}piperidin-1-yl)nocotinic acid (Example 291) and a solution of ammonia in MeOH.

MS (ESP) (MH$^+$): 396 for $C_{17}H_{19}Cl_2N_5O_2$ $^1$H NMR δ: 1.60-1.73 (m, 2H); 1.89-1.92 (m, 2H); 2.17 (s, 3H); 2.98 (t, 2H); 3.79-3.84 (m, 2H); 3.97 (m, 1H); 7.33 (d, 1H); 7.51 (s, 1H); 7.69 (s, 1H); 8.09 (s, 1H); 8.41-8.44 (m, 2H); 12.04 (s, 1H).

Example 285

5-(4-{[(3,4-Dichloro-5-methyl-1H-pyrrol-2-yl)carbonyl]amino}piperidin-1-yl)-N-methoxynicotinamide The title compound was synthesized by an analogous method to Example 8 starting from 5-(4-{[(3,4-dichloro-5-methyl-1H-pyrrol-2-yl)carbonyl]amino}piperidin-1-yl)nocotinic acid (Example 291) and methoxylamine hydrochloride.

MS (ESP) (MH$^+$): 426 for $C_{18}H_{21}Cl_2N_5O_3$ $^1$H NMR δ: 1.59-1.70 (m, 2H); 1.89-1.92 (m, 2H); 2.17 (s, 3H); 2.99 (t, 2H); 3.72 (s, 3H); 3.79-3.84 (m, 2H); 4.00 (m, 1H); 7.25 (d, 1H); 7.56 (s, 1H); 8.27 (s, 1H); 8.47 (d, 1H); 11.85 (s, 1H); 11.96 (s, 1H).

Example 286

4-(4-{[(3,4-Dichloro-5-methyl-1H-pyrrol-2-yl)carbonyl]amino}piperidin-1-yl)-N-methoxypyridine-2-carboxamide The title compound was synthesized by an analogous method to Example 8 starting from 4-(4-{[(3,4-dichloro-5-methyl-1H-pyrrol-2-yl)carbonyl]amino}piperidin-1-yl)pyridine-2-carboxylic acid (Example 293) and methoxylamine hydrochloride.

MS (ESP) (MH$^+$): 426 for $C_{18}H_{21}Cl_2N_5O_3$ $^1$H NMR δ: 1.52-1.62 (m, 2H); 1.87-1.95 (m, 2H); 2.17 (s, 3H); 3.11 (t, 2H); 3.67 (s, 3H); 3.93-3.98 (m, 2H); 4.07 (m, 1H); 7.01 (m, 1H); 7.26 (d, 1H); 7.39 (d, 1H); 8.15 (d, 1H); 11.82 (s, 1H); 11.97 (s, 1H).

Examples 287-294

The following examples were prepared by an analogous method to Example 310 starting from the ester and 2 N lithium hydroxide.

| Ex | Compound | $^1$H NMR δ | M/z (M + 1) | SM |
|---|---|---|---|---|
| 287 | 3-Bromo-5-(4-{[(3,4-dichloro-5-methyl-1H-pyrrol-2-yl)carbonyl]amino}piperidin-1-yl)benzoic acid | 1.53-1.72(m, 2H); 1.82-1.95(m, 2H); 2.17(s, 3H); 2.97(t, 2H); 3.71-3.84(m, 2H); 3.98(m, 1H); 7.26(d, 1H); 7.36(s, 2H); 7.43(s, 1H); 12.02(s, 1H); 13.19(br s, 1H). | 474, 476 (M, M+2) | Example 212 |
| 288 | 3-Allyl-5-(4-{[(3,4-dichloro-5-methyl-1H-pyrrol-2-yl)carbonyl]amino}piperidin-1-yl)benzoic acid | 1.53-1.75(m, 2H); 1.83-1.98(m, 2H); 2.17(s, 3H); 2.90(t, 2H); 3.27-3.44(m overlapping water, 2H); 3.61-3.78(m, 2H); 3.95(m, 1H); 5.00-5.20(m, 2H); 5.94(m, 1H); 7.05(s, 1H); 7.18(s, 1H); 7.26(d, 1H); 7.32(s, 1H); 11.97(s, 1H); 12.78(br s, 1H). | 436 | Example 295 |
| 289 | 3-(4-{[(3,4-Dichloro-5-methyl-1H-pyrrol-2-yl)carbonyl]amino}piperidin-1-yl)-5-(2,3-dihydroxypropyl)benzoic acid | 1.60-1.79(m, 2H); 1.87-2.00(m, 2H); 2.18(s, 3H); 2.69-2.84(m, 1H); 2.99(t, 2H); 3.21-3.38(m, 4H); 3.89-4.04(m, 2H); 7.06-7.46(m, 4H); 11.57(s, 1H). | 470 | Example 296 |
| 290 | 5-(4-{[(3,4-Dichloro-5-methyl-1H-pyrrol-2-yl)carbonyl]amino}piperidin-1-yl)isophthalic acid | 1.72-1.89(m, 2H); 2.06-2.13(m, 2H); 2.21(s, 3H); 3.00(t, 2H); 3.62-3.71(m, 2H); 4.07(m, 1H); 7.70(s, 2H); 7.88(s, 1H). | 440 | Example 297 |
| 291 | 5-(4-{[(3,4-Dichloro-5-methyl-1H-pyrrol-2-yl)carbonyl]amino}piperidin-1-yl)nicotinic acid | 1.60-1.71(m, 2H); 1.89-1.98(m, 2H); 2.17(s, 3H); 3.06(t, 2H); 3.85-3.90(m, 2H); 4.04(m, 1H); 7.38(d, 2H); 7.88(s, 1H); 8.46(s, 1H); 8.57(s, 1H); 12.10(s, 1H). | 397 | Example 214 |
| 292 | 6-(4-{[(3,4-Dichloro-5-methyl-1H-pyrrol-2-yl)carbonyl]amino}piperidin-1-yl)pyridine-2-carboxylic acid | 1.48-1.63(m, 2H); 1.86-1.90(m, 2H); 2.17(s, 3H); 3.05(t, 2H); 4.03(m, 1H); 4.13-4.36(m, 2H); 7.10(d, 1H); 7.21-7.29(m, 2H); 7.67(m, 1H); 11.96(s, 1H); 12.65(br s, 1H). | 397 | Example 215 |
| 293 | 4-(4-{[(3,4-Dichloro-5-methyl-1H-pyrrol-2-yl)carbonyl]amino} | 1.55-1.67(m, 2H); 1.93-1.99(m, 2H); 2.18(s, 3H); 3.31-3.39(m, overlapping water, 2H); 4.13-4.18(m | 397 | Example 299 |

-continued

| Ex | Compound | ¹H NMR δ | M/z (M + 1) | SM |
|---|---|---|---|---|
|  | piperidin-1-yl) pyridine-2-carboxylic acid | 3H); 7.15(d, 1H); 7.41-7.56(m, 2H); 7.99(d, 1H); 12.14(s, 1H). |  |  |
| 294 | 5-(4-{[(3,4-Dichloro-5-methyl-1H-pyrrol-2-yl)carbonyl]amino} piperidin-1-yl) nicotinic acid 1-oxide | 1.55-1.70(m, 2H); 1.80-1.93(m, 2H); 2.17(s, 3H); 3.03(t, 2H); 3.75-3.85(m, 2H); 4.00(m, 1H); 7.20-7.33(m, 2H); 7.90(s, 1H); 8.17(s, 1H); 12.01, s, 1H); 13.73(br s, 1H). | 413 | Example 300 |

Examples 295-300

The following compounds were prepared by an analogous method to Example 118 starting from 3,4-dichloro-5-methyl-1H-pyrrole-2-carboxylic acid (Intermediate 3) and the intermediates shown in the table below.

| Ex | Compound | ¹H NMR δ | M + 1 | SM |
|---|---|---|---|---|
| 295 | Methyl 3-allyl-5-(4-{[(3,4-dichloro-5-methyl-1H-pyrrol-2-yl)carbonyl]amino}piperidin-1-yl) benzoic acid | 1.60-1.70(m, 2H); 1.86-1.93(m, 2H); 2.17(s, 3H); 2.93(t, 2H); 3.37(d, 2H); 3.68-3.73(m, 2H); 3.82(s, 3H); 3.96(m, 1H); 5.05-5.14(m, 2H); 5.94(m, 1H); 7.20-7.33(m, 4H); 11.95(s, 1H). | 450 | Intermediate 143 |
| 296 | Methyl 3-(4-{[(3,4-dichloro-5-methyl-1H-pyrrol-2-yl)carbonyl]amino}piperidin-1-yl)-5-(2,3-dihydroxypropyl) benzoate | 1.55-1.71(m, 2H); 1.88-1.94(m, 2H); 2.17(s, 3H); 2.76(m, 1H); 2.90(t, 2H); 3.22-3.33(m, 3H); 3.57-3.70(m, 4H); 3.81(s, 3H); 3.92-3.96(m, 2H); 7.10(s, 1H); 7.25-7.35(m, 3H); 11.97(s, 1H). | 484 | Intermediate 144 |
| 297 | Dimethyl 5-(4-{[(3,4-dichloro-5-methyl-1H-pyrrol-2-yl)carbonyl]amino}piperidin-1-yl)isophthalate | 1.60-1.70(m, 2H); 1.91-1.98(m, 2H); 2.17(s, 3H); 3.00(t, 2H); 3.76-3.81(m, 2H); 3.87(s, 6H); 4.00(m, 1H); 7.25(d, 1H); 7.71(s, 2H); 7.87(s, 1H); 11.95(s, 1H) | 468 | Intermediate 145 |
| 298 | Dimethyl 2-(4-{[(3,4-dichloro-5-methyl-1H-pyrrol-2-yl)carbonyl]amino}piperidin-1-yl)terephthalate | 1.65-1.76(m, 2H); 1.90-1.98(m, 2H); 2.18(s, 3H); 2.87(t, 2H); 3.24-3.28(m, 2H); 3.85(s, 3H); 3.87(s, 3H); 3.91(m, 1H); 7.29(d, 1H): 7.53-7.69(m, 3H); 11.97(s, 1H). | 468 | Intermediate 146 |
| 299 | Methyl 4-(4-{[(3,4-dichloro-5-methyl-1H-pyrrol-2-yl)carbonyl]amino}piperidin-1-yl)pyridine-2-carboxylate | 1.47-1.63(m, 2H); 1.87-1.92(m, 2H); 2.17(s, 3H); 3.13(t, 2H); 3.85(s, 3H); 3.95-4.06(m, 2H); 4.09(m, 1H); 7.08(m, 1H); 7.23(d, 1H); 7.47(s, 1H); 8.24(d, 1H); 11.96(s, 1H). | 411 | Intermediate 147 |
| 300 | Methyl 5-(4-{[(3,4-dichloro-5-methyl-1H-pyrrol-2-yl)carbonyl]amino}piperidin-1-yl)nicotinate 1-oxide | 1.50-1.66(m, 2H); 1.85-1.88(m, 2H); 2.17(s, 3H); 3.04(t, 2H); 3.78-3.83(m, 2H); 3.87(s, 3H); 4.00(m, 1H); 7.23(d, 1H); 7.35(s, 1H); 7.93(s, 1H); 8.18(s, 1H); 11.96(s, 1H). | 427 | Intermediate 148 |

Example 301

Methyl 1-(4-{[(3,4-dichloro-5-methyl-1H-pyrrol-2-yl)carbonyl]amino}piperidin-1-yl)isoquinoline-3-carboxylate In a sealed high pressure container with a Teflon lining was combined methyl 1-chloroisoquinoline-3-carboxylate (Intermediate 86; 450 mg, 2 mmol), (1.7 g, 4.4 mmol), and $K_2CO_3$ (1.7 g) in 20 ml tert-butanol. The container was heated at 155° C. with stirring for 3 hours. The solution was concentrated by rotary evaporation and reconstituted with EtOAc. The organic layer was washed 4× with $H_2O$, and dried over $MgSO_4$. Crude product was purified by flash Si and 100 mg yellow solid collected.

MS (ES): 461 (M+H)⁺, MS (ES): 459 (M−H)⁻.

¹H NMR δ: 1.89 (m, 2H) 2.03 (s, 2H) 2.19 (s, 3H) 3.06-3.21 (m, 2H) 3.89 (s, 2H) 4.05 (s, 1H) 7.33 (s, 1H) 7.79 (s, 2H) 8.11 (m, 2H) 8.19 (s, 1H) 12.02 (s, 1H).

Example 302

Methyl 5-(4-{[(3,4-dichloro-5-methyl-1H-pyrrol-2-yl)carbonyl]amino}piperidin-1-yl)-1,3,4-oxadiazole-2-carboxylate The title compound was synthesized by an analogous method to Example 42 by coupling methyl 5-{4-[(tert-butoxycarbonyl)amino]piperidin-1-yl}-1,3,4-oxadiazole-2-carboxylate (Intermediate 160) with 3,4-dichloro-5-methyl-1H-pyrrole-2-carboxylic acid (Intermediate 3). De-BOC and coupling should be separate steps.

MS (ESP): 402.0 (M+H) for $C_{15}H_{17}Cl_2N_5O_4$ $^1$H NMR δ: 1.57 (m, 2H); 1.86 (d, 2H); 2.11 (s, 3H); 3.02 (m, 2H); 3.82 (s, 3H); 3.84 (d, 2H); 3.96 (m, 1H); 7.19 (d, 1H); 11.91 (s, 1H).

Example 303

3,4-Dichloro-N-{1-[5-(hydroxymethyl)-1,3,4-oxadiazol-2-yl]piperidin-4-yl}-5-methyl-1H-pyrrole-2-carboxamide Diisobutylaluminum hydride (0.94 ml, 1 M solution in toluene, 0.94 mmol) was added dropwise to a solution of methyl 5-(4-{[(3,4-dichloro-5-methyl-1H-pyrrol-2-yl)carbonyl]amino}piperidin-1-yl)-1,3,4-oxadiazole-2-carboxylate (Example 302) (95 mg, 0.24 mmol) in THF (8 ml) at 0° C. The resultant mixture was allowed to slowly warm to room temperature and was stirred overnight. Potassium sodium tartrate (15 ml, 10% aqueous solution) and EtOAc (100 ml) were added to the reaction mixture and the resultant mixture was stirred vigorously for 1 h. The organic phase was separated, dried over sodium sulfate, filtered and concentrated. The crude residue was purified by preparative reversed-phase HPLC (water/acetonitrile gradient, 10-95%) to yield 45 mg of the title compound.

MS (ESP): 374.0 (M+H) for $C_{14}H_{17}Cl_2N_5O_3$ $^1$H NMR δ: 1.55 (m, 2H); 1.83 (d, 2H); 2.11 (s, 3H); 3.13 (t, 2H); 3.74 (d, 2H); 3.94 (m, 1H); 4.38 (s, 2H); 5.80 (br s, 1H); 7.19 (d, 1H); 11.90 (s, 1H).

Example 304

5-(4-{[(3,4-Dichloro-5-methyl-1H-pyrrol-2-yl)carbonyl]amino}piperidin-1-yl)-1,3,4-oxadiazole-2-carboxylic acid The title compound was synthesized by an analogous method to Example 310 using methyl 5-(4-{[(3,4-dichloro-5-methyl-1H-pyrrol-2-yl)carbonyl]amino}piperidin-1-yl)-1,3,4-oxadiazole-2-carboxylate (Example 302).

MS (ESP): 388.0 (M+H) for $C_{14}H_{15}Cl_2N_5O_4$ $^1$H NMR δ: 1.55 (m, 2H); 1.81 (d, 2H); 2.11 (s, 3H); 3.10 (t, 2H); 3.72 (d, 2H); 3.94 (m, 1H); 7.31 (d, 1H); 6.80-7.40 (br. s, 2H).

Example 305

3,4-Dichloro-5-methyl-N-[1-(1,3,4-oxadiazol-2-yl)piperidin-4-yl]-1H-pyrrole-2-carboxamide The title compound was synthesized by an analogous method to Example 310 using methyl 5-(4-{[(3,4-dichloro-5-methyl-1H-pyrrol-2-yl)carbonyl]amino}piperidin-1-yl)-1,3,4-oxadiazole-2-carboxylate (Example 302) (spontaneous decarboxylation occurred during the hydrolysis).

MS (ESP): 344.2 (M+H) for $C_{13}H_{15}Cl_2N_5O_2$

Example 306

3,4-Dichloro-5-methyl-N-{1-[2-(methylthio)pyrimidin-4-yl]piperidin-4-yl}-1H-pyrrole-2-carboxamide 3,4-Dichloro-N-[1-(2-chloropyrimidin-4-yl)piperidin-4-yl]-5-methyl-1H-pyrrole-2-carboxamide (Example 307, 200 mg, 0.515 mmol) and sodium thiomethoxide (108.2 mg, 1.545 mmol) were combined in DMF (12 ml) and heated at 90° C. for 1 h. The reaction mixture was cooled to room temperature, diluted with EtOAc and water. The phases were separated, and the aqueous phase was extracted three times with EtOAc. The combined organic portions were washed with brine, dried over $Na_2SO_4$, filtered, and concentrated under reduced pressure to give a peach coloured solid (200 mg, 0.499 mmol, 97% yield) that was used without further purification.

MS (ES$^-$): 398.12, 400.05 for $C_{16}H_{19}Cl_2N_5OS$ $^1$H NMR δ: 1.25 (m, 2H); 1.62 (m, 2H); 1.93 (s, 3H); 2.17 (s, 3H); 2.86 (m, 2H); 3.83 (m, 1H); 4.07 (m, 2H); 6.35 (d, 1H); 7.00 (d, 1H); 7.76 (d, 1H); 11.72 (s, 1H)

Example 307

3,4-Dichloro-N-[1-(2-chloropyrimidin-4-yl)piperidin-4-yl]-5-methyl-1H-pyrrole-2-carboxamide 3,4-Dichloro-5-methyl-N-piperidin-4-yl-1H-pyrrole-2-carboxamide hydrochloride (Intermediate 1, 650 mg, 2.08 mmol), 2,4-dichloropyrimidine (309.7 mg, 2.08 mmol), and $Et_3N$ (0.6 ml, 4.16 mmol) were combined in DMF (12 ml) and heated at 90° C. under nitrogen for 1.5 h. Upon cooling to room temperature, the reaction was diluted with EtOAc and water. The phases were separated, and the aqueous portion was extracted twice with EtOAc. The combined organic portions were washed with brine, dried over $Na_2SO_4$, filtered, and concentrated under reduced pressure to give a light brown solid. The crude material was triturated with cold MeOH and filtered to give 458 mg (1.18 mmol, 57%) of the title product.

MS (ES$^-$): 386.09, 388.03, 389.83 for $C_{15}H_{16}Cl_3N_5O$ $^1$H NMR δ: 1.60 (m, 2H); 1.93 (m, 2H); 2.23 (s, 3H); 3.22 (m, 2H); 4.17 (m, 2H); 4.34 (m, 1H); 6.94 (d, 1H); 7.27 (d, 1H); 8.12 (d, 1H); 12.02 (s, 1H)

Example 308

1-(6-Chloro-4-cyanopyridin-2-yl)piperidin-4-yl 3,4-dichloro-5-methyl-1H-pyrrole-2-carboxylate 3,4-Dichloro-5-methyl-1H-pyrrole-2-carboxylic acid (Intermediate 3, 164 mg, 0.84 mmol) was dissolved in anhydrous THF (3 ml). 2-Chloro-6-(4-hydroxypiperidin-1-yl)isonicotinonitrile (Intermediate 26, 200 mg, 0.84 mmol) was added, then DEAD (133 µl, 0.84 mmol) was added dropwise followed by triphenylphosphine (221 mg, 0.84 mmol). The mixture was stirred at room temperature for 18 h. The reaction was concentrated, filtered and purified by semi-preparative reverse phase HPLC eluting with $CH_3CN$/water (0.1% TFA). (135 mg).

MS (ES, M+H): 413 for $C_{17}H_{15}Cl_3N_4O_2$ $^1$H NMR δ: 1.63 (m, 2H); 1.80 (m, 2H); 2.08 (s, 3H); 3.70 (m, 4H); 5.21 (m, 1H); 7.14 (s, 1H); 7.32 (s, 1H); 12.12 (s, 1H)

Example 309

3,4-Dichloro-N-{1-[6-chloro-4-(hydrazinocarbonyl)pyridin-2-yl]piperidin-4-yl}-5-methyl-1H-pyrrole-2-carboxamide Diisopropylethylamine (0.043 ml, 0.25 mmol), HATU (0.048 g, 0.12 mmol) and HOAT (0.017 g 0.12 mmol) were added to a stirred solution of 2-chloro-6-(4-{[(3,4-dichloro-5-methyl-1H-pyrrol-2-yl)carbonyl]amino}piperidin-1-yl)isonicotinic acid (Example 153; 0.055 g, 0.12 mmol) in DMF (2 ml). The resultant solution was stirred for 5 mins and hydrazine (0.04 ml, 0.12 mmol) was added. The mixture was stirred at room temperature for 14 h, partitioned between water and EtOAc. The layers were separated and the organic layer was washed with water two more times. The organic phase was dried over magnesium sulfate and concentrated to give the title compound (30 mg).
MS (ES): 445 (MH$^+$) for $C_{17}H_{19}Cl_3N_6O_2$

Example 310

6-(4-{[(3,4-Dichloro-5-methyl-1H-pyrrol-2-yl)carbonyl]amino}piperidin-1-yl)-2-morpholin-4-ylpyrimidine-4-carboxylic acid Methyl 6-(4-{[(3,4-dichloro-5-methyl-1H-pyrrol-2-yl)carbonyl]amino}piperidin-1-yl)-2-morpholin-4-ylpyrimidine-4-carboxylate (Example 9, 224 mg, 0.45 mmol) was dissolved in MeOH (5 ml). 2 N lithium hydroxide (2 ml) was added and the reaction was stirred at room temperature for 3 h. The mixture was acidified with 1 N HCl and was extracted with EtOAc (3×50 ml), dried over $Na_2SO_4$ and concentrated in vacuo to provide 200 mg of the title compound.
MS (ESP): 483.4 (M+H) for $C_{20}H_{24}Cl_2N_6O_4$

Example 311

6-(4-{[(3,4-Dichloro-5-methyl-1H-pyrrol-2-yl)carbonyl]amino}piperidin-1-yl)-2-methoxypyrimidine-4-carboxylic acid Title compound was synthesized by an analogous method to Example 312 using methyl 2-chloro-6-(4-{[(3,4-dichloro-5-methyl-1H-pyrrol-2-yl)carbonyl]amino}piperidin-1-yl)pyrimidine-4-carboxylate (Example 6) and sodium methoxide.
MS (ES): 428 (M+1) for $C_{17}H_{19}Cl_2N_5O_4$
$^1$H NMR δ: 1.54 (m, 2H); 1.88 (m, 2H); 2.16 (s, 3H); 3.20 (t, 2H); 3.86 (s, 3H); 4.10 (m, 1H); 4.40 (m, 2H); 7.05 (s, 1H); 7.24 (d, 1H); 11.97 (s, 1H).

Example 312

6-(4-{[(3,4-Dichloro-5-methyl-1H-pyrrol-2-yl)carbonyl]amino}piperidin-1-yl)-2-ethoxypyrimidine-4-carboxylic acid Sodium ethoxide solution (1 ml, 3.0 mmol, 21 wt % in EtOH) was added to a stirred solution of methyl 2-chloro-6-(4-{[(3,4-dichloro-5-methyl-1H-pyrrol-2-yl)carbonyl]amino}piperidin-1-yl)pyrimidine-4-carboxylate (Example 6, 0.40 g, 0.89 mmol) in DMF (1.5 ml). The reaction was stirred overnight, then quenched with water (2 ml) and the EtOH removed under reduced pressures. The resulting aqueous solution was acidified with 1 N HCl (pH ~2) and the precipitated product was collected by suction filtration (0.07 g).

MS (ES): 442 (M+1) for $C_{18}H_{21}Cl_2N_5O_4$
$^1$H NMR δ: 1.28 (t, 3H); 1.49 (m, 2H); 1.86 (m, 2H); 2.15 (s, 3H); 3.16 (t, 2H); 4.07 (m, 1H); 4.27 (q, 2H); 4.29 (m, 2H); 6.99 (s, 1H); 7.19 (d, 1H); 11.95 (s, 1H)

Example 313

6-(4-{[(3,4-Dichloro-5-methyl-1H-pyrrol-2-yl)carbonyl]amino}piperidin-1-yl)-2-[(2,2-dimethyl-1,3-dioxolan-4-yl)methoxy]-N-methoxypyrimidine-4-carboxamide The title compound was synthesized by an analogous method to Example 8 starting from 6-(4-{[(3,4-dichloro-5-methyl-1H-pyrrol-2-yl)carbonyl]amino}piperidin-1-yl)-2-[(2,2-dimethyl-1,3-dioxolan-4-yl)methoxy]pyrimidine-4-carboxylic acid (Example 314) and methoxylamine hydrochloride.
MS (ES) MH$^+$: 557 for $C_{23}H_{30}Cl_2N_6O_6$

Example 314

6-(4-{[(3,4-Dichloro-5-methyl-1H-pyrrol-2-yl)carbonyl]amino}piperidin-1-yl)-2-[(2,2-dimethyl-1,3-dioxolan-4-yl)methoxy]pyrimidine-4-carboxylic acid The title compound was synthesized by an analogous method to Example 154 starting from (2,2-dimethyl-1,3-dioxolan-4-yl) MeOH (commercially available) and sodium hydride, and reacting the alkoxide generated in situ with methyl 2-chloro-6-(4-{[(3,4-dichloro-5-methyl-1H-pyrrol-2-yl)carbonyl]amino}piperidin-1-yl)pyrimidine-4-carboxylate (Example 6).
MS (ES) MH$^+$: 528 for $C_{22}H_{27}Cl_2N_5O_6$

Example 315

Methyl 2-(4-{[(3,4-dichloro-5-methyl-1H-pyrrol-2-yl)carbonyl]amino}piperidin-1-yl)-6-methoxypyrimidine-4-carboxylate The title compound was synthesized by an analogous method to Example 6 starting from 3,4-dichloro-5-methyl-N-piperidin-4-yl-1H-pyrrole-2-carboxamide hydrochloride (Intermediate 1) and methyl 2-chloro-6-methoxypyrimidine-4-carboxylate (Intermediate 88).
MS (ES) MH$^+$: 442 for $C_{18}H_{21}Cl_2N_5O_4$

Example 316

Methyl 6-(4-{[(3,4-dichloro-5-methyl-1H-pyrrol-2-yl)carbonyl]amino}piperidin-1-yl)-2-pyrrolidin-1-ylpyrimidine-4-carboxylate The title compound was synthesized by an analogous method to Example 9 starting from methyl 2-chloro-6-(4-{[(3,4-dichloro-5-methyl-1H-pyrrol-2-yl)carbonyl]amino}piperidin-1-yl)pyrimidine-4-carboxylate (Example 6), pyrrolidine, and TEA.
MS (ES$^-$): 479.34, 481.34

Example 317

Methyl 6-(4-{[(3,4-dichloro-5-methyl-1H-pyrrol-2-yl)carbonyl]amino}piperidin-1-yl)-2-piperazin-1-ylpyrimidine-4-carboxylate The title compound was synthesized by an analogous method to Example 9 starting from methyl 2-chloro-6-(4-{[(3,4-dichloro-5-methyl-1H-pyrrol-2-yl)carbonyl]amino}piperidin-1-yl)pyrimidine-4-carboxylate (Example 6), piperazine, and TEA.
MS (ES−): 494.60, 496.59

Example 318

Methyl 6-(4-{[(3,4-dichloro-5-methyl-1H-pyrrol-2-yl)carbonyl]amino}piperidin-1-yl)-2-(4-methylpiperazin-1-yl)pyrimidine-4-carboxylate The title compound was synthesized by an analogous method to Example 9 starting from methyl 2-chloro-6-(4-{[(3,4-dichloro-5-methyl-1H-pyrrol-2-yl)carbonyl]amino}piperidin-1-yl)pyrimidine-4-carboxylate (Example 6), 1-methylpiperazine, and TEA.
MS (ES−): 508.61, 510.60

Example 319

2-(2-Aminoethoxy)-6-(4-{[(3,4-dichloro-5-methyl-1H-pyrrol-2-yl)carbonyl]amino}piperidin-1-yl)-N-methoxypyrimidine-4-carboxamide The title compound was synthesized by a method analogous to Intermediate 70 starting from tert-butyl 2-({4-(4-{[(3,4-dichloro-5-methyl-1H-pyrrol-2-yl)carbonyl]amino}piperidin-1-yl)-6-[(methoxyamino)carbonyl]pyrimidin-2-yl}oxy)ethylcarbamate (Example 322).
MS (ES) MH$^+$: 486 for $C_{19}H_{25}Cl_2N_7O_4$

Example 320

Methyl 2-(4-{[(3,4-dichloro-5-methyl-1H-pyrrol-2-yl)carbonyl]amino}piperidin-1-yl)-1,3-thiazole-5-carboxylate 3,4-Dichloro-5-methyl-N-piperidin-4-yl-1H-pyrrole-2-carboxamide hydrochloride (Intermediate 1, 0.300 g, 0.961 mmol) was dissolved in NMP (3 ml). TEA (267 μl, 1.922 mmol) was added followed by the addition of methyl 2-bromo-1,3-thiazole-5-carboxylate (0.213 g, 0.961 mmol) at room temperature. Using a Smith Microwave Synthesizer, the mixture was subjected to single-mode microwave at 150° C. for 20 minutes and was partitioned between water and EtOAc. The organic layer was washed with water and combined organic phase was dried over magnesium sulfate and concentrated to give the desired product. (432 mg).
MS (ES): 417 (MH$^+$) for $C_{16}H_8Cl_2N_4O_3S$
$^1$H NMR δ: 1.70 (m, 2H); 1.97 (m, 2H); 2.24 (s, 3H); 3.39 (m, 2H); 3.81 (s, 3H); 4.03 (m, 2H); 4.13 (m, 1H); 7.34 (d, 1H); 7.93 (s, 1H); 12.03 (s, 1H)

Example 321

3,4-Dichloro-N-[1-(5-cyano-1,3-thiazol-2-yl)piperidin-4-yl]-5-methyl-1H-pyrrole-2-carboxamide To a solution of 3,4-dichloro-5-methyl-N-piperidin-4-yl-1H-pyrrole-2-carboxamide hydrochloride (Intermediate 1; 0.330 g, 1.058 mmol) in NMP (2 ml) was added TEA (0.150 ml, 1.058 mmol) followed by the addition of 2-bromo-1,3-thiazole-5-carbonitrile (prepared according to F. Campagna et al. *Tet. Lett,* 1977, 21, 1815-1816) (0.200 g, 1.058 mmol) at room temperature. Using a Smith Microwave Synthesizer, the mixture was subjected to single-mode microwave at 150° C. for 20 minutes. The crude mixture was diluted with EtOAc and washed with water several times. The extracts were combined dried over magnesium sulfate and concentrated to give the desired product. (0.450 g).
MS (ES): 384 (MH$^+$) for $C_{15}H_{15}Cl_2N_5OS$
$^1$H NMR δ: 1.77 (m, 2H); 1.98 (m, 2H); 2.24 (s, 3H); 3.47 (m, 2H); 4.02 (m, 2H); 4.16 (m, 1H); 7.36 (d, 1H); 8.09 (s, 1H); 12.03 (s, 1H)

Example 322 tert-Butyl 2-({4-(4-{[(3,4-dichloro-5-methyl-1H-pyrrol-2-yl)carbonyl]amino}piperidin-1-yl)-6-[(methoxyamino)carbonyl]pyrimidin-2-yl}oxy)ethylcarbamate The title compound was synthesized by an analogous method to Example 8 starting from 2-{2-[(tert-butoxycarbonyl)amino]ethoxy}-6-(4-{[(3,4-dichloro-5-methyl-1H-pyrrol-2-yl)carbonyl]amino}piperidin-1-yl)pyrimidine-4-carboxylic acid (Example 154) and methoxylamine hydrochloride.
MS (ES) MH+: 586 for $C_{24}H_{33}Cl_2N_7O_6$

Examples 323-328

The following esters were prepared by an analogous method to Example 134 from 3,4-dichloro-5-methyl-N-piperidin-4-yl-1H-pyrrole-2-carboxamide hydrochloride (Intermediate 1) and the starting materials indicated.

| Example | Compound | $^1$H NMR δ | m/z (ES+) | SM |
| --- | --- | --- | --- | --- |
| 323 | Ethyl 8-methoxy-4-(4-{[(3,4-dichloro-5-methyl-1H-pyrrol-2-yl)carbonyl]amino} piperidin-1-yl) quinoline-2-carboxylate | | 505/507 | Ethyl 4-chloro-8-methoxyquinoline-2-carboxylate (Intermediate 137) |
| 324 | Methyl 8-fluoro-4-(4-{[(3,4-dichloro-5-methyl-1H- | 1.98(m, 2H); 2.03(m, 2H); 2.18(s, 3H); 3.11(m, 2H); 3.33(s, 1H); | 479/481 | Methyl 4-chloro-8-fluoroquinoline- |

-continued

| Example | Compound | ¹H NMR δ | m/z (ES+) | SM |
|---|---|---|---|---|
| | pyrrol-2-yl)carbonyl]amino}piperidin-1-yl)quinoline-2-carboxylate | 3.60(m, 2H); 3.94(s, 3H); 4.03(m, 1H); 7.34(m, 1H); 7.62(m, 2H); 7.83(m, 1H); 12.02(s, 1H) | | 2-carboxylate (Intermediate 138) |
| 325 | Methyl 6-fluoro-4-(4-{[(3,4-dichloro-5-methyl-1H-pyrrol-2-yl)carbonyl]amino}piperidin-1-yl)quinoline-2-carboxylate | 1.92(m, 2H); 2.03(m, 2H); 2.18(s, 3H); 3.11(m, 2H); 3.60(m, 2H); 3.94(s, 3H); 4.05(m, 1H); 7.32(d, 1H, J=7.5); 7.60(s, 1H); 7.63(m, 1H); 7.99(m, 2H); 12.01(s, 1H) | 495/497 | Methyl 4-chloro-6-fluoroquinoline-2-carboxylate (Intermediate 140) |
| 326 | Methyl 8-chloro-4-(4-{[(3,4-dichloro-5-methyl-1H-pyrrol-2-yl)carbonyl]amino}piperidin-1-yl)quinoline-2-carboxylate | 1.92(m, 2H); 2.03(m, 2H); 2.18(s, 3H); 3.11(m, 2H); 3.60(m, 2H); 3.94(s, 3H); 4.05(m, 1H); 7.32(d, 1H, J=7.5); 7.53(m, 1H); 7.60(m, 2H); 7.99(m, 2H); 12.01(s, 1H) | ES⁺ 495/497 | Methyl 4,8-dichloroquinoline-2-carboxylate (Intermediate 141) |
| 327 | Methyl 8-methyl-4-(4-{[(3,4-dichloro-5-methyl-1H-pyrrol-2-yl)carbonyl]amino}piperidin-1-yl)quinoline-2-carboxylate | 1.91(m, 2H); 2.04(m, 2H); 2.17(s, 3H); 2.72(s, 3H); 3.05(m, 2H); 3.55(m, 2H); 3.93(s, 3H); 4.03(m, 1H); 7.32(m, 1H); 7.59(m, 3H); 7.86(m, 1H); 12.01(s, 1H) | ES⁺ 475/477 | Methyl 4-chloro-8-methyl quinoline-2-carboxylate (Intermediate 139) |
| 328 | Ethyl 2-(4-{[(3,4-dichloro-5-methyl-1H-pyrrol-2-yl)carbonyl]amino}piperidin-1-yl)oxazole-4-carboxylate | 1.26(t, 3H, J=7.1); 1.60(m, 2H); 1.88(m, 2H); 2.18(s, 3H); 3.17(m, 2H); 3.90(m, 2H); 4.02(m, 1H); 4.24(q, 2H, J=7.2); 7.27(d, 1H, J=7.9); 8.31(s, 1H); 11.99(s, 1H) | 415/417 | Ethyl 2-chloro-oxazole-4-carboxylate (Intermediate 142) |

Example 329

3,4-Dichloro-5-methyl-N-[1-(1,3-thiazol-2-yl)piperidin-4-yl]-1H-pyrrole-2-carboxamide 3,4-Dichloro-5-methyl-N-piperidin-4-yl-1H-pyrrole-2-carboxamide hydrochloride (Intermediate 1; 1 g, 3.2 mmol) was dissolved in NMP (10 ml). Bromothiazole (2.65 g; 16 mmol) was added followed by the addition of N,N-diisopropylethylamine (2.75 ml, 16 mmol). Using a Smith Microwave Synthesizer, the mixture was subjected to single-mode microwave at 150° C. for a total of 3 h. The mixture was diluted with EtOAc and washed well with water, NaHCO₃, brine. The organic phase was dried over Na₂SO₄ and concentrated in vacuo to give the title compound as a brown solid (692 mg).

MS (ES) MH⁺: 361 for $C_{14}H_{16}Cl_2N_4OS$

¹H NMR δ: 1.78 (m, 2H); 1.98 (m, 2H); 2.26 (s, 3H); 3.28 (m, 2H); 3.95 (m, 2H); 4.12 (m, 1H); 6.93 (d, 1H); 7.22 (s, 1H); 7.31 (d, 1H); 12.10 (s, 1H).

Example 330

1-(6-Chloro-4-cyanopyridin-2-yl)piperidin-4-yl-4-bromo-5-methyl-1H-pyrrole-2-carboxylate The title compound was prepared in a manner analogous to Example 308 from 2-chloro-6-(4-hydroxypiperidin-1-yl)isonicotinonitrile (Intermediate 26) and 4-bromo-5-methyl-1H-pyrrole-2-carboxylic acid (Intermediate 18).

MS (ES) M+H: 425 for $C_{17}H_{16}BrClN_4O$

Example 331

Methyl 2-(4-{[5-methyl-1H-pyrrol-2-yl)carbonyl]amino}piperidin-1-yl)-6-chloroisonicotinate The title compound was prepared in a manner analogous to Example 18 starting from 5-methyl-1H-pyrrole-2-carboxylic acid (Intermediate 29) and methyl 2-(4-aminopiperidin-1-yl)-6-chloroisonicotinate hydrochloride salt (Intermediate 93).

MS (ES, M+H): 376 for $C_{18}H_{21}ClN_4O_3$

Example 332

2-Chloro-6-(4-{[(5-methyl-1H-pyrrol-2-yl)carbonyl]amino}piperidin-1-yl)isonicotinic acid The title compound was prepared in a manner analogous to Example 44 starting from methyl 2-(4-{[5-methyl-1H-pyrrol-2-yl)carbonyl]amino}piperidin-1-yl)-6-chloroisonicotinate (Example 331).

MS (ES, M+H): 362 for $C_{17}H_{19}ClN_4O_3$

Example 333

Methyl 2-chloro-6-(4-{[(3,4-dichloro-5-methyl-1H-pyrrol-2-yl)carbonyl]amino}piperidin-1-yl)isonicotinate The title compound was prepared in a manner analogous to Example 18 starting from 3,4-dichloro-5-methyl-1H-pyrrole-2-carboxylic acid (Intermediate 3) and methyl 2-(4-aminopiperidin-1-yl)-6-chloroisonicotinate hydrochloride salt (Intermediate 93).

MS (ES, M+H): 445,447 for $C_{18}H_{19}Cl_3N_4O_3$

Example 334

Methyl 2-(4-{[(3,4-dichloro-5-methyl-1H-pyrrol-2-yl)carbonyl]amino}piperidin-1-yl)-6-(methylsulfinyl)isonicotinate The title compound was prepared in a manner analogous to Example 6 starting from 3,4-dichloro-5-methyl-N-piperidin-4-yl-1H-pyrrole-2-carboxamide hydrochloride (Intermediate 1) and methyl 2-chloro-6-(methylsulfinyl)isonicotinate (Intermediate 84).

MS (ES, M+H): 473,471 for $C_{19}H_{22}Cl_2N_4O_4S$

Example 335

6-(4-{[(3,4-Dichloro-5-methyl-1H-pyrrol-2-yl)carbonyl]amino}piperidin-1-yl)-2-pyrrolidin-1-ylpyrimidine-4-carboxylic acid The title compound was synthesized by an analogous method to Intermediate 3 starting from methyl 6-(4-{[(3,4-dichloro-5-methyl-1H-pyrrol-2-yl)carbonyl]amino}piperidin-1-yl)-2-pyrrolidin-1-ylpyrimidine-4-carboxylate (Example 316).

MS (ES): 465.3 (M–H) for $C_{20}H_{24}Cl_2N_6O_3$ $^1$H NMR δ: 1.5 (q, 2H); 1.86 (br s, 4H); 2.11 (s, 3H); 3.21 (t, 2H); 3.49 (br s, 4H); 3.6-4.5 (m, 6H); 6.84 (s, 1H); 7.16 (d, 1H); 11.93 (s, 1H).

Example 336

Ethyl 2-(4-{[(3,4-dichloro-5-methyl-1H-pyrrol-2-yl)carbonyl]amino}piperidin-1-yl)-1,3-thiazole-4-carboxylate The title compound was prepared in a manner analogous to Example 320 from 3,4-dichloro-5-methyl-N-piperidin-4-yl-1H-pyrrole-2-carboxamide hydrochloride (intermediate 1) and ethyl 2-bromo-1,3-thiazole-4-carboxylate (commercially available).

MS (ES) M+H: 431,433 for $C_{17}H_{20}Cl_2N_4O_3S$

Example 337

3,4-Dichloro-N-[1-(4-cyano-1,3-thiazol-2-yl)piperidin-4-yl]-5-methyl-1H-pyrrole-2-carboxamide The title compound was prepared as described for Example 321 from 3,4-dichloro-5-methyl-N-piperidin-4-yl-1H-pyrrole-2-carboxamide hydrochloride (Intermediate 1) and 2-bromo-1,3-thiazole-4-carbonitrile (prepared as described in *J. Am. Chem. Soc.* 1952, 74, 5799).

MS (ES) (M+H): 384 for $C_{15}H_{15}Cl_2N_5OS$ $^1$H NMR δ: 1.69-1.77 (m, 2H); 1.98 (dd, 2H); 2.24 (s, 3H); 3.42 (m, 2H); 3.97 (d, 2H); 4.10-4.16 (m, 1H); 7.34-7.36 (d, 1H); 8.09 (s, 1H); 12.03 (s, 1H).

Example 338

4-Bromo-N-[1-(4-cyanopyridin-2-yl)piperidin-4-yl]-5-methyl-1H-pyrrole-2-carboxamide The title compound was prepared in a manner analogous to Example 18 from 3,4-dichloro-5-methyl-1H-pyrrole-2-carboxylic acid (Intermediate 3) and 2-(4-aminopiperidin-1-yl)isonicotinonitrile hydrochloride salt (Intermediate 208).

MS (ES): 412 (M+H) for $C_{17}H_{16}Cl_3N_5O$

Example 339

Ethyl 4-[(tert-butylamino)carbonyl]-2-(4-{[(3,4-dichloro-5-methyl-1H-pyrrol-2-yl)carbonyl]amino}piperidin-1-yl)-1,3-thiazole-5-carboxylate

Example 340

5-Thiazolecarboxylic acid, 4-cyano-2-[4-[[(3,4-dichloro-5-methyl-1H-pyrrol-2-yl)carbonyl]amino]-1-piperidinyl]-, ethyl ester A solution of ethyl 2-{4-[(tert-butoxycarbonyl)amino]piperidin-1-yl)}4-cyano-1,3-thiazole-5-carboxylate (Intermediate 223) (1.9 g) and 15 ml TFA in 20 ml DCM was stirred at room temperature overnight. Solvent was removed and the residue was taken up in DCM and washed with aqueous $Na_2CO_3$ and brine. Drying ($MgSO_4$) and removal of solvent gave 920 mg of a dark brown oil. To a solution of 880 mg (3.1 mmol) of the oil and diisopropylethylamine (0.7 ml, 3.8 mmol) was added 3,4-dichloro-5-methyl-1H-pyrrole-2-carbonyl chloride (Intermediate 224) (800 mg, 3.8 mmol), and the mixture was stirred at room temperature overnight. Additional 3,4-dichloro-5-methyl-1H-pyrrole-2-carbonyl chloride (100 mg) was added, and stirring was continued for 2 hours. The mixture was diluted with EtOAc and washed with water and brine. Drying ($MgSO_4$) and removal of solvent gave a oil which was chromatographed on silica gel (DCM followed by gradient elution to 5% MeOH in DCM). During TFA deprotection, isobuytlene reaction with the nitrile group was observed—the mixture was carried though. The major material was isolated and chromatographed by reverse phase HPLC (45-65% gradient of $CH_3CN$ in water with 0.1% TFA). Two materials were isolated. The first eluting compound was Example 339:

MS (ES): 530.1 (M+H)$^{+1}$, 528.2 (M–H)$^{-1}$ $^1$H NMR δ: 1.22 (t, J=7.06 Hz, 2H); 1.32 (s, 9H); 1.63 (s, 2H); 1.91 (s, 3H); 2.18 (s, 3H); 3.34 (s, 2H); 4.1 (m, 1H); 3.90 (s, 2H); 4.18 (q, J=7.16 Hz, 2H); 7.30 (d, J=7.54 Hz, 1H); 8.01 (s, 1H); 11.99 (s, 1H).

The second eluting compound was Example 340:

MS (ES): 456.0 (M+H)$^{+1}$, 454.1 (M–H)$^{-1}$ $^1$H NMR δ: 1.28 (t, J=7.06 Hz, 3H); 1.55-1.75 (m, 2H); 1.82-2.02 (m, 2H); 2.18 (s, 3H); 3.33-3.52 (m, 2H); 3.85-4.02 (m, 2H); 4.04 (s, 1H); 4.30 (q, J=7.10 Hz, 2H); 7.29 (d, J=7.72 Hz, 1H); 11.80-12.17 (m, 1H).

Example 341

4-Cyano-2-(4-{[(3,4-dichloro-5-methyl-1H-pyrrol-2-yl)carbonyl]amino}piperidin-1-yl)-1,3-thiazole-5-carboxylic acid A solution of ethyl 4-[(tert-butylamino)carbonyl]-2-(4-{[(3,4-dichloro-5-methyl-1H-pyrrol-2-yl)carbonyl]amino}piperidin-1-yl)-1,3-thiazole-5-carboxylate (Example 340; 140 mg, 0.31 mmol) and 2 N LiOH in water (0.93 ml, 1.86 mmol) in 6 ml 1:1 THF:MeOH was heated at 80° C. for 30 min in a microwave reactor. 1 N HCl (1.86 ml) was added and the mixture was diluted with water. Precipitated material was filtered and rinsed well with water. Drying of the precipitate in vacuo gave 105 mg of product.

MS (ES): 428.0 (M+H)

$^1$H NMR δ: 1.67 (s, 1H); 1.80-2.04 (m, 2H); 2.18 (s, 3H); 3.33 (s, 2H); 3.89 (s, 2H); 4.06 (d, J=5.09 Hz, 1H); 7.30 (s, 1H); 12.03 (s, 1H); 13.92 (s, 1H).

Example 342

4-[(tert-Butylamino)carbonyl]-2-(4-{[(3,4-dichloro-5-methyl-1H-pyrrol-2-yl)carbonyl]amino}piperidin-1-yl)-1,3-thiazole-5-carboxylic acid A solution of 5-thiazolecarboxylic acid, 4-cyano-2-[4-[[(3,4-dichloro-5-methyl-1H-pyrrol-2-yl)carbonyl]amino]-1-piperidinyl]-, ethyl ester (Example 339; 186 mg, 0.35 mmol) and 2 N LiOH in water (0.35 ml, 0.7 mmol) in 6 ml MeOH was heated at 80° C. for 30 min in a microwave reactor. 1 N HCl (0.7 ml) was added and the mixture was diluted with water. Precipitated material was filtered, rinsed well with water and dried in vacuo to give 164 mg of product

MS (ES): 502.1 (M+H)

$^1$H NMR δ:1.20-1.57 (m, 9H); 1.66 (s, 2H); 1.90 (s, 2H); 2.18 (s, 3H); 3.34 (s, 2H); 4.00 (s, 3H); 7.31 (d, J=7.72 Hz, 1H); 12.01 (s, 1H); 16.06 (s, 1H).

Examples 343-346

The following examples were prepared by the procedure of Example 223 from the starting materials indicated.

The invention claimed is:

1. A compound of the formula (1) or a pharmaceutically acceptable salt thereof:

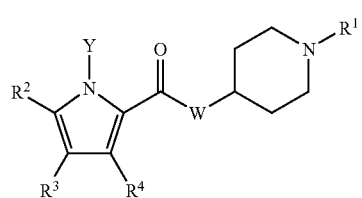

(1)

wherein:

W is O or $NR^5$;

Y is hydrogen;

$R^1$ is $R^1$a;

$R^1$a is a 4 to 7 membered saturated, partially unsaturated or unsaturated heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from:

nitro, cyano, sulfo, formyl, hydroxyiminomethyl, (2-6C)alkenyl, (2-6C)alkynyl, —CO(1-6C)alkyl, —COO(1-6C)alkyl (optionally substituted with —COO(1-6C)alkyl), trifluoromethyl, —CONR$^6$R$^7$, —OCONR$^6$R$^7$,

| Ex. | R | $^1$H NMR δ | M + 1 | SM |
|---|---|---|---|---|
| 343 | 2-(4-{[(3,4-Dichloro-5-methyl-1H-pyrrol-2-yl)carbonyl]amino}piperidin-1-yl)-4-methyl-1,3-thiazole-5-carboxylic acid | 1.62(q, 2H); 1.89(d, 2H); 2.16(s, 3H); 2.91(t, 2H); 3.55(s, 3H); 3.69(d, 2H); 3.87-4.04(m, 1H); 7.26(d, 1H); 11.95(s, 1H). | 417 | Ethyl 2-(4-{[(3,4-dichloro-5-methyl-1H-pyrrol-2-yl)carbonyl]amino}piperidin-1-yl)-4-methyl-1,3-thiazole-5-carboxylate (Example 218) |
| 344 | 3-(4-{[(3,4-Dichloro-5-methyl-1H-pyrrol-2-yl)carbonyl]amino}piperidin-1-yl)benzoic acid | 1.65(q, 2H); 1.89(d, 2H); 2.16(s, 3H); 2.91(t, 2H); 3.70(d, 2H); 3.83-4.04(m, 1H); 7.17-7.27(m, 2H); 7.27-7.40(m, 2H); 7.45(s, 1H); 11.94(s, 1H). | 396 | Methyl 3-(4-{[(3,4-dichloro-5-methyl-1H-pyrrol-2-yl)carbonyl]amino}piperidin-1-yl)benzoate (Example 211) |
| 345 | 3-(4-{[(3,4-Dichloro-5-methyl-1H-pyrrol-2-yl)carbonyl]amino}piperidin-1-yl)-5-morpholin-4-ylbenzoic acid | 1.63-1.85(q, 2H); 1.90-2.06(m, 2H); 2.13(s, 3H); 3.05-3.23(m, 6H); 3.59(d, 2H); 3.71(bs, 4H); 3.89-4.02(m, 1H); 6.94(s, 1H); 7.13(s, 1H); 7.19(s, 1H). | 481 | Methyl 3-(4-{[(3,4-dichloro-5-methyl-1H-pyrrol-2-yl)carbonyl]amino}piperidin-1-yl)-5-morpholin-4-ylbenzoate (Example 216) |
| 346 | 3-(4-{[(3,4-Dichloro-5-methyl-1H-pyrrol-2-yl)carbonyl]amino}piperidin-1-yl)-5-(4-methylpiperazin-1-yl)benzoic acid | 1.51-1.73(m, 2H); 1.80-1.97(m, 2H); 2.14(s, 3H); 2.53(s, 4H); 2.81(s, 3H); 2.87-3.01(m, 3H); 3.04-3.24(m, 2H); 3.39-3.56(m, 2H); 3.65(d, 2H); 6.76(s, 1H); 6.94(s, 1H); 7.04(s, 1H). | 495 | Methyl 3-(4-{[(3,4-dichloro-5-methyl-1H-pyrrol-2-yl)carbonyl]amino}piperidin-1-yl)-5-(4-methylpiperazin-1-yl)benzoate (Example 217) |

—N(R$^7$)COR$^6$, —CONHCH(CO$_2$R$^7$)R$^6$, halo, hydroxy, carboxy, (1-6C)alkyl [optionally substituted by 1 or 2 substituents independently selected from hydroxy, halo, cyano, nitro, —COO(1-6C)alkyl, —OCO(1-4C)alkyl, (1-6C)alkoxy, (1-4C)alkoxy(1-4C)alkoxy, hydroxy(1-4C)alkoxy-, (2-4C)alkenyloxy, trifluoromethyl, —CONR$^6$R$^7$, carboxy, —NHC(O)O(1-4C)alkyl, —OCONR$^6$R$^7$, —C(=NOH)(1-4C)alkyl, —C(=NOH)NR$^6$R$^7$, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl (optionally substituted by 1 or 2 substituents selected from (1-6C)alkyl and the optional substituents described for (1-6C)alkyl hereinbefore), —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, aryl, —NHC(O)O(1-4C)alkyl, —C(=NOR$^7$)(1-4C)alkyl, —C(=NOR$^7$)NR$^6$R$^7$, —S(O)pNR$^6$R$^7$, —S(O)p(1-4C)alkylCONHR$^7$, —NR$^7$S(O)pNR$^6$R$^7$, —NR$^7$S(O)p(1-4C)alkyl, —NR$^7$S(O)p-aryl, —C(O)NHS(O)p(1-4C)alkyl, —C(O)NHS(O)p-aryl, —NR$^6$R$^7$, —CH$_2$CH(CO$_2$R$^6$)OH, -(1-4C)alkylCH(NR$^6$R$^7$)CO$_2$R$^6$ and -(1-4C)alkylCH(NR$^6$R$^7$)CO(NR$^6$R$^7$);

wherein any aryl or heterocyclyl group in any of the preceding values for substituents on R$^1$a may optionally be substituted by 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl-, (1-4C)alkoxy(1-4C)alkyl-, halo(1-4C)alkyl-, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl and —S(O)$_2$N[di(1-4C)alkyl];

R$^2$ is selected from hydrogen, (1-4C)alkyl, cyclopropyl, (2-4C)alkenyl, (2-4C)alkynyl, halo, cyano, fluoromethyl, difluoromethyl and trifluoromethyl;

R$^3$ is selected from hydrogen, (1-4C)alkyl, cyclopropyl, (2-4C)alkenyl, (2-4C)alkynyl, halo, hydroxy, cyano, fluoromethyl, difluoromethyl trifluoromethyl, —CO(1-6C)alkyl, and (1-6C)alkoxy;

R$^4$ is selected from hydrogen, (1-4C)alkyl, (2-4C)alkenyl, (2-4C)alkynyl, nitro, hydroxy, halo, cyano, (3-6C)cycloalkyl, -(1-6C)alkyl(3-6C)cycloalkyl, halo(1-4C)alkyl-, difluoromethyl, trifluoromethyl, —CO(1-6C)alkyl, and (1-6C)alkoxy;

R$^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —NH(1-4C)alkyl, —N[di(1-4C)alkyl], (1-4C)alkoxy, (1-4C)alkoxy(1-4C)alkoxy, (1-4C)alkoxy(1-4C)alkoxy(1-4C)alkoxy, (1-4C)alkoxy(1-4C)alkyl-, (1-4C)alkylthio(1-4C)alkyl-, hydroxy(1-4C)alkyl-, -(1-4C)alkylNH$_2$, -(1-4C)alkylNH(1-4C)alkyl, -(1-4C)alkylN[di(1-4C)alkyl], and -(1-4C)alkylheterocyclyl;

R$^7$ is independently at each occurrence selected from hydrogen and (1-4C)alkyl;

or R$^6$ and R$^7$ may together with the nitrogen to which they are attached form a 5 or 6-membered heterocyclyl ring, optionally substituted with 1 or 2 substituents independently selected from (1-4C)alkyl, (2-4C)alkenyl, (2-4C)alkynyl, hydroxy, (1-4C)alkoxy, halo, cyano, nitro, carboxy, hydroxy(1-4C)alkyl-, (1-4C)alkoxy(1-4C)alkyl-, halo(1-4C)alkyl-, difluoromethyl, trifluoromethyl, trifluoromethoxy, formyl, —CO(1-4C)alkyl, —COO(1-4C)alkyl, —C(O)NH$_2$, —C(O)NH(1-4C)alkyl, —C(O)N[di(1-4C)alkyl], —S(O)$_2$NH$_2$, —S(O)$_2$NH(1-4C)alkyl, —S(O)$_2$N[di(1-4C)alkyl] and —S(O)p(1-4C)alkyl;

R$^5$ is selected from hydrogen and (1-4C)alkyl;

p is (independently at each occurrence) 0, 1 or 2.

2. A compound of claim 1 or a pharmaceutically acceptable salt thereof wherein W is O.

3. A compound of claim 1 or a pharmaceutically acceptable salt thereof wherein W is NR$^5$.

4. A compound of claim 1 or a pharmaceutically acceptable salt thereof wherein R$^1$ is R$^1$a; wherein R$^1$a is a 5 or 6 membered saturated, partially unsaturated or unsaturated heterocyclic ring containing 1, 2, 3, or 4 heteroatoms independently selected from O, S and N (provided that such a ring does not contain O—O or S—S bonds), wherein a —CH$_2$— group can optionally be replaced by a —C(O)—, a ring sulphur atom may be optionally oxidised to form the S-oxide(s), and a ring nitrogen atom may be optionally oxidised to form the N-oxide, and wherein said ring may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR$^6$R$^7$, —N(R$^7$)COR$^6$, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR$^6$R$^7$, —NHC(O)NR$^6$R$^7$, —NHC(O)(1-4C)alkyl, —NHC(O)heterocyclyl, —NHC(O)aryl, —NHS(O)p(1-4C)alkyl, —S(O)p(1-4C)alkyl, —S(O)pNR$^6$R$^7$, —NHSO$_2$R$^6$, —NR$^6$R$^7$, and heterocyclyl], (3-6C)cycloalkyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), heterocyclyl, —NHC(O)O(1-4C)alkyl, —C(=NOR$^7$)(1-4C)alkyl, —C(=NOR$^7$)NR$^6$R$^7$, —S(O)p(1-4C)alkylCONHR$^7$, —C(O)NHS(O)p(1-4C)alkyl, and —NR$^6$R$^7$, wherein any aryl or heterocyclyl group in any of the preceding values for substituents on R$^1$a may optionally be substituted by 1 or 2 substituents independently selected from (1-4C)alkyl and carboxy.

5. A compound of claim 1 or a pharmaceutically acceptable salt thereof wherein R$^2$ is selected from (1-4C)alkyl, halo and cyano.

6. A compound of claim 1 or a pharmaceutically acceptable salt thereof wherein R$^3$ is selected from hydrogen, (1-4C)alkyl, halo, cyano and —CO(1-6C)alkyl.

7. A compound of claim 1 or a pharmaceutically acceptable salt thereof wherein R$^4$ is selected from hydrogen, (1-4C)alkyl, halo and cyano.

8. A compound of claim 1 or a pharmaceutically acceptable salt thereof wherein:

$R^6$ is independently at each occurrence selected from hydrogen, (1-4C)alkyl, (3-4C)alkenyl, (3-6C)cycloalkyl, -(1-4C)alkylC(O)O(1-4C)alkyl, hydroxy, amino, —N[di(1-4C)alkyl], (1-4C)alkoxy and -(1-4C)alkylheterocyclyl;

$R^7$ is independently at each occurrence selected from hydrogen and (1-6C)alkyl;

or $R^6$ and $R^7$ may together with the nitrogen to which they are attached form a 5 or 6-membered heterocyclyl ring, optionally substituted with 1 or 2 substituents independently selected from (1-4C)alkyl.

9. A compound of claim 1 or a pharmaceutically acceptable salt thereof:

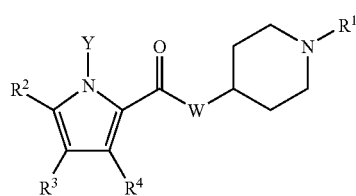

(1)

wherein:

$R^1$ is $R^1a$; wherein $R^1a$ is pyridinyl, N-oxopyridinyl, pyrimidinyl, thiazolyl, thiadiazolyl, tetrazolyl, imidazolyl, triazinyl, pyrrolidinyl, thienyl, furanyl, oxadiazolyl, isoxazolyl, oxazolyl or pyrrolyl, wherein said $R^1a$ may be optionally substituted by 1, 2 or 3 substituents independently selected from:

nitro, cyano, sulfo, formyl, hydroxyiminomethyl, (2-6C)alkenyl, —CO(1-6C)alkyl, —COO(1-6C)alkyl trifluoromethyl, —CONR⁶R⁷, —N(R⁷)COR⁶, halo, hydroxy, carboxy, (1-6C)alkyl [optionally substituted by 1 or 2 substituents independently selected from hydroxy, —OCO(1-4C)alkyl, (1-6C)alkoxy, (1-4C)alkoxy(1-4C)alkoxy, hydroxy(1-4C)alkoxy, (2-4C)alkenyloxy, —NHC(O)O(1-4C)alkyl, —NHC(=NH)NR⁶R⁷, —NHC(O)NR⁶R⁷, —NHC(O)(1-4C)alkyl, —NHC(O)tetrahydrofuranyl, —NHC(O)phenyl, —NHS(O)p(1-4C)alkyl, —S(O)p(1-4C)alkyl, —S(O)pNR⁶R⁷, —NHSO₂R⁶, —NR⁶R⁷, morpholino, 1,3-dioxo-1,3-dihydro-2H-isoindolyl and 1,3-dioxolanyl], cyclopropyl, —O(1-6C)alkyl (optionally substituted by 1 or 2 substituents as described for (1-6C)alkyl hereinbefore), —S(O)p(1-4C)alkyl (optionally substituted by 1 or 2 substituents as described for (1-6C)alkyl hereinbefore), tetrazolyl, 2-oxo-1,3,4-oxadiazolyl, 1,2,4-oxadiazolyl, morpholino, piperazinyl, pyrrolidinyl, —NHC(O)O(1-4C)alkyl, —C(=NOR⁷)(1-4C)alkyl, —C(=NOR⁷)NR⁶R⁷, —S(O)p(1-4C)alkylCONHR⁷, —C(O)NHS(O)p(1-4C)alkyl and —NR⁶R⁷;

wherein any phenyl, tetrahydrofuranyl, morpholino, 1,3-dioxo-1,3-dihydro-2H-isoindolyl, 1,3-dioxolanyl, tetrazolyl, 2-oxo-1,3,4-oxadiazolyl, 1,2,4-oxadiazolyl, morpholino, piperazinyl, pyrrolidinyl, in any of the preceding values for substituents on $R^1a$ may optionally be substituted by 1 or 2 substituents independently selected from (1-4C)alkyl and carboxy;

$R^2$ is selected from methyl, ethyl, isopropyl, chloro and cyano;

$R^3$ is selected from hydrogen, methyl, ethyl, chloro, bromo, cyano and —COMe;

$R^4$ is selected from hydrogen, chloro, methyl, ethyl and cyano;

$R^5$ is hydrogen or methyl;

$R^6$ is independently at each occurrence selected from hydrogen, (1-4C)alkyl, (3-4C)alkenyl, cyclopropyl, -(1-4C)alkylC(O)O(1-4C)alkyl, hydroxy, amino, —N[di(1-4C)alkyl], (1-4C)alkoxy and -(1-4C)alkylmorpholino;

$R^7$ is independently at each occurrence selected from hydrogen and (1-4C)alkyl;

or $R^6$ and $R^7$ may together with the nitrogen to which they are attached form piperazinyl or morpholino optionally substituted with 1 or 2 substituents independently selected from (1-4C)alkyl;

p is (independently at each occurrence) 0, 1 or 2.

10. A compound of claim 1 or a pharmaceutically acceptable salt thereof selected from:

2-chloro-6-(4-{[(3,4-dichloro-5-methyl-1H-pyrrol-2-yl)carbonyl]amino}piperidin-1-yl)-N-methoxypyrimidine-4-carboxamide;

2-chloro-6-(4-{[(3,4-dichloro-5-methyl-1H-pyrrol-2-yl)carbonyl]amino}piperidin-1-yl)isonicotinamide;

1-[4-(aminocarbonyl)-6-chloro-2-pyridinyl]4-piperidinyl 4-bromo-5-methyl-1H-pyrrole-2-carboxylate;

1-{4-[amino(hydroxyimino)methyl]6-chloro-2-pyridinyl}-4-piperidinyl 3,4-dichloro-5-methyl-1H-pyrrole-2-carboxylate;

2-butoxy-6-(4-{[(3,4-dichloro-5-methyl-1H-pyrrol-2-yl)carbonyl]amino}piperidin-1-yl)isonicotinic acid;

2-(4-{[(3,4-dichloro-5-methyl-1H-pyrrol-2-yl)carbonyl]amino}piperidin-1-yl)-6-(2-methoxyethoxy) isonicotinic acid;

2-(4-{[(3,4-dichloro-5-methyl-1H-pyrrol-2-yl)carbonyl]amino}piperidin-1-yl)-N-methoxy-6-(methylsulfonyl)isonicotinamide;

2-(butylthio)-6-(4-{[(3,4-dichloro-5-methyl-1H-pyrrol-2-yl)carbonyl]amino}piperidin-1-yl)pyrimidine-4-carboxylic acid;

2-(tert-butylthio)-6-(4-{[(3,4-dichloro-5-methyl-1H-pyrrol-2-yl)carbonyl]amino}piperidin-1-yl)pyrimidine-4-carboxylic acid;

2-tert-butyl-6-(4-{[(3,4-dichloro-5-methyl-1H-pyrrol-2-yl)carbonyl]amino}piperidin-1-yl)pyrimidine-4-carboxylic acid;

4-(4-{[(3,4-dichloro-5-methyl-1H-pyrrol-2-yl)carbonyl]amino}piperidin-1-yl)quinoline-2-carboxylic acid;

2-(4-{[(3,4-dichloro-5-methyl-1H-pyrrol-2-yl)carbonyl]amino}piperidin-1-yl)-1,3-thiazole-5-carboxylic acid;

2-(4-{[(3,4-dichloro-5-methyl-1H-pyrrol-2-yl)carbonyl]amino}piperidin-1-yl)-1,3-thiazole-4-carboxylic acid;

6-chloro-4-(4-{[(3,4-dichloro-5-methyl-1H-pyrrol-2-yl)carbonyl]amino}piperidin-1-yl)quinoline-2-carboxylic acid;

5-(4-{[(3,4-dichloro-5-methyl-1H-pyrrol-2-yl)carbonyl]amino}piperidin-1-yl)-N-methoxynicotinamide;

6-(4-{[(3,4-dichloro-5-methyl-1H-pyrrol-2-yl)carbonyl]amino}piperidin-1-yl)pyridine-2-carboxylic acid;

4-[(tert-butylamino)carbonyl]-2-(4-{[(3,4-dichloro-5-methyl-1H-pyrrol-2-yl)carbonyl]amino}piperidin-1-yl)-1,3-thiazole-5-carboxylic acid; and 2-(4-{[(3,4-dichloro-5-methyl-1H-pyrrol-2-yl)carbonyl]amino}piperidin-1-yl)-4-methyl-1,3-thiazole-5-carboxylic acid.

11. A process for preparing a compound of claim 1 or a pharmaceutically acceptable salt thereof, comprising:

a) for compounds of formula (1) where W is NR$^5$; reacting an acid of the formula (2a):

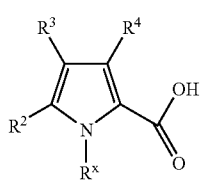

(2a)

(wherein R$^x$ is hydrogen or a suitable protecting group) or an activated derivative thereof; with an amine of formula (3a); or

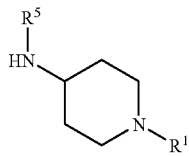

(3a)

b) reacting a compound of formula (4a):

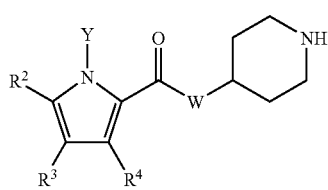

(4a)

with a compound of formula (5a):

X—R$^1$ (5a)

wherein X is a displaceable group;

c) for compounds of formula (1) where W is O; reacting an acid of the formula (2a) or an activated derivative thereof, with an alcohol of formula (6a); or

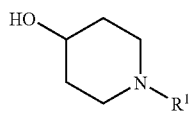

(6a)

and thereafter if necessary:
  i) converting a compound of the formula (1) into another compound of the formula (1);
  ii) removing any protecting groups;
  iii) forming a pharmaceutically acceptable salt.

12. A pharmaceutical composition which comprises a compound of claim 1 or a pharmaceutically acceptable salt thereof, and a pharmaceutically acceptable diluent or carrier.

* * * * *